US012751836B2

(12) United States Patent
Campbell et al.

(10) Patent No.: US 12,751,836 B2
(45) Date of Patent: Oct. 6, 2026

(54) SYSTEMS AND METHODS FOR JOINT FUSION

(71) Applicant: Crossroads Extremity Systems, LLC, Memphis, TN (US)

(72) Inventors: Michael Campbell, Virginia Beach, VA (US); Scott Shawen, Charlotte, NC (US); Daniel Sayger, Olive Branch, MS (US); Michael Chad Hollis, Collierville, TN (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 768 days.

(21) Appl. No.: 17/748,301

(22) Filed: May 19, 2022

(65) Prior Publication Data

US 2022/0370211 A1 Nov. 24, 2022

Related U.S. Application Data

(60) Provisional application No. 63/364,943, filed on May 18, 2022, provisional application No. 63/233,582,
(Continued)

(51) Int. Cl.
*A61F 2/46* (2006.01)
*A61B 17/064* (2006.01)
(Continued)

(52) U.S. Cl.
CPC ........ *A61F 2/4606* (2013.01); *A61B 17/0642* (2013.01); *A61B 17/15* (2013.01);
(Continued)

(58) Field of Classification Search
CPC .......................... A61B 17/1682; A61F 2/4606
See application file for complete search history.

(56) References Cited

U.S. PATENT DOCUMENTS 4,069,824 A 1/1978 Weinstock
4,335,715 A 6/1982 Kirkley
(Continued)

FOREIGN PATENT DOCUMENTS

EP 0570187 A1 11/1993
JP 2004-174265 A 6/2004
(Continued)

OTHER PUBLICATIONS

Arthrex Hallux Valgus Solutions, Arthrex, Inc., www.arthrex.com 2009, 2 pp.
(Continued)

*Primary Examiner* — Andrew Yang

(57) ABSTRACT

Methods and apparatus are disclosed for excising a joint between first and second bones to define a resected joint, approximating the first and second bones to reduce the resected joint, and fixing the first and second bones relative to each other. The excising step can be performed using a cut guide that is movable from a first orientation to cut the first bone to a second orientation to cut the second bone. A compressor block can be driven over temporary fixation members that extends into the first and second bones to reduce the resected joint. A staple, along or in combination with other fixation elements, can then permanently fix the first bone to the second bone.

24 Claims, 93 Drawing Sheets

Related U.S. Application Data filed on Aug. 16, 2021, provisional application No. 63/201,940, filed on May 19, 2021.

(51) Int. Cl.

| | |
|---|---|
| ***A61B 17/15*** | (2006.01) |
| *A61B 17/56* | (2006.01) |
| *A61F 2/30* | (2006.01) |
| *A61F 2/42* | (2006.01) |

(52) U.S. Cl.

CPC .................. *A61B 2017/565* (2013.01); *A61F 2002/30622* (2013.01); *A61F 2002/4238* (2013.01)

(56) References Cited

U.S. PATENT DOCUMENTS

| | | | |
|---|---|---|---|
| 4,349,018 | A | 9/1982 | Chambers |
| 4,409,973 | A | 10/1983 | Neufeld |
| 4,440,168 | A | 4/1984 | Warren |
| 4,501,268 | A | 2/1985 | Comparetto |
| 4,502,474 | A | 3/1985 | Comparetto |
| 4,509,511 | A | 4/1985 | Neufeld |
| 4,565,191 | A | 1/1986 | Slocum |
| 4,627,425 | A | 12/1986 | Reese |
| 4,632,102 | A | 12/1986 | Comparetto |
| 4,664,102 | A | 5/1987 | Comparetto |
| 4,708,133 | A | 11/1987 | Comparetto |
| 4,736,737 | A | 4/1988 | Fargie et al. |
| 4,750,481 | A | 6/1988 | Reese |
| 4,757,810 | A | 7/1988 | Reese |
| 4,852,558 | A | 8/1989 | Outerbridge |
| 4,913,144 | A | 4/1990 | Del Medico |
| 4,952,214 | A | 8/1990 | Comparetto |
| 4,959,066 | A | 9/1990 | Dunn et al. |
| 5,035,698 | A | 7/1991 | Comparetto |
| 5,042,983 | A | 8/1991 | Rayhack |
| 5,049,149 | A | 9/1991 | Schmidt |
| 5,053,039 | A | 10/1991 | Hofmann et al. |
| 5,078,719 | A | 1/1992 | Schreiber |
| 5,112,334 | A | 5/1992 | Alchermes et al. |
| 5,147,364 | A | 9/1992 | Comparetto |
| 5,176,685 | A | 1/1993 | Rayhack |
| 5,246,444 | A | 9/1993 | Schreiber |
| D357,534 | S | 4/1995 | Hayes |
| 5,413,579 | A | 5/1995 | Tom Du Toit |
| 5,449,360 | A | 9/1995 | Schreiber |
| 5,470,335 | A | 11/1995 | Du Toit |
| 5,540,695 | A | 7/1996 | Levy |
| 5,578,038 | A | 11/1996 | Slocum |
| 5,601,565 | A | 2/1997 | Huebner |
| 5,613,969 | A | 3/1997 | Jenkins, Jr. |
| 5,620,448 | A | 4/1997 | Puddu |
| 5,643,270 | A | 7/1997 | Combs |
| 5,667,510 | A | 9/1997 | Combs |
| H1706 | H | 1/1998 | Mason |
| 5,722,978 | A | 3/1998 | Jenkins, Jr. |
| 5,749,875 | A | 5/1998 | Puddu |
| 5,779,709 | A | 7/1998 | Harris et al. |
| 5,843,085 | A | 12/1998 | Graser |
| 5,911,724 | A | 6/1999 | Wehrli |
| 5,980,526 | A | 11/1999 | Johnson et al. |
| 5,984,931 | A | 11/1999 | Greenfield |
| 6,007,535 | A | 12/1999 | Rayhack et al. |
| 6,027,504 | A | 2/2000 | Mcguire |
| 6,030,391 | A | 2/2000 | Brainard et al. |
| 6,203,545 | B1 | 3/2001 | Stoffella |
| 6,248,109 | B1 | 6/2001 | Stoffella |
| 6,391,031 | B1 | 5/2002 | Toomey |
| 6,547,793 | B1 | 4/2003 | Mcguire |
| 6,676,662 | B1 | 1/2004 | Bagga et al. |
| 6,755,838 | B2 | 6/2004 | Trnka |
| 6,796,986 | B2 | 9/2004 | Duffner |
| 7,018,383 | B2 | 3/2006 | Mcguire |
| 7,112,204 | B2 | 9/2006 | Justin et al. |
| 7,182,766 | B1 | 2/2007 | Mogul |
| 7,540,874 | B2 | 6/2009 | Trumble et al. |
| 7,572,258 | B2 | 8/2009 | Stiernborg |
| 7,691,108 | B2 | 4/2010 | Lavallee |
| 7,763,026 | B2 | 7/2010 | Egger et al. |
| D630,746 | S | 1/2011 | Richter et al. |
| 7,967,823 | B2 | 6/2011 | Ammann et al. |
| 7,972,338 | B2 | 7/2011 | O'Brien |
| 8,062,301 | B2 | 11/2011 | Ammann et al. |
| 8,083,746 | B2 | 12/2011 | Novak |
| 8,137,406 | B2 | 3/2012 | Novak et al. |
| 8,236,000 | B2 | 8/2012 | Ammann et al. |
| 8,262,664 | B2 | 9/2012 | Justin et al. |
| 8,277,459 | B2 | 10/2012 | Sand et al. |
| 8,282,645 | B2 | 10/2012 | Lawrence et al. |
| 8,313,492 | B2 | 11/2012 | Wong et al. |
| 8,409,209 | B2 | 4/2013 | Ammann et al. |
| 8,496,662 | B2 | 7/2013 | Novak et al. |
| 8,529,571 | B2 | 9/2013 | Horan et al. |
| 8,540,777 | B2 | 9/2013 | Ammann et al. |
| 8,545,508 | B2 | 10/2013 | Collazo |
| D695,402 | S | 12/2013 | Dacosta et al. |
| 8,652,142 | B2 | 2/2014 | Geissler |
| 8,657,820 | B2 | 2/2014 | Kubiak et al. |
| 8,702,715 | B2 | 4/2014 | Ammann et al. |
| 8,771,279 | B2 | 7/2014 | Philippon et al. |
| 8,777,948 | B2 | 7/2014 | Bernsteiner |
| 8,888,785 | B2 | 11/2014 | Ammann et al. |
| 8,900,247 | B2 | 12/2014 | Tseng et al. |
| 8,906,026 | B2 | 12/2014 | Ammann et al. |
| 9,060,822 | B2 | 6/2015 | Lewis et al. |
| 9,113,920 | B2 | 8/2015 | Ammann et al. |
| 9,351,742 | B2 | 5/2016 | Appenzeller et al. |
| 9,622,805 | B2 | 4/2017 | Santrock et al. |
| 9,687,250 | B2 | 6/2017 | Dayton et al. |
| 9,814,474 | B2 | 11/2017 | Montoya et al. |
| 9,907,558 | B2 | 3/2018 | Fallin et al. |
| 9,936,994 | B2 | 4/2018 | Smith et al. |
| 10,045,807 | B2 | 8/2018 | Santrock et al. |
| 10,245,086 | B2 | 4/2019 | Treace et al. |
| 10,245,088 | B2 | 4/2019 | Dayton et al. |
| 10,292,713 | B2 | 5/2019 | Fallin et al. |
| 10,299,842 | B2 | 5/2019 | Hollis et al. |
| 10,335,220 | B2 | 7/2019 | Smith et al. |
| 10,342,590 | B2 | 7/2019 | Bays et al. |
| 10,376,268 | B2 | 8/2019 | Fallin et al. |
| 10,470,779 | B2 | 11/2019 | Fallin et al. |
| 10,512,470 | B1 | 12/2019 | Bays et al. |
| 10,555,757 | B2 | 2/2020 | Dayton |
| 10,561,426 | B1 | 2/2020 | Dayton et al. |
| 10,575,862 | B2 | 3/2020 | Bays et al. |
| 10,743,995 | B2 | 8/2020 | Fallin et al. |
| 10,898,211 | B2 | 1/2021 | Fallin et al. |
| 11,058,546 | B2 | 7/2021 | Hollis et al. |
| 11,116,558 | B2 | 9/2021 | Smith et al. |
| 11,147,590 | B2 | 10/2021 | Dayton et al. |
| 11,160,567 | B2 | 11/2021 | Fallin et al. |
| 11,304,735 | B2 | 4/2022 | Sayger et al. |
| 12,133,655 | B2 | 11/2024 | Gazonnet et al. |
| 2002/0165552 | A1 | 11/2002 | Duffner |
| 2002/0198530 | A1 | 12/2002 | Sanford et al. |
| 2003/0167091 | A1 | 9/2003 | Scharf |
| 2004/0097946 | A1 | 5/2004 | Dietzel et al. |
| 2004/0138669 | A1 | 7/2004 | Horn |
| 2005/0070909 | A1 | 3/2005 | Egger et al. |
| 2005/0149042 | A1 | 7/2005 | Metzger |
| 2005/0228389 | A1 | 10/2005 | Stiernborg |
| 2005/0251147 | A1 | 11/2005 | Novak |
| 2005/0273112 | A1 | 12/2005 | Mcnamara |
| 2006/0129163 | A1 | 6/2006 | Mcguire |
| 2006/0241637 | A1 | 10/2006 | Hodorek et al. |
| 2006/0264961 | A1 | 11/2006 | Murray-Brown |
| 2006/0276795 | A1 | 12/2006 | Orbay et al. |
| 2007/0010818 | A1 | 1/2007 | Stone et al. |
| 2007/0265634 | A1 | 11/2007 | Weinstein |
| 2007/0276383 | A1 | 11/2007 | Rayhack |
| 2008/0015603 | A1 | 1/2008 | Collazo |
| 2008/0039850 | A1 | 2/2008 | Rowley et al. |
| 2008/0147073 | A1 | 6/2008 | Ammann et al. |

(56) References Cited

U.S. PATENT DOCUMENTS

| | | | |
|---|---|---|---|
| 2008/0172056 | A1 | 7/2008 | Edwards |
| 2008/0195215 | A1 | 8/2008 | Morton |
| 2008/0269908 | A1 | 10/2008 | Warburton |
| 2009/0036931 | A1 | 2/2009 | Pech et al. |
| 2009/0054899 | A1 | 2/2009 | Ammann et al. |
| 2009/0210010 | A1 | 8/2009 | Strnad et al. |
| 2009/0222047 | A1 | 9/2009 | Graham |
| 2010/0125300 | A1 | 5/2010 | Blitz et al. |
| 2010/0130981 | A1 | 5/2010 | Richards |
| 2010/0152782 | A1 | 6/2010 | Stone et al. |
| 2011/0178524 | A1 | 7/2011 | Lawrence et al. |
| 2011/0188550 | A1 | 8/2011 | Wajcer et al. |
| 2011/0213376 | A1 | 9/2011 | Maxson et al. |
| 2011/0224734 | A1 | 9/2011 | Schelling |
| 2011/0245835 | A1 | 10/2011 | Dodds et al. |
| 2012/0016426 | A1 | 1/2012 | Robinson |
| 2012/0095465 | A1 | 4/2012 | Graham |
| 2012/0185056 | A1 | 7/2012 | Warburton |
| 2012/0191199 | A1 | 7/2012 | Raemisch |
| 2012/0303033 | A1 | 11/2012 | Weiner et al. |
| 2013/0012949 | A1 | 1/2013 | Fallin et al. |
| 2013/0090662 | A1 | 4/2013 | Hanson et al. |
| 2013/0172942 | A1 | 7/2013 | Lewis et al. |
| 2013/0184708 | A1 | 7/2013 | Robinson et al. |
| 2013/0226248 | A1 | 8/2013 | Hatch et al. |
| 2013/0226252 | A1 | 8/2013 | Mayer |
| 2013/0231668 | A1 | 9/2013 | Olsen et al. |
| 2013/0317559 | A1 | 11/2013 | Leavitt et al. |
| 2013/0331845 | A1 | 12/2013 | Horan et al. |
| 2014/0188139 | A1 | 7/2014 | Fallin et al. |
| 2014/0194999 | A1 | 7/2014 | Orbay et al. |
| 2014/0343555 | A1 | 11/2014 | Russi et al. |
| 2015/0057667 | A1 | 2/2015 | Ammann et al. |
| 2015/0245858 | A1 | 9/2015 | Weiner et al. |
| 2016/0015426 | A1 | 1/2016 | Dayton |
| 2016/0135858 | A1 | 5/2016 | Dacosta et al. |
| 2016/0192950 | A1 | 7/2016 | Dayton et al. |
| 2016/0192970 | A1 | 7/2016 | Dayton et al. |
| 2016/0213384 | A1 | 7/2016 | Fallin et al. |
| 2016/0235414 | A1 | 8/2016 | Hatch et al. |
| 2016/0235454 | A1 | 8/2016 | Treace et al. |
| 2016/0324532 | A1 | 11/2016 | Montoya et al. |
| 2016/0324555 | A1 | 11/2016 | Brumfield et al. |
| 2016/0354127 | A1 | 12/2016 | Lundquist et al. |
| 2017/0007305 | A1 | 1/2017 | Hollis et al. |
| 2017/0014143 | A1 | 1/2017 | Dayton et al. |
| 2017/0014173 | A1 | 1/2017 | Smith et al. |
| 2017/0042598 | A1 | 2/2017 | Santrock et al. |
| 2017/0042599 | A1 | 2/2017 | Bays et al. |
| 2017/0049576 | A1 | 2/2017 | Guilford et al. |
| 2017/0056031 | A1 | 3/2017 | Awtrey et al. |
| 2017/0079669 | A1 | 3/2017 | Bays et al. |
| 2017/0156717 | A1 | 6/2017 | Triplett et al. |
| 2017/0164989 | A1 | 6/2017 | Weiner et al. |
| 2017/0172638 | A1 | 6/2017 | Santrock et al. |
| 2017/0196602 | A1 | 7/2017 | Lundquist et al. |
| 2018/0110530 | A1 | 4/2018 | Wagner et al. |
| 2018/0125504 | A1 | 5/2018 | Dayton et al. |
| 2018/0168746 | A1 | 6/2018 | Swayze et al. |
| 2018/0256223 | A1 | 9/2018 | Lueth et al. |
| 2018/0296257 | A1 | 10/2018 | Penzimer et al. |
| 2018/0317906 | A1 | 11/2018 | Hollis et al. |
| 2018/0317992 | A1 | 11/2018 | Santrock et al. |
| 2018/0353172 | A1 | 12/2018 | Hartdegen et al. |
| 2019/0125418 | A1 | 5/2019 | Muller et al. |
| 2019/0175238 | A1 | 6/2019 | Dayton et al. |
| 2019/0274745 | A1 | 9/2019 | Smith et al. |
| 2019/0328435 | A1 | 10/2019 | Bays et al. |
| 2019/0328436 | A1 | 10/2019 | Bays et al. |
| 2019/0336140 | A1* | 11/2019 | Dacosta ............... A61B 17/151 |
| 2019/0357919 | A1 | 11/2019 | Fallin et al. |
| 2020/0000464 | A1* | 1/2020 | Gaston ................... A61B 17/10 |
| 2020/0015856 | A1 | 1/2020 | Treace et al. |
| 2020/0078025 | A1 | 3/2020 | Fallin et al. |
| 2020/0138491 | A1 | 5/2020 | Brigido et al. |
| 2020/0197021 | A1 | 6/2020 | Dayton et al. |
| 2020/0375644 | A1 | 12/2020 | Smith et al. |
| 2021/0022879 | A1 | 1/2021 | Hollis et al. |
| 2021/0026357 | A1 | 1/2021 | Okubi et al. |
| 2021/0077162 | A1 | 3/2021 | Muller et al. |
| 2021/0077192 | A1 | 3/2021 | Perler et al. |
| 2021/0251670 | A1 | 8/2021 | Sayger et al. |
| 2021/0282823 | A1 | 9/2021 | Day et al. |
| 2021/0307763 | A1 | 10/2021 | Fallin et al. |
| 2021/0338450 | A1 | 11/2021 | Hollis et al. |
| 2022/0273346 | A1 | 9/2022 | Sayger et al. |
| 2022/0323085 | A1 | 10/2022 | Hales et al. |
| 2023/0043795 | A1 | 2/2023 | Hollis et al. |

FOREIGN PATENT DOCUMENTS

| | | | |
|---|---|---|---|
| JP | 2018-525111 | A | 9/2018 |
| JP | 2019-024741 | A | 2/2019 |
| WO | 00/06036 | A1 | 2/2000 |
| WO | 2004/075775 | A2 | 9/2004 |
| WO | 2004/089227 | A2 | 10/2004 |
| WO | 2005/041785 | A1 | 5/2005 |
| WO | 2007/008348 | A2 | 1/2007 |
| WO | 2008/097781 | A1 | 8/2008 |
| WO | 2016/134154 | A1 | 8/2016 |
| WO | 2016/134160 | A1 | 8/2016 |
| WO | 2017/011589 | A1 | 1/2017 |
| WO | 2017/031000 | A1 | 2/2017 |
| WO | 2017/049056 | A1 | 3/2017 |
| WO | 2018/081185 | A1 | 5/2018 |
| WO | 2019/113394 | A1 | 6/2019 |
| WO | 2021/021640 | A1 | 2/2021 |
| WO | 2021/026357 | A1 | 2/2021 |
| WO | 2021/167992 | A1 | 8/2021 |

OTHER PUBLICATIONS

Comprehensive Solutions for Forefoot and Midfood Sungery using the Mini TightRope System, Arthrex, Inc., www arthrex com 2012, 15 pp.

DiDomenico, Lawrence A., et al. "Lapidus Bunionectomy: First Metatarsal-Cuneiform Arthrodesis," Souhterland, Chapter 31, Aug. 18, 2012.

Distal Extremities Orthopaedic Update, Arthrex, Inc., www.arthrex.com, 2014, 24 pp.

Dobbe, et al, "Computer-Assisted and Patent-Specific 3-D Planning and Evaluation of a Single-Cut Rotational Osteotomy for Complex long-Bone Deformities". Med Biol Eng Comput (2011) 49:1363-1370.

Foot & Ankle Repair and Reconstruction Technology Brochure, Arthrex, Inc., www.athrex.com, 2016, 86 pp.

Gregg, Julie, et al., "Plantar Plate Repair and Weil Osteotomy for Metatarsophalangeal Joint Instability", Foot and Ankle Surgery 13(2007) 116-121.

International Search Report and Written Opinion dated Jul. 22, 2021 in application No. PCT/US21/18398 (CROAD.023WO).

International Search Report for International Application No. PCT/US2021/018398 dated Jul. 22, 2021.

Meyer, D.C., et al., "A New Methodology for the Planning of Single Cut Corrective Osteotornles of Mai-Aligned Long Bones", Clinical Blomechanics 20(2005) 223-227.

Oscillating Saw Attachment fo, EPD/APD, Colibri II and Small Electric Drive, Synthes GmbH, www.synthes.com, 2012, 2 pp.

Scarf Osteotomy Technical Information Sheet, Talus group of GECO, www.geco-medical.org, 2004, 2 pp.

Shurnas, Paul S., M.D., et al., Proximal Metatarsal Opening Wedge Osteotomy: PMOW-Arthrex LPS System, Arthrex, Inc., www.arthrex.com, 2008, 1 pp.

Speed Triad Medial Technique, BioMedical Enterprises, www.bme-tx.com, 2015, 2 pp.

The Accu-Cut Osteotomy Guide System, BioPro Implants, www.bioproimpiants.com, Brochure No. 16932 Rev07, 2 pp.

The Accu-Cut Osteotomy Guide System, BioProimplants. www.bioproimplants.com, Brochure No. 17136, Rev4, 2 pp.

(56) References Cited

OTHER PUBLICATIONS

The Next Generation in Foot & Ankle Repair and Reconstruction Technology 2016, Arthrex, Inc., www.arthrex.com, 2016, 76 pp.
Weil, Lowell Jr., el al., "Anatomic Plantar Plate Repair Using the Weil Metatarsal Osteotomy Approach", Foot & Ankle Specialist, http://fas.sagepub.com/, 2011, 7 pp.

* cited by examiner

SYSTEMS AND METHODS FOR JOINT FUSION

CROSS-REFERENCE TO RELATED APPLICATIONS

This claims priority to U.S. Patent Application Ser. No. 63/201,940 filed May 19, 2021, U.S. Patent Application Ser. No. 63/233,582 filed Aug. 16, 2021, and U.S. Patent Application Ser. No. 63/364,943 filed May 18, 2022, the disclosure of each of which is hereby incorporated by reference as if set forth in its entirety herein.

FIELD

The present disclosure relates to medical devices and more particularly to systems and methods for fusion of the tarsometatarsal joint.

BACKGROUND

Tarsometatarsal joint fusion is a surgical procedure that fuses a cuneiform bone with a respective metatarsal bone within the middle foot. Fusion of the tarsometatarsal joint stiffens the joint to correct deformities in the tarsometatarsal region. Conventional methods involve the cutting of the cuneiform and the metatarsal at the joint, reducing the resulting gap between the cuneiform and the metatarsal, and fixing the cuneiform and metatarsal, for instance with a bone plate. Unfortunately, conventional methods suffer from inconsistent cuts at the cuneiform and the metatarsal, which can produce unpredictable compression and alignment of the cuneiform and metatarsal during final fixation, particularly at the second and third cuneiforms and metatarsals.

What is therefore needed is an improved method and apparatus that can consistently produce predictable cuts, and achieves subsequent reliable compression and alignment of the cuneiform and metatarsal prior to final fixation.

BRIEF DESCRIPTION OF THE DRAWINGS

Aspects and advantages of the embodiments provided herein are described with reference to the following detailed description in conjunction with the accompanying drawings. Throughout the drawings, reference numbers may be re-used to indicate correspondence between referenced elements. The drawings are provided to illustrate example embodiments described herein and are not intended to limit the scope of the disclosure.

FIG. 63 is a perspective view of the human foot of FIG. 62, showing the reamer placed over another of the temporary bone fixation elements to create another pilot hole in accordance with an alternative embodiment;

FIG. 64 is a perspective view of the human foot of either of FIG. 61 or 63, showing an applicator driving a staple into the pilot holes;

FIG. 65 is a perspective view of the human foot of FIG. 64, showing the staple released from the applicator;

FIG. 66 is a perspective view of the bones of a human foot, showing a step of a portion of an example fusion procedure of the TMT joint performed using the example joint fusion devices disclosed herein, showing a joint between first and second bones that have been cut, and further showing first and second temporary bone fixation elements positioned in the first and second bones, respectively;

FIG. 67 is a perspective view of the human foot of FIG. 66, showing a bone plate placed across the joint over the temporary bone fixation elements so as to overlay respective portions of the first and second bones;

FIG. 68 is a perspective view of the human foot of FIG. 67, showing a bone fastener inserted through the bone plate and driven into one of the first and second bones;

FIG. 69 is a perspective view of the human foot of FIG. 68, showing the compressor block of FIG. 52A applied over the temporary bone fixation elements toward the bone plate to move the first and second bones and closer together;

FIG. 70 is a perspective view of the human foot of FIG. 69, showing a second bone screw 2022 driven into the other of the first and second bones with respect to FIG. 68;

FIG. 71 is a perspective view of the human foot of FIG. 70, showing the compression block and temporary bone fixation elements removed;

FIG. 72 is a perspective view of the human foot of FIG. 71, showing a staple inserted through a staple aperture of the bone plate;

FIG. 73A is a perspective view of an example bone plate configured to be used in the joint fusion procedures described herein;

FIG. 73B is another perspective view of the bone plate of FIG. 73A;

Figure 73A:
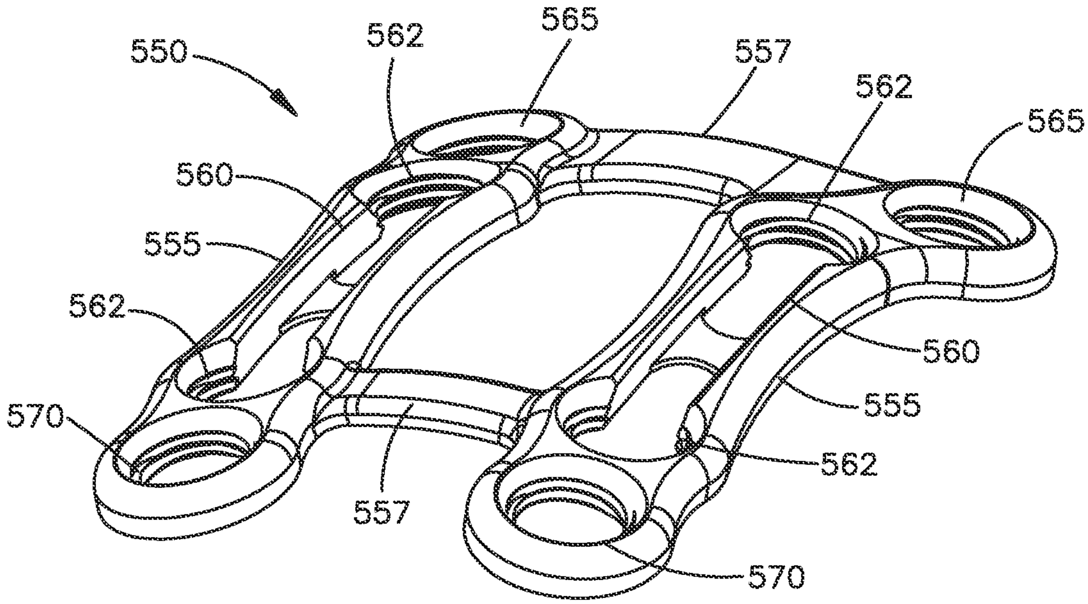
Figure 73B:
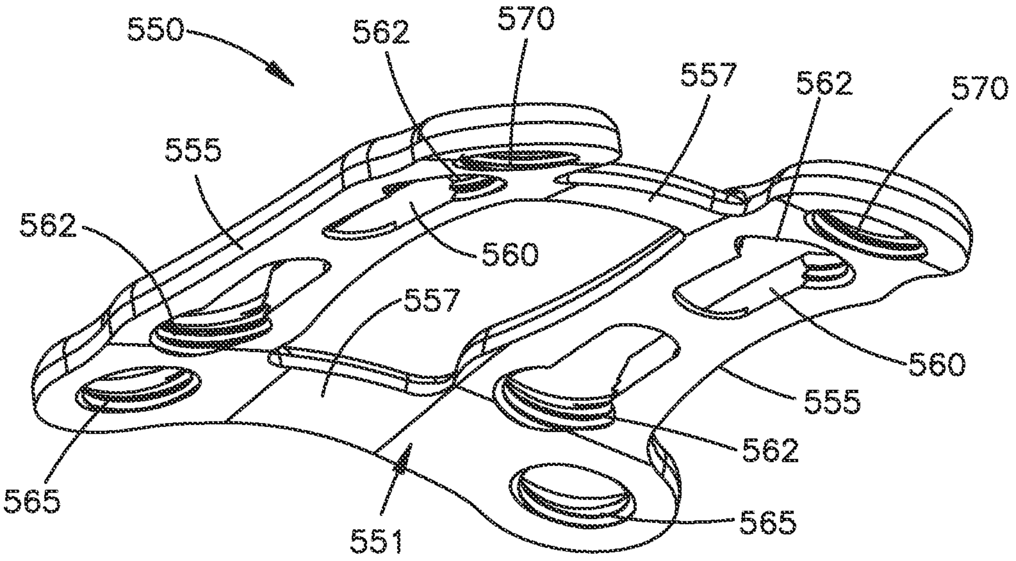
Figure 73C:
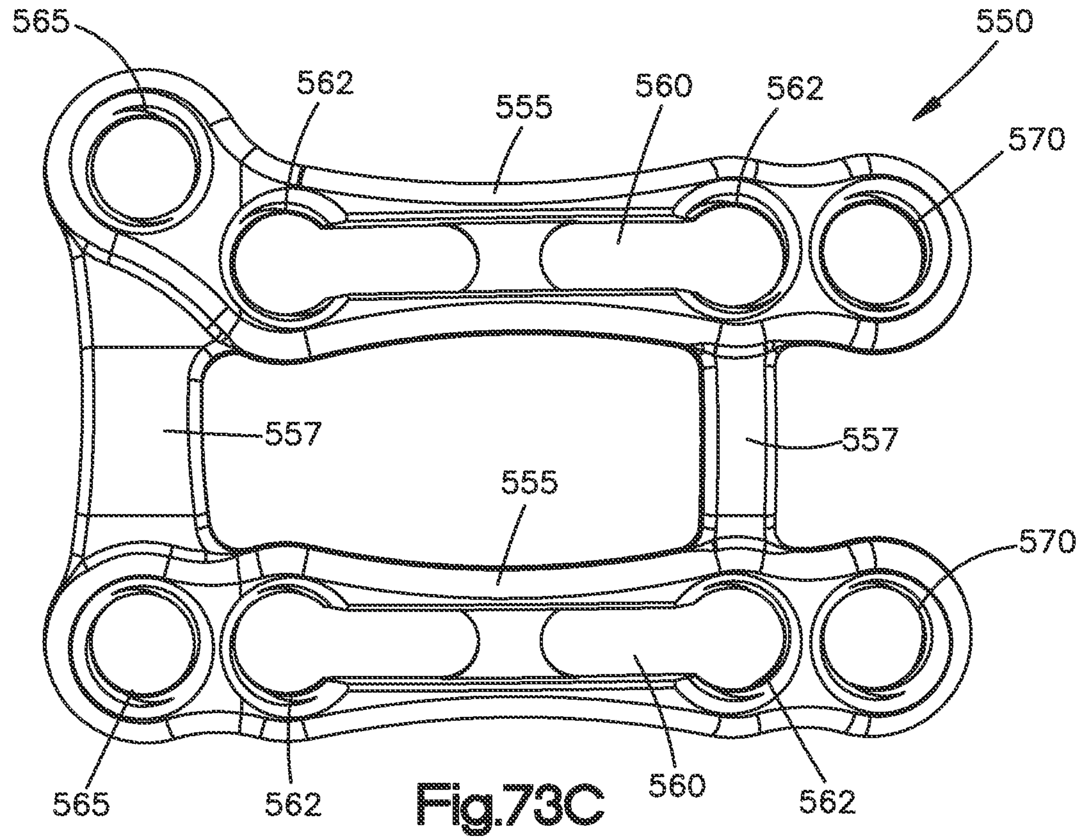
Figure 73D:
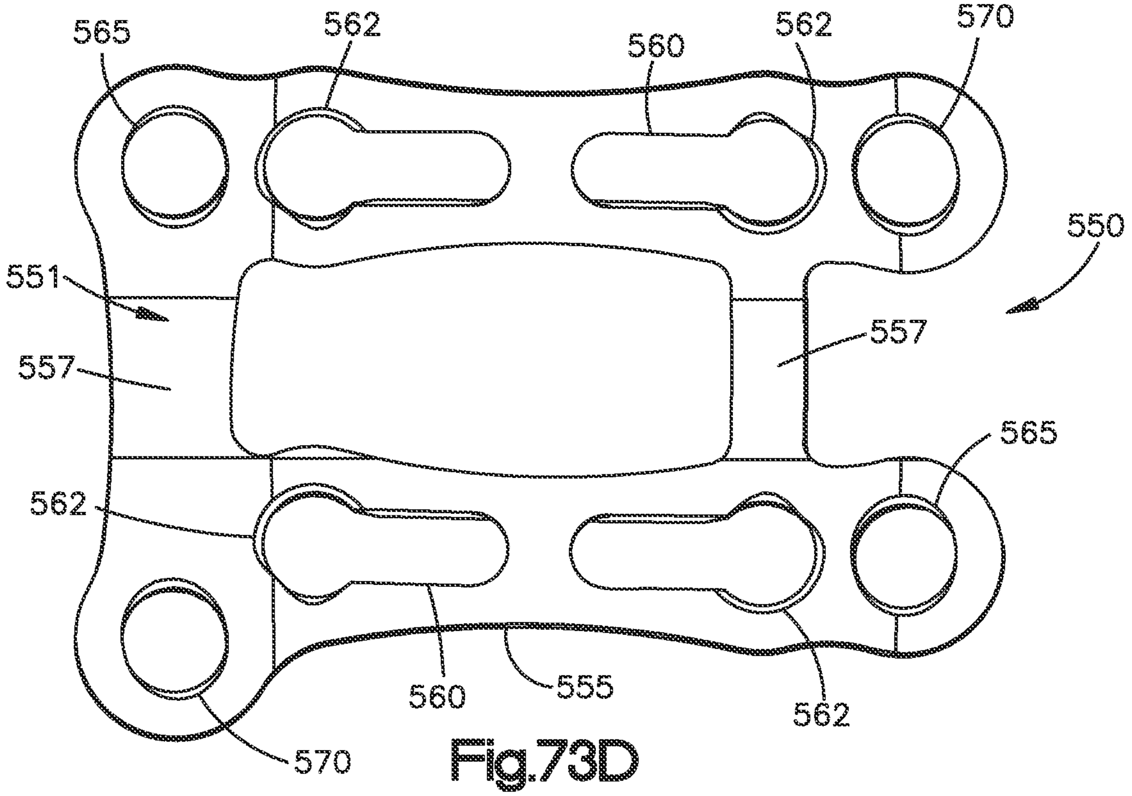
Figure 73E:
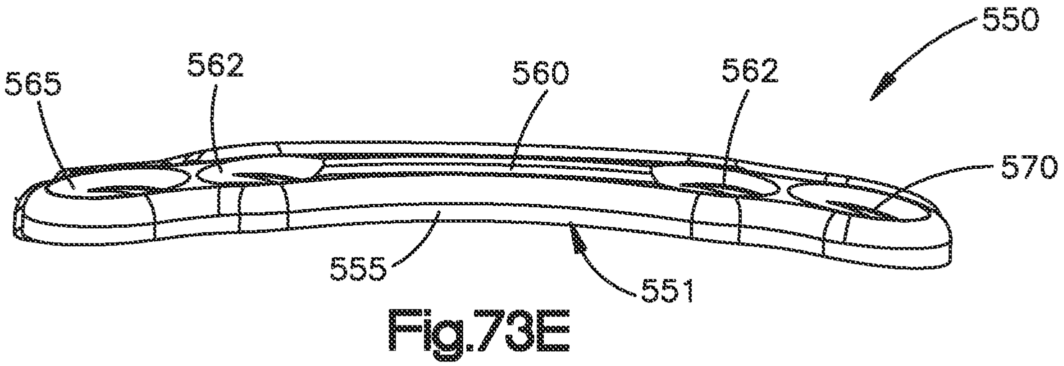
Figure 73F:
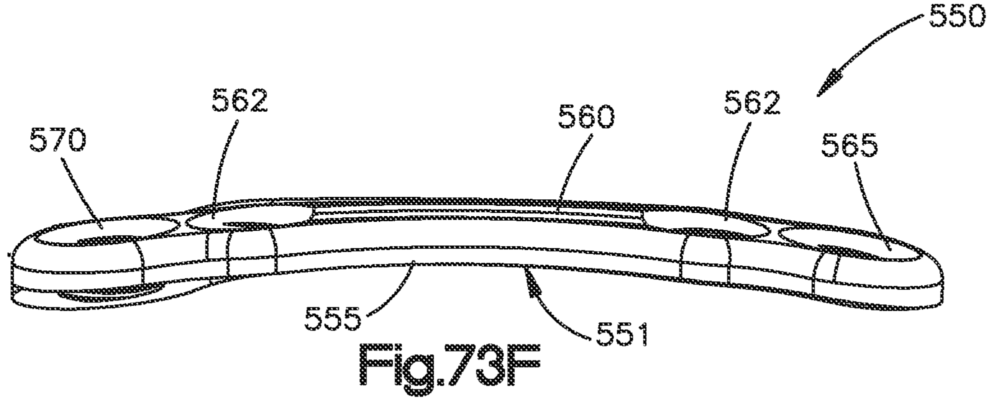
Figure 73G:
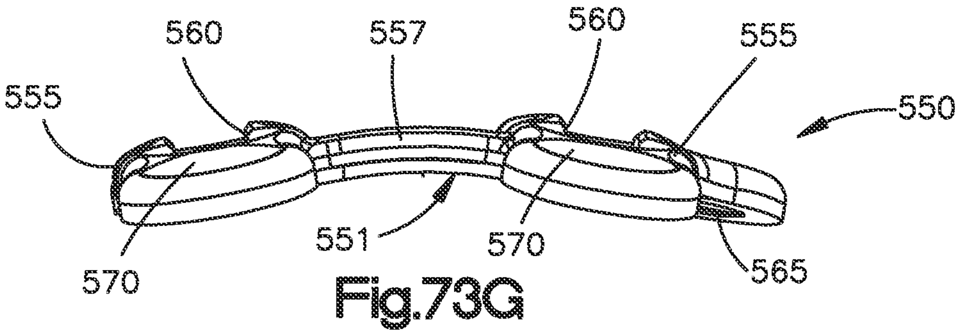
Figure 73H:
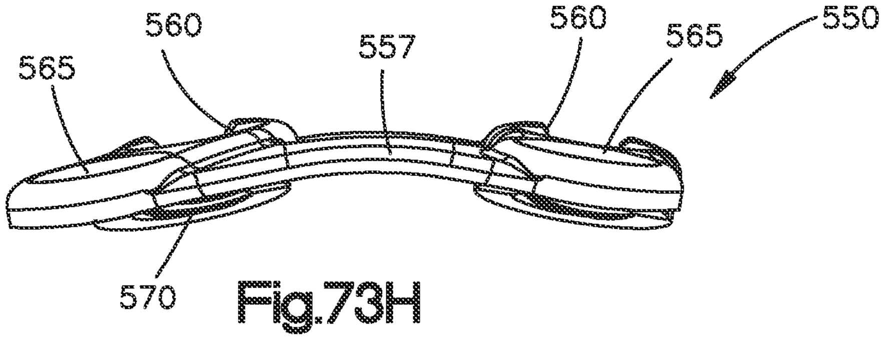
Figure 74:
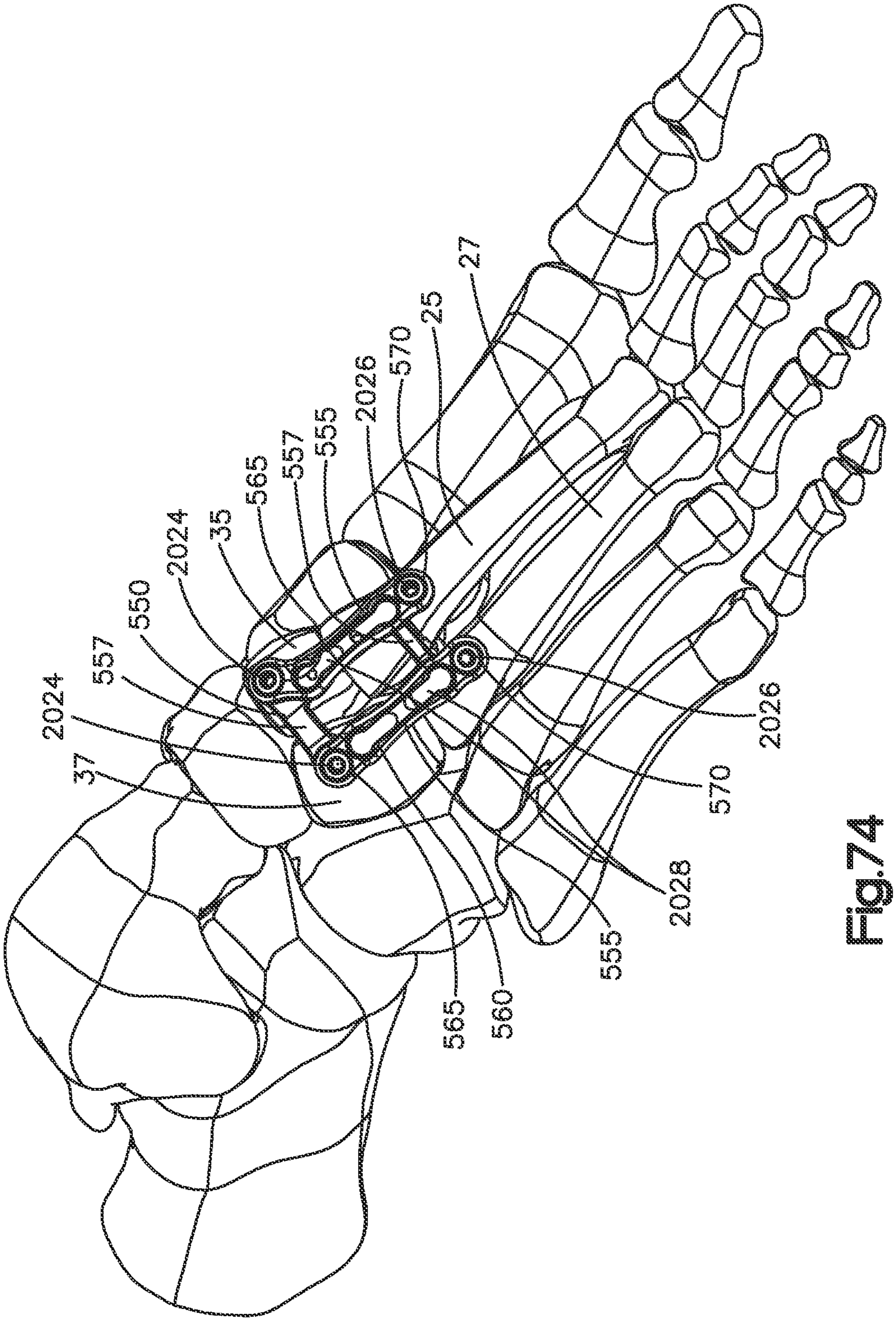

FIG. 73C is a top plan view of the bone plate of FIG. 73A;

FIG. 73D is a bottom plan view of the bone plate of FIG. 73A;

FIG. 73E is a side elevation view of the bone plate of FIG. 73A;

FIG. 73F is an opposite side elevation view of the bone plate of FIG. 73A;

FIG. 73G is a distal end elevation view of the bone plate of FIG. 73A;

FIG. 73H is a proximal end elevation view of the bone plate of FIG. 73A; and FIG. 74 is a perspective view of the bones of a foot illustrating an application of the example bone plate of FIGS. 73A-73H.

DETAILED DESCRIPTION

The following description is directed to certain implementations for the purpose of describing the innovative aspects of this disclosure. However, a person having ordinary skill in the art will readily recognize that the teachings herein can be applied in a multitude of different ways.

Generally described, the systems, devices, and methods described herein provide improved methods and tools that can be used to perform a Lapidus bunionectomy with desirable precision. Some or all of the tools and/or components described herein may be provided in a kit and can include a plurality of optional and/or interchangeable components that may be selected, positioned, secured, and or used at the time of the bunionectomy procedure. Accordingly, the systems, devices, and methods disclosed herein may allow a surgeon to perform a bunionectomy, or otherwise correct alignment of two or more misaligned bones or bone segments, more effectively, efficiently, and/or precisely than would be possible with conventional devices and procedures.

The embodiments described herein can be manufactured from a number of different materials or combinations of materials. Nitinol, stainless steel, titanium, and/or other materials may have desirable material properties for certain components described herein. Stainless steel and/or titanium may not possess shape memory or super elasticity, but may possess the mechanical properties for embodiments that may benefit from mechanical manipulation to achieve multiple configurations. Still other materials such as PEEK or other polymers may also possess material properties beneficial for the embodiments described herein. A combination of materials may also be preferred. For example, a combination of nitinol and titanium (e.g., a nitinol plate with titanium screws) may be the materials of choice for some embodiments. Those skilled in the art are aware of the typical materials and combinations of materials applicable to the current technology.

Figure 1:
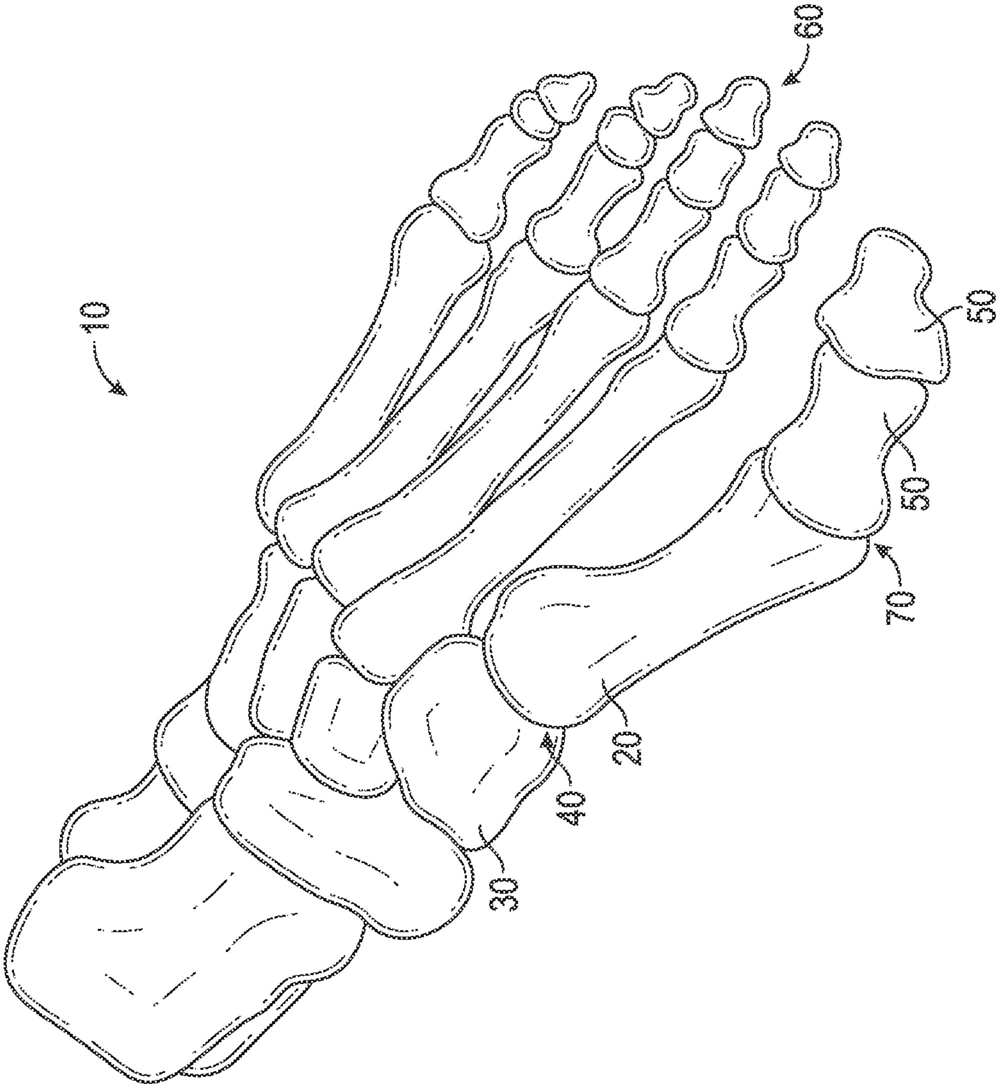
FIG. 1 is a perspective view of the bones of a foot having a bunion.

FIG. 1 is a perspective view of the bones of a foot 10 having a bunion, also known as a metatarsus primus varus with associated hallux valgus. The foot 10 includes a first metatarsal 20 which articulates at its proximal end with the first cuneiform 30 (also known as the medial cuneiform) at the first tarsometatarsal (TMT) joint 40. The distal end of the first metatarsal 20 articulates with the phalanges 50 of the big toe. Intermetatarsal angle is defined as the angle between an axis of one metatarsal in relation to a second metatarsal, in the anatomic transverse plane. Rotation is defined as axial rotation about the axis of the metatarsal, in the anatomic frontal plane. A bunion as shown in FIG. 1 is characterized by an increased intermetatarsal angle and/or rotation of the first metatarsal 20 at the first TMT joint 40 such that the first metatarsal 20 extends away, or medially, from the remainder of the foot 10. When a bunion is present, the phalanges 50 of the big toe are typically angled inward, or laterally, toward the other phalanges 60, resulting in the characteristic bump at the metatarsophalangeal joint 70 which is the most prominent external indication of a bunion. The protruding metatarsophalangeal joint 70 may further be associated with a swollen bursal sac or osseous anomaly which may cause discomfort, difficulty with wearing shoes, and other inconveniences to the person having the bunion.

With reference to FIGS. 2A-7F, various devices and components are provided for use with an improved Lapidus bunionectomy procedure for correcting the TMT joint deformity of FIG. 1. Although the following description is made with reference to the Lapidus bunionectomy procedure, it will be understood that the various devices and components described herein are not limited to such procedures and may equally be used in other orthopedic procedures as will be understood by those skilled in the art.

Figure 2A:
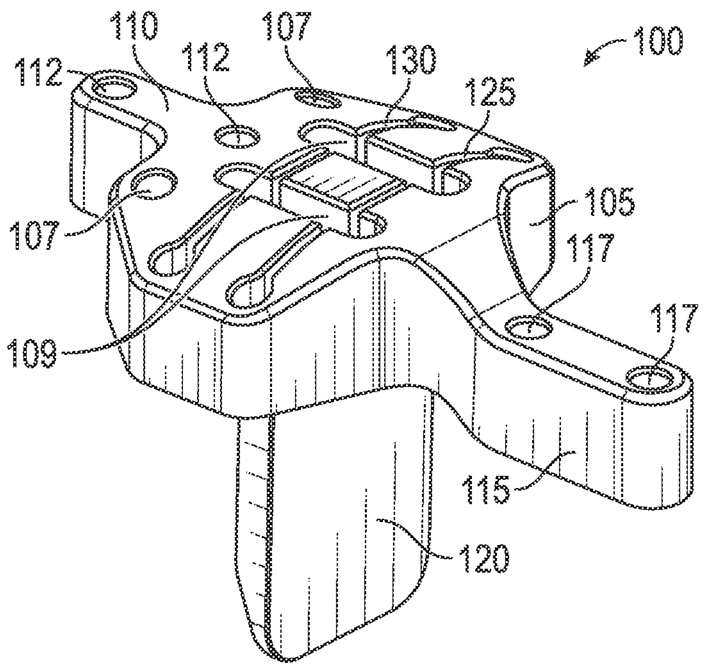
FIG. 2A is a perspective view of an example cut guide configured as a cutting guide and a pin guide for a corrective osteotomy procedure as described herein.
Figure 2B:
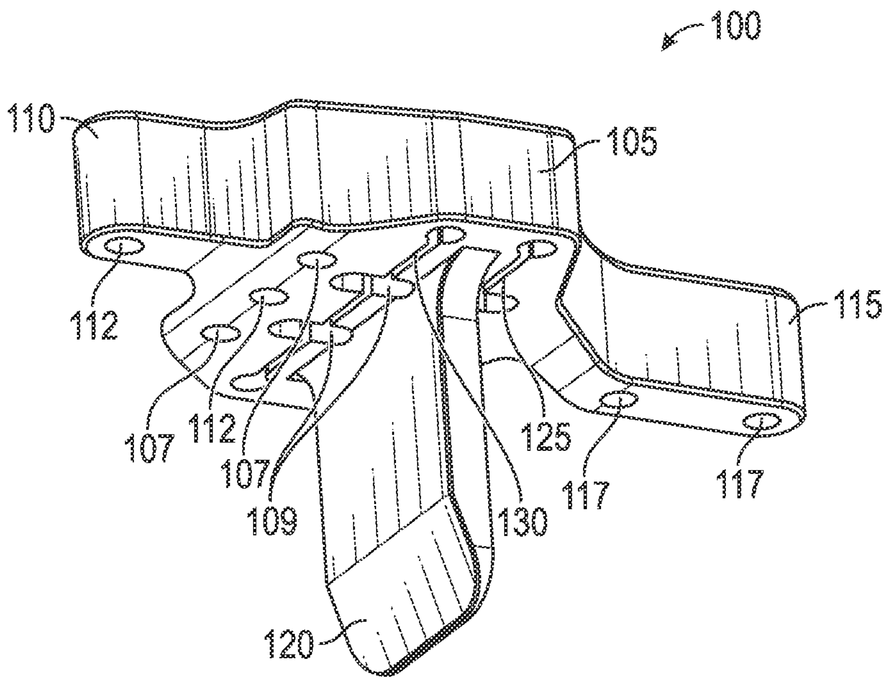
FIG. 2B is another perspective view of the cut guide of FIG. 2A.
Figure 2C:
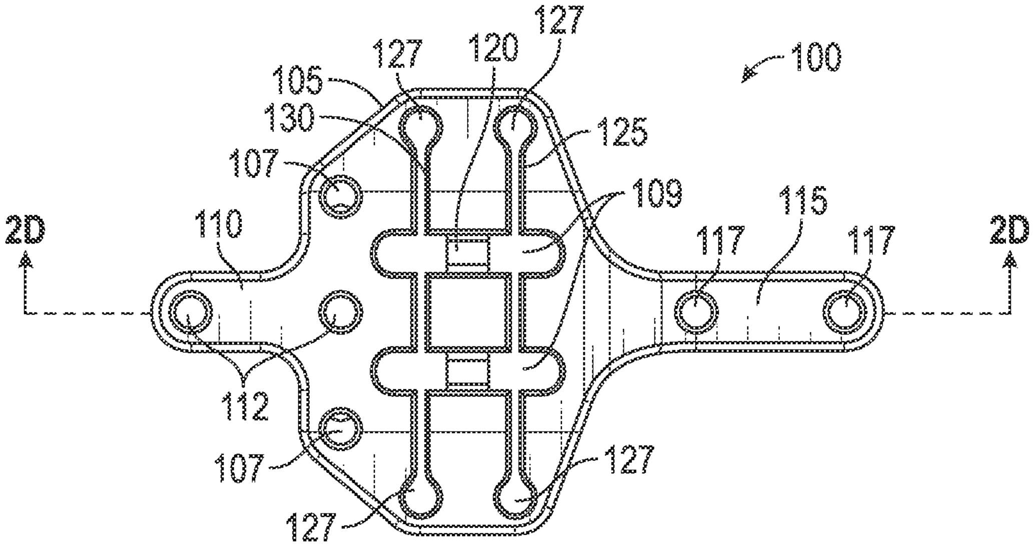
FIG. 2C is a top plan view of the cut guide of FIG. 2A.
Figure 2D:
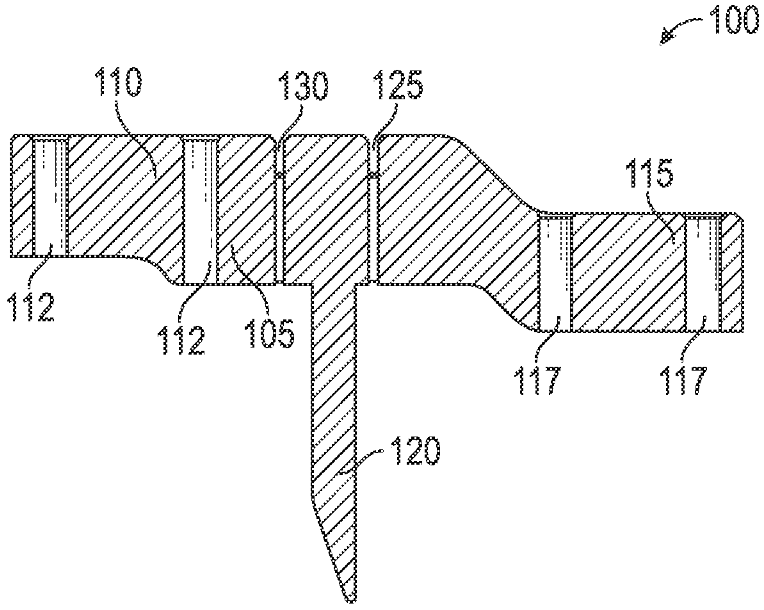
FIG. 2D is a sectional side elevation view of the cut guide of FIG. 2C taken along line 2D-2D.

FIGS. 2A-2D depict an example cut guide 100 configured as a cutting guide and a pin guide for the Lapidus bunionectomy procedures described herein. FIGS. 2A and 2B are upper and lower perspective views of the cut guide 100, respectively. FIG. 2C is a top plan view of the cut guide 100. FIG. 2D is a cross-sectional side elevation view of the cut guide 100 taken about the line 2D-2D in FIG. 2C. The cut guide 100 may be a single integrally formed component and may comprise a metal, a plastic, or other suitable material.

The cut guide 100 generally includes a body 105, a proximal extension 110, a distal extension 115, and a paddle 120. The paddle 120 is sized and shaped to seat within a joint such as a TMT joint (e.g., between the first metatarsal and the first cuneiform), for example, after removing soft tissue such as the joint capsule around the joint. The relatively narrower and sloped terminal portion of the paddle 120 may facilitate insertion of the paddle 120 into the joint. In some embodiments, the paddle 120 is integrally formed with the body 105.

The body 105 of the cut guide 100 includes a distal slot 125 and a proximal slot 130. The distal slot 125 and the proximal slot 130 each pass through the full thickness of the body 105 and are sized and shaped to serve as a positioning guide for a sawblade (or other cutting instrument, e.g., a bur) in order to facilitate precise saw cuts at each side of the joint. For example, the distal slot 125 may be positioned at a predetermined distance relative to the distal plane of the paddle 120 to facilitate cutting the base of the first metatarsal when the paddle 120 is positioned within the first TMT joint. Similarly, the proximal slot 130 may be positioned on the opposite side (proximal plane) of the paddle to facilitate cutting the first cuneiform. The distal slot 125 and the proximal slot 130 may be identically or similarly shaped (e.g., may have the same length and/or width) such that the metatarsal and cuneiform cuts can be performed with the same or same type of saw blade. In some embodiments, the distal slot 125 and the proximal slot 130 may be parallel to each other and/or to the paddle 120, or may be angled relative to the plane of the paddle 120. In some embodiments, relatively wider terminal sections 127 at the ends of the slots 125, 130 may be provided for the placement of additional guide wires during cutting to prevent a saw blade from making an excessively wide cut when using the cut guide 100.

Proximal pin holes 112 extend through the full thickness of the cut guide 100. One or both of the proximal pin holes 112 can be disposed on the proximal extension 110 or within the body 105. The proximal pin holes 112 can each have a substantially circular profile sized to accommodate a surgical pin or wire for temporarily securing the cut guide to the foot. The proximal pin holes 112 serve as a guide such that two proximal pins or wires can be inserted at a predetermined spacing relative to each other and relative to the plane along which the first cuneiform is cut by a saw blade through the proximal slot 130. It should be appreciated that pins or wires are examples of temporary bone fixation elements as described herein. The proximal pin holes 112 extend vertically parallel to each other, as shown in FIG. 2D.

Distal pin holes 117 extend through the full thickness of the distal extension 115. Similar to the proximal pin holes 112, the distal pin holes 117 can each have a substantially circular profile sized to accommodate a surgical pin or wire for temporarily securing the cut guide to the foot, and may have the same diameter as the proximal pin holes 112. The distal pin holes 117 serve as a guide such that two distal pins or wires can be inserted at a predetermined spacing relative to each other and relative to the plane along which the first metatarsal is cut by a saw blade through the distal slot 125. The distal pin holes 117 extend vertically parallel to each other and parallel to the proximal pin holes 112, as shown in FIG. 2D. A plane which intersects the axes of the proximal pin holes 112 may be coplanar with a plane which intersects the axes of distal pin holes 117. The combination of the pin holes form a linear array of holes, spanning the TMT joint. A Bottom or bone-facing surface of the distal extension 115 may not be coplanar with a bottom or bone-facing surface of the body 105 and/or the proximal extension 110, which may allow the cut guide 100 to be placed closer to the bone while allowing space for the osseous anatomy of the proximal metatarsal and the medial cuneiform. Further details are provided in U.S. Pat. No. 10,292,713, which is incorporated herein by reference.

In some embodiments, the body 105 of the cut guide 100 further includes one or more additional openings, such as additional convergent pin holes 107 and/or longitudinal apertures 109. The convergent pin holes 107 may be utilized to insert one or more additional pins or wires if additional stability is desired during a bunionectomy procedure. The longitudinal apertures 109 extend transverse to the slots 125, 130 and may provide an opening to facilitate x-ray visualization and/or any other suitable surgical imaging procedure to confirm and/or monitor the alignment of the cut guide during a bunionectomy procedure.

Figure 2E:
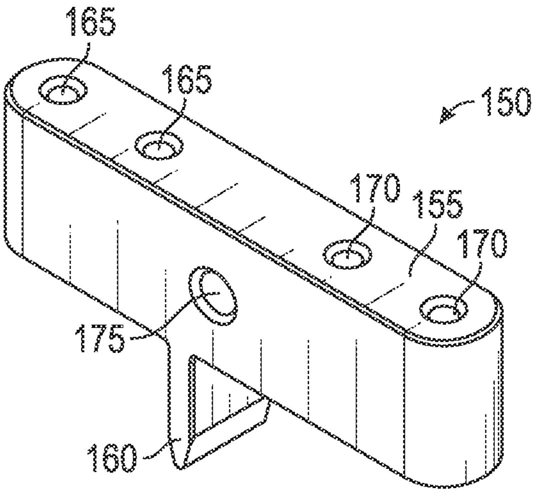
FIG. 2E is a perspective view of an example free-hand pin guide for orienting the insertion of pins in the absence of the cut guide of FIGS. 2A-2D.
Figure 2F:
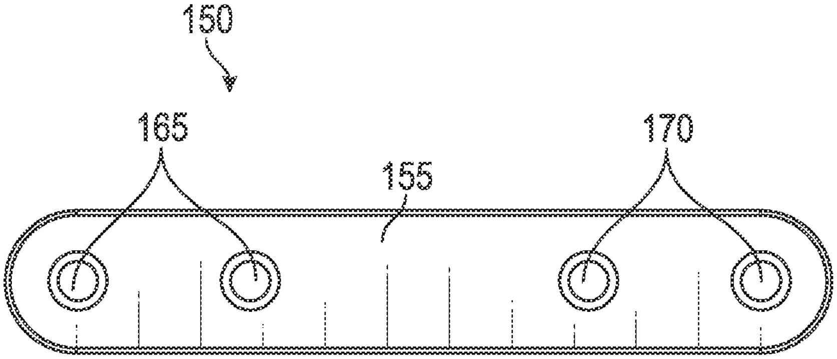
FIG. 2F is a top plan view of the free-hand pin guide of FIG. 2E.
Figure 2G:
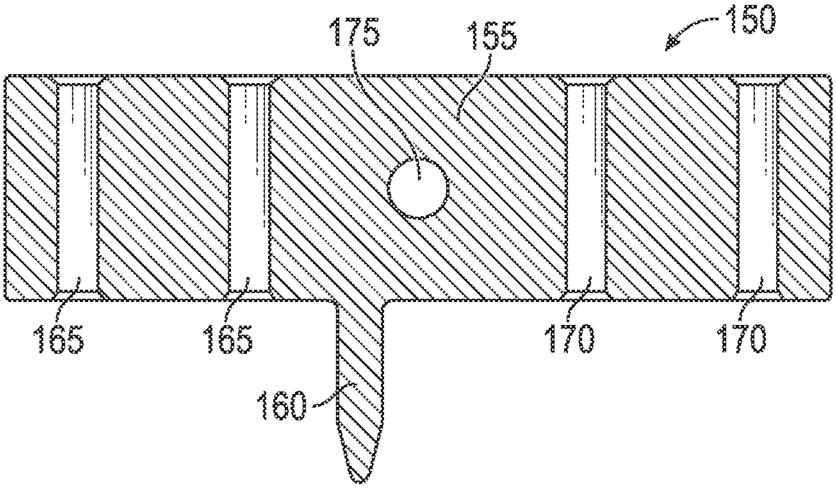
FIG. 2G is a sectional elevation view of the free-hand pin guide of FIG. 2E.

FIGS. 2E-2G depict an example free-hand pin guide 150 including an array of pin holes spanning the TMT joint for orienting the insertion of pins in the absence of the cut guide 100 of FIGS. 2A-2D. In some bunionectomy procedures, the cut guide 100 may not be used, for example, if the cut guide 100 does not fit within a joint, due to a surgeon's preference, or for any other reason that causes free-hand joint cuts to be made rather than cuts using the cut guide 100. The free-hand pin guide 150 generally comprises a body 155 and a paddle 160. Proximal pin holes 165 and distal pin holes 170 extend through the full thickness of the body 155. The proximal pin holes 165 may have the same relative spacing as the proximal pin holes 112 of the cut guide 100. Similarly, the distal pin holes 170 may have the same relative spacing as the distal pin holes 117 of the cut guide 100. A handle attachment aperture 175, which may be threaded, is provided for attaching a side-mounted handle which may assist the user in placing the free-hand pin guide 150. Similar to the proximal pin holes 112 and distal pin holes 117 of the cut guide 100, the proximal pin holes 165 and distal pin holes 170 of the free-hand pin guide 150 extend vertically parallel to each other. However, the spacing from the paddle 160 of the proximal pin holes 165 and the distal pin holes 170 of the free-hand pin guide 150 is slightly smaller than that of the proximal and distal pin holes 112, 117 relative to the paddle 120 of the cut guide 100 to compensate for the free-hand pin guide 150 being applied after the cuts have been made. Thus, the free-hand pin guide 150 allows the placement of pins or wires following a free-hand cut with the same spacing relative to the first TMT joint as if the cut guide 100 had been used to perform the cuts.

Figure 2H:
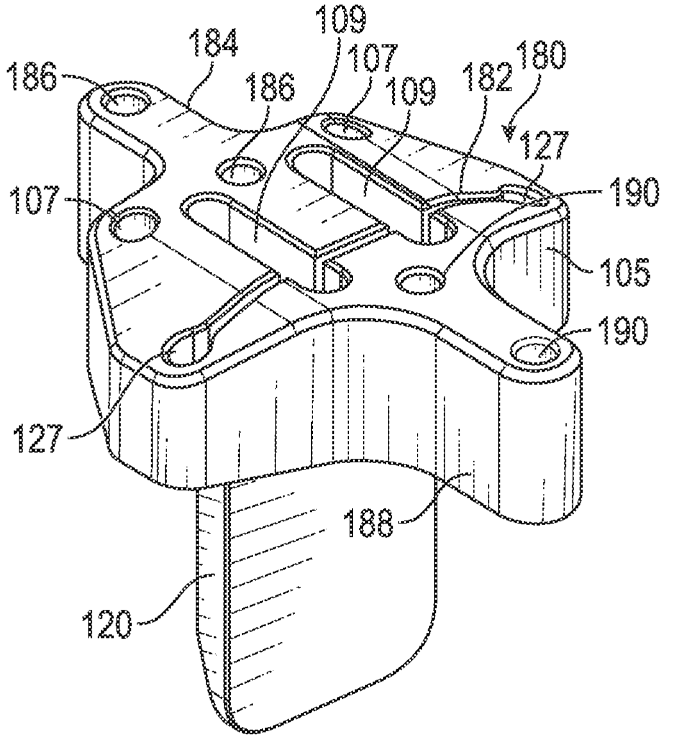
FIG. 2H is a perspective view of an example of a cut guide configured as a cutting guide and a pin guide for a corrective osteotomy procedure described herein.
Figure 2I:
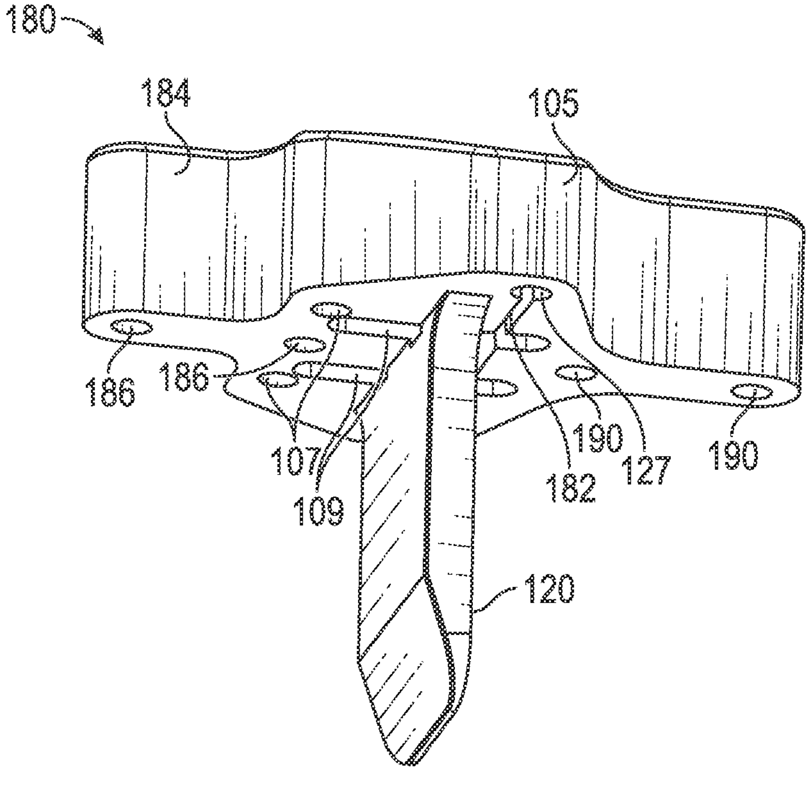
FIG. 2I is another perspective view of the cut guide configured as a cutting guide and pin guide of FIG. 2H.
Figure 2J:
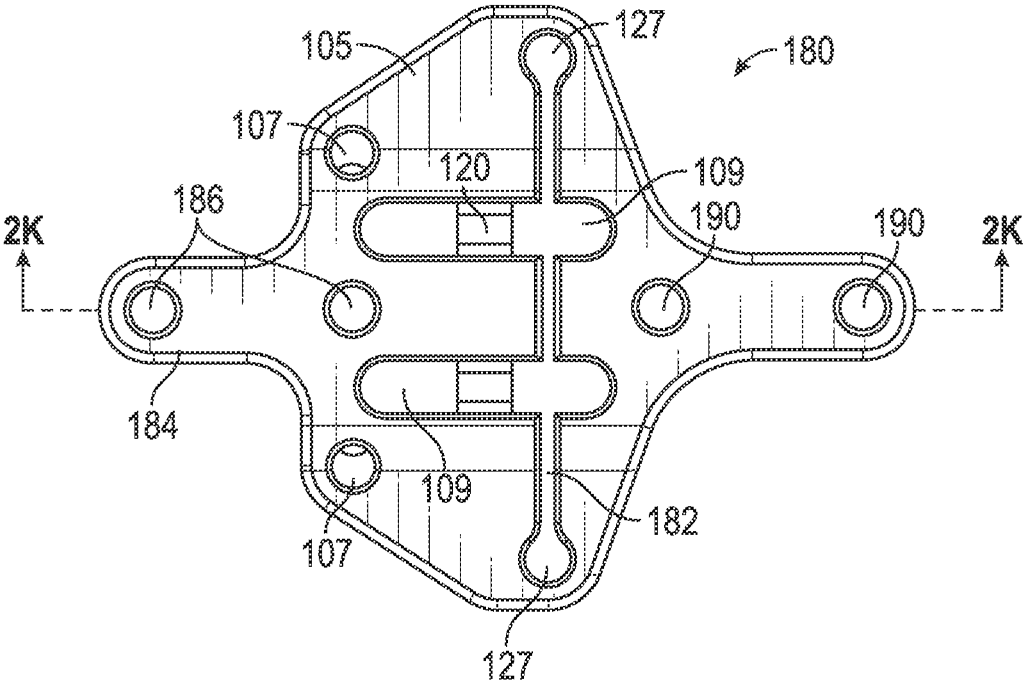
FIG. 2J is a top plan view of the cut guide configured as a cutting guide and pin guide of FIG. 2H.
Figure 2K:
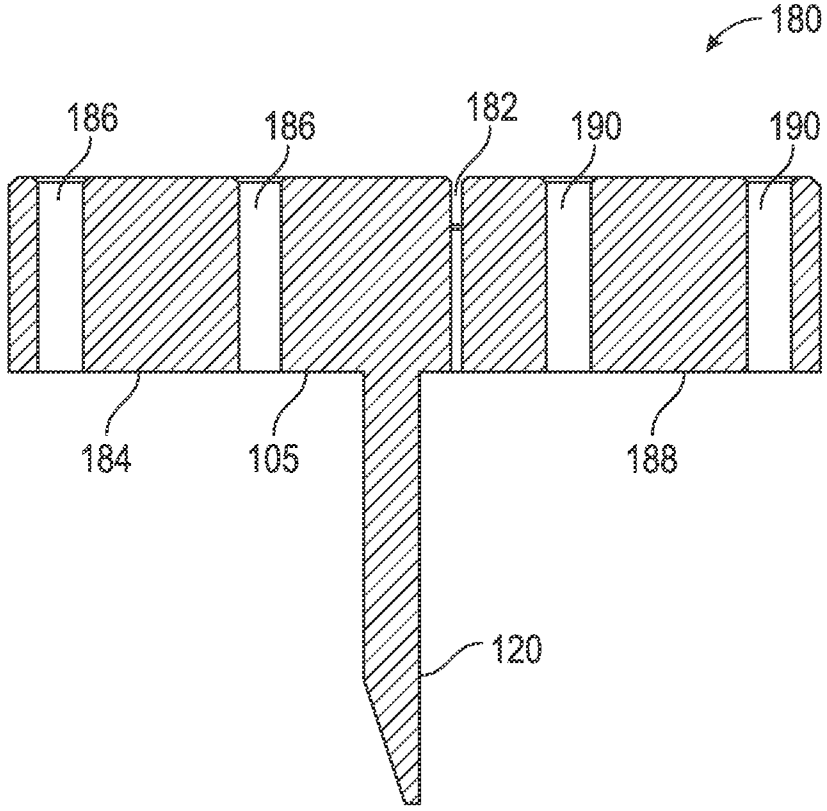
FIG. 2K is a sectional elevation view of the cut guide configured as a cutting guide and pin guide of FIG. 2J, taken along line 2K-2K.

FIGS. 2H-2K depict an example reversible cut guide 180 configured as a cutting guide and a pin guide for the Lapidus bunionectomy procedures described herein. FIGS. 2H and 2I are upper and lower perspective views of the cut guide 180, respectively. FIG. 2J is a top plan view of the cut guide 180. FIG. 2K is a cross-sectional side elevation view of the cut guide 180 taken about the line 2K-2K in FIG. 2J. The cut guide 180 may be a single integrally formed component and may comprise a metal, a plastic, or other suitable material. The cut guide 180 is similar to the cut guide 100 of FIGS. 2A-2D, but may be reversible and is configured with a single slot 182 rather than proximal and distal slots 125, 130 of FIGS. 2A-2D.

The cut guide 180 generally includes a body 105, a first extension 184, a second extension 188, and a paddle 120. The paddle 120 is sized and shaped to seat within a joint such as a TMT joint (e.g., between the first metatarsal and the first cuneiform), for example, after removing soft tissue such as the joint capsule around the joint. The relatively narrower and sloped terminal portion of the paddle 120 may facilitate insertion of the paddle 120 into the joint. In some embodiments, the paddle 120 is integrally formed with the body 105.

The body 105 of the cut guide 180 includes a single cutting slot 182. The slot 182 passes through the full thickness of the body 105 and is sized and shaped to serve as a positioning guide for a sawblade or other type of cutting instrument in order to facilitate precise saw cuts at each side of the joint. For example, the slot 182 may be positioned at a predetermined distance relative to the plane of the adjacent surface of the paddle 120 to facilitate cutting the base of the first metatarsal or the first cuneiform, depending on the orientation of the cut guide 180, when the paddle 120 is positioned within the first TMT joint. In some embodiments, the slot 182 may be parallel to the paddle 120, or may be angled relative to the plane of the paddle 120. In some embodiments, relatively wider terminal sections 127 at the ends of the slot 182 may be provided for the placement of additional guide wires during cutting to prevent a saw blade from making an excessively wide cut when using the cut guide 180.

First pin holes 186 extend through the full thickness of the cut guide 180. One or both of the first pin holes 186 can be disposed on the first extension 184 or within the body 105. The first pin holes 186 can each have a substantially circular profile sized to accommodate a surgical pin or wire for temporarily securing the cut guide to the foot. The first pin holes 186 serve as a guide such that two pins or wires can be inserted at a predetermined spacing relative to each other and relative to the second pin holes 190. The first pin holes 186 extend vertically parallel to each other, as shown in FIG. 2K.

Second pin holes 190 extend through the full thickness of the cut guide 180. Similar to the first pin holes 186, the second pin holes 190 can each have a substantially circular profile sized to accommodate a surgical pin or wire for temporarily securing the cut guide 180 to the foot, and may have the same diameter as the first pin holes 186. The second pin holes 190 serve as a guide such that two distal pins or wires can be inserted at a predetermined spacing relative to each other and relative to the plane along which the first metatarsal or first cuneiform is cut by a saw blade through the slot 182. The second pin holes 190 extend vertically parallel to each other and parallel to the first pin holes 186, as shown in FIG. 2K. A plane which intersects the axes of the first pin holes 186 may be coplanar with a plane which intersects the axes of second pin holes 190. The combination of the pin holes form a linear array of holes, spanning the TMT joint. A bottom or bone-facing surface of the second extension 188 may be coplanar or substantially coplanar with a bottom or bone-facing surface of the body 105 and/or the first extension 184, which may allow the cut guide 180 to be placed across the TMT joint in either of two opposite orientations with the paddle 120 seated within the joint.

In some embodiments, the body 105 of the cut guide 180 further includes one or more additional openings, such as additional convergent pin holes 107 and/or longitudinal apertures 109. The convergent pin holes 107 may be utilized to insert one or more additional pins or wires if additional stability is desired during a bunionectomy procedure. The longitudinal apertures 109 extend transverse to the slot 182 and may provide an opening to facilitate x-ray visualization and/or any other suitable surgical imaging procedure to confirm and/or monitor the alignment of the cut guide during a bunionectomy procedure.

Figure 2L:
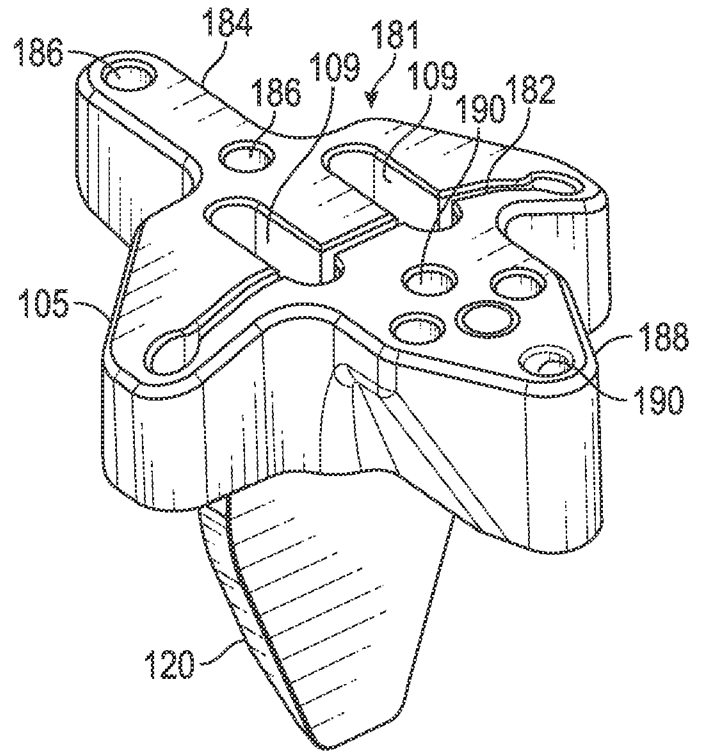
FIG. 2L is a perspective view of an example cut guide configured as a cutting guide and a pin guide for the Lapidus bunionectomy procedures described herein.
Figure 2M:
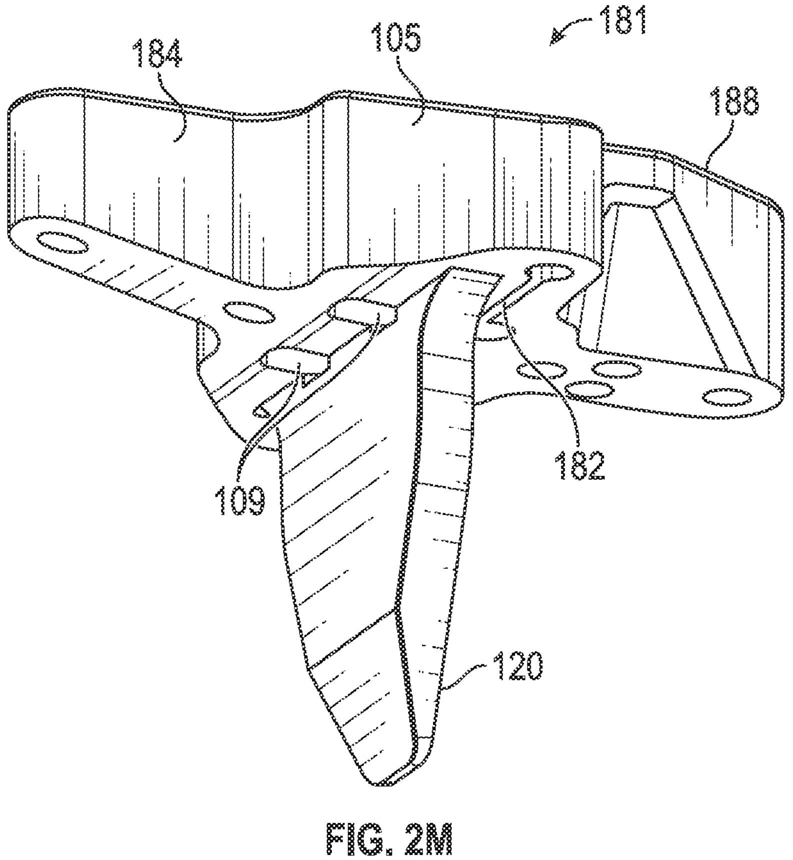
FIG. 2M is another perspective view of the example cut guide configured as a cutting guide and a pin guide of FIG. 2L.
Figure 2N:
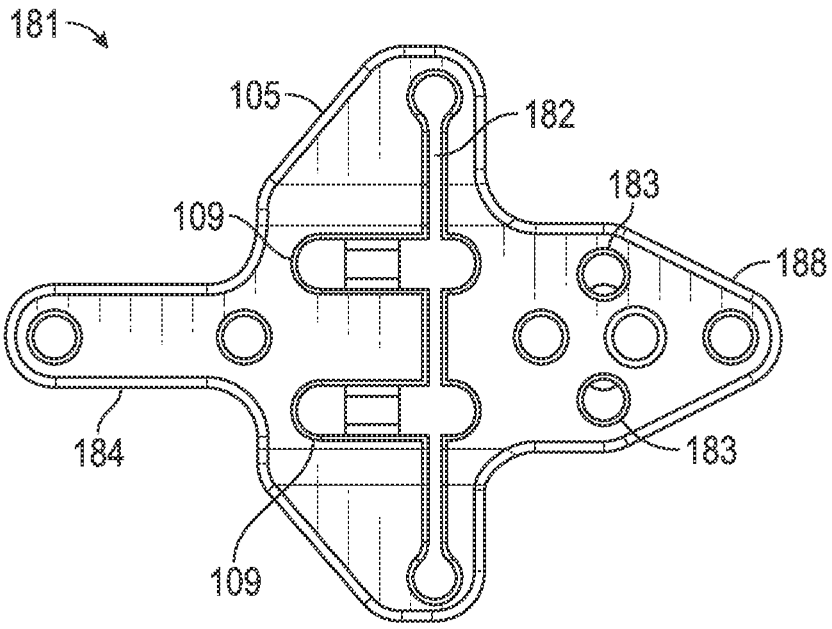
FIG. 2N is a top plan view of the example cut guide configured as a cutting guide and a pin guide of FIG. 2L.

FIGS. 2L-2N depict a further example reversible cut guide 181 configured as a cutting guide and a pin guide for the Lapidus bunionectomy procedures described herein. FIGS. 2L and 2M are upper and lower perspective views of the cut guide 181, respectively. FIG. 2N is a top plan view of the cut guide 181. The cut guide 181 may be a single integrally formed component and may comprise a metal, a plastic, or other suitable material. The cut guide 181 is similar to the cut guide 180 of FIGS. 2H-2K, including a reversible configuration with a single slot 182.

The cut guide 181 generally includes a body 105, a first extension 184, a second extension 188, and a paddle 120. The first extension 184 and the second extension 188 can include first pin holes 186 and second pin holes 190 as described above with reference to FIGS. 2H-2K. The paddle 120 is sized and shaped to seat within a joint such as a TMT joint (e.g., between the first metatarsal and the first cuneiform), for example, after removing soft tissue such as the joint capsule around the joint. The relatively narrower and sloped terminal portion of the paddle 120 may facilitate insertion of the paddle 120 into the joint. In some embodiments, the paddle 120 is integrally formed with the body 105.

In the example embodiment of FIGS. 2L-2N, the body 105 of the cut guide 181 further includes one or more additional openings, such as additional convergent pin holes 183, extending through the second extension 188. The convergent pin holes 183 may be utilized to insert one or more additional pins or wires if additional stability is desired during a bunionectomy procedure. Similar to the cut guide 180 of FIGS. 2H-2K, longitudinal apertures 109 extend transverse to the slot 182 and may provide an opening to facilitate x-ray visualization and/or any other suitable surgical imaging procedure to confirm and/or monitor the alignment of the cut guide during a bunionectomy procedure.

Figure 3A:
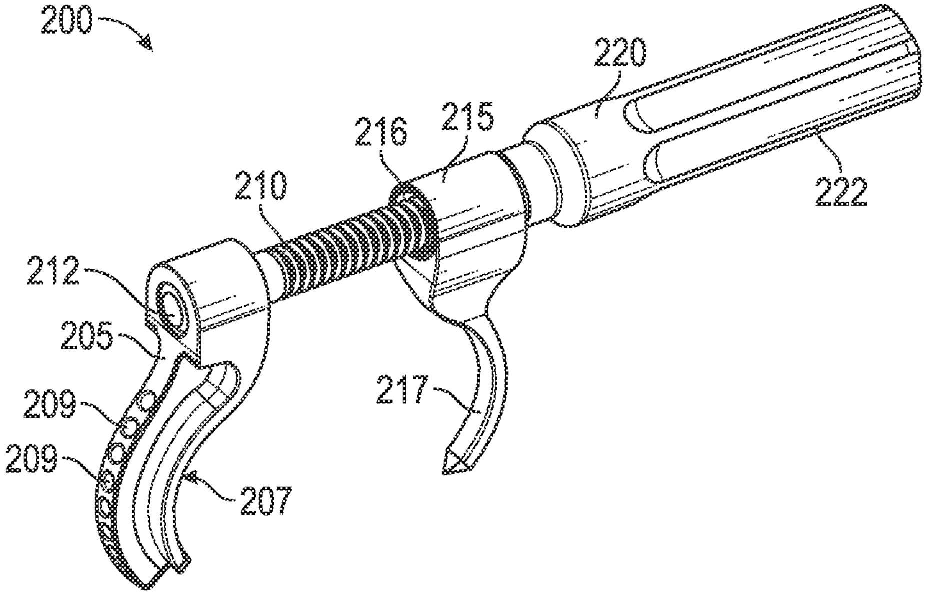
FIG. 3A is a perspective view of example linear reducers configured to be used in the Lapidus bunionectomy procedures described herein.
Figure 3B:
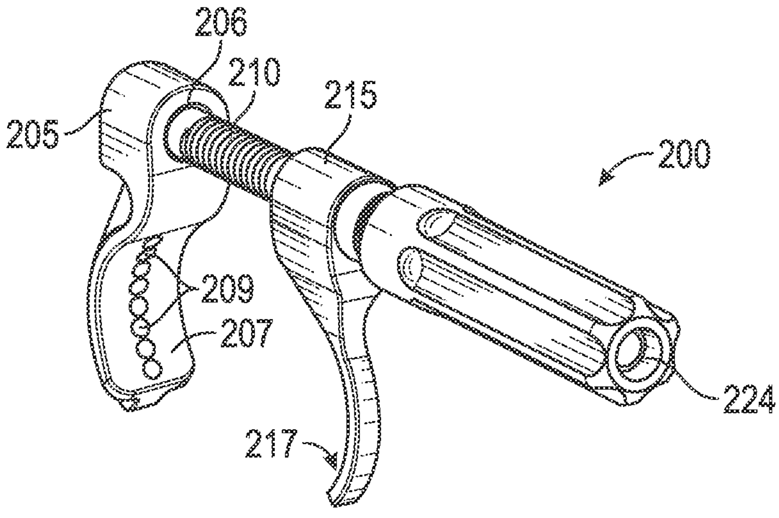
FIG. 3B is another perspective view of the example linear reducers of FIG. 3A.
Figure 3C:
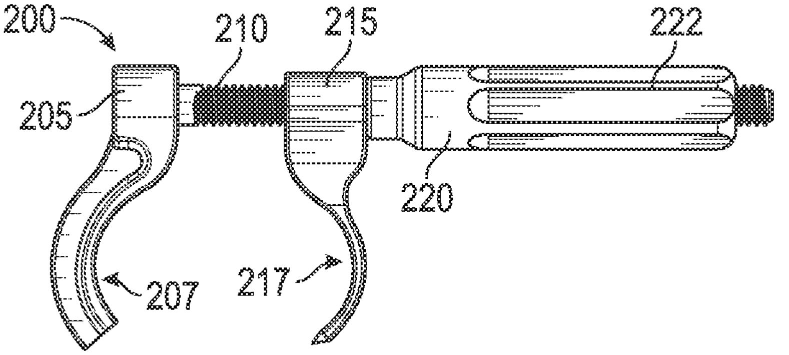
FIG. 3C is a side elevation view of the example linear reducers of FIG. 3A.

FIGS. 3A-3H depict an example linear reducer 200 configured to be used in the Lapidus bunionectomy procedures described herein. With reference to FIGS. 3A-3C, the linear reducer 200 includes a medial hook 205, a threaded shaft 210, a lateral hook 215, and a handle 220. As will be described in greater detail with reference to FIGS. 10-14, the linear reducer 200 is suitable for applying correction within the transverse plane during a Lapidus bunionectomy procedure by moving the first and second metatarsals closer together to reduce the intermetatarsal angle, as well as maintaining the desired correction of the frontal plane when a pin is placed within medial hook pin holes 209.

The medial hook 205 includes a coupling aperture 206 sized and shaped to couple to a first end 212 of the threaded shaft 210. In some embodiments, the medial hook 205 may be fixedly coupled to the threaded shaft 210 such that the medial hook 205 is neither rotatable nor translatable relative to the threaded shaft 210. The medial hook 205 includes a curved engagement surface 207 configured to rest against the medial side of the foot. One or more medial hook pin holes 209 extend from the engagement surface 207 through the full thickness of the medial hook 205 such that a pin may be placed through the medial hook 205 to temporarily secure the medial hook 205 to the toe.

The lateral hook 215 includes a coupling aperture 216 sized and shaped to receive the threaded shaft 210 therethrough. The lateral hook 215 may have a smooth interior surface having a diameter at least as large as the full diameter of the threaded shaft 210 such that the lateral hook 215 can translate along the threaded shaft 210 without rotating. Other features of the coupling aperture may include a non-cylindrical profile such that, when the lateral hook 215 is assembled to the threaded shaft 210, the non-cylindrical profile prevents rotation of the lateral hook 215 about the axis of the threaded shaft 210. The lateral hook 215 includes a curved engagement surface 217 configured to rest against the lateral side of a bone such as the second metatarsal. In some embodiments, the engagement surface 217 may be inserted through an incision between, for example, the second and third toes such that the engagement surface 217 can be placed against the lateral side of the foot for transverse plane correction. For instance, the engagement surface 217 can be placed against the lateral surface of the second metatarsal or any other lateral surface of the foot.

In various embodiments, the components of the linear reducer 200 may comprise a variety of materials. For example, the handle 220, the threaded shaft 210, the medial hook 205, and/or the lateral hook 205 may comprise a metal, a plastic or polymeric material, or the like. In some embodiments, the medial hook 205 and/or the lateral hook 215 may comprise a radiolucent material. Advantageously, a radiolucent material may be at least partially transmissive to x-rays or other radiation associated with medical imaging, so as to facilitate imaging of the bones of the foot while the linear reducer 200 is applied. Example radiolucent materials suitable for the medial hook 205 and/or the lateral hook 215 include carbon fiber, polymeric materials, and/or composite materials such as a carbon fiber reinforced polymer.

The handle 220 includes one or more grip features 222 such as knurling to facilitate a user's grip while rotating the handle 220. A threaded aperture 224 extends longitudinally through the handle 220. The interior threading of the threaded aperture 224 is sized and spaced to mesh with the exterior threading of the threaded shaft 210. In some embodiments, only a portion of the threaded aperture 224 is threaded, for example, with any remaining length drilled to a larger diameter to allow clear pass-through of the threaded shaft 210. Thus, the interior threading of the threaded aperture 224 allows the handle 220 to be translated to a desired position along the threaded shaft 210 by rotating the handle 220 about the threaded shaft 210. Accordingly, when a user wishes to decrease the spacing between the medial hook 205 and the lateral hook 215, the user twists the handle 220 clockwise about the threaded shaft 210 such that the handle 220 pushes the lateral hook 215 along the threaded shaft 210 toward the medial hook 205. Friction between the interior threading of the threaded aperture 224 and the exterior threading of the threaded shaft 210 prevents the lateral hook 215 and handle 220 from being pushed outward away from the medial hook 205 unless the handle 220 is twisted.

Figure 3F:
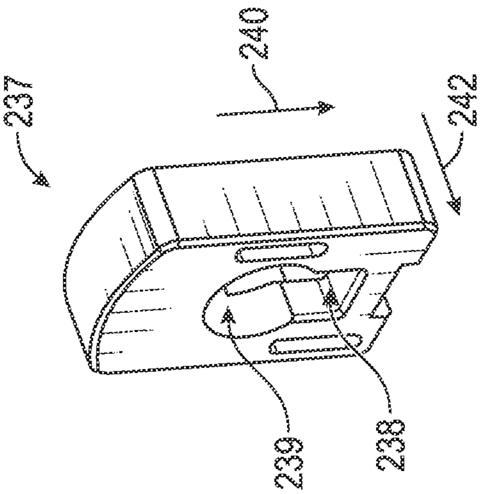
FIG. 3F is a perspective view of a quick-release insert of the example linear reducers of FIG. 3A.
Figure 3E:
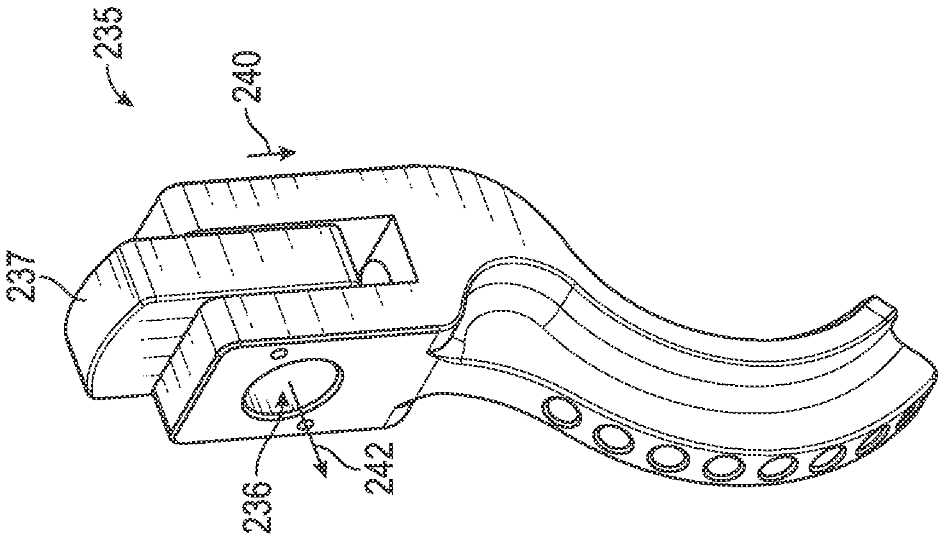
FIG. 3E is a perspective view of a medial hook of the example linear reducers of FIG. 3A.
Figure 3D:
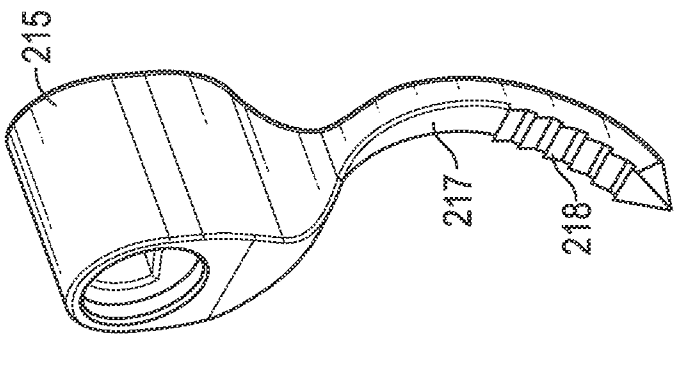
FIG. 3D is a perspective view of a lateral hook of the example linear reducers of FIG. 3A.

FIG. 3D illustrates an alternative embodiment of the lateral hook 215. In the alternative lateral hook 215 of FIG. 3D, the engagement surface 217 includes one or more bone engagement features 218 configured to provide an improved grip on the lateral surface of the second metatarsal bone during a Lapidus bunionectomy. In some cases, the bone engagement features 218 may reduce the probability of the lateral hook 215 sliding upward away from the second metatarsal during or following reduction of the intermetatarsal angle within the transverse plane.

Figure 3G:
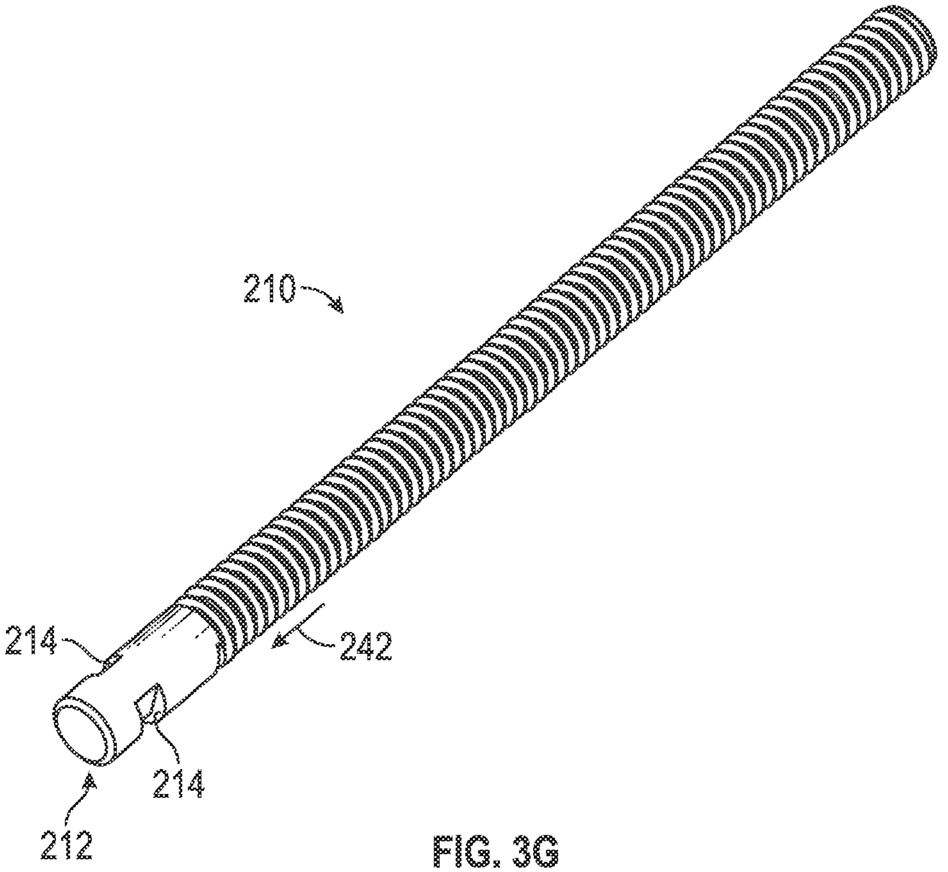
FIG. 3G is a perspective view of a threaded shaft of the example linear reducers of FIG. 3A.

FIGS. 3E-3G illustrate a quick-release feature that may be incorporated at the medial hook of the linear reducer 200. In a quick-release embodiment of the linear reducer 200, the fixedly coupled medial hook 205 of FIGS. 3A-3C is replaced by a quick-release medial hook 235. The quick-release medial hook 235 includes an aperture 236 large enough to slidably accommodate the threaded shaft 210. A quick-release insert 237 is insertable within the upper portion of the quick-release medial hook 235. The quick-release insert 237 has a coupling aperture 239 including a locking portion 238 configured to interlock with notches 214 near the first end 212 of the threaded shaft 210. Thus, when the quick-release insert 237 is in the raised position shown in FIG. 3E, the locking portion 238 is engaged within the notches 214 to fixedly couple the quick-release medial hook 235 to the threaded shaft.

When it is desired to remove the linear reducer 200 from the foot, the quick-release insert 237 is pushed downward along the direction 240. As the quick-release insert 237 moves downward, the locking portion 238 disengages from the notches 214 in the threaded shaft 210, such that the entire quick-release medial hook becomes slidable along a longitudinal direction 242 relative to the threaded shaft 210. For example, with the quick-release medial hook 235 pinned to the bone, the threaded shaft 210 may be removed through the coupling aperture 216 of the lateral hook 215, and the lateral hook 215 may be removed from the foot substantially vertically. The medial hook 205 may then be unpinned and removed from the foot easily.

Figure 3H:
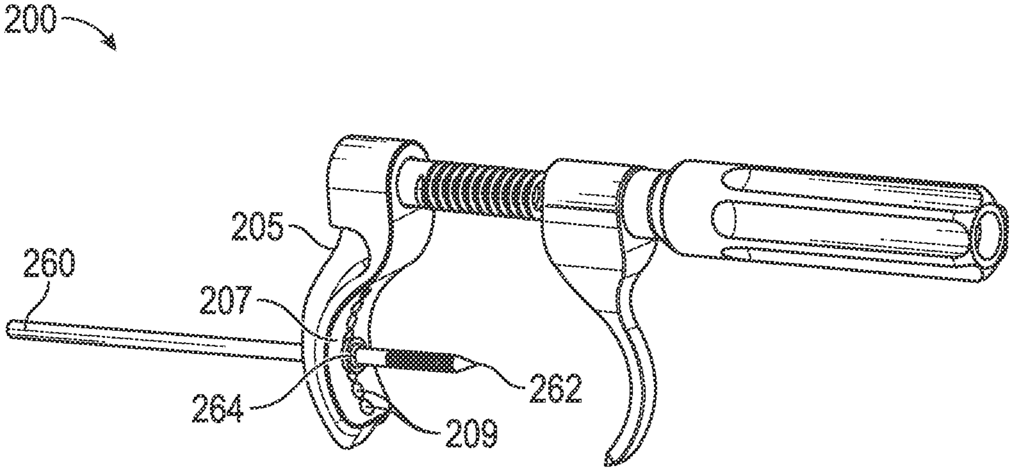
FIG. 3H is a perspective view of the example linear reducers of FIG. 3A including a shouldered pin.

Referring now to FIG. 3H, in some embodiments a shouldered pin 260 may be used in conjunction with the linear reducer 200. Although any type of pin may be used, a shouldered pin 260 may advantageously prevent damage to the skin of the medial side of a foot when the linear reducer 200 is used. The shouldered pin 260 includes a tip 262 which enters the foot and a shoulder 264 which extends radially outward from the sides of the shouldered pin 260. The shoulder 264 is preferably larger than the medial hook pin holes 209 such that the shoulder 264 prevents the shouldered pin 260 from sliding outward through the medial hook pin hole 209. Accordingly, when the shouldered pin 260 is inserted into the medial side of a first metatarsal and the linear reducer 200 is manipulated to reduce the intermetatarsal angle of the foot, the lateral force exerted by the medial hook 205 is transferred to the first metatarsal via the shoulder 264, rather than through the skin along the engagement surface 207, reducing the probability of compression and/or damage to the skin of the foot. In some embodiments, a shouldered pin 260 may be used in conjunction with the quick-release medial hook 235 depicted in FIGS. 3E-3G.

Figure 4A:
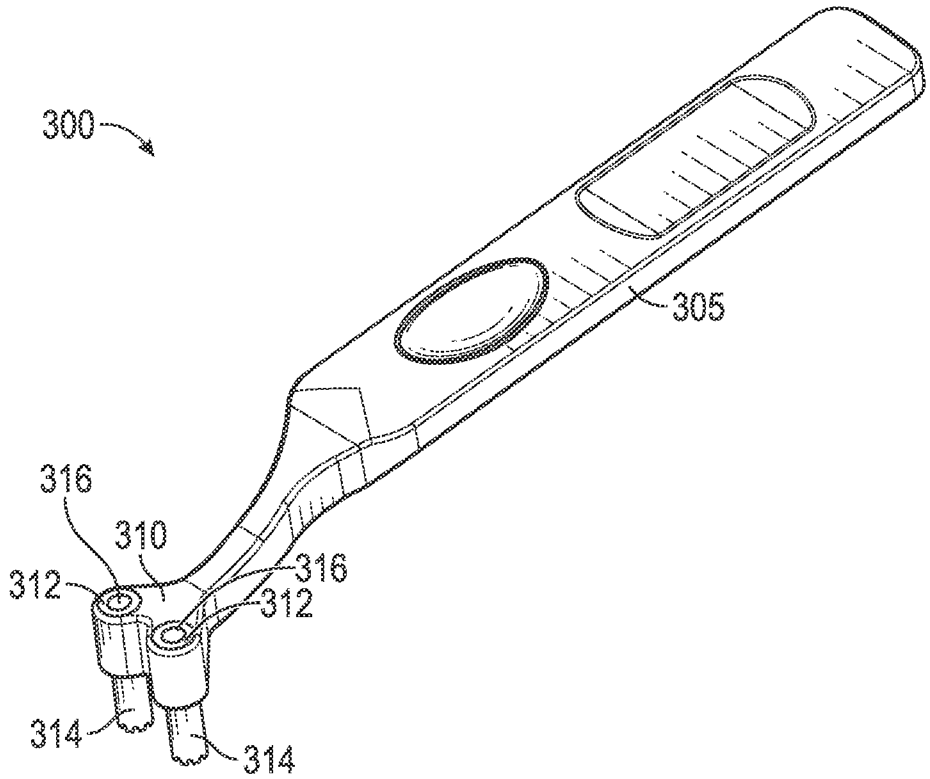
FIG. 4A is a perspective view of an example control handle configured to be used in the Lapidus bunionectomy procedures described herein.
Figure 4B:
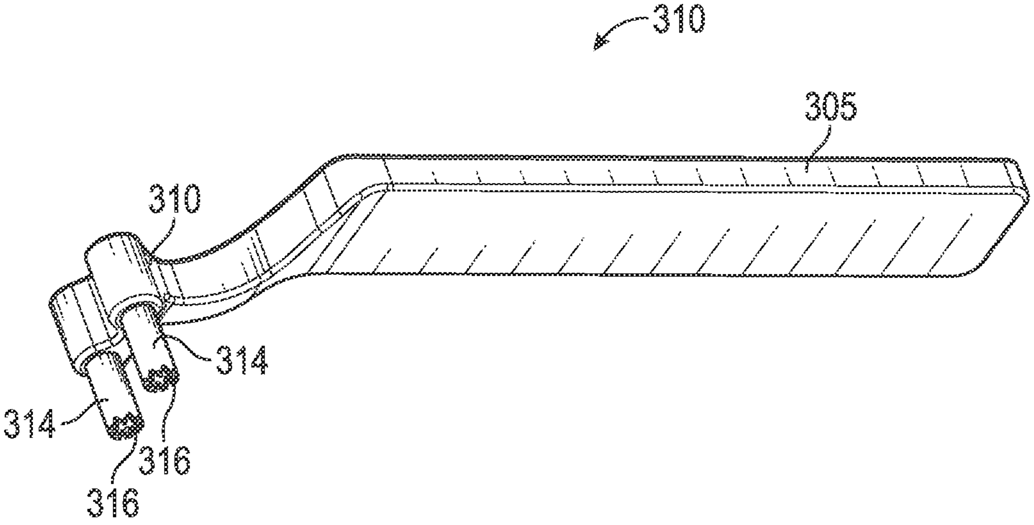
FIG. 4B is another perspective view of the example control handle of FIG. 4A.

FIGS. 4A and 4B depict an example control handle 300 configured to be used in the Lapidus bunionectomy procedures described herein. As will be described in greater detail with reference to FIGS. 11-14, the linear reducer 200 is suitable for applying correction within the frontal plane or other planes during a Lapidus bunionectomy procedure by rotating the first metatarsal relative to the first cuneiform. The control handle 300 is only one example of a handle that could be attached to the cut guide 100. Those skilled in the art will appreciate that a variety of attachments may be made between a control handle and the cut guide 100 without departing from the scope of the present technology.

The control handle 300 includes a handle 305 and an engagement portion 310 connected to the handle. Apertures 312 within the engagement portion 310 and/or pin guides 314 disposed within the apertures 312 are spaced to receive pins placed within the first metatarsal according to the spacing of the distal pin holes 117 or 170 of the cut guide 100 or the free-hand pin guide 150. The spacing of the apertures 312 also corresponds to the spacing of the proximal pin holes 112 or 165. The spaces 316 within the pin guides 314 are suitably large to receive surgical pins or wires.

Figure 5A:
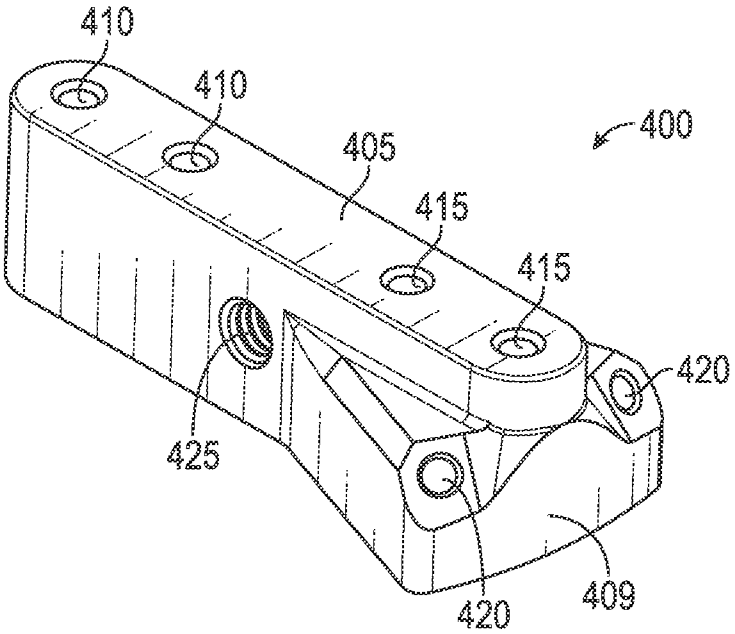
FIG. 5A is a perspective view of an example compressor block configured to be used in the Lapidus bunionectomy procedures described herein.
Figure 5B:
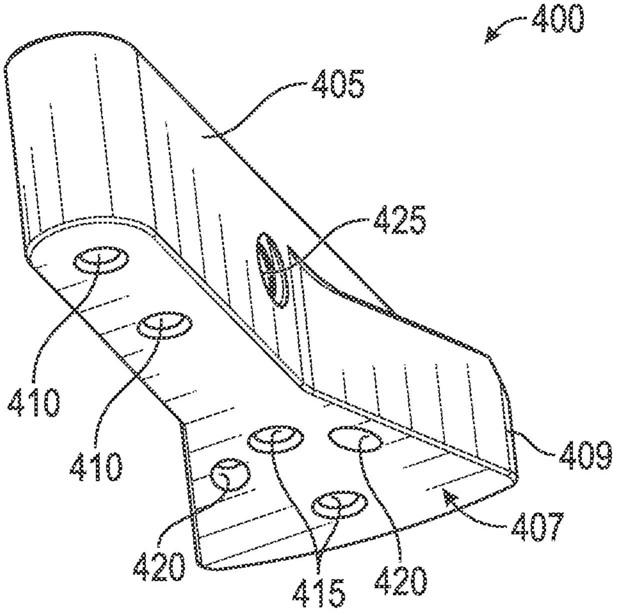
FIG. 5B is another perspective view of the example compressor block of FIG. 5A.
Figure 5C:
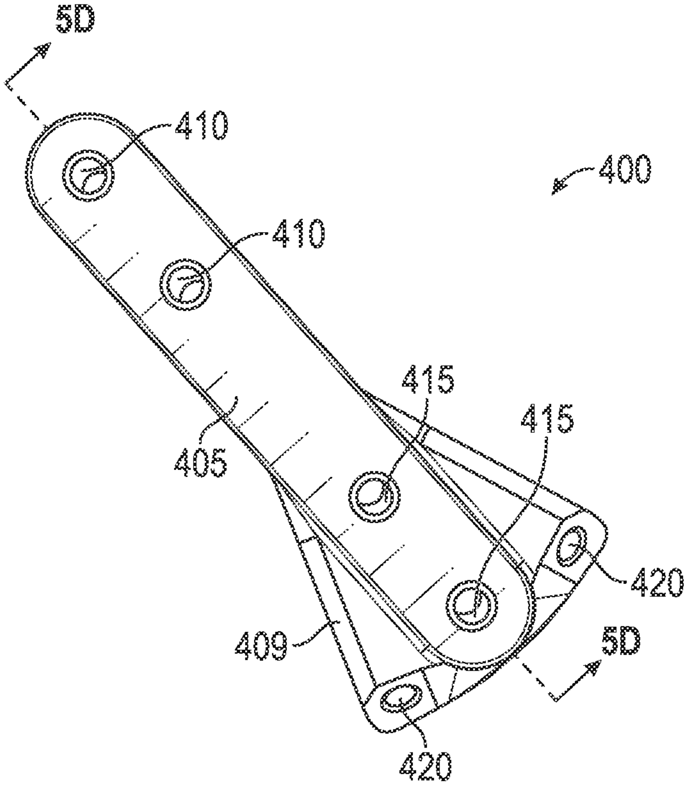
FIG. 5C is a top plan view of the example compressor block of FIG. 5A.
Figure 5D:
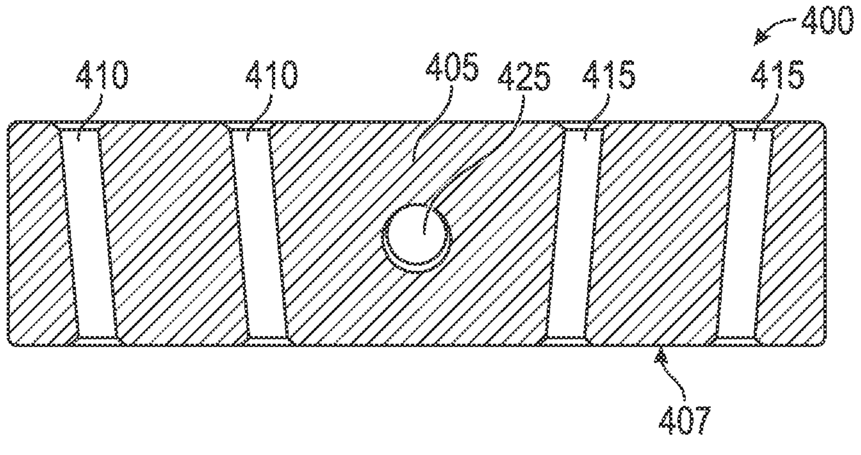
FIG. 5D is a sectional elevation view of the example compressor block of FIG. 5C, taken along line 5D-5D.

FIGS. 5A-5D depict an example compressor block 400 configured to be used in the Lapidus bunionectomy procedures described herein. As will be appreciated from the description below, the compressor block 400 may be configured for a combination of realignment and compression of first and second bones, and thus can be referred to as a "realignment and compression block" (e.g., a RAC block). FIGS. 5A and 5B are upper and lower perspective views of the compressor block 400, respectively. FIG. 5C is a top plan view of the compressor block 400. FIG. 5D is a cross-sectional side elevation view of the compressor block 400 taken about the line 5D-5D in FIG. 5C. As will be described in greater detail, with reference to FIGS. 16-18, the compression block 400 is configured to assist in compressing and fixing a resected joint that has been free-hand cut or cut using the cut guide 100.

Figure 15:
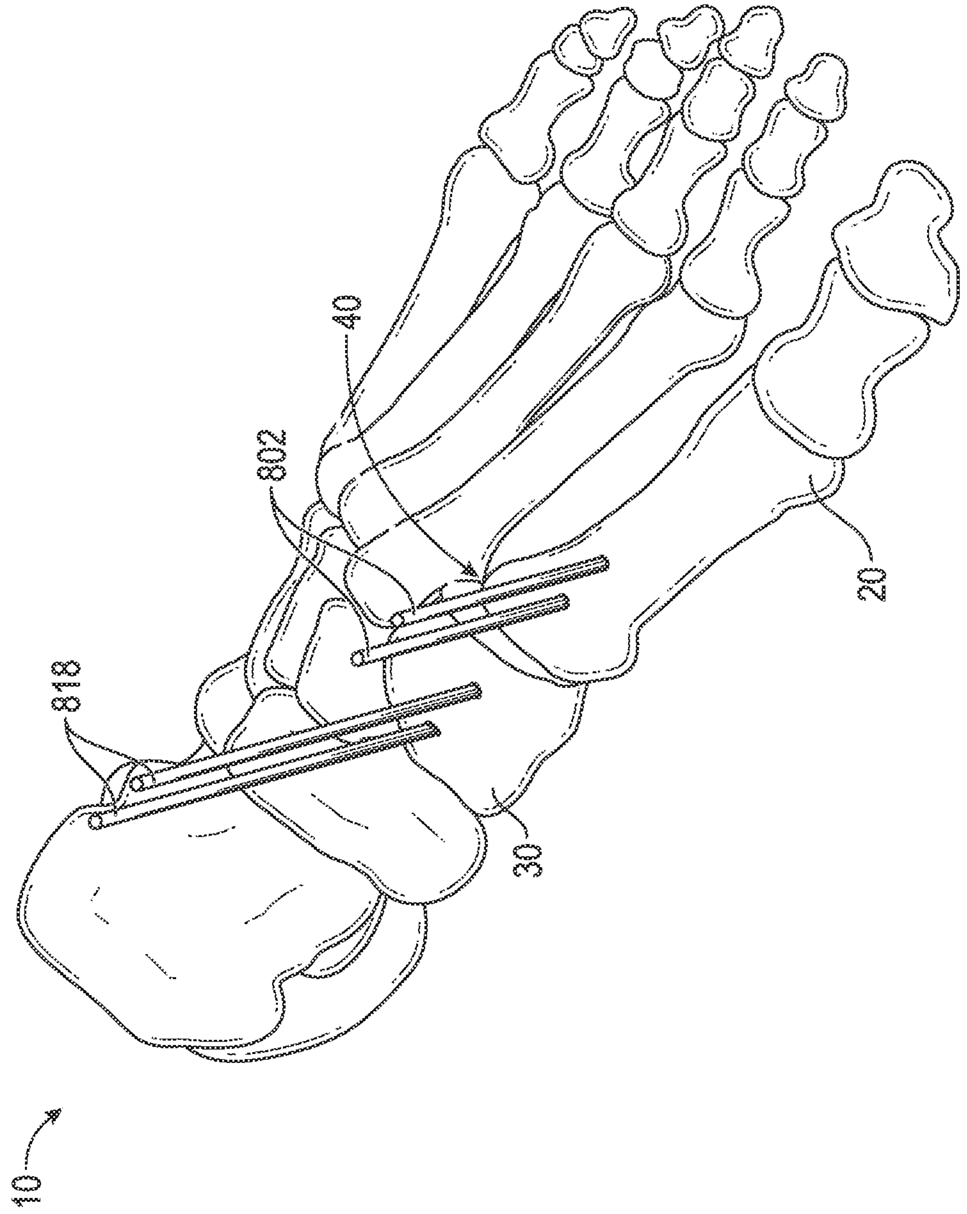
FIG. 15 is a perspective view of the human foot of FIG. 14, showing the cut guide, the linear reducer, and the control handle removed.
Figure 16:
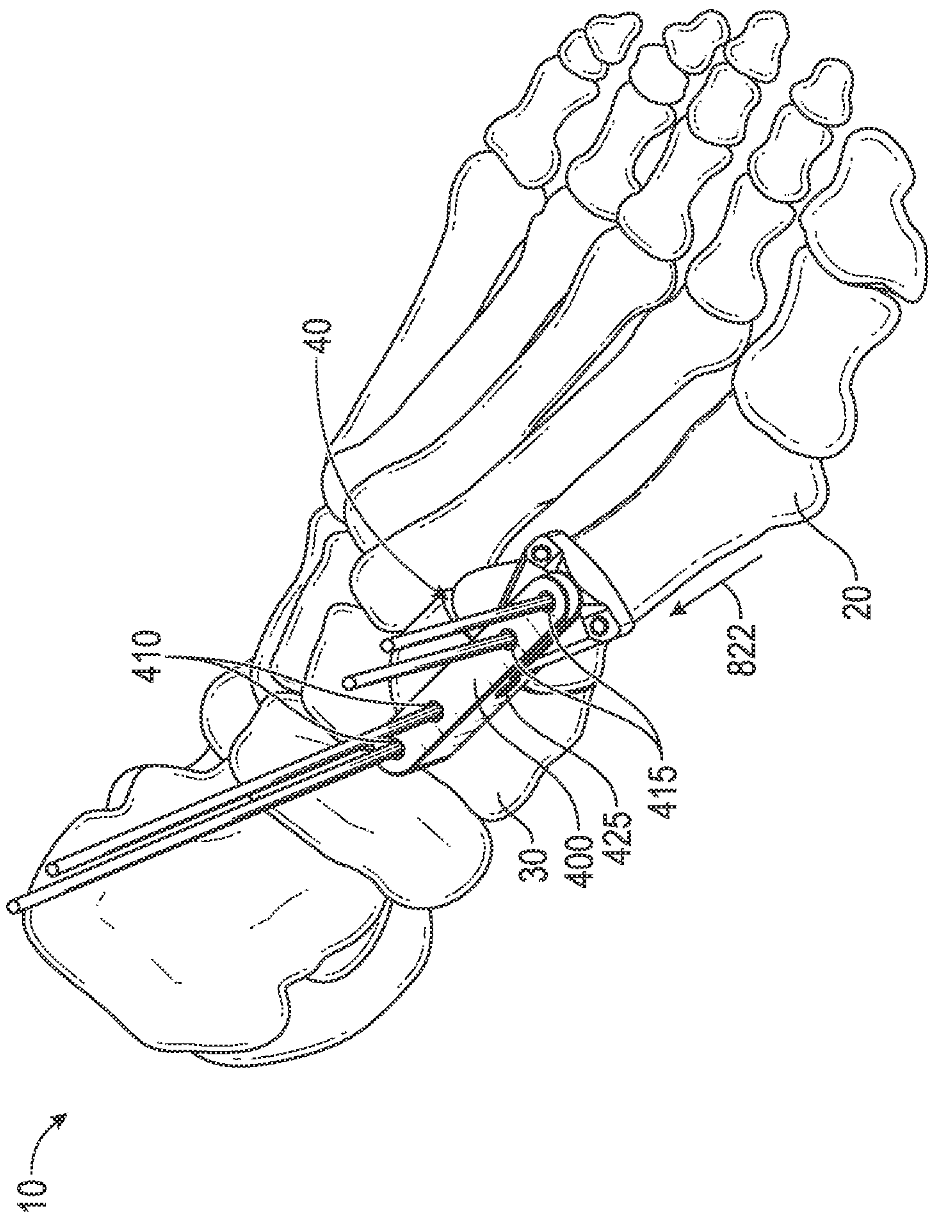
FIG. 16 is a perspective view of the human foot of FIG. 15, showing the compressor block of FIG. 5A applied over the metatarsal pins and cuneiform pins.

The compressor block 400 includes a body 405 having proximal pin holes 410 and distal pin holes 415 extending therethrough. The proximal pin holes 410 are spaced relative to each other by the same spacing as that of the proximal pin holes 112, 165 of the cut guide 100 and the free-hand pin guide 150. Similarly, the distal pin holes 415 are spaced relative to each other by the same spacing as that of the distal pin holes 117, 170 of the cut guide 100 and the free-hand pin guide 150. However, the proximal pin holes 410 and the distal pin holes 415 are each located closer to the center of the compressor block 400 than the proximal pin holes 112, 165 and the distal pin holes 117, 170 of the cut guide 100 and the free-hand pin guide 150. Additionally, as shown in the cross-sectional view of FIG. 5D, the proximal pin holes 410 and the distal pin holes 415 are not parallel and are disposed at converging angles such that their spacing at the bottom edge 407 of the compressor block 400 is relatively closer. Thus, parallel pins threaded into the proximal apertures 410 and the distal apertures 415 are compressed closer together as the compressor block 400 slides downward over the pins, as shown in FIGS. 15-16. A handle attachment aperture 425, which may be threaded, is provided for attaching a side-mounted handle which may assist the user in sliding the compressor block 400 downward to compress pins or wires passing through the compressor block 400.

Figure 17:
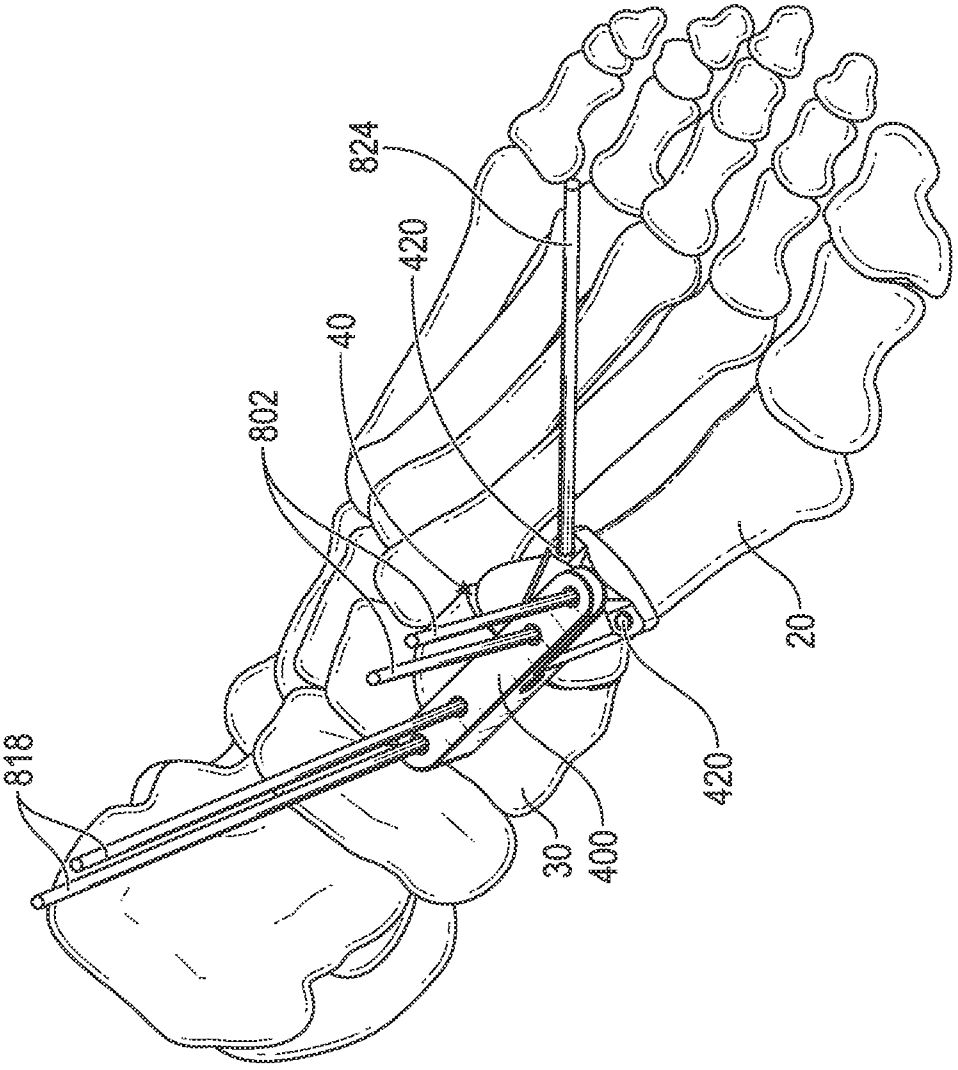
FIG. 17 is a perspective view of the human foot of FIG. 16, showing a cross pin inserted through one of the cross pin holes of the compressor block.
Figure 18:
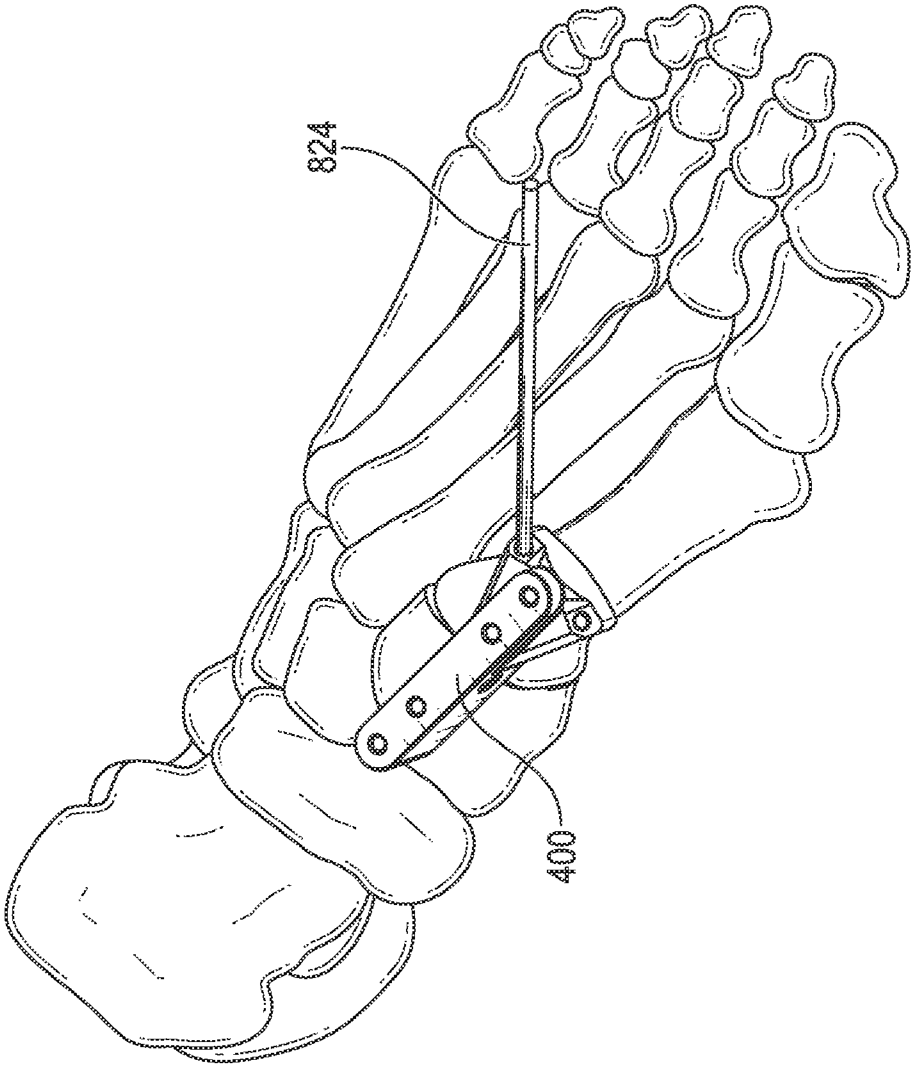
FIG. 18 is a perspective view of the human foot of FIG. 17, showing the metatarsal pins and the cuneiform pins removed.

The compressor block 400 further includes widened section 409 containing cross pin holes 420. As shown in FIGS. 5A and 5B, each cross pin hole 420 extends downward and inward from an outer edge of the widened section 409 such that a pin or wire inserted into a cross pin hole 420 exits the bottom edge 407 of the compressor block 400 relatively nearer the centerline of the compressor block 400. As shown in FIGS. 16-18, the cross pin holes 420 are aligned such that, when the compressor block 400 is used in conjunction with the cut guide 100 or free-hand pin guide 150 at the first TMT joint, the compressor block 400 brings the cut faces of the resected first TMT joint into contact with each other and a pin inserted through either cross pin hole 420 will extend at an angle through the interface of the compressed joint to temporarily maintain contact at the joint face until the first cuneiform and the first metatarsal can be fixed by a plate or other fixing component.

FIGS. 6A-6G depict an example bone plate 500 and cross screw 530 configured to be used in the Lapidus bunionectomy procedures described herein. The bone plate 500 and/or the cross screw 530 can be formed of a variety of metals or alloys. For example, the bone plate may be formed of titanium, a shape-memory alloy such as nitinol, or the like.

The bone plate 500 is sized and shaped to be applied across a resected first TMT joint. Accordingly, the bone plate 500 comprises a body 505 including a staple aperture 510, cuneiform screw apertures 515, a metatarsal screw aperture 520, and a cross screw aperture 525. The staple aperture 510 includes two holes 512 sized and shaped to accommodate the two legs of a bone staple such that one of the legs is seated within the first cuneiform near the cuneiform screw apertures 515 and the other leg is seated within the first metatarsal near the metatarsal screw aperture 520 and the cross screw aperture 525.

The staple aperture 510 and each of the screw apertures 515, 520, 525 is shaped to include a countersink to reduce motion of staples and/or screws seated therein. In addition, the countersinks may allow a staple or screw applied therein to not extend significantly above the outer surface of the body 505 of the bone plate 500. Due to the angle at which a cross screw must be applied in the cross screw aperture 525, the cross screw aperture 525 has an elliptical shape when viewed perpendicular to the bone plate 500 (e.g., corresponding to a cylindrical profile along a screw path through the cross screw aperture 525) and includes a shelf 527 occupying approximately one half of the perimeter of the cross screw aperture 525. The shelf 527 is shaped to engage with the head of a cross screw when the cross screw is inserted at a pre-drilled angle, such that the cross screw securely engages the bone plate 500 and seats within the countersink.

Figure 6A:
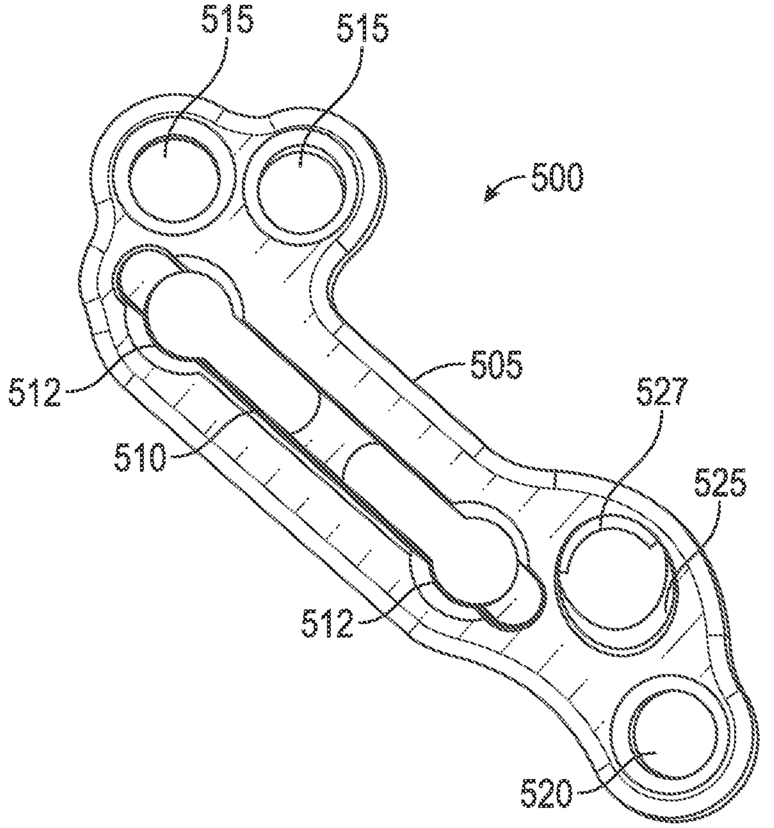
FIG. 6A is a plan view of an example bone plate configured to be used in the Lapidus bunionectomy procedures described herein.
Figure 6B:
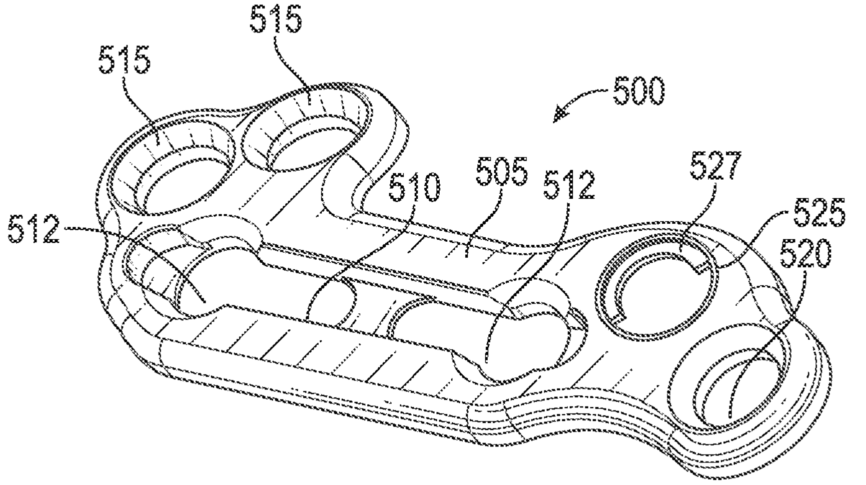
FIG. 6B is a perspective view of the example bone plate of FIG. 6A.
Figure 6C:
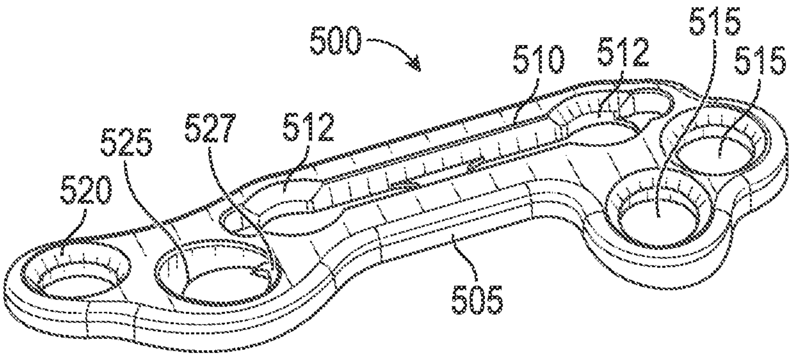
FIG. 6C is another perspective view of the example bone plate of FIG. 6A.
Figure 6D:
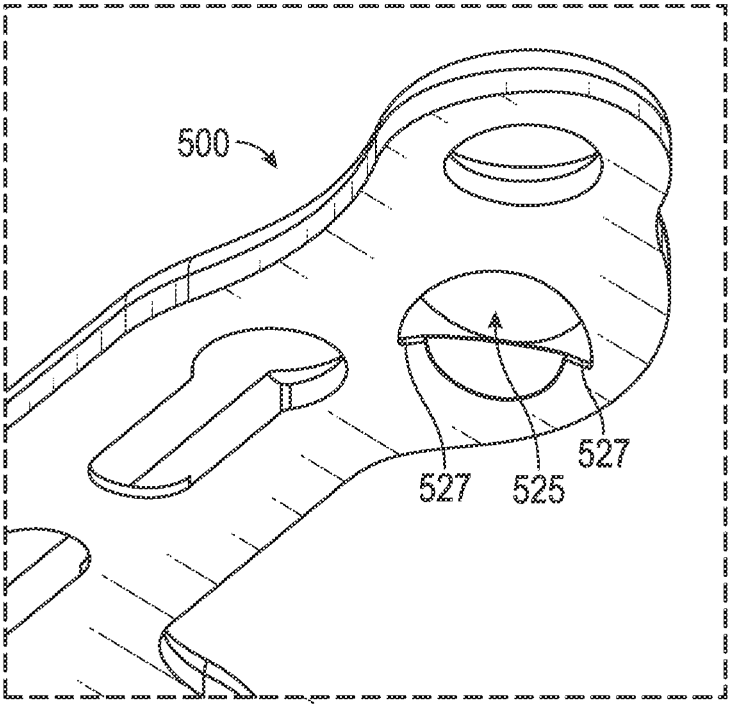
FIG. 6D is an enlarged perspective view of a portion of the example bone plate of FIG. 6A.
Figure 6E:
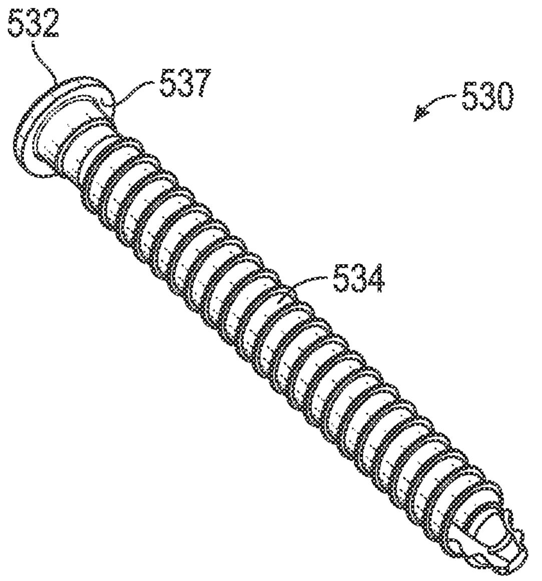
FIG. 6E is a perspective view of a cross screw configured to be used with the bone plate of FIG. 6A.
Figure 6F:
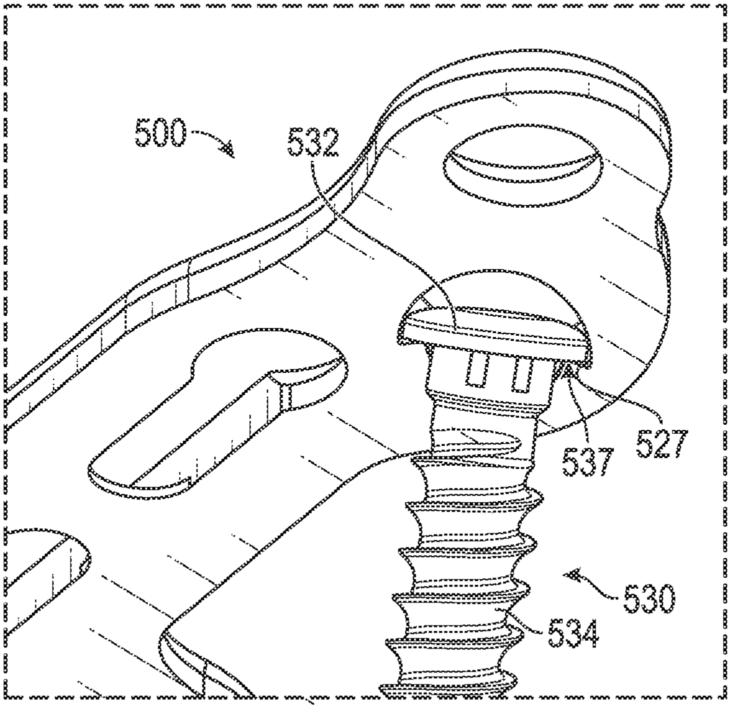
FIG. 6F is a perspective view of portion of the bone plate of FIG. 6D showing the cross screw of FIG. 6E inserted therein.
Figure 6G:
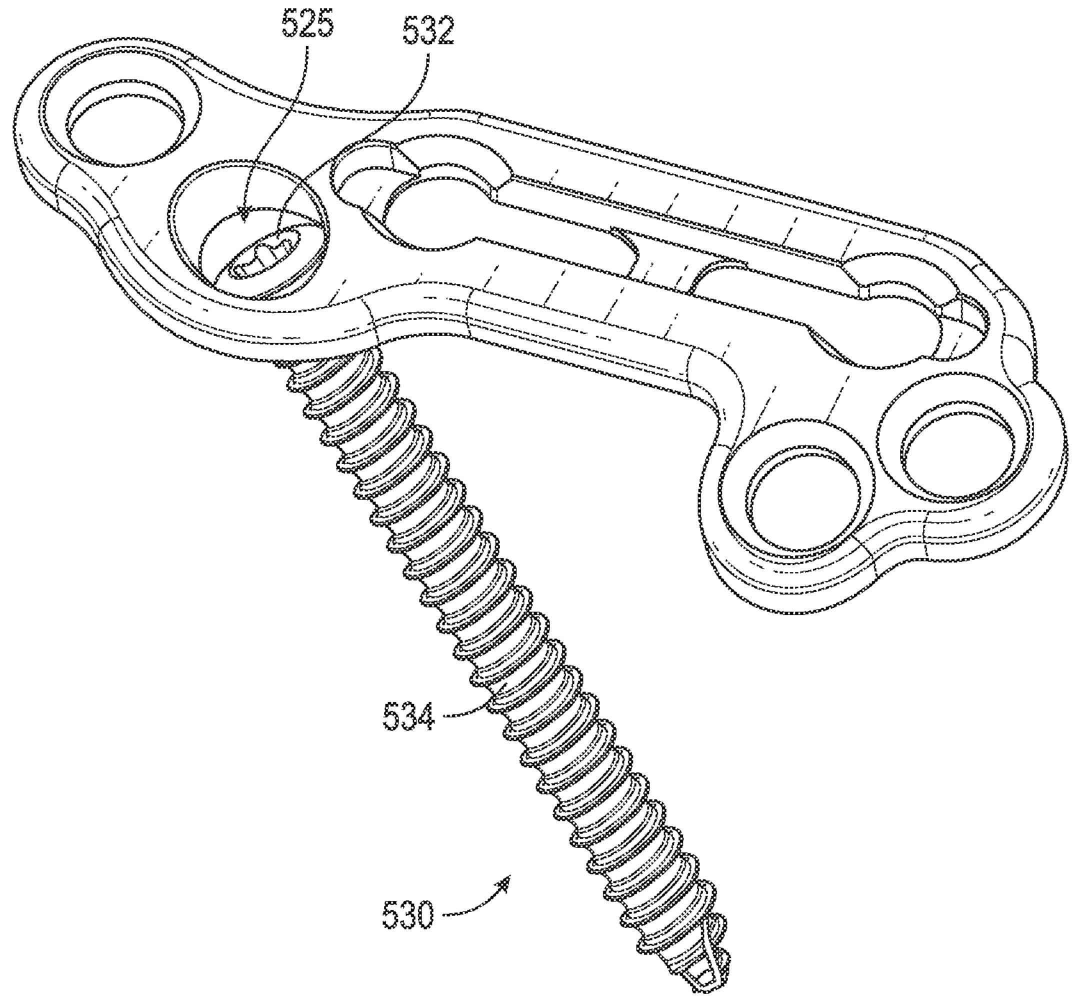
FIG. 6G is a perspective view of the bone plate of FIG. 6D showing the cross screw of FIG. 6E inserted therein.

FIG. 6D is an expanded partial view of the bone plate 500, illustrating in detail the cross screw aperture 525 and the shelf 527. FIG. 6E illustrates an example cross screw 530 configured to be seated within the cross screw aperture 525, including a head 532 and a threaded shaft 534. As shown in FIG. 6D, which is taken perpendicular to an axis of a cross screw path, the shelf 527 can be canted or tapered such that an inner edge of the shelf 527 is higher relative to an outer edge where the shelf 527 meets the interior wall of the cross screw aperture 525. As shown in FIG. 6E, the head 532 of the cross screw 530 has an undercut shelf 537. The shelf 537 is tapered downward as the diameter increases in this embodiment. Accordingly, as shown in FIGS. 6F and 6G, when the cross screw 530 is inserted through the cross screw aperture 525, the undercut shelf 537 of the head 532 of the cross screw 530 engages with the upwardly tapering shelf 527 of the bone plate 500 such that the bone screw 530 seats at the desired angle within the bone.

Figure 7A:
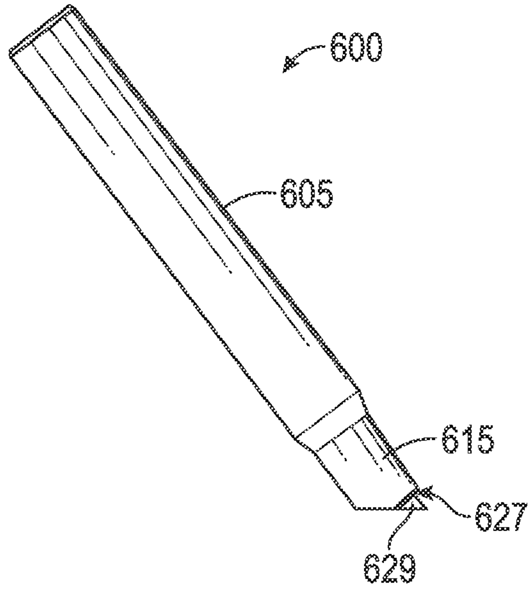
FIG. 7A is a perspective view of an example fixed-angle cross screw drill guide configured to be used in the Lapidus bunionectomy procedures described herein.
Figure 7B:
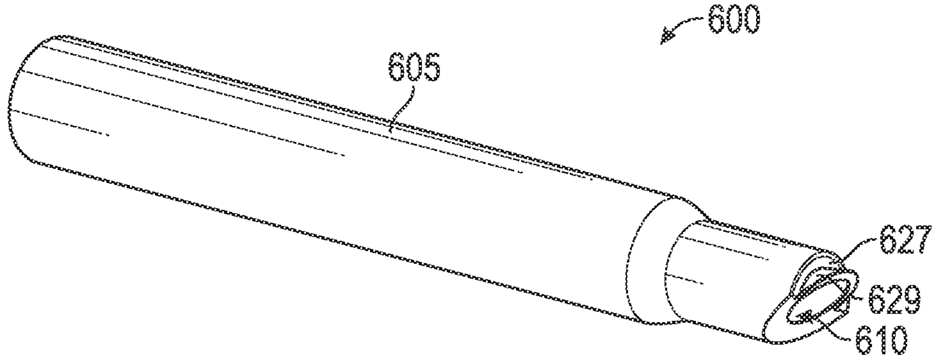
FIG. 7B is another perspective view of the example fixed-angle cross screw drill guide of FIG. 7A.
Figure 7C:
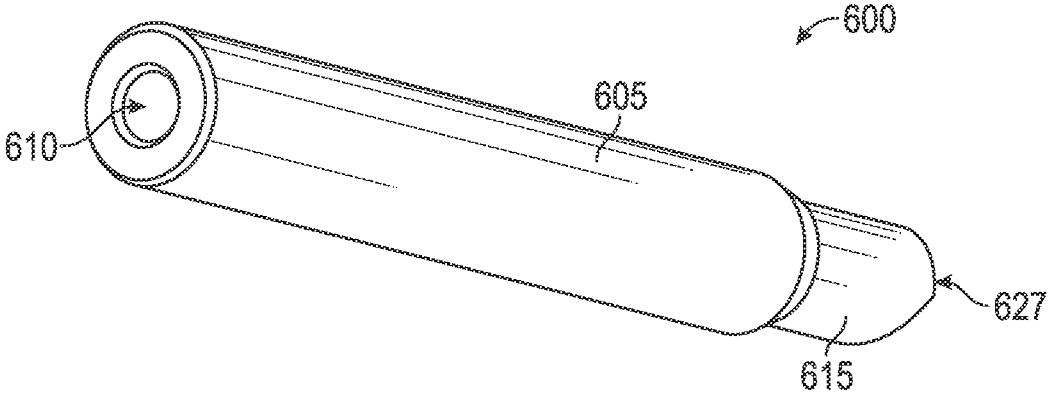
FIG. 7C is yet another perspective view of the example fixed-angle cross screw drill guide of FIG. 7A.
Figure 7D:
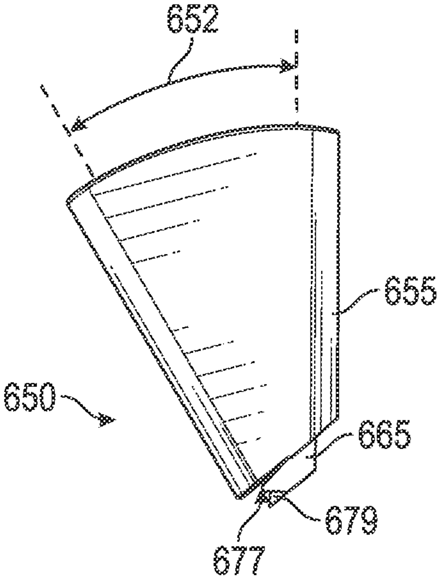
FIG. 7D is a side elevation view of an example variable-angle cross screw drill guide configured to be used in the Lapidus bunionectomy procedures described herein.
Figure 7E:
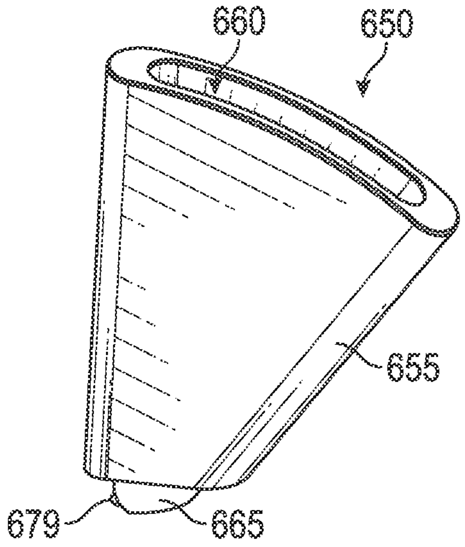
FIG. 7E is a perspective view of the variable-angle cross screw drill guide of FIG. 7D.
Figure 7F:
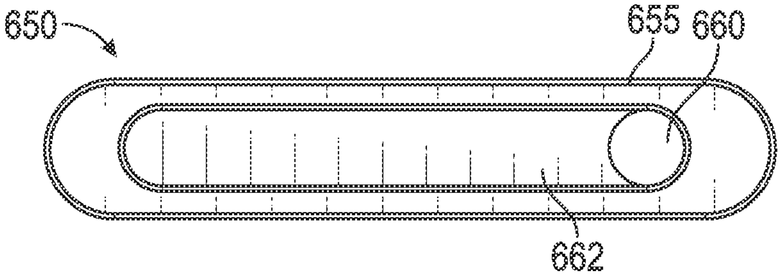
FIG. 7F is an end elevation view of the variable-angle cross screw drill guide of FIG. 7D.

FIGS. 7A-7F depict example cross screw drill guides configured to be used in conjunction with the bone plate 500 when applying the cross screw through the cross screw aperture 525. FIGS. 7A-7C depict an example fixed-angle cross screw drill guide 600. FIGS. 7D-7F depict an example variable-angle cross screw drill guide 650 which allows a surgeon to select one of a range of angles for insertion of the cross screw.

The fixed-angle cross screw drill guide 600 includes a body 605 and a tip 615. A lengthwise aperture 610 extends through the full length of the body 605. The diameter of the lengthwise aperture 610 may be selected such that a drill bit, suitably sized to drill a pilot hole for a cross screw, can fit through the lengthwise aperture 610. In some embodiments, the diameter of the lengthwise aperture 610 may be selected such that a k-wire or other guide structure can fit through the lengthwise aperture 610, such that the guide may be removed and a cannulated drill bit may be used to drill a pilot hole. The tip 615 includes a shelf engagement surface 627 and a toe 629. The toe 629 and the shelf engagement surface 627 are shaped such that the toe 629 can be seated within the cross screw aperture 525 with the shelf engagement surface 627 seated against the shelf 527 of the cross screw aperture 525. The elliptical shape of the cross screw aperture 525 defines a single stable orientation for seating the tip 615 of the fixed-angle cross screw drill guide 600 therein. The fixed-angle cross screw drill guide 600 facilitates consistent and reproducible application of a cross screw at a predetermined suitable angle to prevent bunion recurrence. Additionally, the fixed-angle cross screw drill guide 600 can force the entry of the drill bit into bone at a location concentric with the radius of curvature of the shelf 527 of the bone plate 500 (e.g., because a screw may still be able to pass through the bone plate 500 even if the hole is incorrectly drilled). Moreover, the fixed-angle cross screw drill guide 600 establishes the drill bit at an angle that prevents the cross screw from interfering with the staple leg, prevents the cross screw from crossing the TMT joint, and directs the cross screw toward the base of the second metatarsal or the second cuneiform.

The variable-angle cross screw drill guide 650 similarly includes a body 655 and a tip 665, as well as an aperture 660 extending through the body 655. The tip 665 has the same shape as the tip 615 of the fixed-angle cross screw drill guide 600, including a shelf engagement surface 677 and a toe 679, such that the elliptical shape of the cross screw aperture 525 similarly defines a single stable orientation for seating the tip 665 of the variable-angle cross screw drill guide 650 therein. The variable-angle cross screw drill guide 650 has a generally wedge-shaped body 655 surrounding a wedge-shaped slot 662 in communication with the aperture 660. The wedge-shaped slot 662 accommodates a range 652 of drilling angles whose paths pass through the aperture 660. Thus, while the elliptical shape of the cross screw aperture 525 defines a single seating orientation of the variable-angle cross screw drill guide 650, the wedge-shaped slot 662 allows the surgeon to select a variety of angles within a predetermined plane. The available drilling paths can range from a first extreme path which is perpendicular or nearly perpendicular relative to the bone plate 500, to a second extreme path at a smaller angle relative to the bone plate 500. Depending on the geometry of the bone structure of an individual foot, the variable-angle cross screw drill guide 650 can allow a surgeon to select a cross screw trajectory, for example, to enter the second metatarsal or the second cuneiform as desired.

With reference to FIGS. 8-24, an example Lapidus bunionectomy using certain devices disclosed herein will be described. Although the procedure of FIGS. 8-24 illustrates a particular implementation of a Lapidus bunionectomy using a specific subset of the devices disclosed herein, it will be understood that the components and steps illustrated and described with reference to FIGS. 8-24 may equally be applied in different sequences and/or with different combinations of components to correct a bunion.

Figure 8:
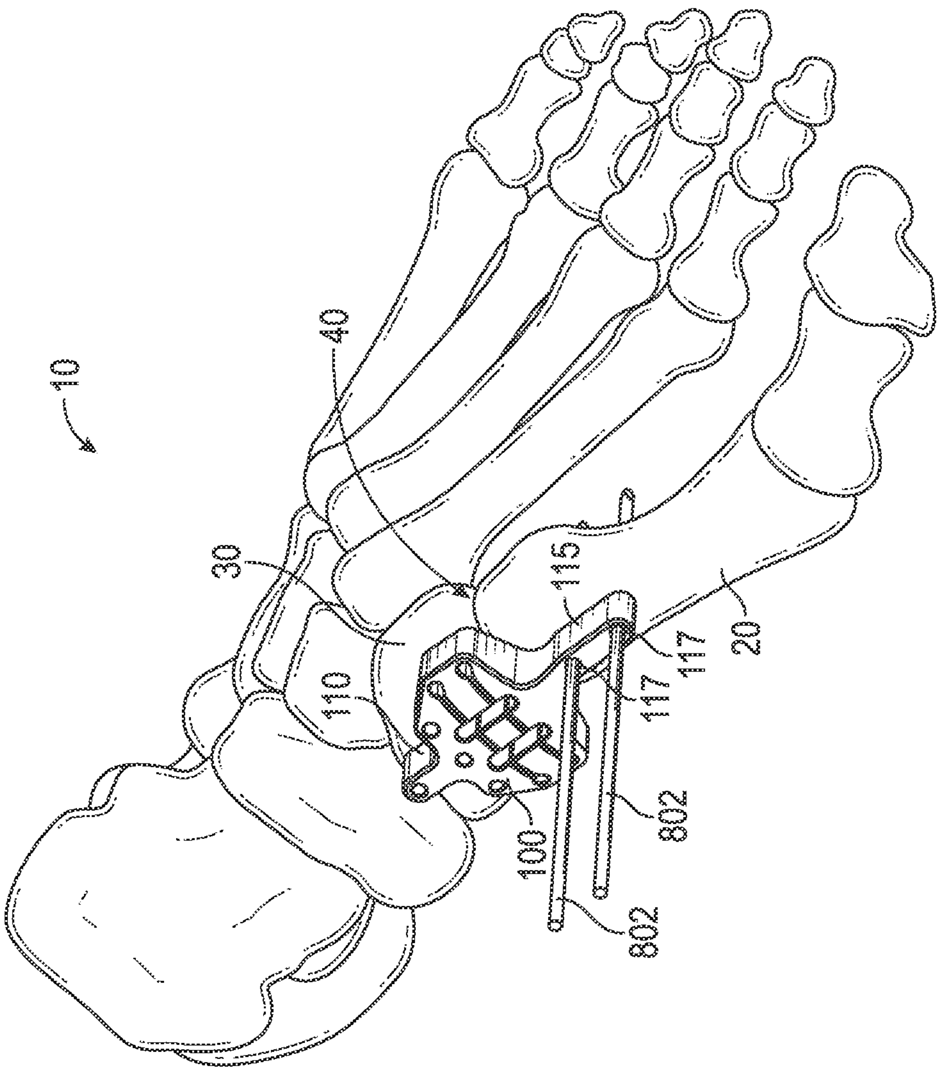
FIG. 8 is a perspective view of the bones of a human foot, showing one of a plurality of steps of an example Lapidus bunionectomy procedure performed using the example bunionectomy devices disclosed herein, whereby the cut guide of FIG. 2A is temporarily secured to the foot.

FIGS. 8-24 depict the bones of a foot 10 initially having a bunion. Similar to the foot 10 of FIG. 1, the foot 10 includes a first metatarsal 20 that is angled and rotated relative to the first cuneiform 30 at the first TMT joint 40 such that the big toe has an undesirable medial protrusion and an increased intermetatarsal angle. As shown in FIG. 8, the procedure may begin by placing and temporarily securing the cut guide 100 of FIGS. 2A-2D. Prior to placing the cut guide, the surgeon may prepare the first TMT joint 40 by making an incision such as a dorsomedial incisions to expose the first TMT joint 40 and excising soft tissue around the joint, such as the joint capsule or other soft tissue, to expose the first TMT joint 40 and create a space in which the paddle 120 (FIGS. 2A-2D) of the cut guide 100 can be seated.

Once the joint has been prepared, the cut guide 100 is placed by seating the paddle 120 (not visible in FIG. 8) within the first TMT joint 40 such that proximal extension 110 sits adjacent to or against the first cuneiform 30 and the distal extension 115 sits adjacent to or against the first metatarsal 20. The paddle 120 is inserted into the first TMT joint 40 such that the cut guide 100 is oriented along the axis of the first metatarsal 20. The alignment of the cut guide 100 may be confirmed under fluoroscopy or other suitable imaging technique before proceeding.

When the cut guide 100 has been placed and is suitably aligned, the cut guide 100 is temporarily secured relative to the first metatarsal 20 by inserting two metatarsal pins 802 or wires through the distal pin holes 117 of the distal extension 115 and into or through the first metatarsal 20. The metatarsal pins 802 or wires, as well as any of the other pins or wires described in the following description, may be, for example, a Kirschner wire ("K-wire"), or any other suitable type of wire or pin that can be placed into the bone to secure the cut guide 100.

Figure 9:
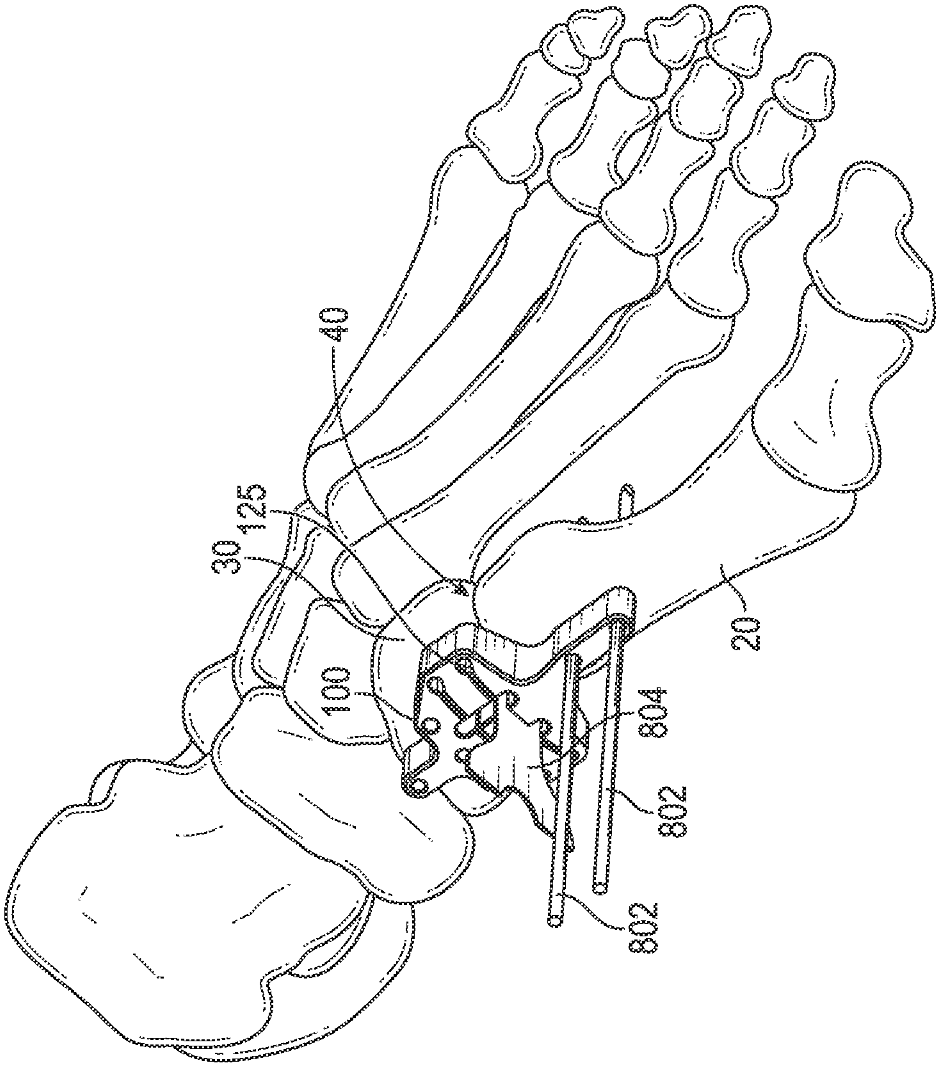
FIG. 9 is a perspective view of the human foot of FIG. 8, showing metatarsal pins inserted through the cut guide and into a first metatarsal, and further showing a saw blade that cuts a base of the first metatarsal.

Continuing to FIG. 9, once the metatarsal pins 802 or wires are inserted, the base of the first metatarsal 20 is cut using a saw blade 804 inserted through the distal slot 125 of the cut guide 100.

Figure 10:
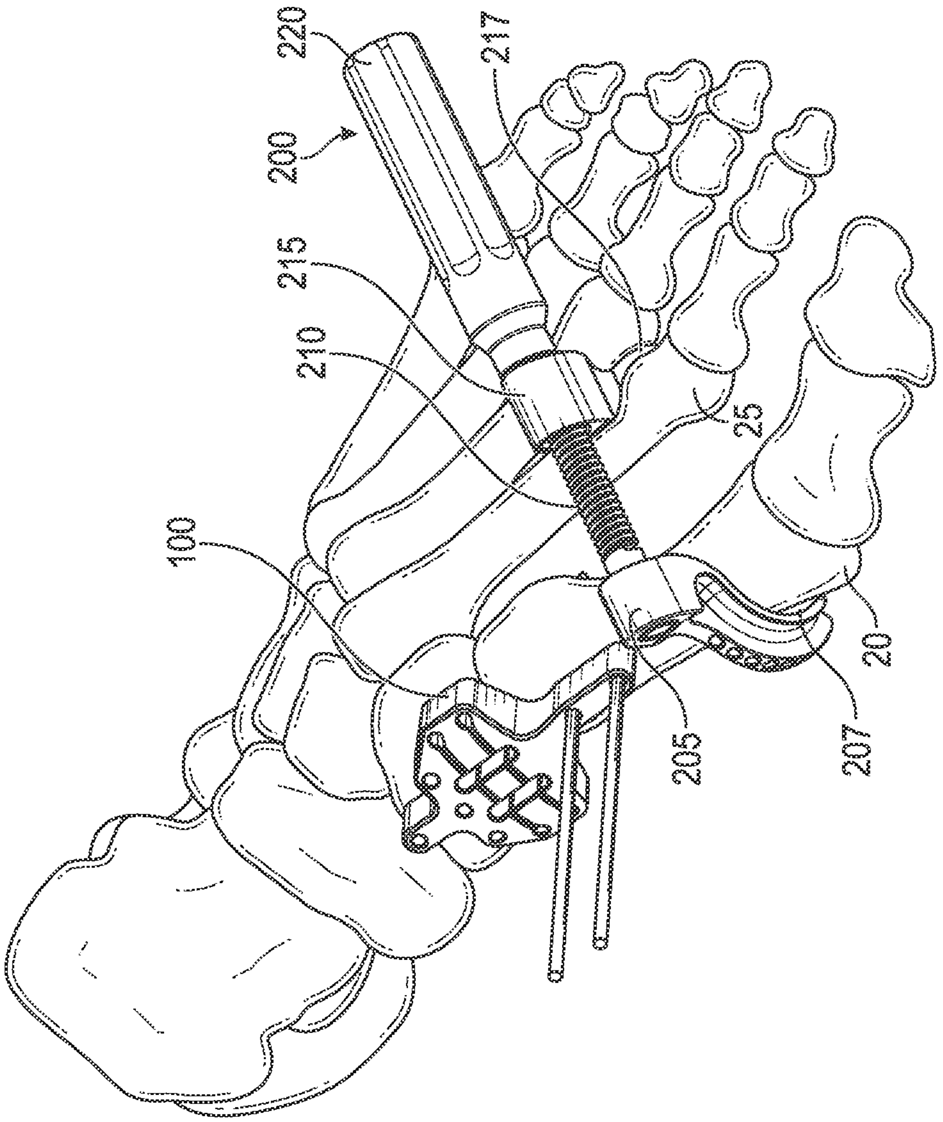
FIG. 10 is a perspective view of the human foot of FIG. 9, showing the linear reducer of FIG. 3A provisionally placed around the first metatarsal and the second metatarsal.

With reference to FIG. 10, a linear reducer 200 may be provisionally placed around the first metatarsal 20 and the second metatarsal 25. In some embodiments, an incision is made lateral of the second metatarsal 25 between the second and third toes to accommodate insertion of the lateral hook 215 such that the engagement surface 217 contacts the lateral side of the second metatarsal 25. The engagement surface 207 of the medial hook 205 is placed against a medial surface of the foot adjacent the first metatarsal 20, and the handle 220 of the linear reducer 200 may be turned clockwise relative to the threaded shaft 210 until the handle 220 contacts the lateral fork 215. The initial placement of the linear reducer 200 may be a provisional placement, without initially inserting any pins through the medial fork 205.

Figure 11:
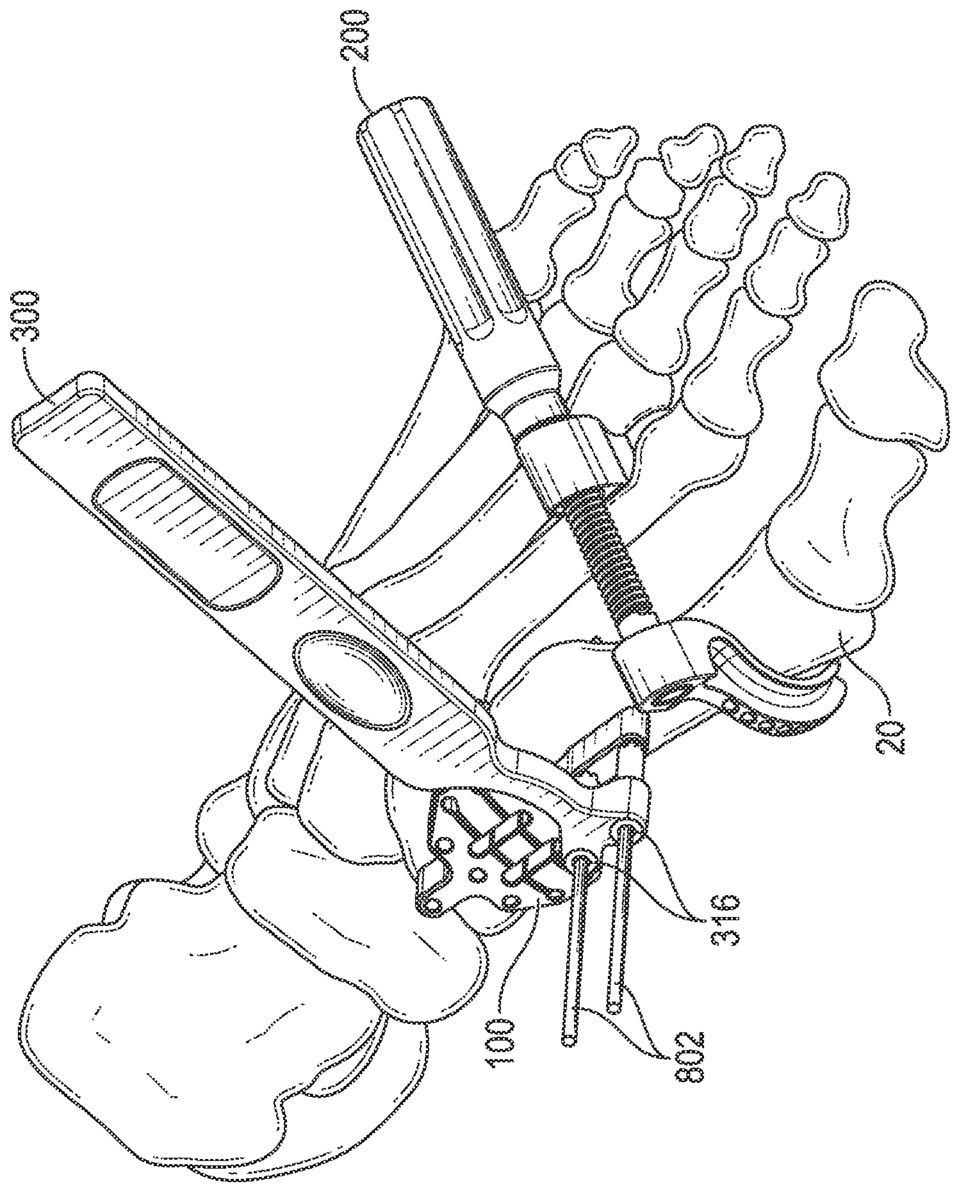
FIG. 11 is a perspective view of the human foot of FIG. 10, showing the control handle of FIG. 4A placed over the pins.
Figure 12:
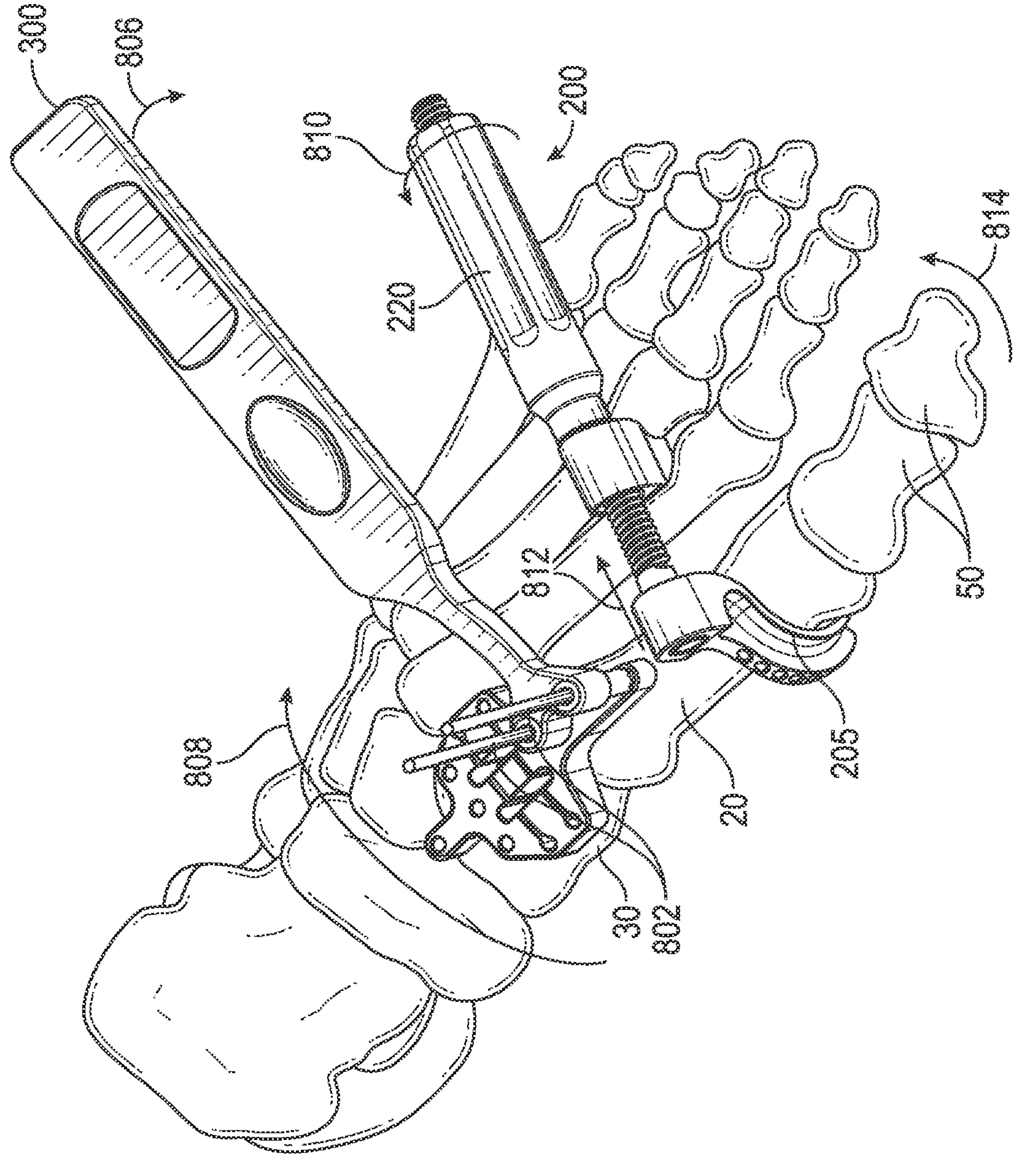
FIG. 12 is a perspective view of the human foot of FIG. 11, but whereby the control handle has been rotated.

Continuing to FIG. 11, a control handle 300 may further be placed by inserting the metatarsal pins 802 through the spaces 316 within the pin guides 314 of the control handle 300. With reference to FIG. 12, the control handle 300 may then be rotated within the frontal plane to correct for rotation about the axis of the first metatarsal 20. For example, when a clockwise rotation 806 imparted to the control handle 300, the torque applied to the control handle 300 is transferred via the metatarsal pins 802 such that the first metatarsal and the phalanges 50 of the big toe are rotated clockwise 808. Additionally, any necessary adjustment of the joint within the sagittal plane may be applied manually at this time. In some embodiments, other corrections, such as application of torque in the transverse plane to reduce the intermetatarsal angle, could also be applied using the control handle 300. When the frontal plane and sagittal plane have been suitably corrected using the control handle 300, the surgeon may then proceed to adjust the position of the first metatarsal 20 in the transverse plane.

Figure 13:
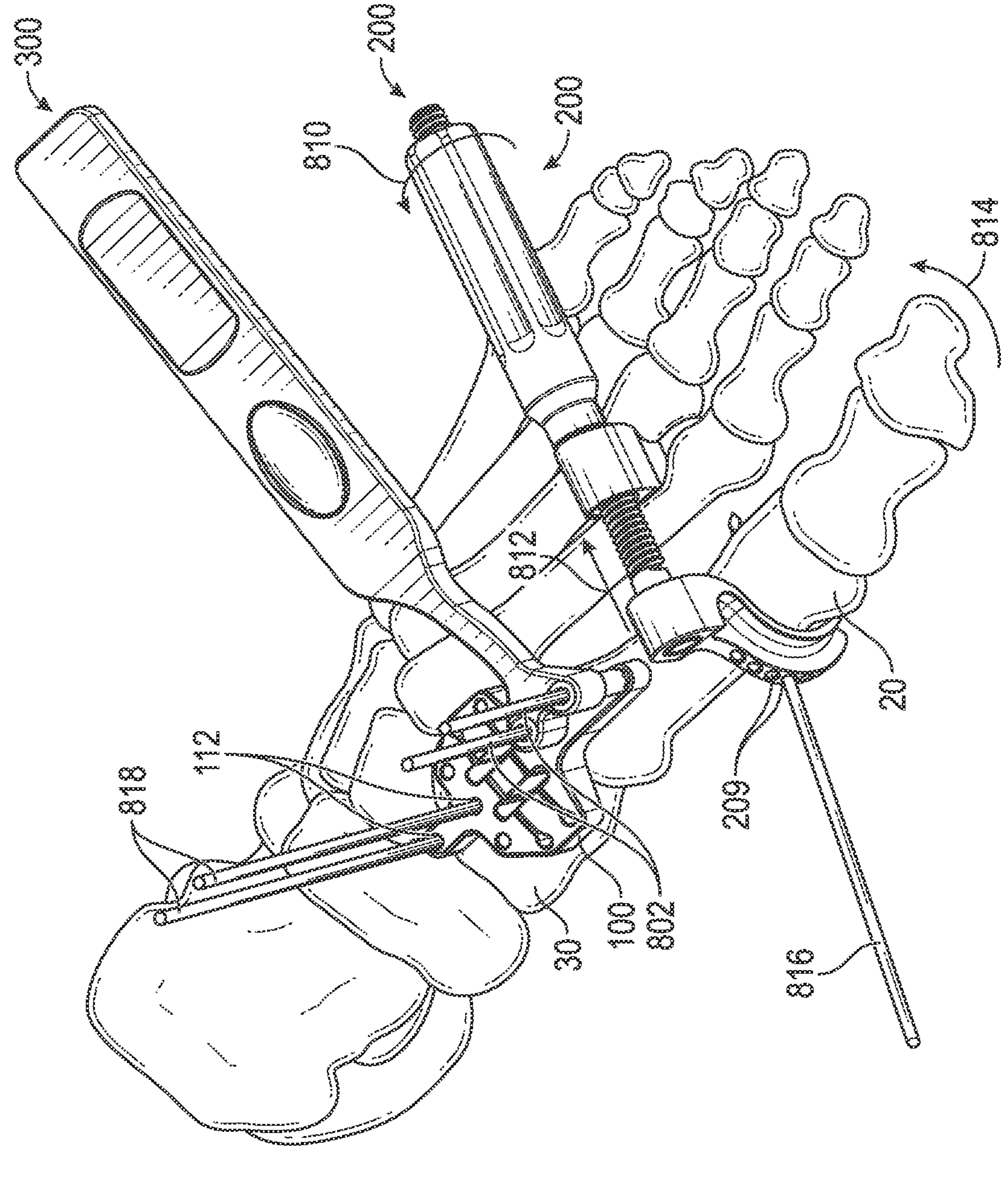
FIG. 13 is a perspective view of the human foot of FIG. 12, showing cuneiform pins inserted through proximal pin holes of the cut guide and into or through the first cuneiform, and a medial hook pin inserted through a medial hook pin holes of the linear reducer and into or through the first metatarsal to fix the rotational position of the first metatarsal.

Referring jointly to FIGS. 12 and 13, the transverse plane may be corrected using the linear reducer 200. In some implementations, a medial hook pin 816 is inserted through one of the medial hook pin holes 209 and into or through the first metatarsal 20 to fix the rotational position of the first metatarsal 20 in the frontal plane (e.g., locking in the frontal plane correction previously applied using the control handle 300). The medial hook pin may be a shouldered pin, such that lateral pressure exerted by the medial hook 205 is applied directly to the first metatarsal 20 through the pin shoulder rather than being applied through the skin along the engagement surface 207 of the medial hook.

With or without insertion of a medial hook pin 816, a transverse plane correction may be applied by turning the handle 220 of the linear reducer 200. For example, a clockwise rotation 810 of the handle 220 reduces the distance along the threaded shaft between the medial fork 205 and the lateral fork 215, causing the medial fork 205 to move laterally along direction 812 relative to the lateral fork 215. As a result, the medial fork 205 applies a lateral force to the first metatarsal 20 in the transverse plane, causing a corresponding lateral movement 814 of the first metatarsal 20 within the transverse plane.

At this stage, the misalignment of the first TMT joint 40 has been addressed. With continued reference to FIG. 13, two cuneiform pins 818 or wires are inserted through the proximal pin holes 112 of the cut guide and into or through the first cuneiform 30. The cuneiform pins 818 or wires temporarily secure the cut guide 100 relative to the first cuneiform 30. At this point, the four pins 802 and 814 form an array that establishes and/or locks the surgeon's desired correction.

Figure 14:
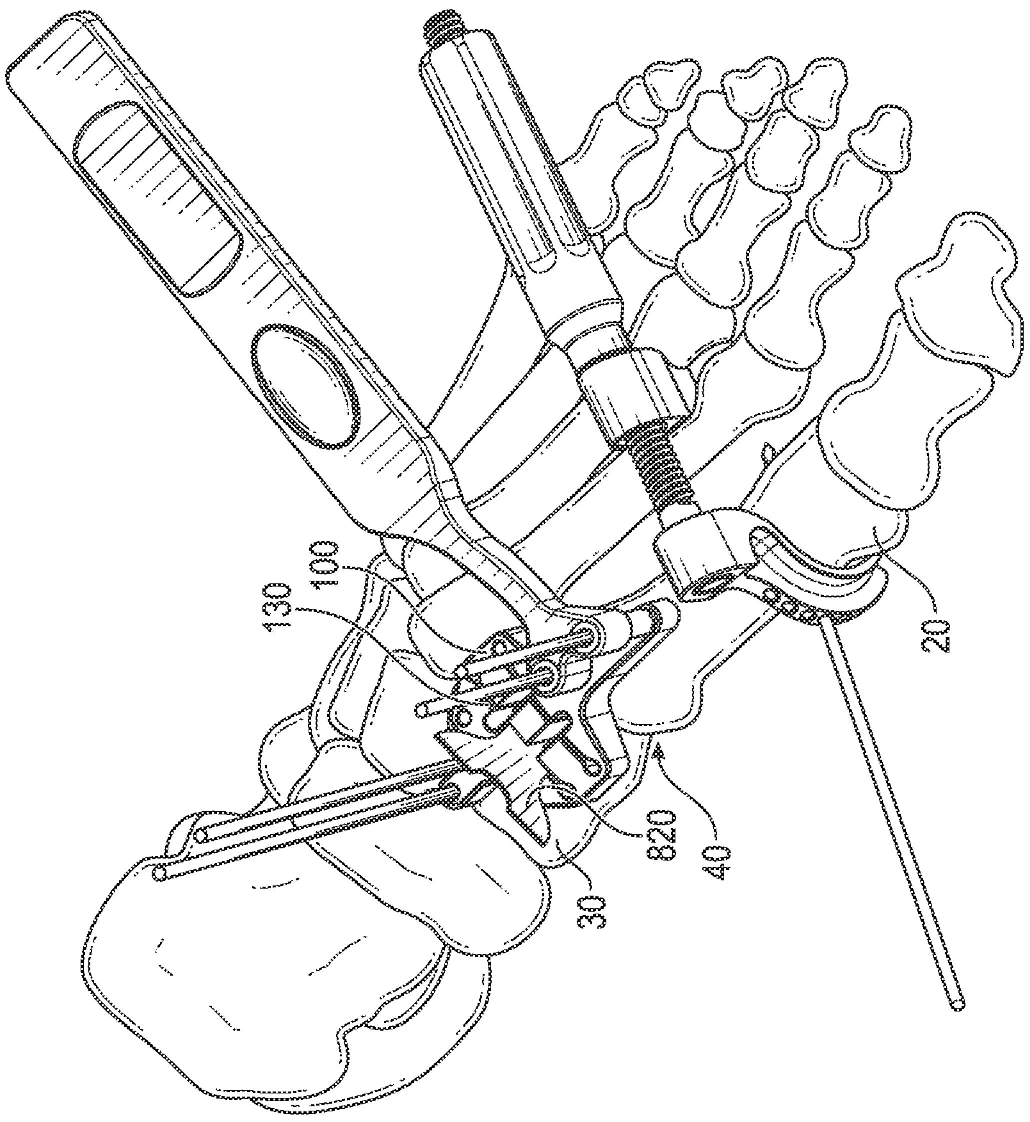
FIG. 14 is a perspective view of the human foot of FIG. 13, showing a saw blade inserted through a proximal slot of the cut guide and configured to cut a base of the first cuneiform.

Continuing to FIG. 14, once the cuneiform pins 818 or wires are inserted, the base of the first cuneiform 30 is cut using a saw blade 820 inserted through the proximal slot 130 of the cut guide 100. Cutting the base of the first cuneiform 30 completes the excision of the first TMT joint 40. With reference to FIG. 15, the cut guide 100, the linear reducer 200, and the control handle 300 are removed from the foot 10. The control handle 300 can be removed by sliding upward until the control handle is free of the metatarsal pins 802 or wires. The cut guide 100 can similarly be removed by sliding the cut guide 100 upward until it is free of the metatarsal pins 802 or wires and the cuneiform pins 818 or wires. The linear reducer 200 is removed by removing the medial hook pin 816 and lifting the medial and lateral hooks 205, 215 away from the foot 10. In some embodiments, a quick-release medial hook 235 may be used to facilitate removal of the linear reducer. After removal of the cut guide 100, linear reducer 200, and control handle 300, the fully disarticulated first TMT joint is left with the metatarsal pins 802 or wires and cuneiform pins 818 or wires remaining in place. At this point, the surgeon may further use any desired means to distract and further prepare the joint in preparation for fusion. It is recognized that the pins 802 in the metatarsal 20 and the pins 818 in the cuneiform 30 can return to their original orientation, which is a misaligned relative orientation between the metatarsal and the cuneiform.

Referring now to FIG. 16, the compressor block 400 is applied over the metatarsal pins 802 or wires and cuneiform pins 818 or wires. Preferably, the metatarsal pins 802 or wires are either shorter or longer than the cuneiform pins 818 or wires (e.g., by approximately the height of the compressor block 400 or more, as shown in FIG. 16). In the example of FIG. 16, the compressor block 400 is applied by first threading the proximal pin holes 410 onto the relatively longer cuneiform pins 818 or wires, followed by threading the distal pin holes 415 onto the relatively shorter metatarsal pins 802 or wires. As discussed above with reference to FIGS. 5A-5D, unlike the pin holes of the cut guide 100, the pin holes of the compressor block 400 are slightly closer together and tapered inward such that it may be difficult to attempt to insert all four pins or wires through the compressor block 400 simultaneously.

Figure 19:
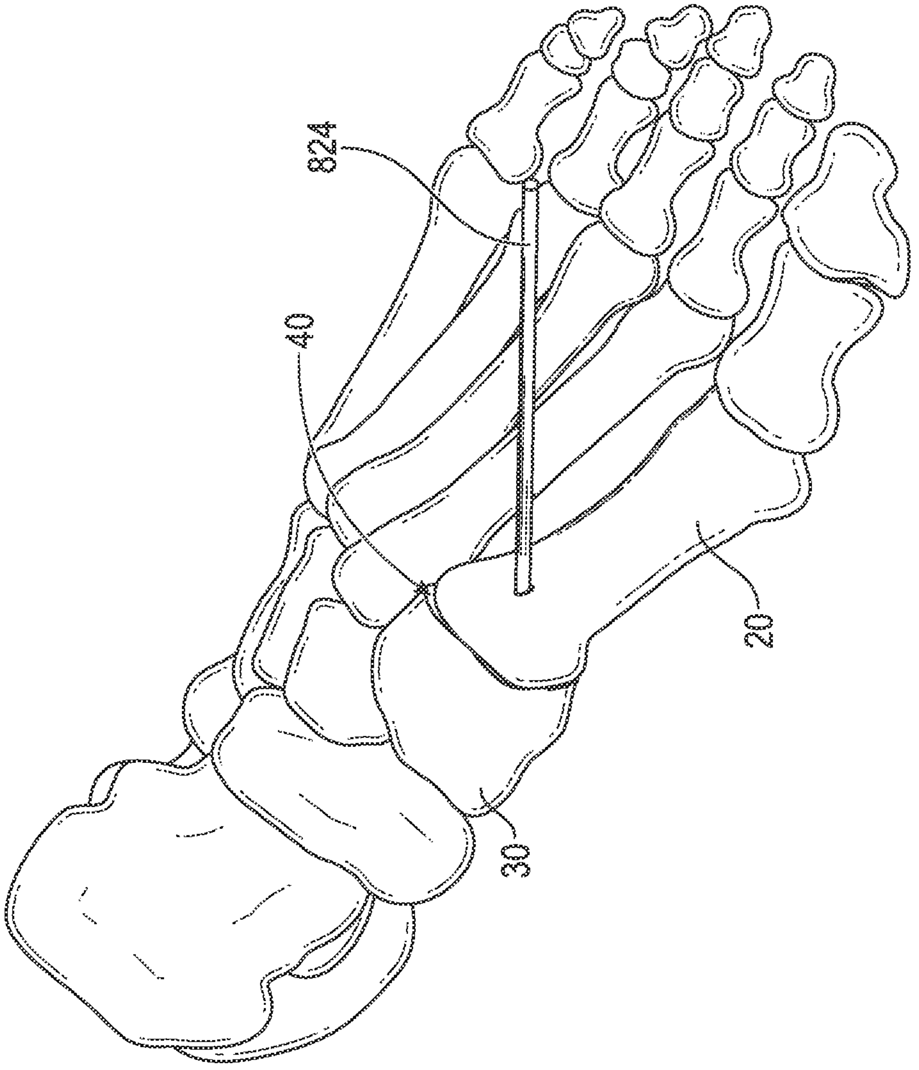
FIG. 19 is a perspective view of the human foot of FIG. 18, showing the compressor block removed.

Due to the convergent angle of the proximal pin holes 410 to the distal pin holes 415, sliding the compressor block 400 downward over the cuneiform pins 818 or wires and the metatarsal pins 802 or wires pulls the metatarsal pins 802 or wires closer to the cuneiform pins 818 or wires. Thus, the application of the compressor block 400 causes the first metatarsal 20 to move along direction 822 toward the first cuneiform 30, bringing the cut face of the first metatarsal 20 into contact with the cut face of the first cuneiform 30. The angled holes cause a rotation of the pins in the sagittal plane so that the plantar side of the joint is compressed. This may be desirable, as compression on only the dorsal aspect of the bones may in some cases cause a plantar gapping of the joint which is undesirable for fusion. Further, application of the compressor block 400 aligns the pins 802 and 818 in a single plane which corresponds to the plane of the cut guide, which thus returns the alignment of the metatarsal and cuneiform to the desired aligned position Continuing to FIG. 17, a cross pin 824 is then inserted through one of the cross pin holes 420 such that the cross pin 824 passes through the compressed joint to temporarily fix the joint in place. As shown in FIG. 18, the metatarsal pins 802 or wires and the cuneiform pins 818 or wires are removed. As shown in FIG. 19, the compressor block 400 may then be removed by sliding the compressor block outward along the cross pin 824, which remains in place to fix the joint until the bone plate 500 can be applied. Any number of cross pin hole trajectories could be applied to the compression block 400 for placement of the crossing wire. Although the cross pin 824 is shown as being inserted distally and extending proximally into the joint, in other embodiments the compression block 400 may have cross pin holes 420 located proximally instead of or in addition to distally. In such embodiments, the cross pin 824 would be inserted from a proximal end of the compression block 400 and would extend distally through the joint.

Figure 20:
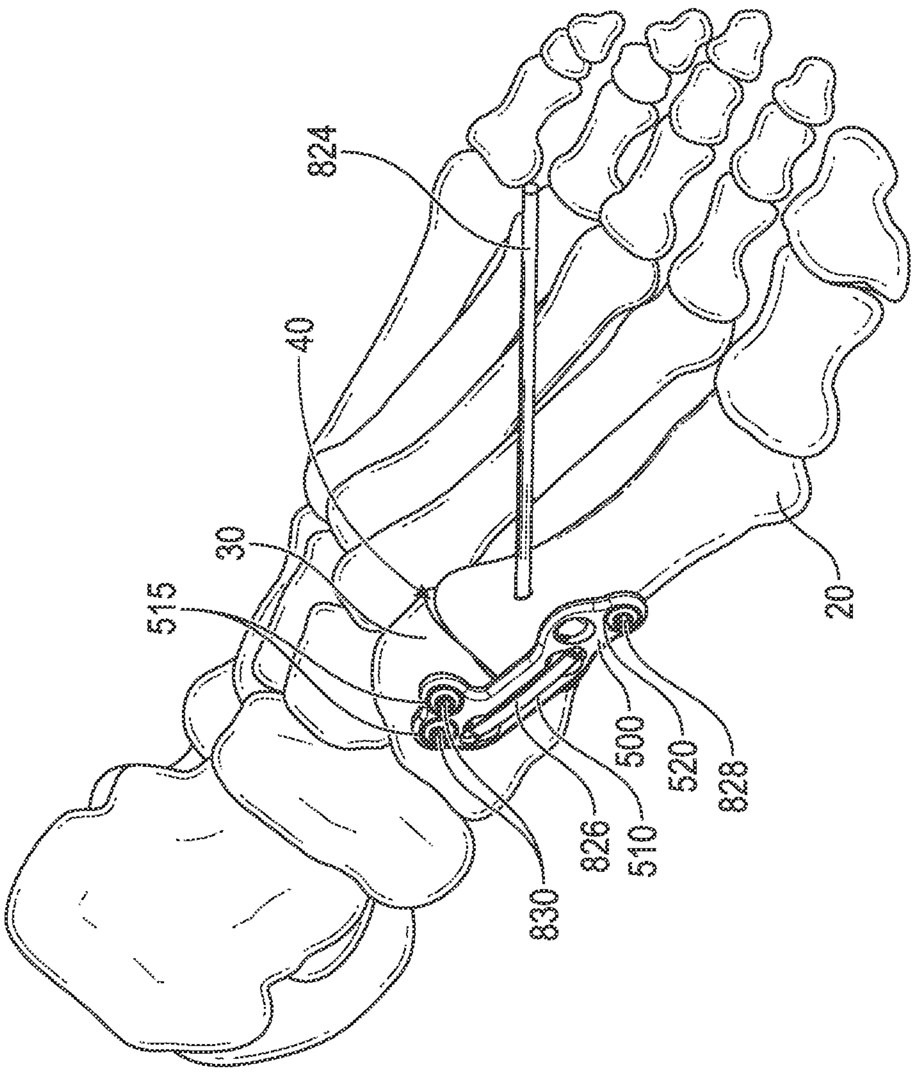
FIG. 20 is a perspective view of the human foot of FIG. 19, showing the bone plate of FIG. 6A placed across the resected first tarsometatarsal joint.
Figure 21:
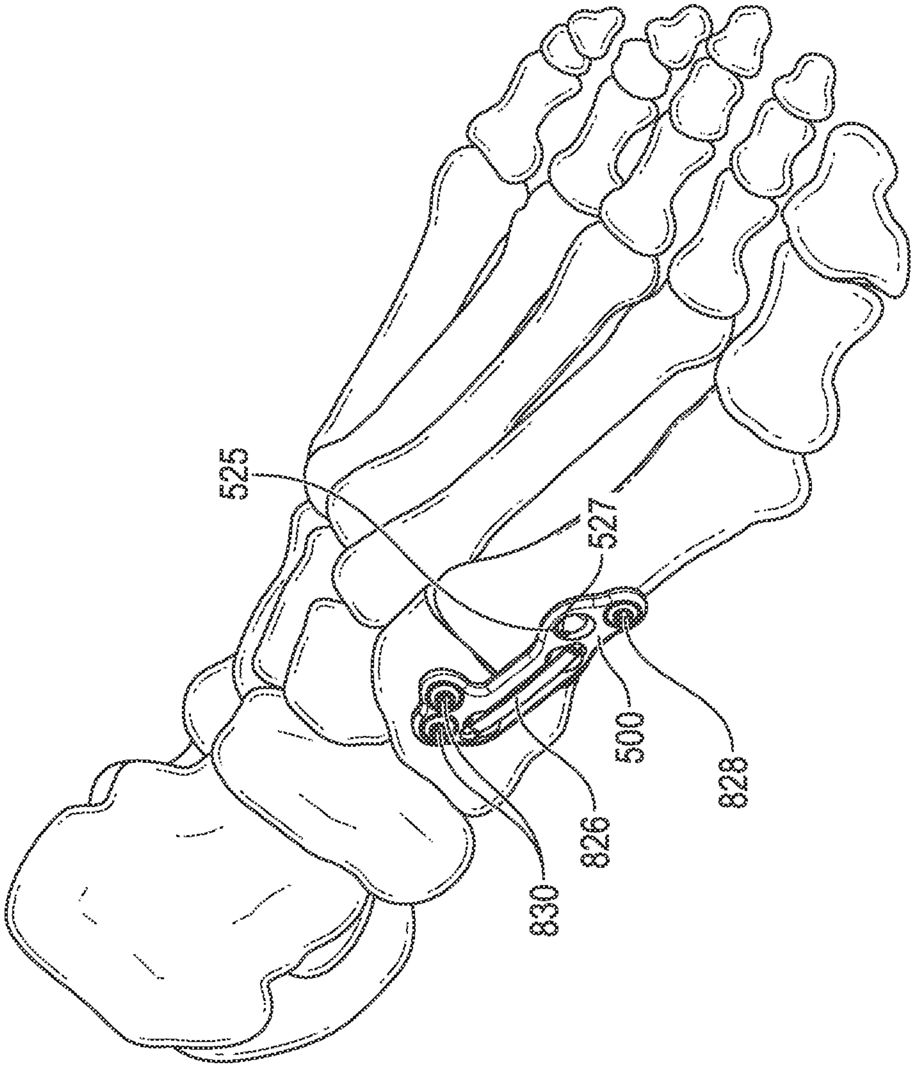
FIG. 21 is a perspective view of the human foot of FIG. 20, showing the cross pin of FIG. 17 removed.

With reference to FIG. 20, while the joint is fixed in place by the cross pin 824, the bone plate 500 is placed across the resected first TMT joint 40. Pilot holes are drilled as necessary. In order to fix the first metatarsal 20 relative to the first cuneiform 30, a staple 826 is placed at the staple aperture 510, a metatarsal screw 828 is placed at the metatarsal screw aperture 520, and cuneiform screws 830 are placed at the cuneiform screw apertures 515. The staple 826, metatarsal screw 828, and cuneiform screws 830 can be placed in any order; however, it may be preferable to place the staple 826 and the metatarsal screw 828 prior to placing the cross screw 834. As shown in FIG. 21, when the first metatarsal 20 and the first cuneiform 30 have been fixed using the bone plate 500, the cross pin 824 is no longer necessary and can be removed. The staple 826 may be made of a shape-memory material. In some embodiments, the staple 826 is held in a deformed configuration wherein the staple legs are approximately parallel during insertion through the plate 500. After insertion, the staple 826 may be allowed to relax toward a non-deformed configuration, where the legs are angled towards each other. Thus, after insertion, the staple 826 provides a compression force across the TMT joint 40. More details regarding the plate-staple system may be found in U.S. Pat. No. 10,299,842, which is incorporated herein by reference in its entirety. More details regarding staples suitable for use as described herein can be found in U.S. Publication No. 2018/0317906, which is incorporated herein by reference in its entirety.

Figure 22:
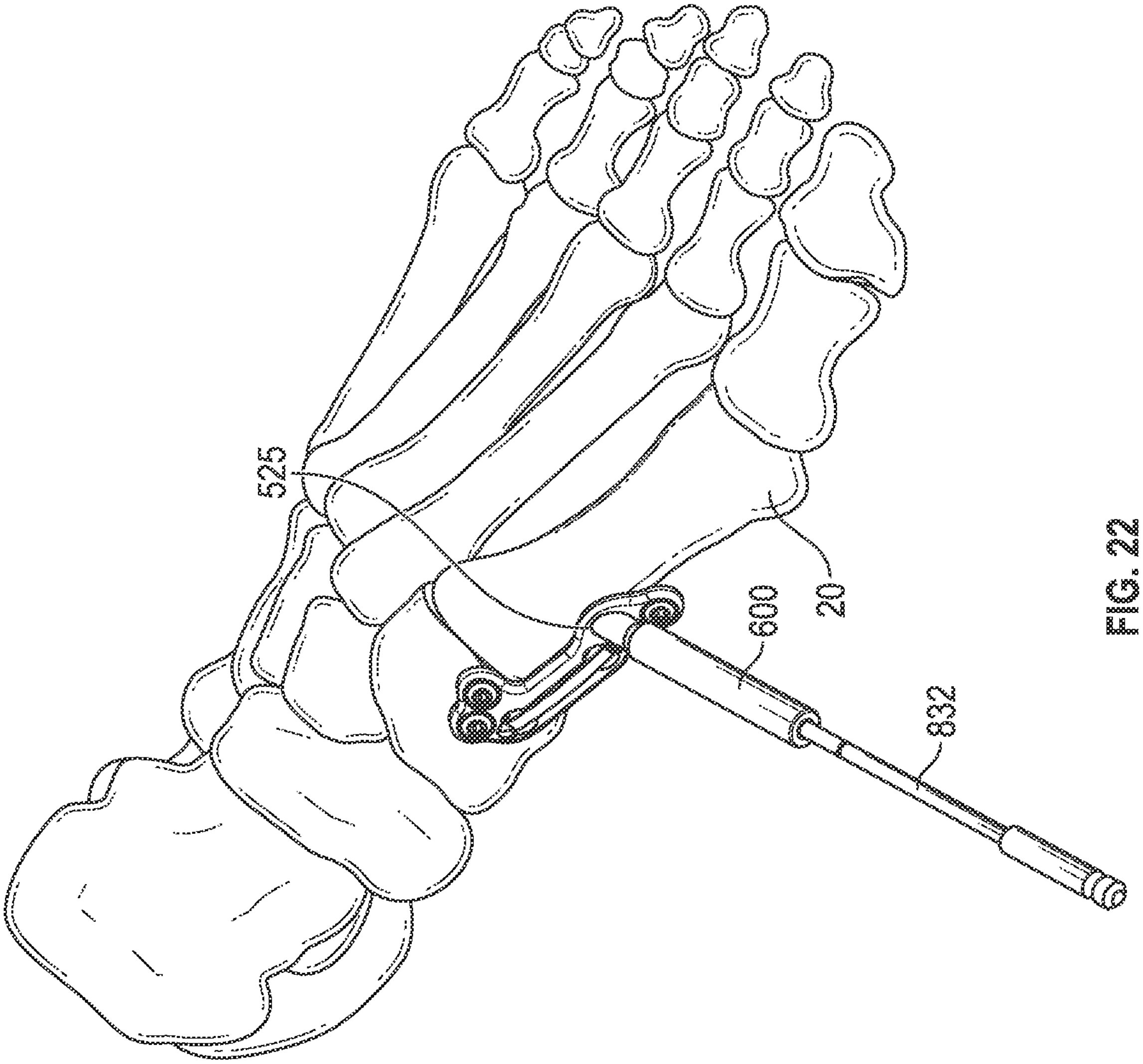
FIG. 22 is a perspective view of the human foot of FIG. 21, showing a cross screw drill guide placed within a cross screw aperture of the bone plate.

Continuing to FIG. 22, a cross screw drill guide is placed within the cross screw aperture 525 of the bone plate 500. Although the fixed-angle cross screw drill guide 600 of FIGS. 7A-7C is shown in FIG. 22, the procedure may equally be implemented using the variable-angle cross screw drill guide 650 of FIGS. 7D-7F. The cross screw drill guide 600 is seated in the cross screw aperture 525 by seating the shelf engagement surface 627 (or the shelf engagement surface 677 if the variable-angle cross screw drill guide 650 is used) against the shelf 527 of the cross screw aperture 525. A drill bit 832 is inserted through the cross screw drill guide 600 and turned to drill a pilot hole for a cross screw within the cross screw aperture 525. The drill bit 832 and the cross screw drill guide 600 are removed, and the cross screw 834 is placed at the cross screw aperture 525, completing the Lapidus bunionectomy procedure.

Figure 23:
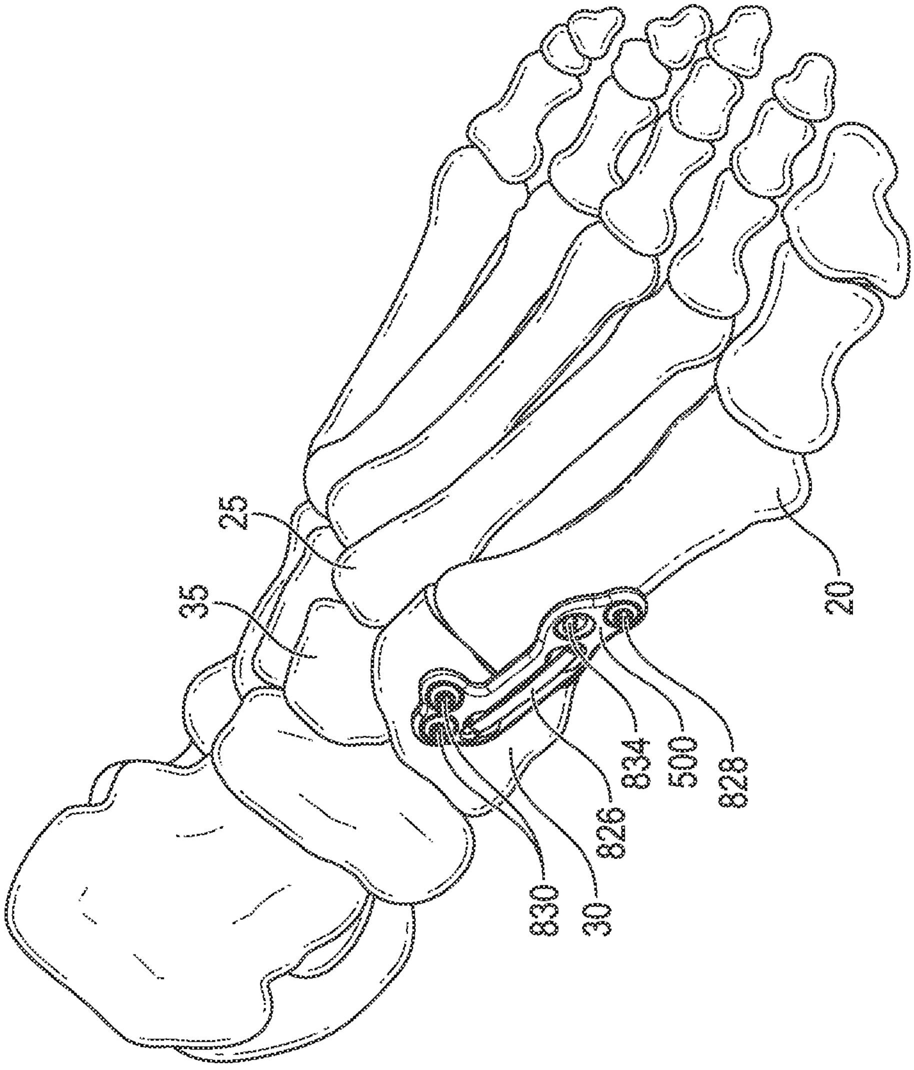
FIG. 23 is a perspective view of the human foot of FIG. 22, showing a completed state of the Lapidus bunionectomy illustrated in FIG. 8-23.
Figure 24:
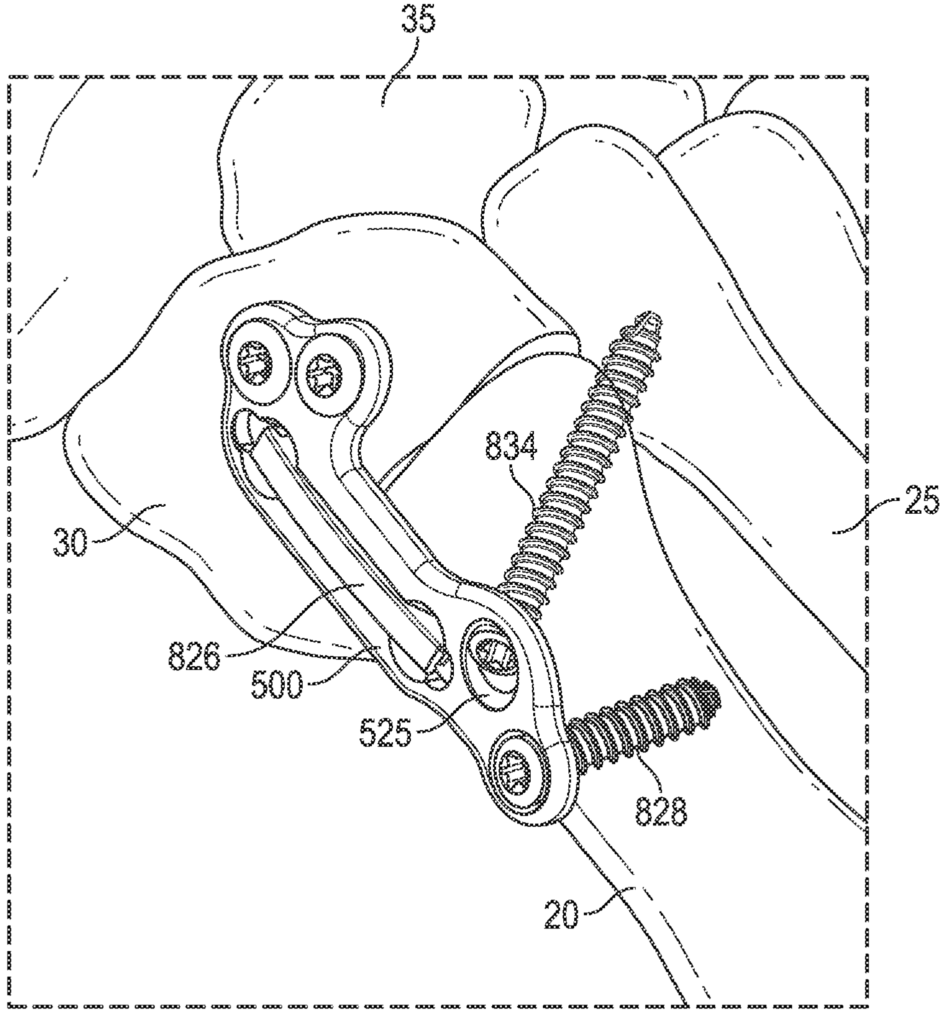
FIG. 24 is a perspective view of the human foot of FIG. 22, showing an enlarged portion of the foot in which the first metatarsal is transparent to illustrate the internal placement of screws.

FIGS. 23 and 24 show the completed state of the Lapidus bunionectomy in accordance with the present technology. FIG. 24 is an enlarged view of a portion of the foot, in which the first metatarsal 20 is shown with transparency to illustrate the internal placement of the cross screw 834. As shown in FIGS. 23 and 24, the first metatarsal 20 is fixed in a desired orientation relative to the first cuneiform 30, with a reduced intermetatarsal angle relative to the second metatarsal 25, by the bone plate 500, the staple 826, the metatarsal screw 828, and the cuneiform screws 830.

Advantageously, the cross screw 834 further functions to prevent future recurrence of the bunion. As the foot may still experience daily pressure that could cause the bunion to return, the cross screw 834 anchors the first metatarsal 20 to either the second metatarsal 25 or the second cuneiform 35, depending on the geometry of the foot and the angle of insertion of the cross screw 834. Thus, the Lapidus bunionectomy of FIGS. 8-24 advantageously goes beyond merely repairing the bunion by providing an additional structural connection to more laterally disposed bones of the midfoot to prevent recurrence.

With reference to FIGS. 25-29, a portion of an alternative Lapidus bunionectomy using certain devices herein will be described. The portion of the Lapidus bunionectomy illustrated in FIGS. 25-29 provides an alternative method of performing the first metatarsal and first cuneiform cuts using the single-slotted cut guide 180 illustrated in FIGS. 2H-2K. Thus, as will be described in greater detail below, the portion of the Lapidus bunionectomy illustrated in FIGS. 25-29 may be used in conjunction with portions of the Lapidus bunionectomy illustrated in FIGS. 8-24 and/or with other bunionectomy procedures. Although the procedure of FIGS. 25-29 illustrates a particular implementation of a Lapidus bunionectomy using a specific subset of the devices disclosed herein, it will be understood that the components and steps illustrated and described with reference to FIGS. 25-29 may equally be applied in different sequences and/or with different combinations of components to correct a bunion.

Figure 25:
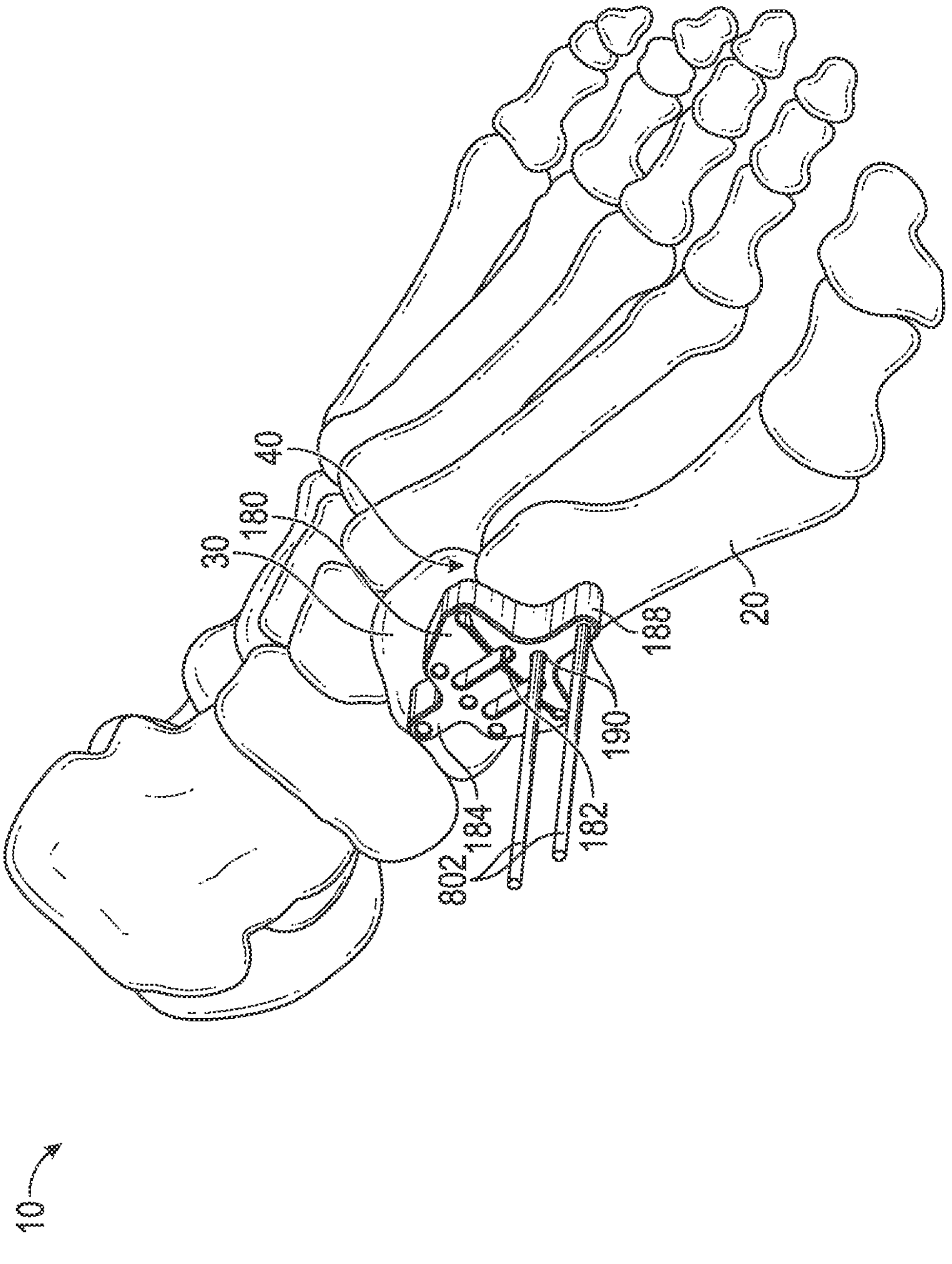
FIG. 25 is a perspective view of the bones of a human foot, showing a step of an example Lapidus bunionectomy procedure performed using the example bunionectomy devices disclosed herein, showing the cut guide of FIG. 2H secured to the foot using metatarsal pins.

As shown in FIG. 25, the procedure may begin by placing and temporarily securing the cut guide 180 of FIGS. 2H-2K to the foot 10. Similar to the beginning configuration of FIG. 8, the first TMT joint 40 may have been prepared by making an incision such as a dorsomedial incision to expose the first TMT joint 40 and excising soft tissue around the joint, such as the joint capsule or other soft tissue, to expose the first TMT joint 40 and create a space in which the paddle 120 (FIGS. 2H-2K) of the cut guide 180 can be seated.

Once the joint has been prepared, the cut guide 180 is placed by seating the paddle 120 (not visible in FIG. 25) within the first TMT joint 40 such that the first extension 184 sits adjacent to or against the first cuneiform 30 and the second extension 188 sits adjacent to or against the first metatarsal 20. The paddle 120 is inserted into the first TMT joint 40 such that the cut guide 180 is oriented along the axis of the first metatarsal 20 with the slot 182 positioned over the first metatarsal 20. Alternatively, in some embodiments, the cut guide 180 may be oriented with the slot 182 positioned over the first cuneiform 30, and the bunionectomy may be performed such that the first cuneiform 30 is cut before the first metatarsal 20. The alignment of the cut guide 180 may be confirmed under fluoroscopy or other suitable imaging technique before proceeding.

When the cut guide 180 has been placed and is suitably aligned, the cut guide 180 is temporarily secured relative to the first metatarsal 20 by inserting one or more metatarsal pins 802 or wires through the second pin holes 190 of the second extension 188 and into or through the first metatarsal 20. The metatarsal pins 802 or wires, as well as any of the other pins or wires described in the following description, may be, for example, a Kirschner wire ("K-wire"), or any other suitable type of wire or pin that can be placed into the bone to secure the cut guide 180. Although two metatarsal pins 802 or wires are illustrated in this example, the cut guide 180 may be suitably robust and stable when held in place by the paddle 120 and a single metatarsal pin 802 or wire.

Figure 26:
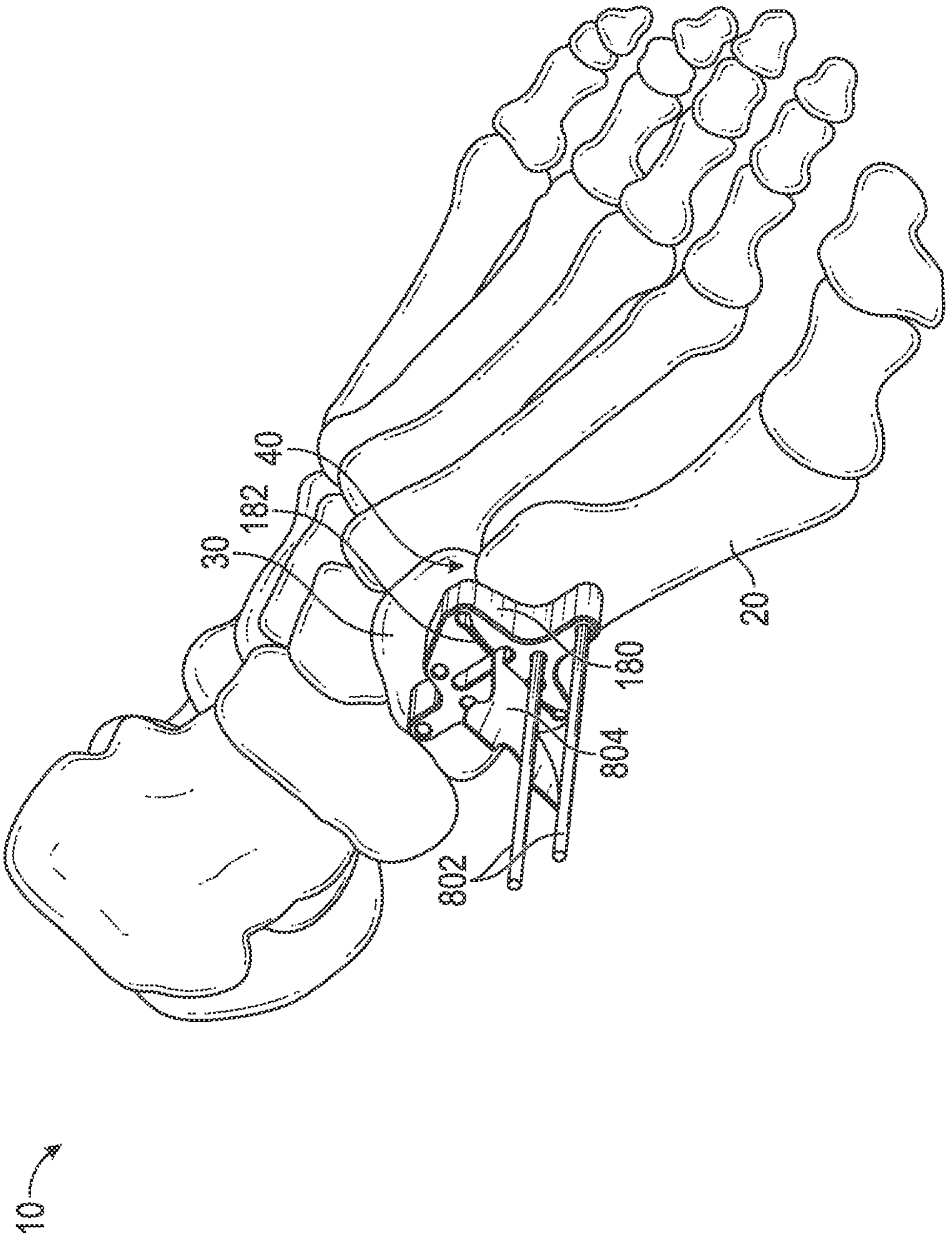
FIG. 26 is a perspective view of the foot of FIG. 25, showing a saw blade inserted through a slot of the cut guide to cut the base of the first metatarsal.

Continuing to FIG. 26, once the metatarsal pins 802 or wires are inserted, the base of the first metatarsal 20 is cut using a saw blade 804 inserted through the slot 182 of the cut guide 180.

Figure 27:
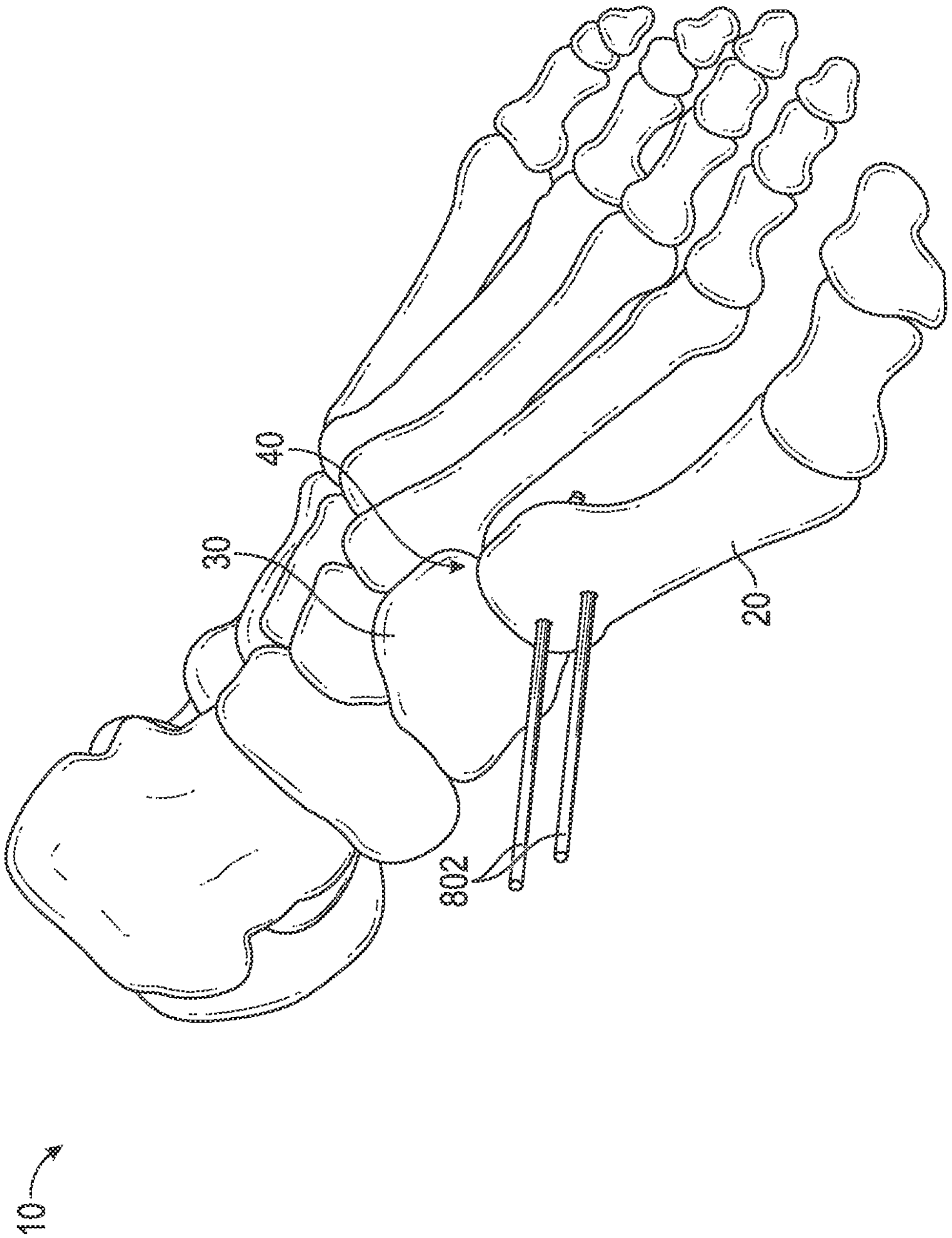
FIG. 27 is a perspective view of the foot of FIG. 26, showing the saw blade and the cut guide removed.
Figure 28:
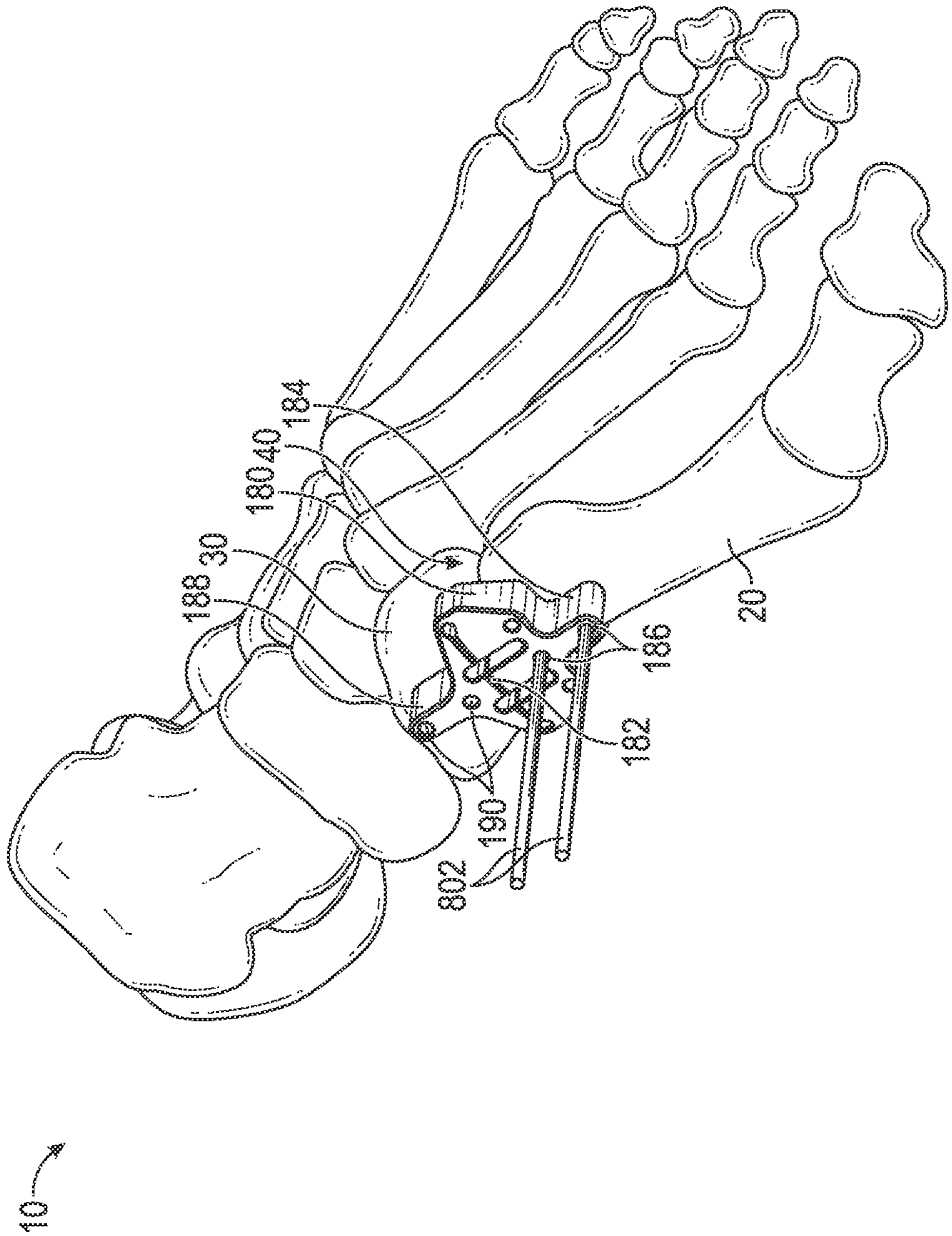
FIG. 28 is a perspective view of the foot of FIG. 27, showing the cut guide secured to the foot in a different position such that the same slot is aligned to cut the first cuneiform.

With reference to FIGS. 27 and 28, after the base of the first metatarsal 20 is cut, the cut guide 180 can be reoriented such that the same slot 182 can be used to guide the cutting of the first cuneiform 30 which occurs later in the Lapidus bunionectomy procedure. The cut guide 180 can be removed by sliding the cut guide 180 upward until the second pin holes 190 are free of the metatarsal pins 802 or wires, as shown in FIG. 27. At this stage, the resected portion of the bone from the first metatarsal 20 (or from the first cuneiform 30 if the first cuneiform 30 was cut first) can be removed from the foot 10. The cut guide 180 can then be reversed (e.g., rotated 180 degrees about an axis parallel to the metatarsal pines 802 or wires). The metatarsal pins 802 or wires may then be inserted through the first pin holes 186, and the cut guide 180 may be moved downward along the metatarsal pins 802 or wires until the paddle 120 is again seated within the first TMT joint 40, as shown in FIG. 28. In some embodiments, the first pin holes 186 and second pin holes 190 have a different spacing about the center of the paddle 120. For example, the first pin holes 186 may be closer to the paddle 120 by a distance equal to the thickness of the bone removed by the first cut, such that reversing the cut guide 180 results in the paddle 120 resting firmly against the cut surface of the first metatarsal 20.

In the configuration of FIG. 28, due to the reversal of the cut guide 180, the second holes 190 are disposed above the first cuneiform 30 and the slot 182 is positioned to guide cutting of the first cuneiform 30 rather than the first metatarsal 20. From the state illustrated in FIG. 28, the Lapidus bunionectomy procedure can proceed substantially as shown and described with reference to FIGS. 10-13 for correction of the position of the first metatarsal 20 and phalanges 50 in the frontal and transverse planes. In the same process described with reference to FIG. 13, two cuneiform pins 818 or wires are inserted through the second pin holes 190 of the cut guide 180 and into or through the first cuneiform 30. The cuneiform pins 818 or wires temporarily secure the cut guide 180 relative to the first cuneiform 30. At this point, the four pins 802 and 814 form an array that establishes and/or locks the surgeon's desired correction.

Figure 29:
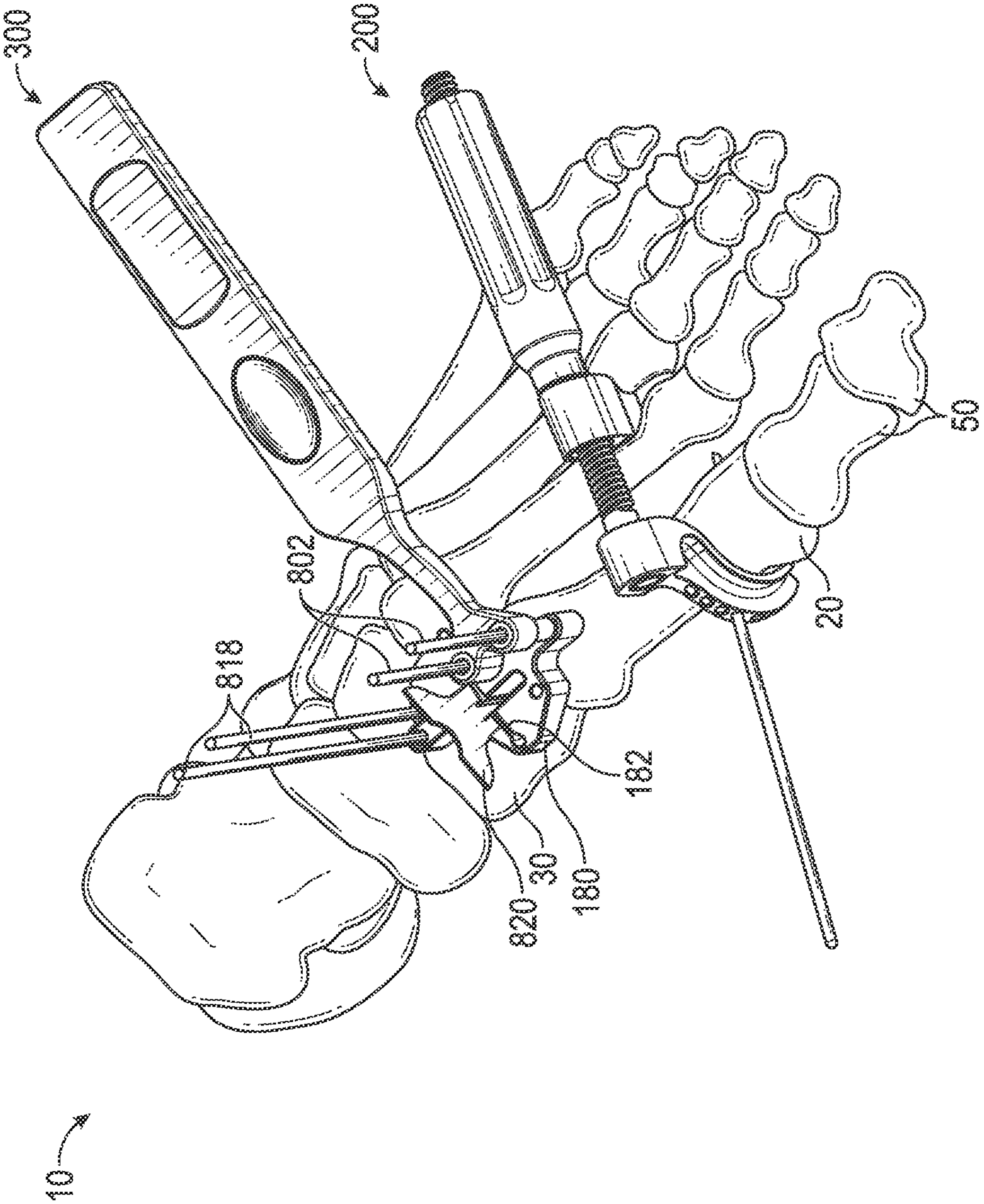
FIG. 29 is a perspective view of the foot of FIG. 28, showing a saw blade inserted through the slot of the cut guide 180 to cut the base of the first cuneiform, and further showing a linear reducer attached to the foot, and a control handle attached to the cut guide.

Referring now to FIG. 29, due to the reversal of the cut guide 180 following cutting of the first metatarsal 20, the slot 182 is now positioned on the cuneiform side of the first TMT joint 40. Thus, following correction of the bunion in at least the frontal and/or transverse planes and the placing of the cuneiform pins 818 or wires, the slot 182 is positioned to guide the cutting of the first cuneiform 30. It is appreciated that, prior to driving the cuneiform pins 818 into the cuneiform 30, the windlass mechanism of the foot can be engaged by dorsiflexing the hallux, which thereby compresses the paddle 120 (see FIG. 2A) against the cuneiform 30. Compression of the paddle 120 against the cuneiform 30 can ensure that the slot 182 is aligned with a portion of the cuneiform 30 at a position that ensures that an adequate section is cut from the cuneiform 30.

Once the cuneiform pins 818 or wires are inserted, the base of the first cuneiform 30 is cut using a saw blade 820 inserted through the slot 182 of the cut guide 180. Cutting the base of the first cuneiform 30 completes the excision of the first TMT joint 40. The cut guide 180, the linear reducer 200, and the control handle 300 may then be removed from the foot 10 by the same or similar operations to those described above with reference to FIG. 15. After removal of the cut guide 180, linear reducer 200, and control handle 300, the fully disarticulated first TMT joint 40 is left with the metatarsal pins 802 or wires and cuneiform pins 818 or wires remaining in place. At this point, the surgeon may further use any desired means to distract and further prepare the joint in preparation for fusion. The remainder of the Lapidus bunionectomy procedure may then proceed substantially as shown and described with reference to FIGS. 16-24.

With reference to FIGS. 30A-32C, various additional devices and components are provided for use with an improved Lapidus bunionectomy procedure for correcting the TMT joint deformity of FIG. 1. The devices and components of FIGS. 30A-32C may be used to perform additional optional steps in the Lapidus bunionectomy procedures described herein, such as additional removal of bone and/or additional rotational correction of the frontal plane prior to fixation. Although the following description is made with reference to the Lapidus bunionectomy procedure, it will be understood that the various devices and components described herein are not limited to such procedures and may equally be used in other orthopedic procedures as will be understood by those skilled in the art.

Figure 30A:
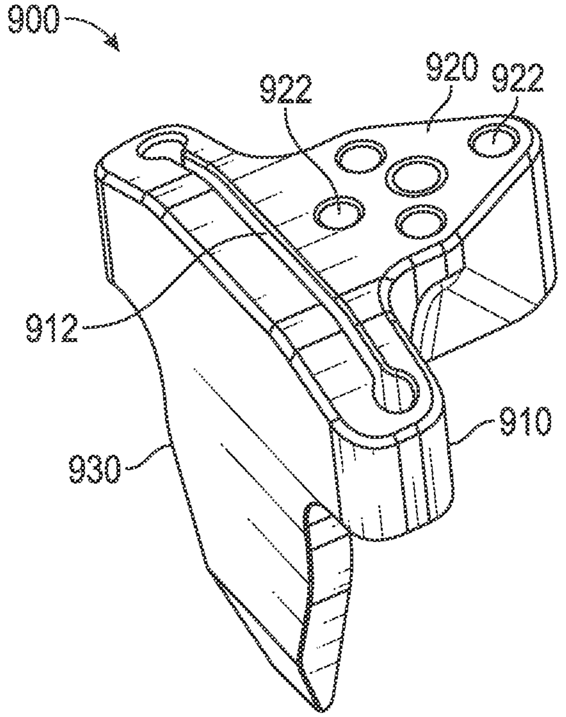
FIG. 30A is a perspective view of an example cut guide configured as a re-cutting guide and a pin guide for the Lapidus bunionectomy procedures described herein.
Figure 30B:
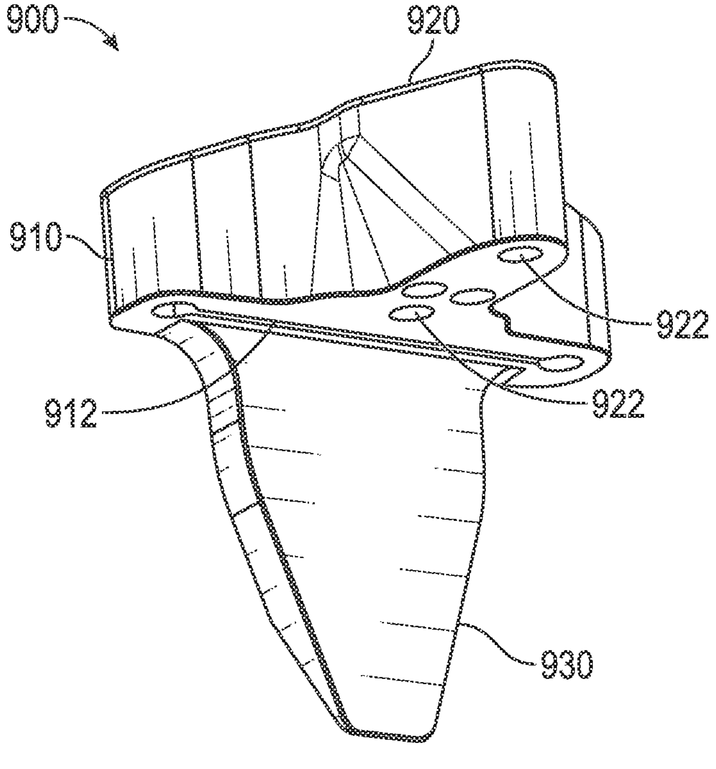
FIG. 30B is another perspective view of the re-cutting guide and a pin guide of FIG. 30A.
Figure 30C:
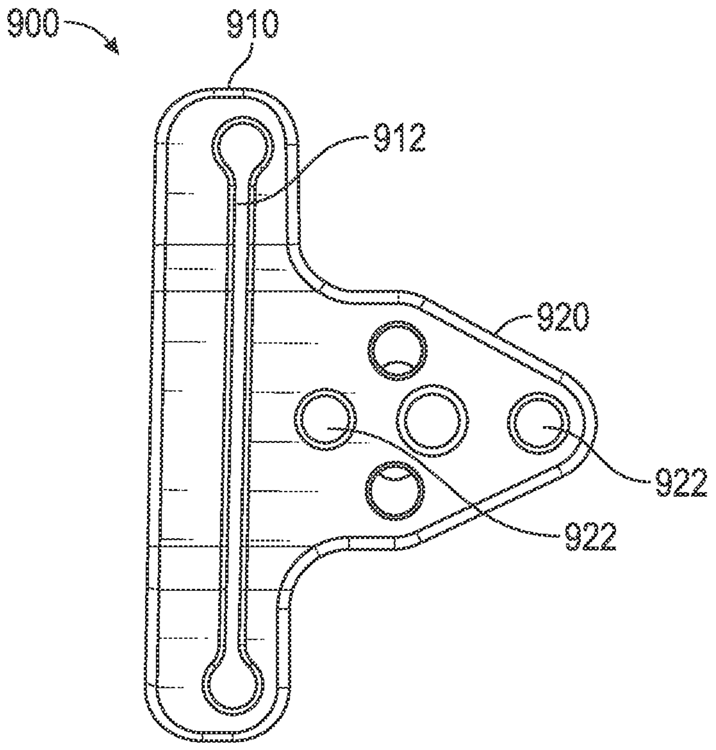
FIG. 30C is a top plan view of the re-cutting guide and a pin guide of FIG. 30A.

FIGS. 30A-30C depict a cut guide 900 configured as a re-cut guide and a pin guide for the Lapidus bunionectomy procedures described herein. In some Lapidus bunionectomy procedures, a surgeon may desire to remove additional bone from the first metatarsal and/or from the first cuneiform at the first TMT joint during the procedure. For example, the edges of the first metatarsal and/or first cuneiform forming the TMT joint may have varying levels of concavity in different individuals, such that some first metatarsals and/or first cuneiforms may need to have more bone cut away in order to reach a plane at which interior bone is exposed over the full cross-section of the cut area.

FIGS. 30A and 30B are upper and lower perspective views of the cut guide 900, respectively. FIG. 30C is a top plan view of the cut guide 900. The cut guide 900 may be a single integrally formed component and may comprise a metal, a plastic, or other suitable material. The cut guide 900 may be sized and shaped to be used in conjunction with (e.g., after) another cut guide such as the cut guide 181 of FIGS. 2L-2N.

The cut guide 900 generally comprises a body 910, an extension 920, and a paddle 930. The extension 920 can have a size and shape similar or identical to the second extension 188 of the cut guide 181 and can include pin holes 922 having a spacing corresponding to the spacing of second pin holes 190 of the cut guide 181. The body 910 includes a slot 912. The paddle 930 is sized and shaped to seat within a joint such as a TMT joint, for example.

To accomplish the desired re-cut functionality, the spacing between the slot 912 and the pin holes 922 of the cut guide 900 is closer than the corresponding spacing in an associated cut guide used for the initial joint cutting. For example, in a kit including a cut guide 900 and a cut guide 181 (FIGS. 2L-2N), the distance between the slot 912 and the nearer of the pin holes 922 is shorter than the distance between the slot 182 and the nearer of the second pin holes 190 of the cut guide 180. Accordingly, after cut is made using the cut guide 181 held in place by pins extending through the second pin holes 190, the cut guide 181 can be removed and the cut guide 900 can be placed over the same pins through pin holes 922 such that the slot 912 defines a cutting plane closer to the pins for re-cutting. Use of the cut guide 900 as a re-cut guide will be described in greater detail with reference to FIGS. 33-35.

Figure 31A:
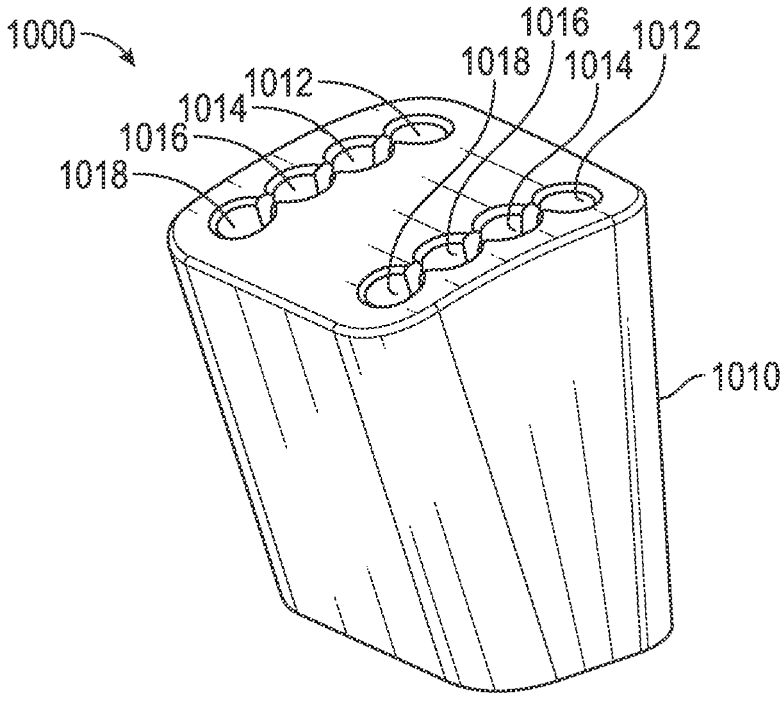
FIG. 31A is a perspective view of an example realignment guide configured as a pin guide for frontal plane adjustment in the Lapidus bunionectomy procedures described herein.
Figure 31B:
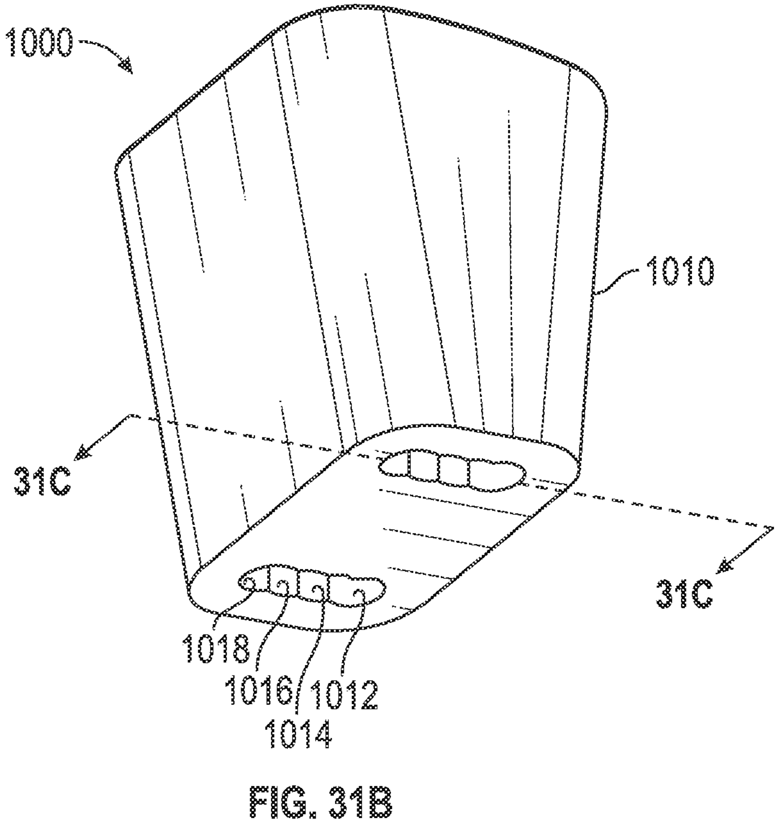
FIG. 31B is another perspective view of the realignment guide of FIG. 31A.
Figure 31C:
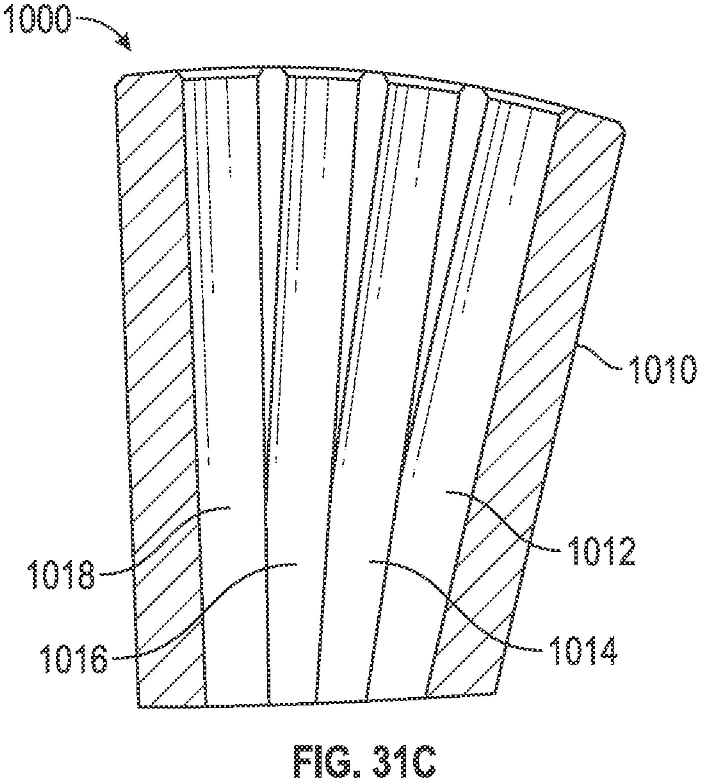
FIG. 31C is a sectional elevation view of the realignment guide of FIG. 31B taken along line 31C-31C.

FIGS. 31A-31C depict an example realignment guide 1000 configured as a pin guide for frontal plane adjustment in the Lapidus bunionectomy procedures described herein. FIGS. 31A and 31B are upper and lower perspective views of the realignment guide 1000, respectively. FIG. 31C is a cross-sectional side elevation view of the realignment guide 100 taken about the line 31C-31C in FIG. 31B. The realignment guide 1000 includes a body 1010 having two or more pairs of pin holes therethrough. The body 1010 is generally wedge-shaped and may be integrally formed from a metal, a plastic, or other suitable material.

In the example realignment guide 1000 of FIGS. 31A-31C, the body 1010 includes four pairs of pin holes 1012, 1014, 1016, and 1018. Each pair of pin holes 1012, 1014, 1016, 1018 may be parallel, and the pairs are oriented in a converging configuration. Each pair of pin holes 1012, 1014, 1016, 1018 may be spaced apart by a distance corresponding to the pin hole spacing of an associated cut guide (e.g., cut guide 180, 181, 900, etc.). The pin holes 1012, 1014, 1016, 1018 may thus be used to implement further frontal plane correction by being placed over an existing pair of pins and serving as a guide for placement of a second pair of similarly spaced, parallel pins at a predetermined angular offset about a metatarsal bone relative to the existing pair. the use of the realignment guide 100 will be described in greater detail with reference to FIGS. 39-48.

Figure 32A:
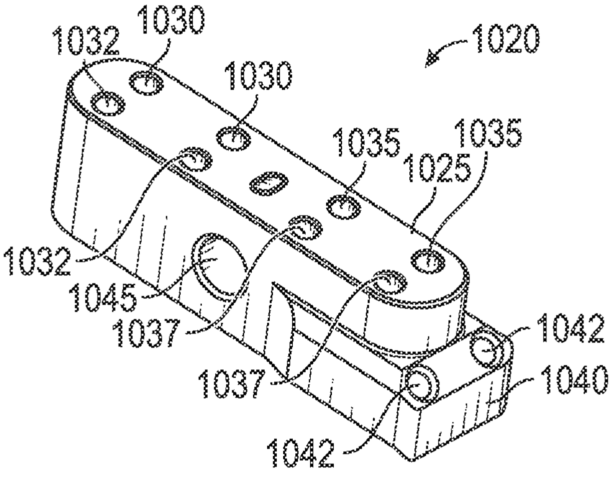
FIG. 32A is a perspective view of an example realignment guide configured as a pin guide for frontal plane adjustment in the Lapidus bunionectomy procedures described herein.
Figure 32B:
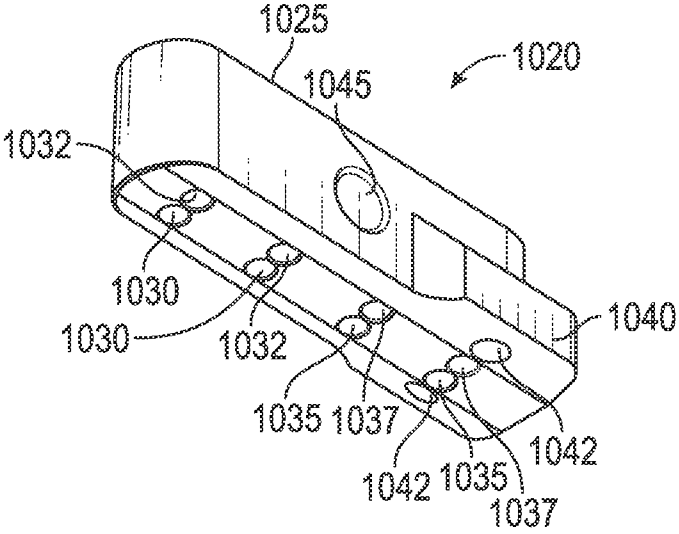
FIG. 32B is another perspective view of the realignment guide of FIG. 32A.
Figure 32C:
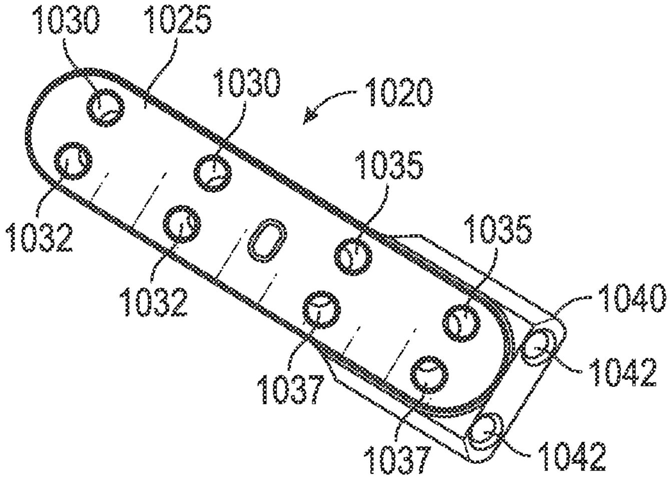
FIG. 32C is a top plan view of the realignment guide of FIG. 32A.

FIGS. 32A-32C depict an example realignment guide 1020 configured as a pin guide and a compression block for frontal plane adjustment in the Lapidus bunionectomy procedures described herein. FIGS. 32A and 32B are upper and lower perspective views of the realignment guide 1020, respectively. FIG. 32C is a top plan view of the realignment guide 1020. The realignment guide 1020 may be integrally formed form a metal, a plastic, or other suitable material. The realignment guide 1020 may have a shape generally similar to the compressor block 400 and can function as both a realignment guide and a compressor block in operation.

The realignment guide 1020 includes a body 1025 having two pairs of proximal pin holes 1030, 1032 and two pairs of distal pin holes 1035, 1037. Similar to the proximal pin holes 410 and the distal pin holes 415 of the compressor block 400, the proximal pin holes 1030, 1032 and distal pin holes 1035, 1037 are convergent toward the middle of the realignment guide 1020. A widened section 1040 can include cross pin holes 1042 for additional stabilization and/or for temporary fixation while permanent fixation devices are placed. As will be described in greater detail with reference to FIGS. 36-38, the realignment guide 1020 may be used to implement additional frontal plane correction of the first metatarsal without requiring the insertion of additional pins into the bone.

Figure 33:
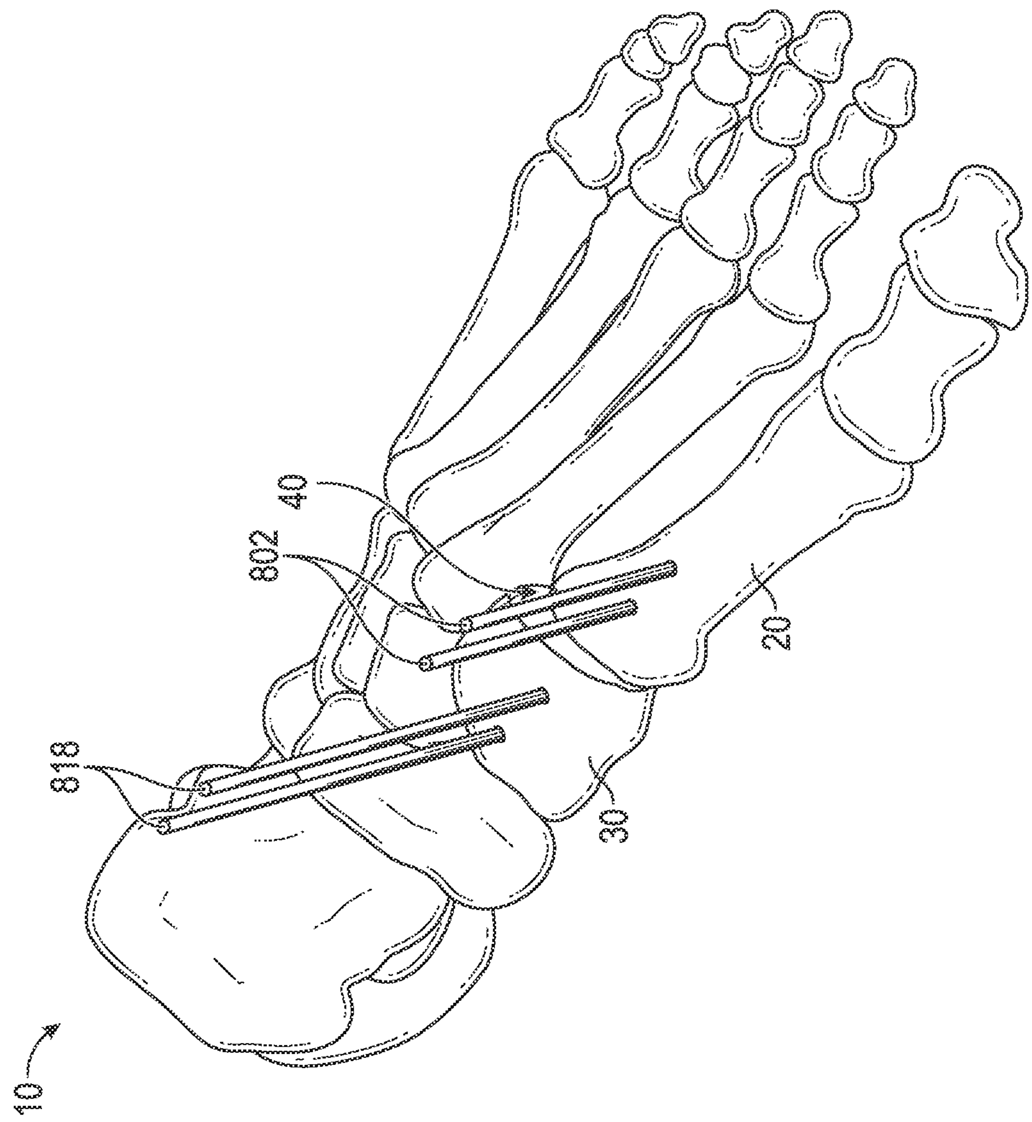
FIG. 33 is a perspective view of the bones of a human foot in a configuration similar to that of FIG. 15, showing a step of a re-cutting portion of an example Lapidus bunionectomy procedure performed using the example bunionectomy devices disclosed herein, whereby metatarsal pins and/or cuneiform pins remain in the foot.
Figure 34:
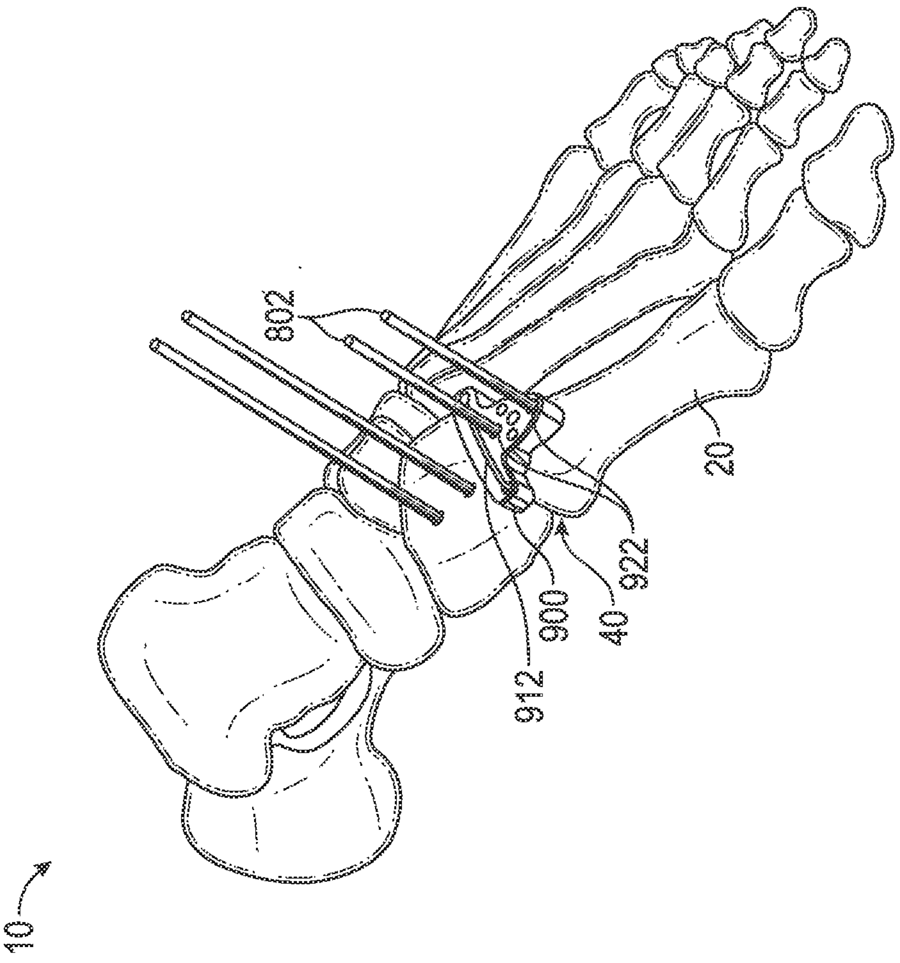
FIG. 34 is a perspective view of the human foot of FIG. 33, showing the cut guide of FIG. 30A placed over the metatarsal pins.
Figure 35:
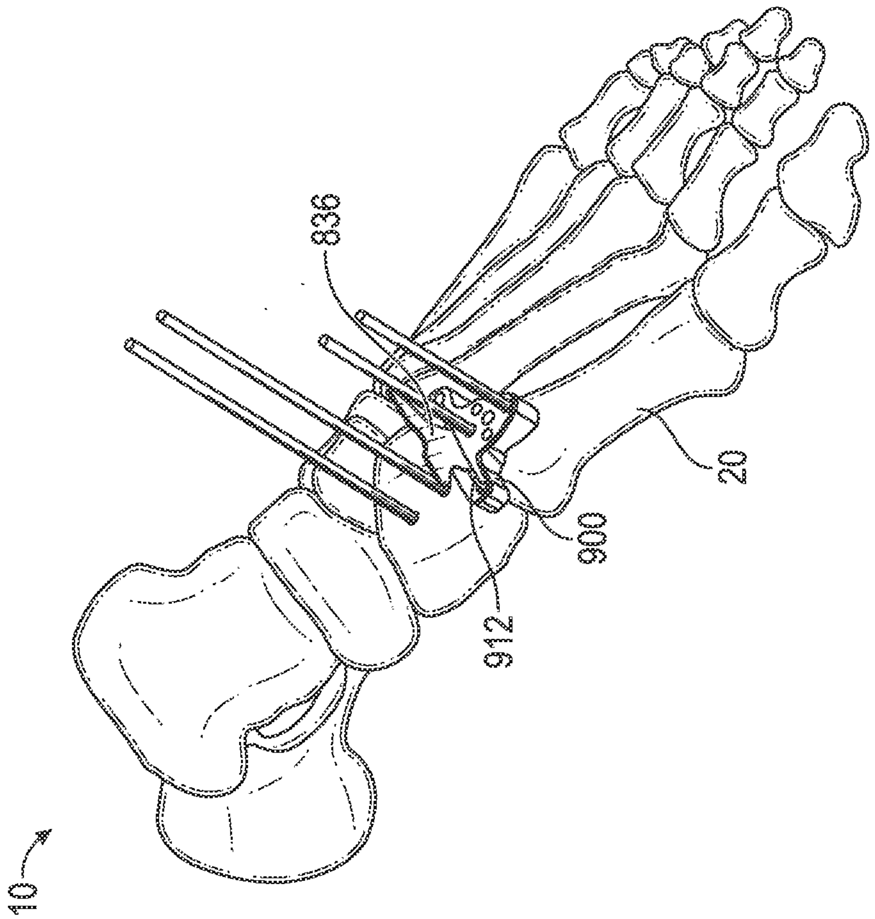
FIG. 35 is a perspective view of the human foot of FIG. 34, showing a saw blade 836 inserted through a slot of the cut guide.

FIGS. 33-35 are perspective views of the bones of a foot 10, sequentially illustrating a re-cutting portion of an example Lapidus bunionectomy procedure performed using the example bunionectomy devices disclosed herein. The re-cutting portion of the Lapidus bunionectomy illustrated in FIGS. 33-35 may be performed at any time after an initial cut has been made to the first metatarsal 20 and/or to the first cuneiform 30, where further removal of bone is desired. For example, in some procedures, a surgeon may examine the cut end of a first metatarsal 20 and/or first cuneiform 30 and determine that further bone should be removed due to concavity of the bone or a desired spacing. Thus, as will be described in greater detail below, the portion of the Lapidus bunionectomy illustrated in FIGS. 33-35 may be used in conjunction with any of the other Lapidus bunionectomy procedures described herein.

As shown in FIG. 33, the re-cutting portion may begin with the foot 10 in a configuration similar to that of FIG. 15. In the configuration of FIG. 33, a cut guide (e.g., cut guide 100, cut guide 180, cut guide 181, etc. as disclosed elsewhere herein) may have been used to remove a portion of the first metatarsal 20 and/or the first cuneiform 30. Metatarsal pins 802 and/or cuneiform pins 818 may remain in the foot 10 following removal of the cut guide that was used to make the initial cuts to the first metatarsal 20 and/or first cuneiform 30. In the example re-cutting portion illustrated in FIGS. 33-35, it is desired to remove an additional portion of the first metatarsal 20 facing the first TMT joint 40.

Continuing to FIG. 34, the cut guide 900, configured as a re-cut guide, is placed by inserting the metatarsal pins 802 through the pin holes 922 of the cut guide 900 and sliding the cut guide 900 onto the metatarsal pins 802 until the cut guide 900 is seated against the previously cut face of the first metatarsal 20. In this configuration of FIG. 34, the slot 912 of the cut guide 900 is aligned closer to the metatarsal pins 802 than the TMT joint-facing end of the first metatarsal 20 due to the closer spacing of the cut guide 900 relative to that of the cut guides 100, 180, 181. Once the cut guide 900 is placed, the base of the first metatarsal 20 can be re-cut using a saw blade 836 inserted through the slot 912 of the cut guide 900. The remainder of the Lapidus bunionectomy procedure may the proceed substantially as shown and described with reference to FIGS. 16-24 or as described elsewhere herein. It will be understood that the re-cutting described above may be applied equally to the first metatarsal 20 or to the first cuneiform 30. If re-cutting is desired, another RAC block can be used in the manner described above that is configured to provide additional compression.

Figure 36:
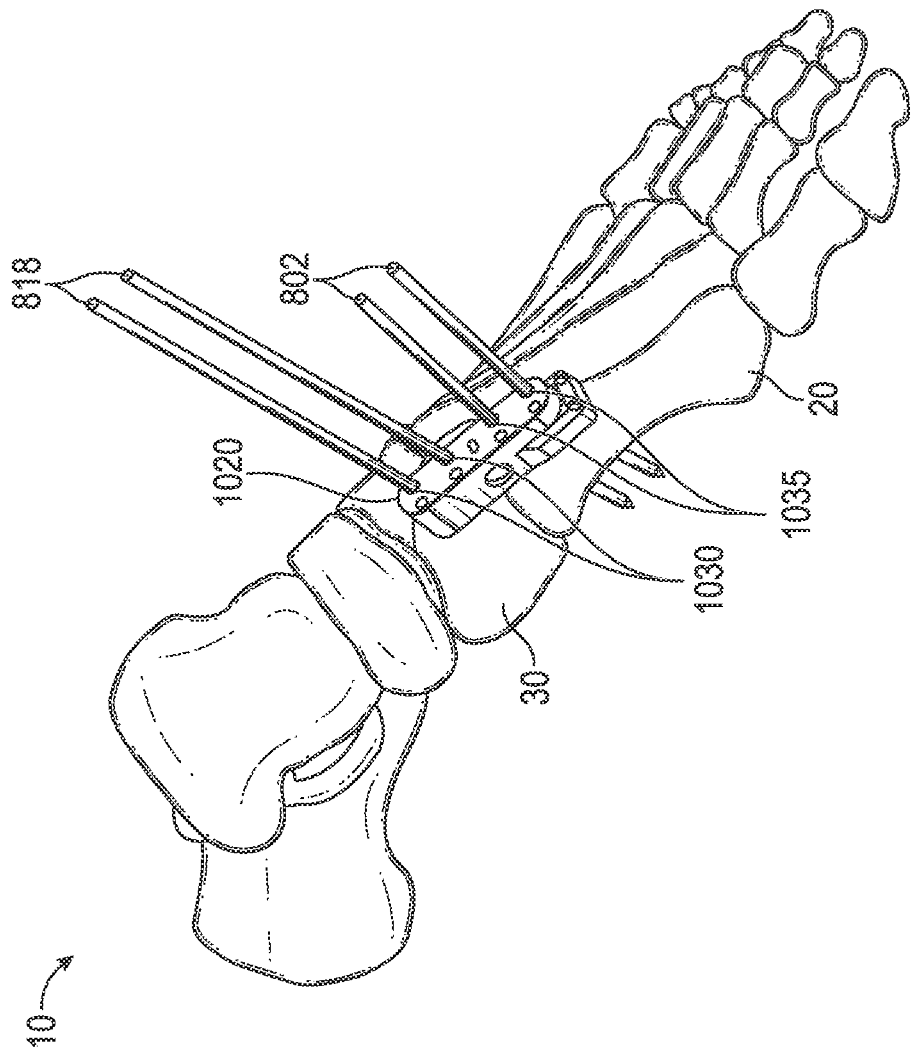
FIG. 36 is a perspective view of the bones of a human foot, showing a step of a frontal plane realignment portion of an example Lapidus bunionectomy procedure using the example bunionectomy devices disclosed herein, whereby the foot is in a configuration as illustrated in FIG. 15 or 33, and the realignment guide of FIG. 32A is installed.
Figure 37:
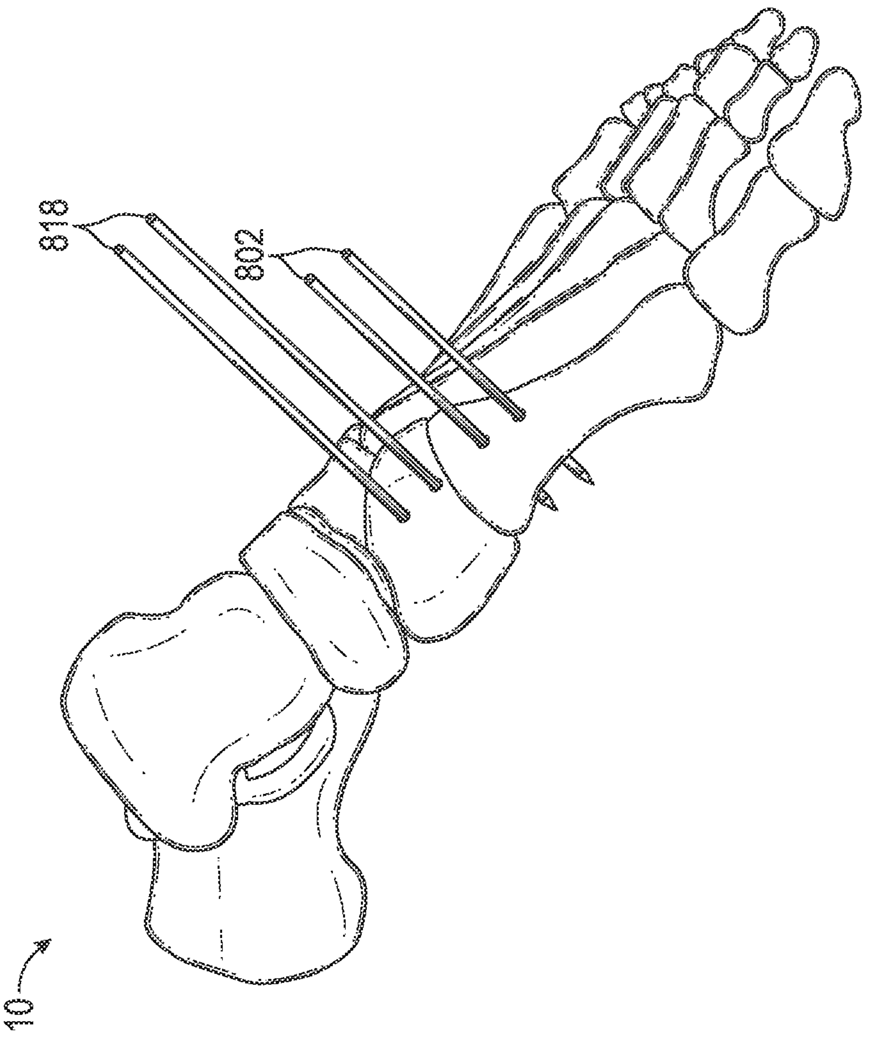
FIG. 37 is a perspective view the human foot of FIG. 36, whereby the realignment guide has been removed.
Figure 38:
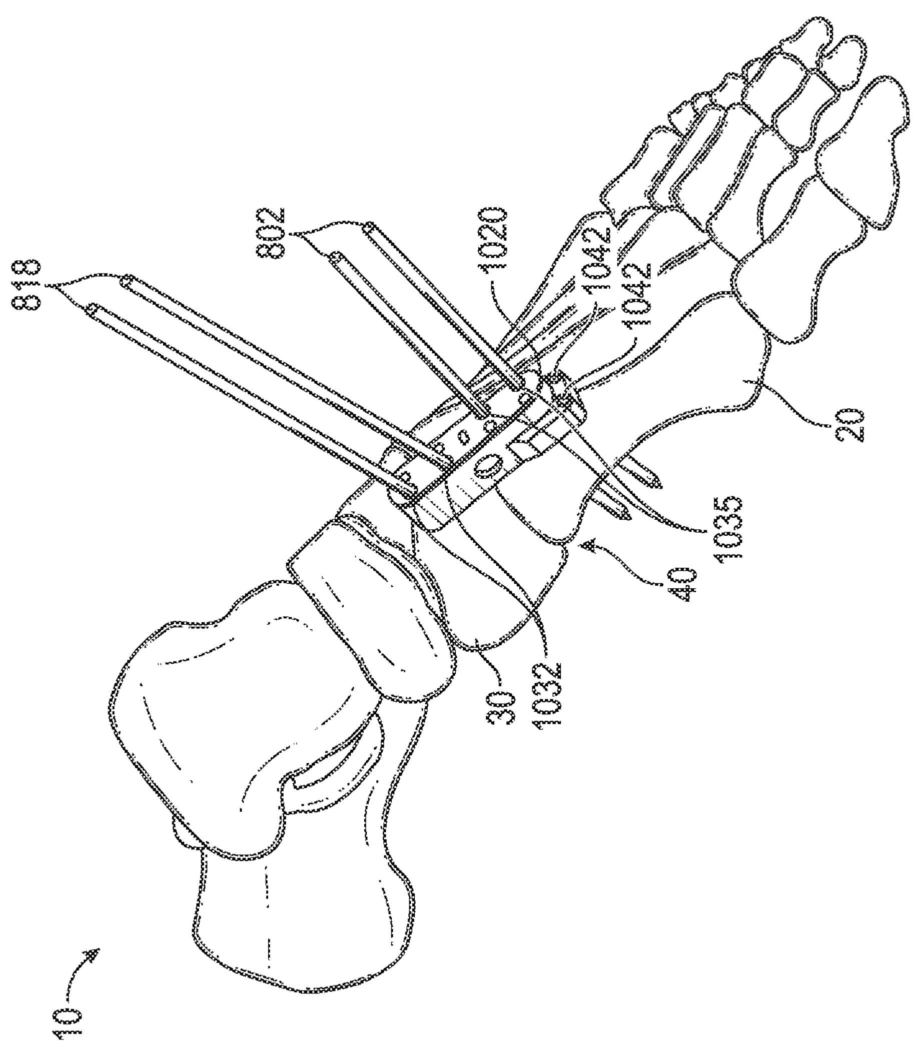
FIG. 38 is a perspective view the human foot of FIG. 37, whereby the realignment guide has been replaced over the metatarsal pins and the cuneiform pins that are inserted through a second pair of proximal pin holes of the realignment guide.
Figure 39:
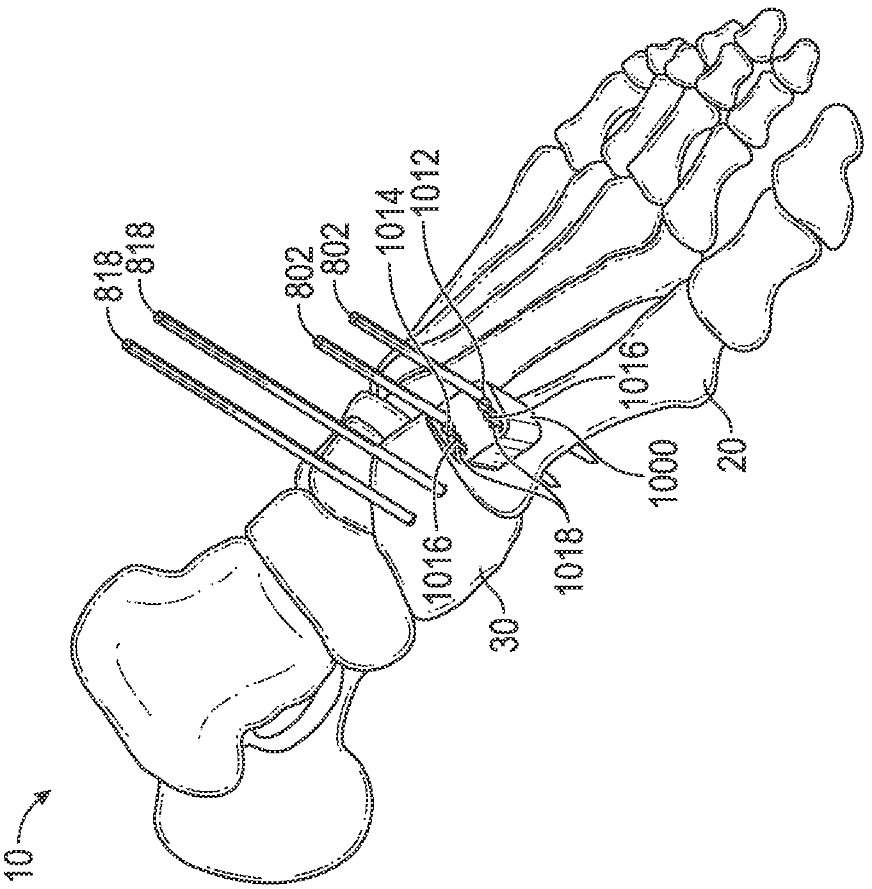
FIG. 39 is a perspective view of the bones of a human foot, showing a step of a frontal plane realignment portion of an example Lapidus bunionectomy procedure using the example bunionectomy devices disclosed herein, whereby the realignment guide of FIG. 31A is installed over the metatarsal pins.

FIGS. 36-38 are perspective views of the bones of a foot 10, sequentially illustrating a frontal plane realignment portion of an example Lapidus bunionectomy procedure using the realignment guide 1020 illustrated in FIGS. 32A-32C. The frontal plane realignment portion of the Lapidus bunionectomy illustrated in FIGS. 36-38 may be performed at any time after the first metatarsal 20 and the first cuneiform 30 have been cut, and prior to fixation, as described elsewhere herein. As the realignment guide 1020 is configured as both a pin guide and a compression block for frontal plane realignment, the realignment portion illustrated in FIGS. 36-38 may be performed instead of or in addition to (e.g., before or after) the compression portion of the Lapidus bunionectomy as illustrated in FIGS. 16-18. For example, in some procedures, a surgeon may perform an initial frontal plane correction and may subsequently determine, such as when initially fitting the compression block as shown in FIG. 16, that further correction or realignment of the first metatarsal 20 in the frontal plane is needed.

The frontal plane realignment begins with the foot 100 in a configuration as illustrated in FIG. 15 or 33 described above, in which metatarsal pins 802 remain in the first metatarsal 20 and cuneiform pins 818 remain in the first cuneiform 30 following cutting of the bones using the cut guides described herein. The realignment portion continues to the configuration shown in FIG. 36, as the realignment guide 1020 is placed by inserting the metatarsal pins 802 through a first pair of distal pin holes 1035 and inserting the cuneiform pins 818 through a first pair of proximal pin holes 1030. When the metatarsal pins 802 and the cuneiform pins 818 are disposed within pairs of holes on the same side of the realignment guide 1020 as shown in FIG. 36, the realignment guide 1020 functions similarly to the compression block 400, compressing the cut ends of the first metatarsal 20 and the first cuneiform 30 without applying any frontal plane realignment. At the stage illustrated in FIG. 36, the surgeon may determine that the initial frontal plane adjustment was insufficient, and that the first metatarsal 20 should be realigned by further clockwise rotation to reach a desired alignment.

As shown in FIGS. 37 and 38, the realignment guide 1020 is removed from the foot 10 (FIG. 37) and replaced over the cuneiform pins 818 and metatarsal pins 802. However, in replacing the realignment guide 1020, the cuneiform pins 818 are inserted through the second pair of proximal pin holes 1032, which are angularly displaced relative to the first pair of proximal pin holes 1030. The metatarsal pins 802 are inserted through the same first pair of distal pin holes 1035 through which they were previously inserted in FIG. 36. Thus, the replacement of the realignment guide 1020 effects a further clockwise rotational adjustment of the first metatarsal 20 and compresses the TMT joint 40 for fixation. Alternatively, a counterclockwise adjustment may be performed by reinserting the cuneiform pins 818 through the same first pair of proximal pin holes 1030 and inserting the metatarsal pins 802 through the second set of distal pin holes 1037. Following realignment as shown in FIGS. 36-38, the Lapidus bunionectomy procedure can proceed to fixation of the bones of the TMT joint 40, for example, as shown and described with reference to FIGS. 17-24. The cross pin 824 for temporary fixation, as shown in FIGS. 18-20, can be inserted through either of the cross pin holes 1042.

FIGS. 39-48 are perspective views of the bones of a foot, sequentially illustrating a frontal plane realignment portion of an example Lapidus bunionectomy procedure using the realignment guide 1000 illustrated in FIGS. 31A-31C. The frontal plane realignment portion of the Lapidus bunionectomy illustrated in FIGS. 39-48 may be performed at various stages of the procedure, for example, prior to placement of the compression block as illustrated in FIG. 16. In some embodiments, the frontal plane realignment portion of the Lapidus bunionectomy illustrated in FIGS. 39-48 may be performed after an initial placement of the compression block 400 indicates that more or less frontal plane correction is needed prior to fixation. As will be described in greater detail, realignment using the realignment guide 1000 differs from realignment using the realignment guide 1020 (e.g., FIGS. 36-38) in that the realignment guide 1000 guides the placement of a second pair of metatarsal pins, rotationally displaced relative to the initial pair of metatarsal pins, which may then be used in combination with the compression block 400 to complete the frontal plane realignment.

The frontal plane realignment begins with the foot 100 in a configuration as illustrated in FIG. 15 or 33 described above, in which metatarsal pins 802 remain in the first metatarsal 20 and cuneiform pins 818 remain in the first cuneiform 30 following cutting of the bones using the cut guides described herein. The realignment portion continues to the configuration shown in FIG. 39, as the realignment guide 1000 is placed by inserting the metatarsal pins 802 through a first pair of pin holes 1012 of the realignment guide 1000. In this configuration, the other three pairs of pin holes 1014, 1016, 1018 define pin placement locations for three increasing amounts of clockwise frontal plane realignment. Alternatively, if counterclockwise frontal plane realignment is desired, the realignment guide 1000 would be placed by inserting the metatarsal pins 802 through the fourth pair of pin holes 1018 such that the other three pairs of pin holes 1012, 1014, 1016 would define pine placement locations for counterclockwise frontal plane realignment.

Figure 40:
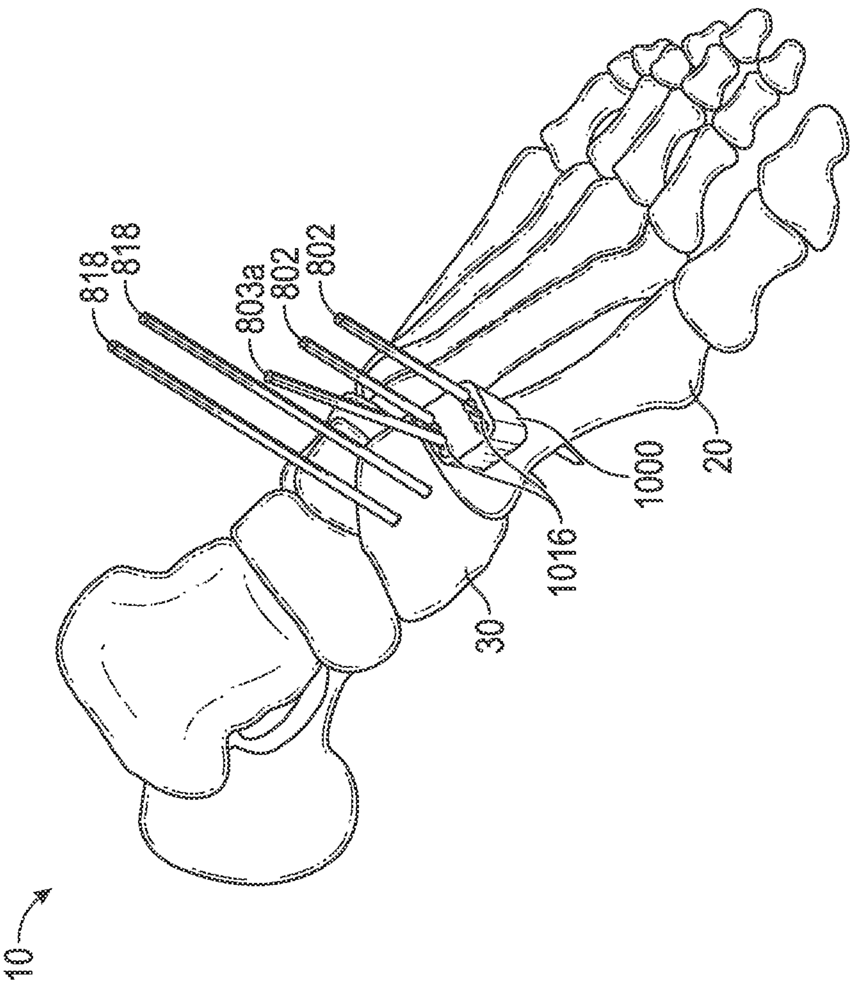
FIG. 40 is a perspective view of the human foot of FIG. 39, whereby a first substitute metatarsal pin is partially inserted into the first metatarsal through one of a pair of pin holes of the realignment guide.

After the realignment guide 1000 is placed, the process continues to FIG. 40 as a first substitute metatarsal pin 803*a* is partially inserted into the first metatarsal 20 through one of the pair of pin holes 1016. Due to the convergence of the paths of the pin holes 1012, 1014, 1016, 1018 within the first metatarsal 20, it may be impossible or undesirable to fully insert substitute metatarsal pin while the metatarsal pins 802 remain inserted. Accordingly, the first substitute metatarsal pin 803*a* may be only partially inserted such that the first substitute metatarsal pin 803*a* does not impinge upon the corresponding metatarsal pin 802. Preferably, the first substitute metatarsal pin 803*a* extends sufficiently into the bone so as to retain the position and orientation of the realignment guide 1000 relative to the first metatarsal 802 if one of the metatarsal pins 802 is removed.

Figure 41:
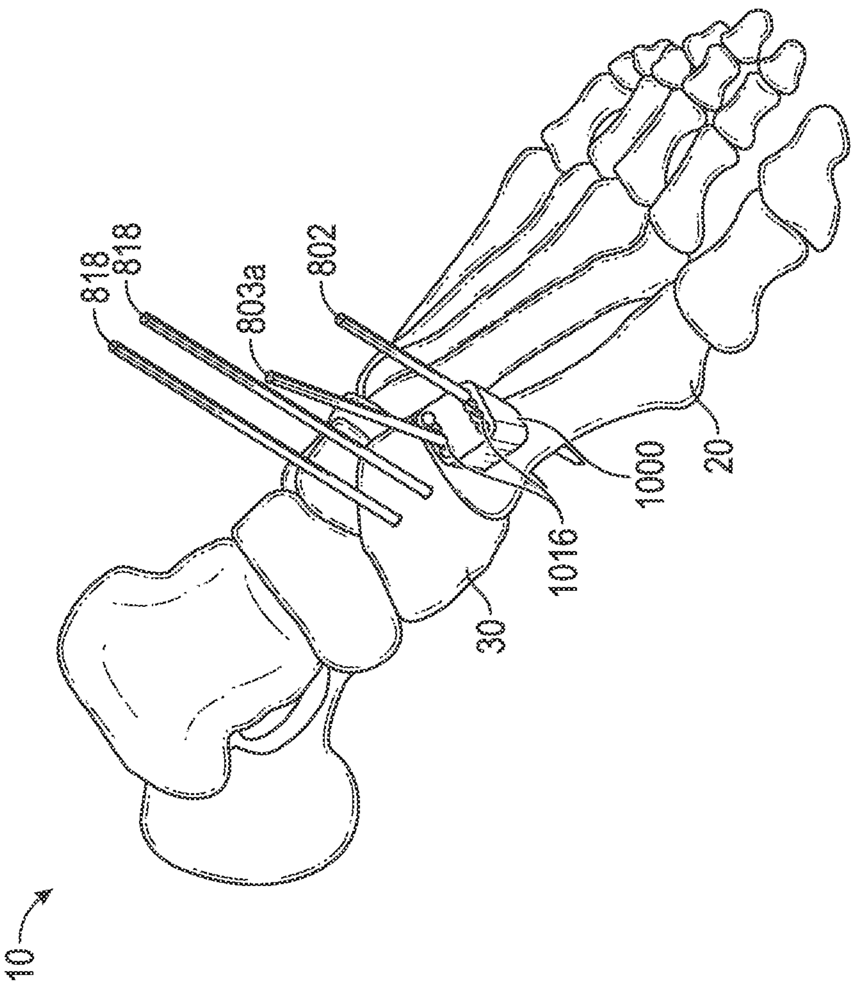
FIG. 41 is a perspective view of the human foot of FIG. 40, whereby a proximal metatarsal pin is removed from the first metatarsal.
Figure 42:
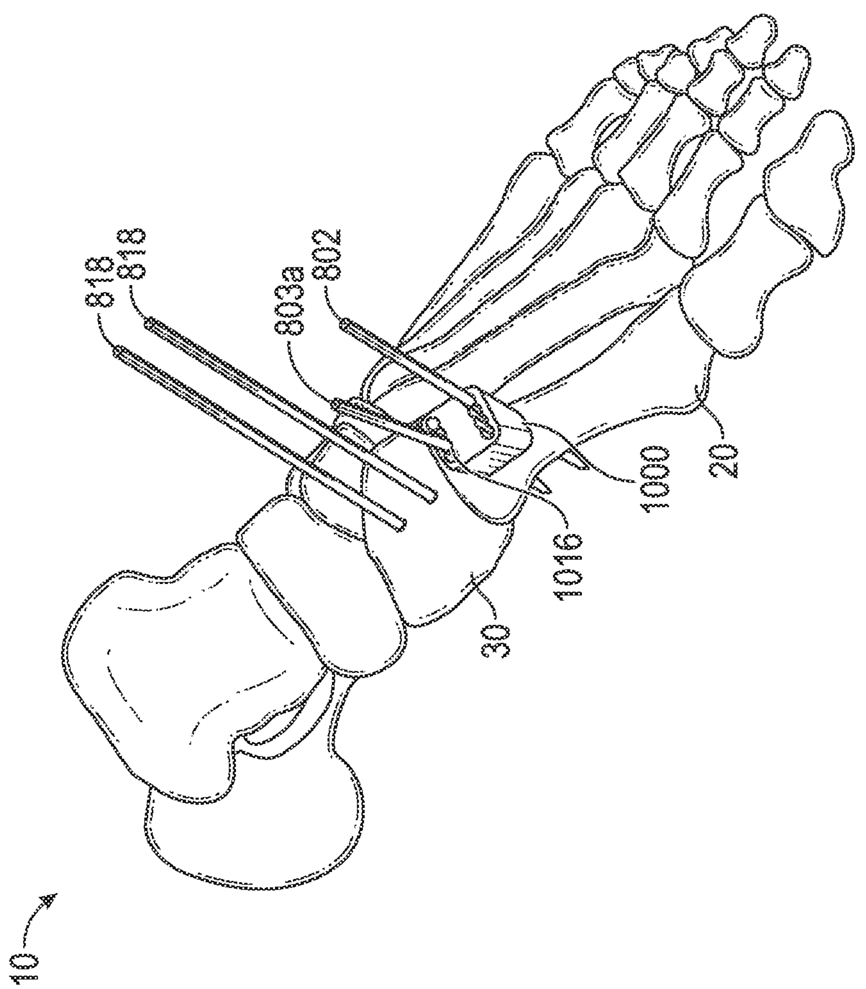
FIG. 42 is a perspective view of the human foot of FIG. 41, whereby the first substitute metatarsal pin is inserted further through the pin hole and the first metatarsal to a fully inserted position.

Continuing to FIG. 41, the proximal metatarsal pin 802 corresponding to the first substitute metatarsal pin 803*a* is removed from the first metatarsal 20. In this configuration, the partially inserted first substitute metatarsal pin 803*a* and the remaining metatarsal pin 802 are sufficient to maintain the position and orientation of the realignment guide 1000 relative to the first metatarsal. As shown in FIG. 42, the first substitute metatarsal pin 803*a* can then be inserted further through the pin hole 1016 and the first metatarsal to a fully inserted position, with the realignment guide 1000 serving as a pin placement guide for the first substitute metatarsal pin 803*a*.

Figure 43:
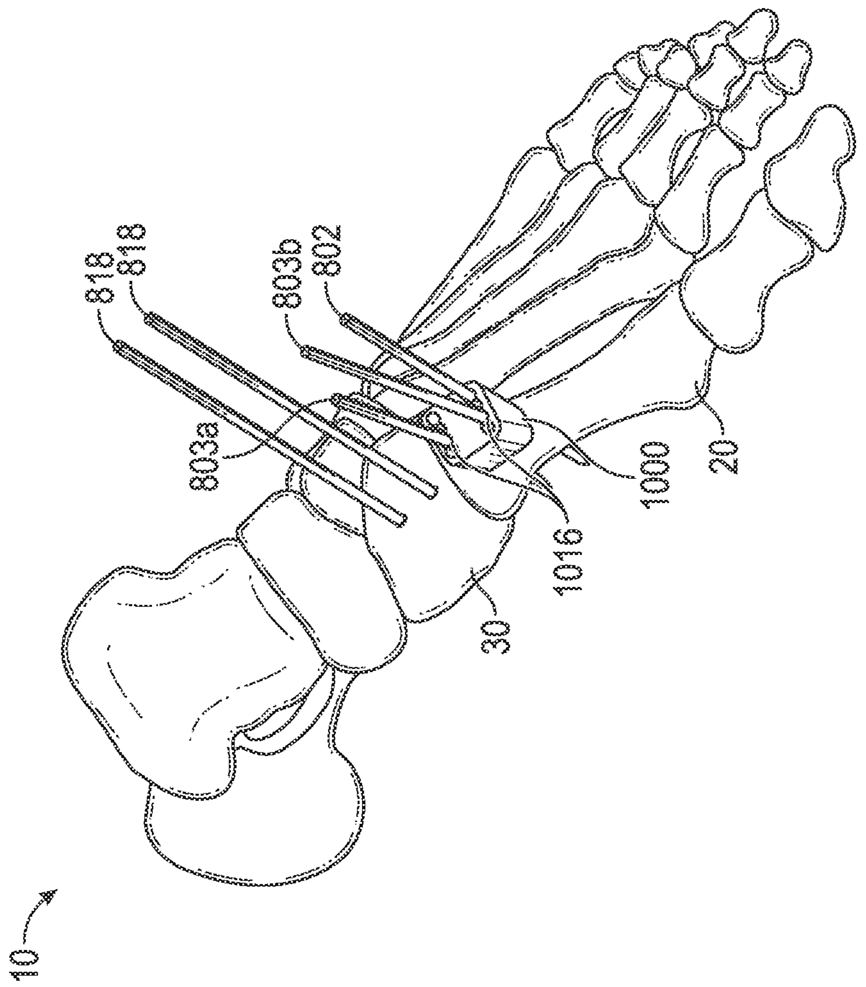
FIG. 43 is a perspective view of the human foot of FIG. 42, showing a step of a replacement procedure for a remaining metatarsal pin, whereby a second replacement metatarsal pin is partially inserted through another pin hole of the pair of pin holes of the realignment guide.
Figure 44:
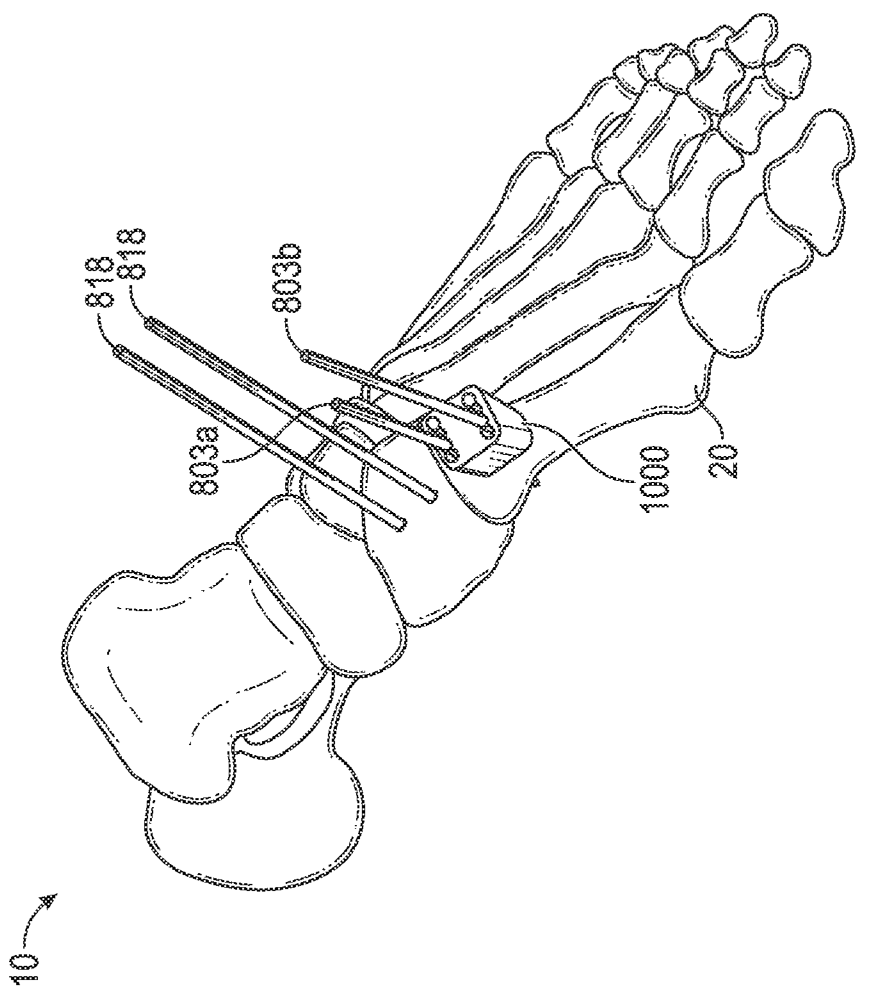
FIG. 44 is a perspective view of the human foot of FIG. 43, whereby the remaining metatarsal pin is removed.
Figure 45:
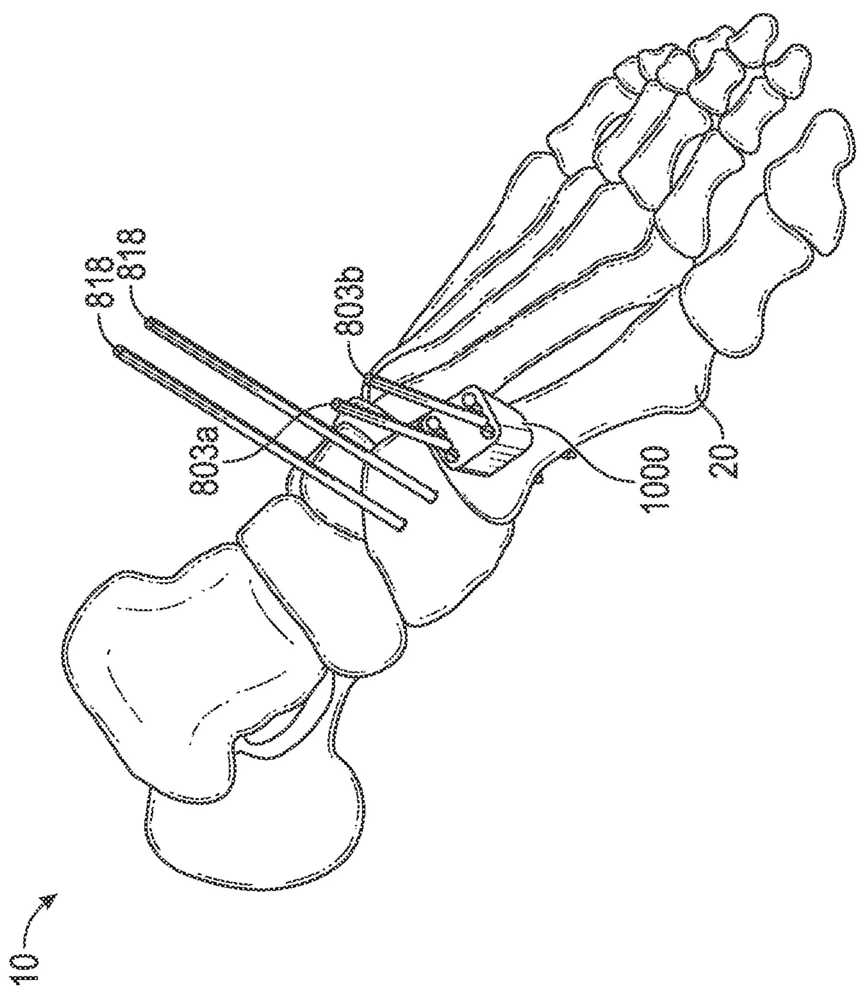
FIG. 45 is a perspective view of the human foot of FIG. 44, whereby the second replacement metatarsal pin is further inserted through the realignment guide.

Continuing to FIGS. 43-45, a similar replacement procedure is performed for the remaining metatarsal pin 802. As shown in FIG. 43, a second replacement metatarsal pin 803*b* is partially inserted through the other pin hole of the pair of pin holes 1016. As shown in FIG. 44, the remaining metatarsal pin 802 is removed to allow the second replacement metatarsal pin 803*b* to be fully inserted. As shown in FIG. 45, the second replacement metatarsal pin 803*b* is further inserted through the realignment guide 1000.

Figure 46:
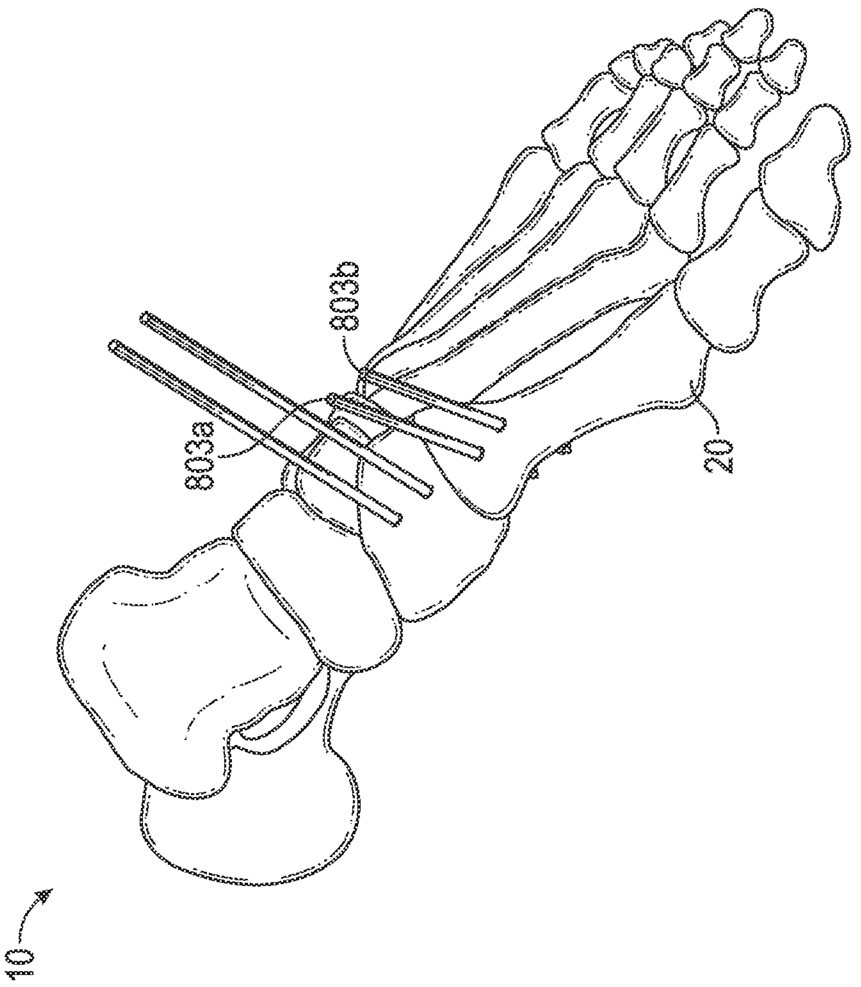
FIG. 46 is a perspective view of the human foot of FIG. 45, showing the realignment guide removed from the foot.
Figure 47:
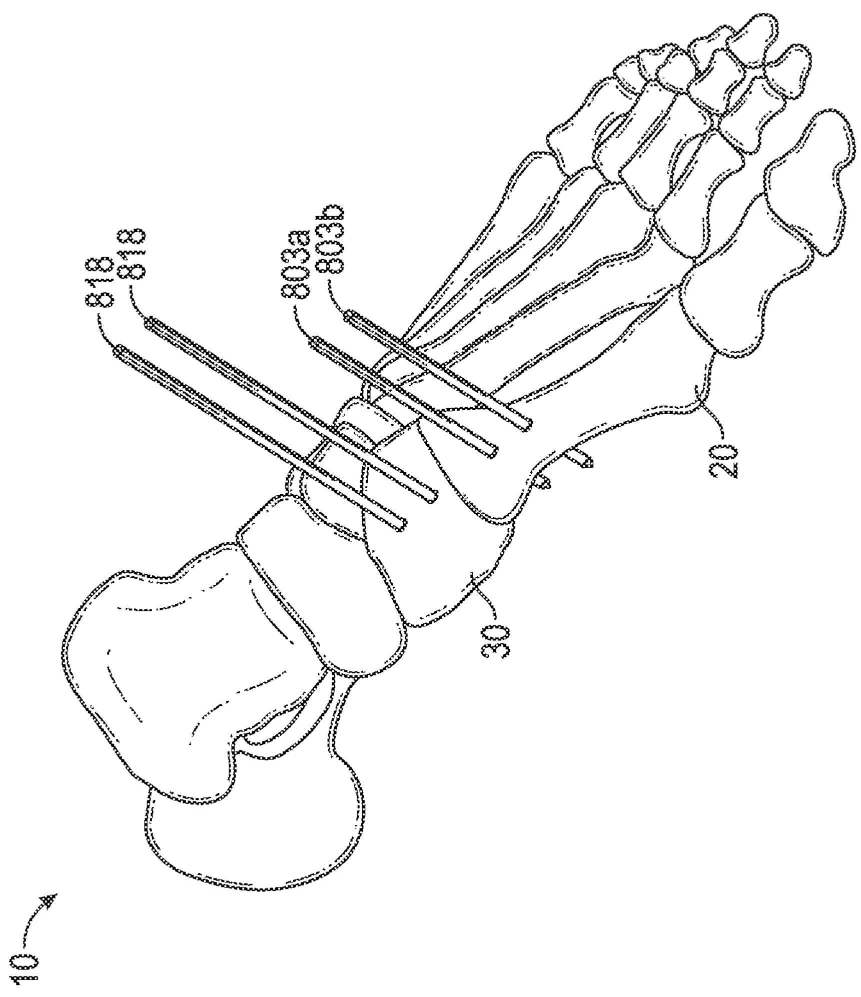
FIG. 47 is a perspective view of the human foot of FIG. 46, whereby the first metatarsal is rotated within the frontal plane relative to the first cuneiform.
Figure 48:
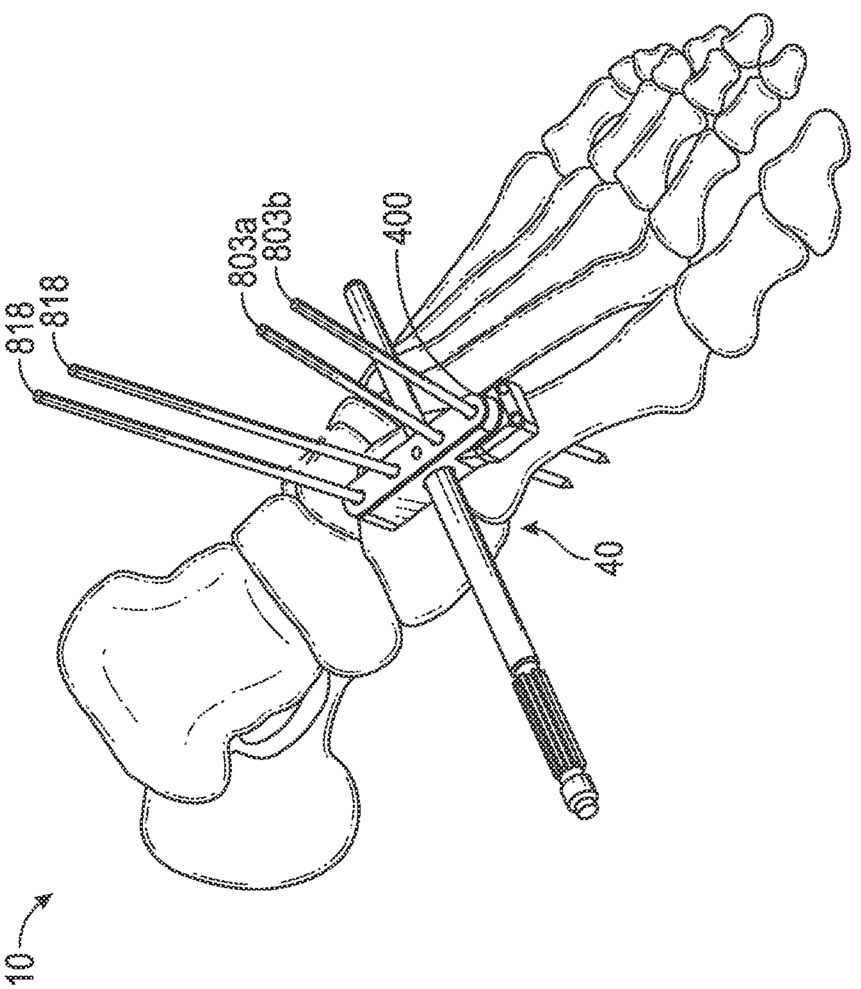
FIG. 48 is a perspective view of the human foot of FIG. 47, whereby the compressor block is installed over the cuneiform pins and the replacement metatarsal pins.
Figure 49B:
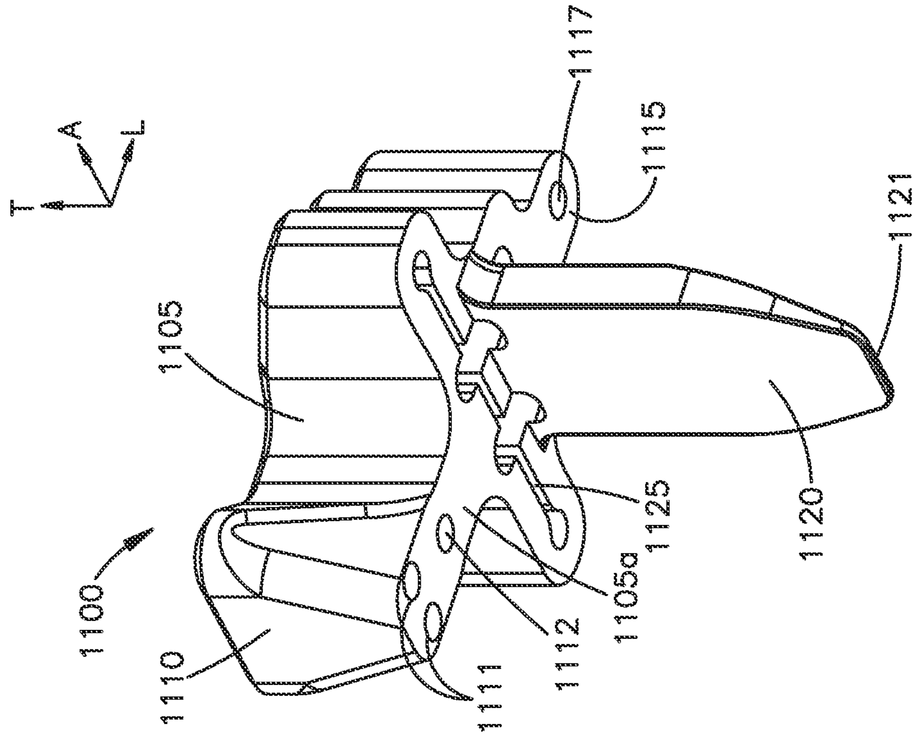
FIG. 49B is another perspective view of the cut guide of FIG. 49A.
Figure 49A:
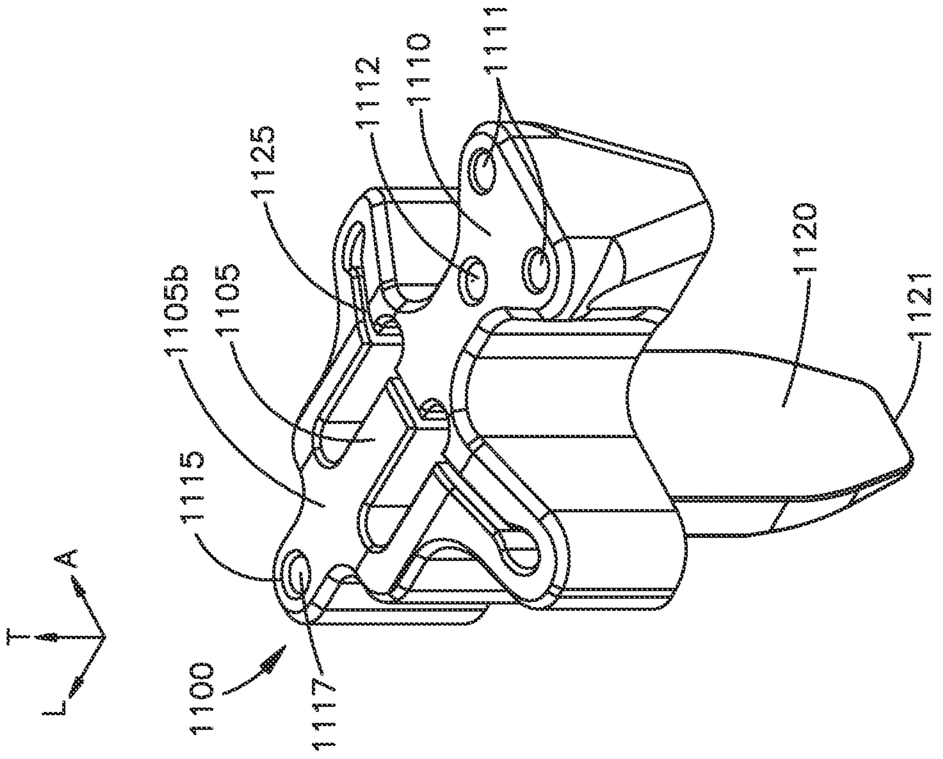
FIG. 49A is a perspective view of another example of a cut guide configured as a cutting guide and a fixation guide for joint fusion procedures described herein.
Figure 49D:
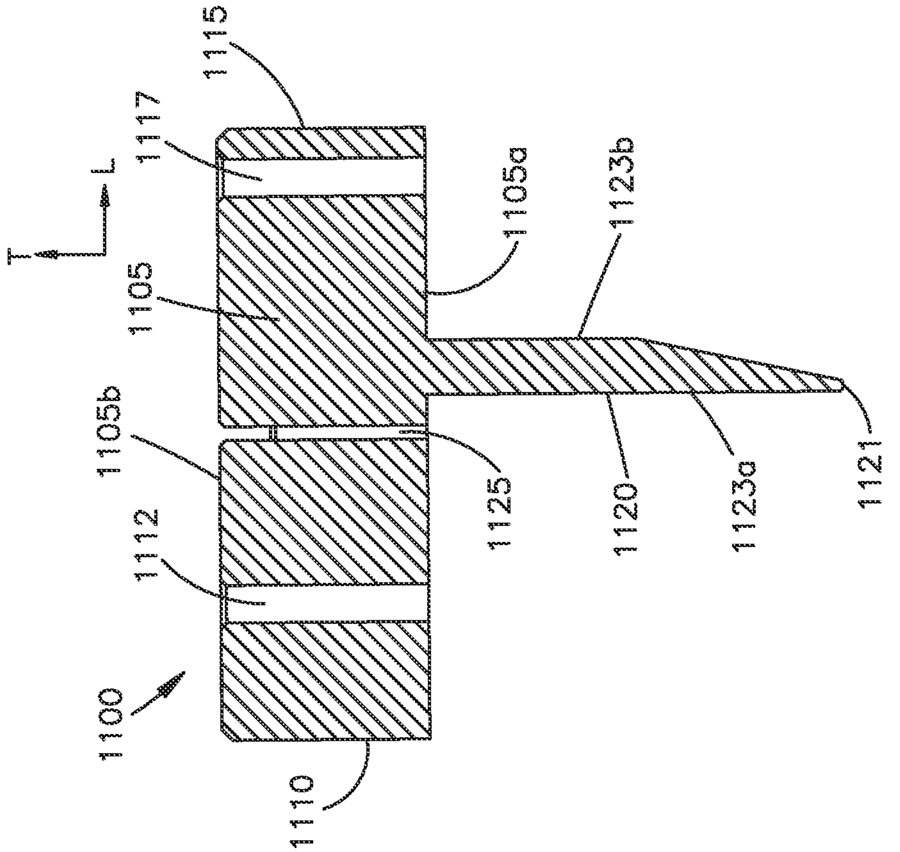
FIG. 49D is a sectional elevation view of the cut guide of FIG. 49C taken along line 49D-49D.
Figure 49C:
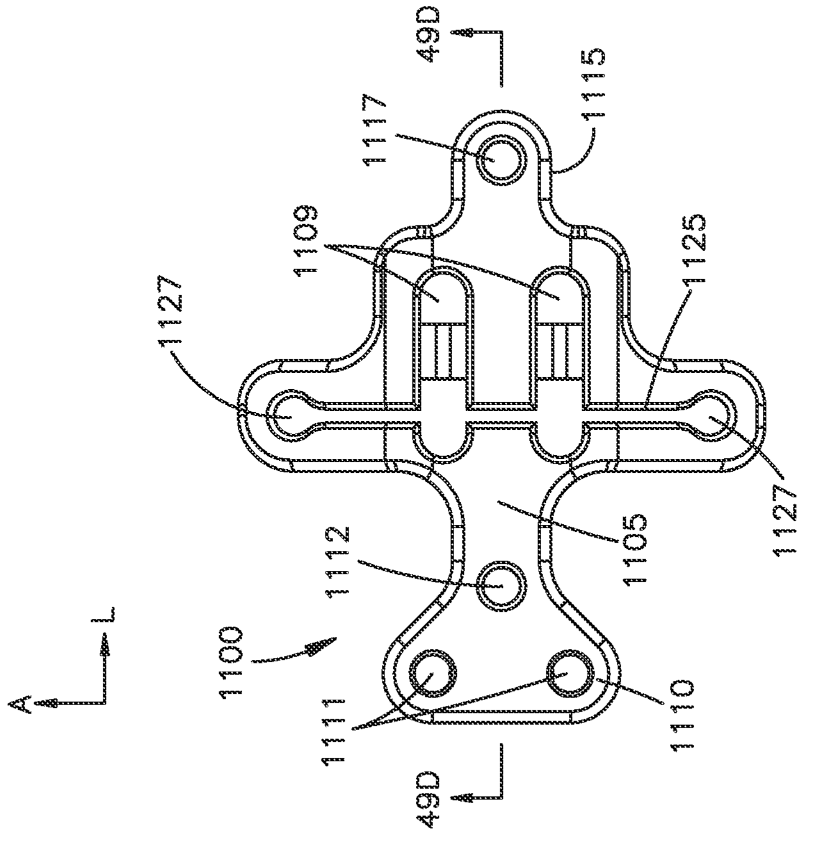
FIG. 49C is a top plan view of the cut guide of FIG. 49A.
Figure 50B:
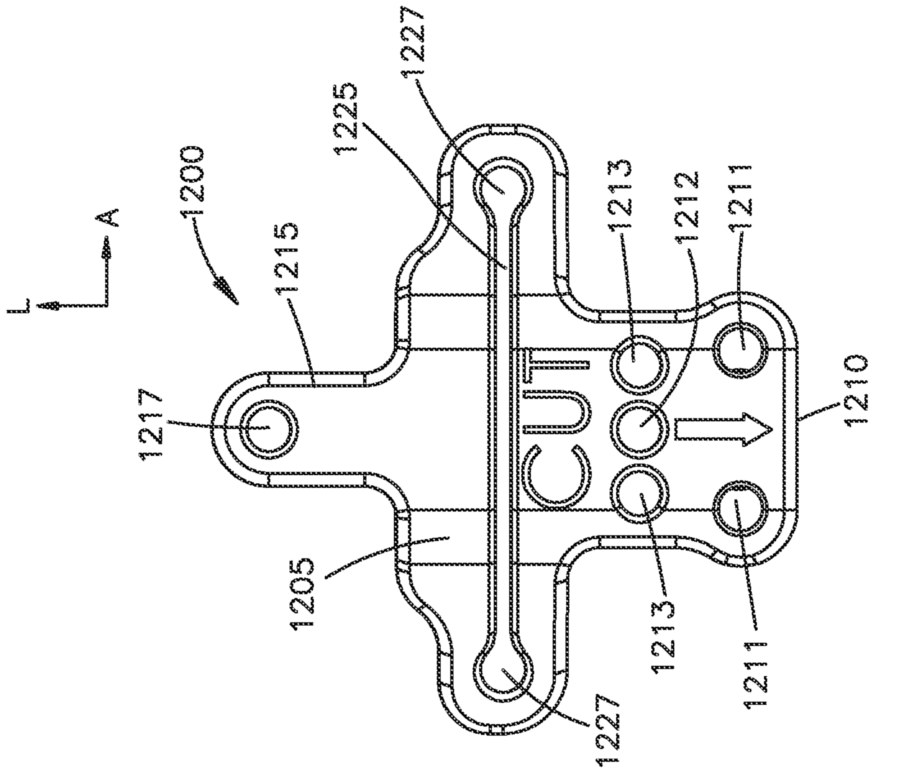
FIG. 50B is a top plan view of the cutting guide of FIG. 50A.
Figure 50A:
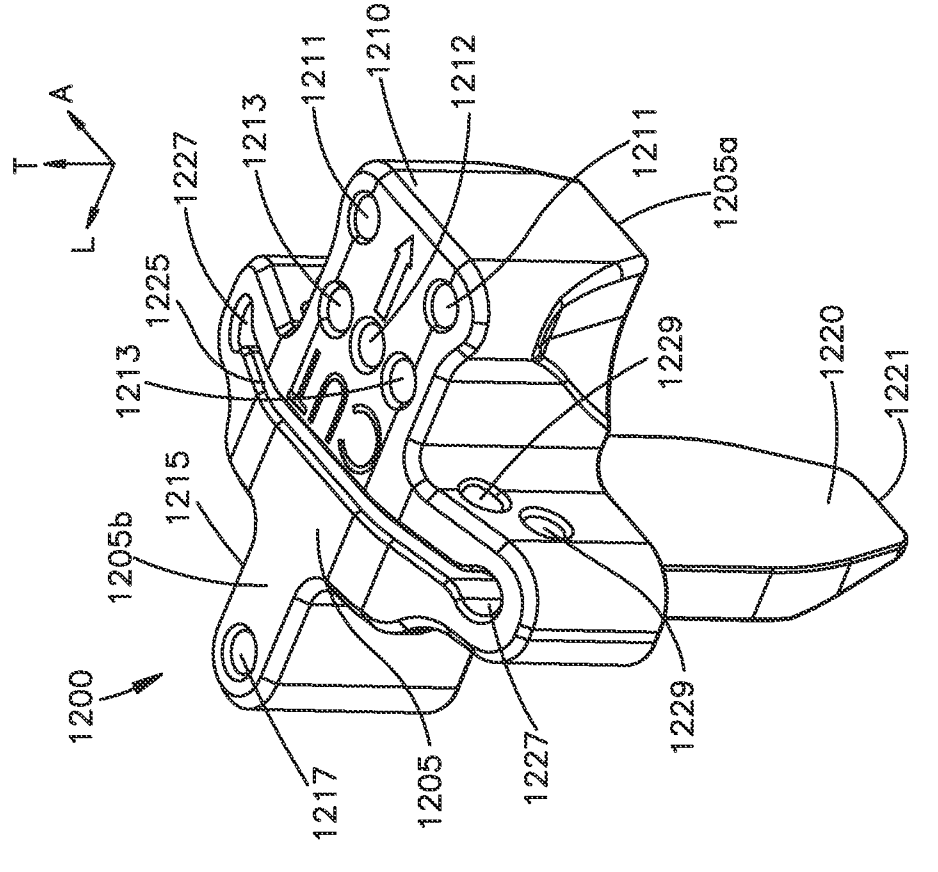
FIG. 50A is a perspective view of another example of a cutting guide configured as a cutting guide and a fixation guide for joint fusion procedures described herein.
Figure 50D:
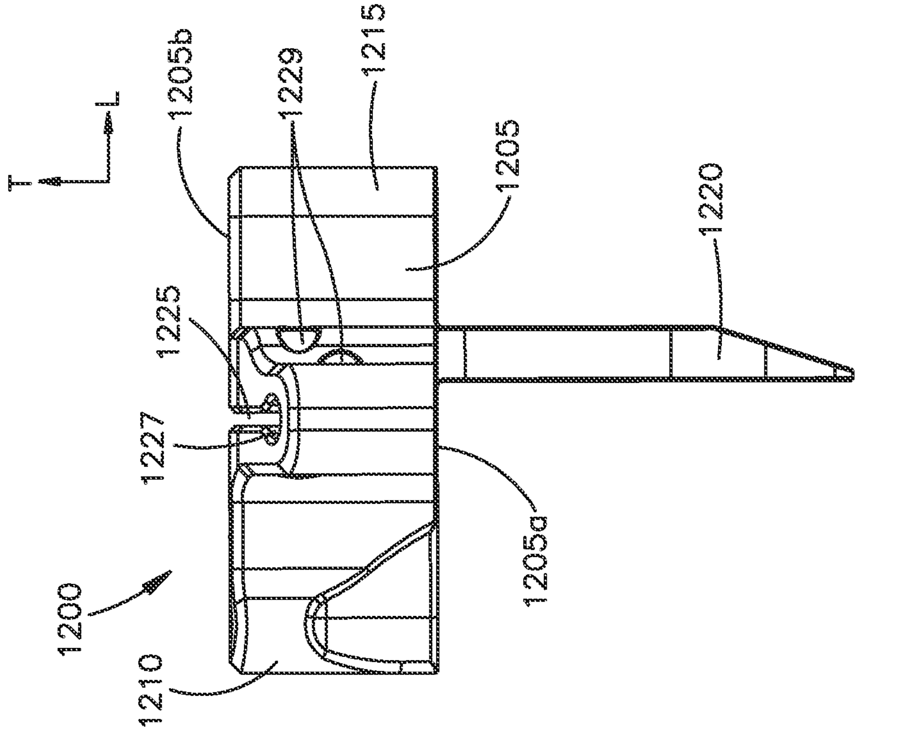
FIG. 50D is an end elevation view of the cutting guide of FIG. 50A.
Figure 50C:
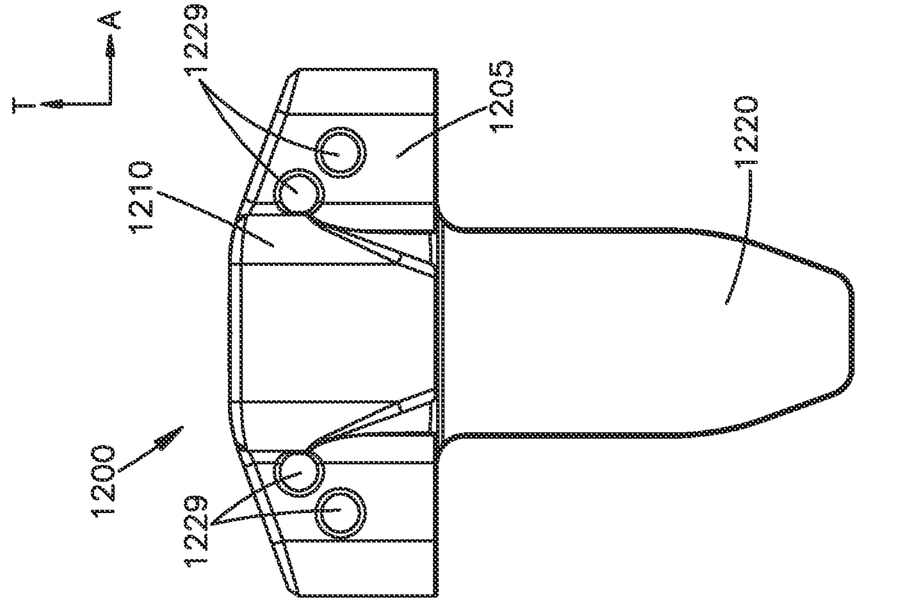
FIG. 50C is a side elevation view of the cutting guide of FIG. 50A.
Figure 51B:
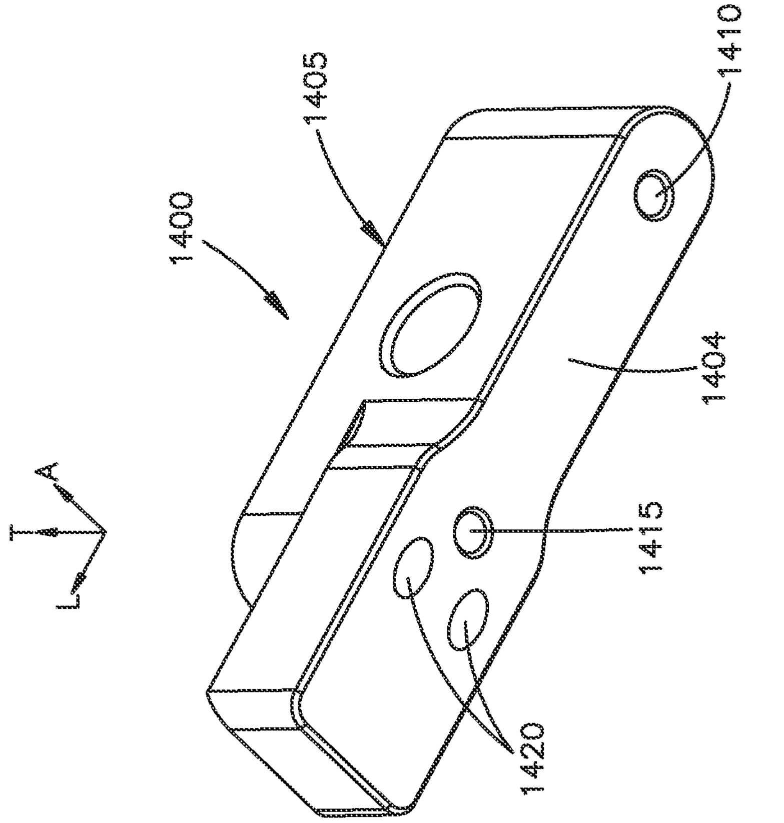
FIG. 51B is another perspective view of the compressor block of FIG. 51A.
Figure 51A:
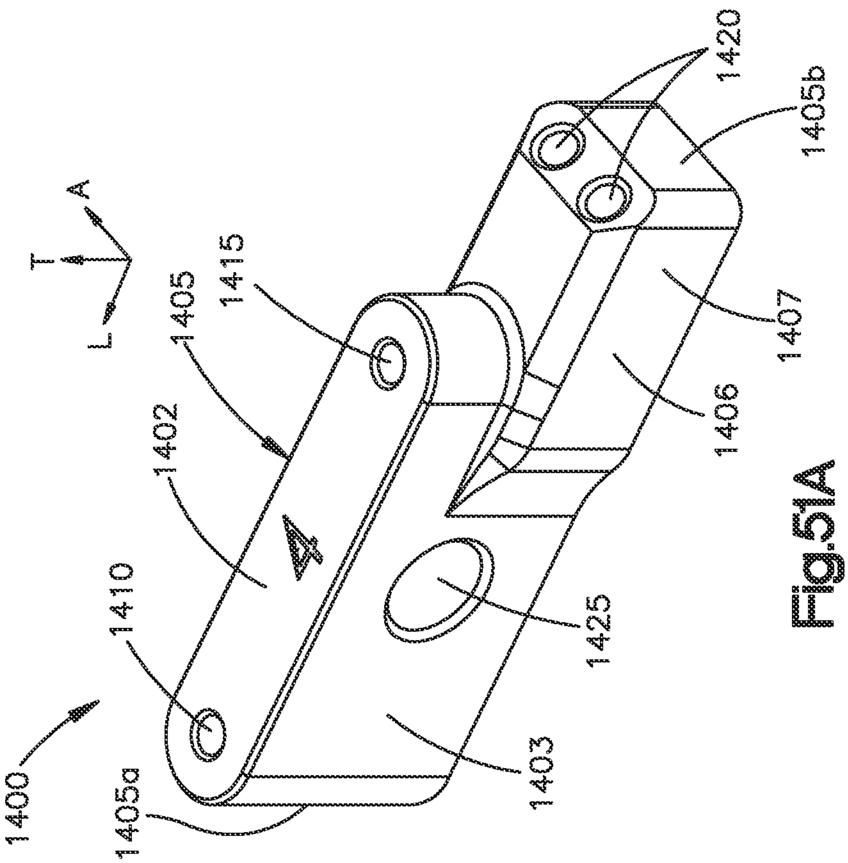
FIG. 51A is a perspective view of another example of a compressor block configured to be used in the joint fusion procedures described herein.
Figures 51C, 51D, 51E:
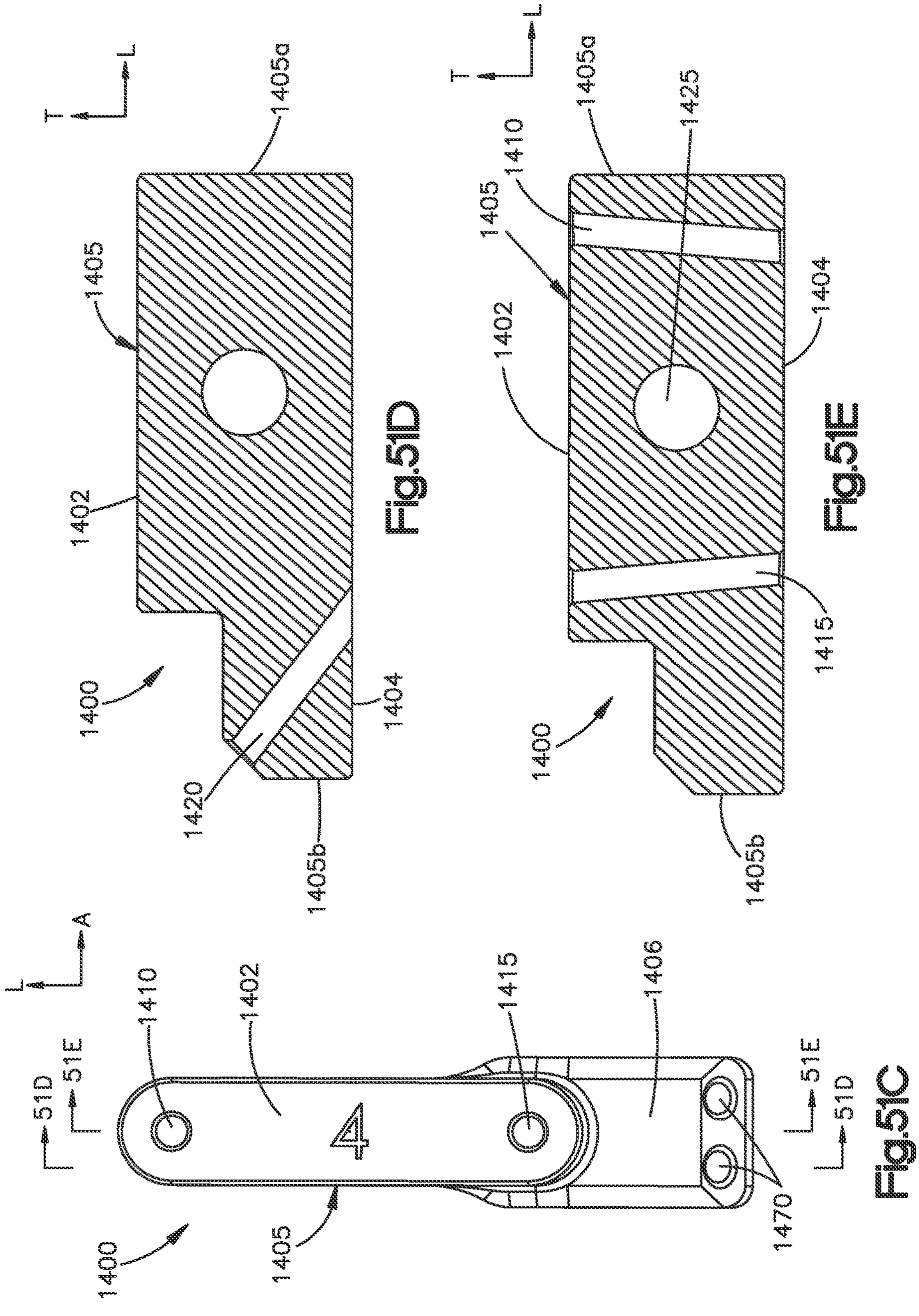
FIG. 51C is a top plan view of the compressor block of FIG. 51A.
FIG. 51D is a sectional elevation view of the compressor block of FIG. 51C taken along line 51D-51D.
FIG. 51E is a sectional elevation view of the compressor block of FIG. 51C taken along line 51E-51E.
Figure 52D:
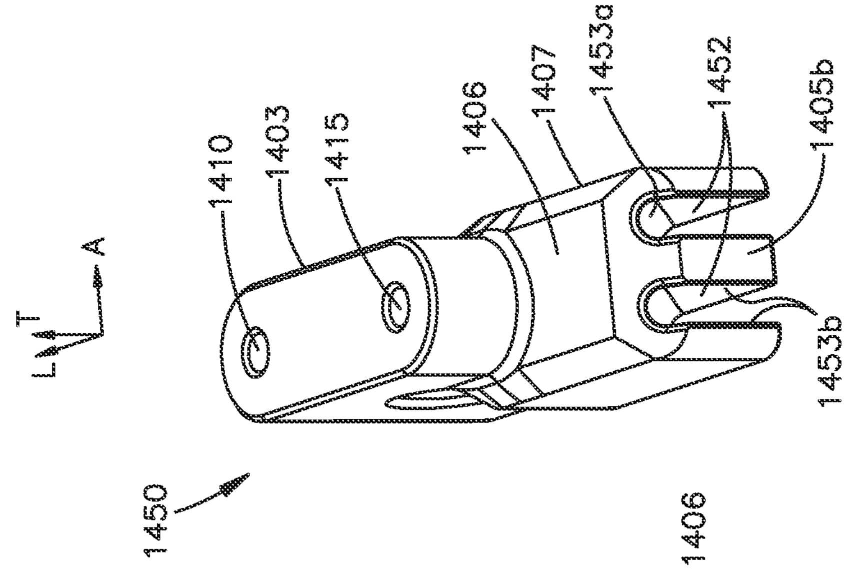
FIG. 52D is a perspective view of the compressor block of FIG. 52A.
Figure 52C:
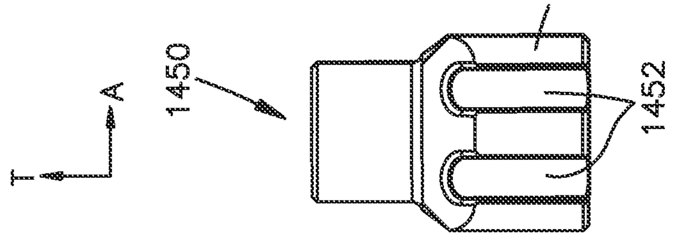
FIG. 52C is an end elevation view of the compressor block of FIG. 52A.
Figure 52B:
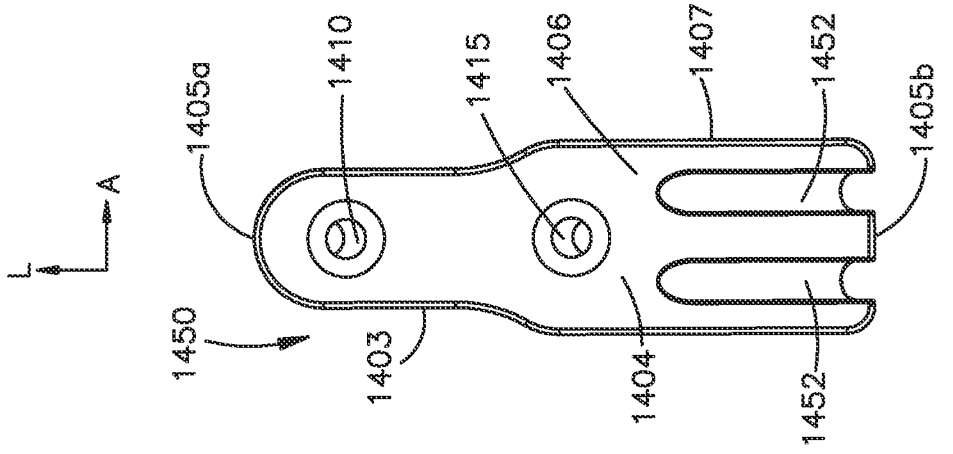
FIG. 52B is a bottom plan view of the compressor block of FIG. 52A.
Figure 52A:
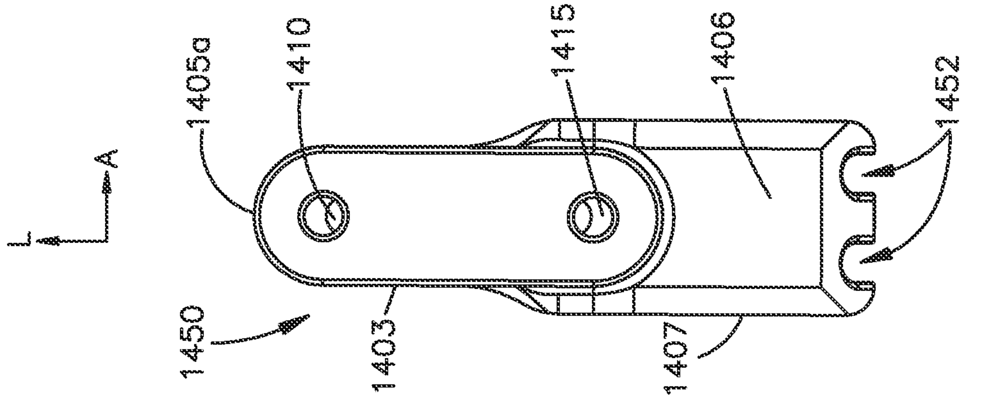
FIG. 52A is a top plan view of another example of a compressor block configured to be used in the joint fusion procedures described herein.

Continuing to FIG. 46, the realignment guide 1000 is removed from the foot 10 such that the replacement metatarsal pins 803*a*, 803*b* remain in the first metatarsal 20 with the same spacing but angularly displaced relative to the metatarsal pins 802 that were removed. As shown in FIG. 47, the first metatarsal 20 is then rotated within the frontal plane relative to the first cuneiform 30 into the final orientation in which the replacement metatarsal pins 803*a*, 803*b* are aligned with the cuneiform pins 818. Following this final frontal plane realignment process, a compression block such as compression block 400 may then be placed over the cuneiform pins 818 and the replacement metatarsal pins 803*a*, 803*b* to compress the TMT joint 40 for fixation as shown in FIG. 48. The Lapidus bunionectomy procedure may then proceed to conclusion, for example, as shown and described with reference to FIGS. 17-24.

Referring now to FIGS. 49A-49D a bone fixation kit can include an example cut guide 1100 can be configured as a cutting guide and a temporary fixation guide for a joint fusion procedure and particularly for fusion of the TMT joint (for example, fusion of the second or third TMT joint). As will be described, the cut guide 1100 can be configured to guide a cutting instrument to resect a first bone on one side of a joint, and then repositioned to guide the cutting instrument to resect a second bone on an opposite side of a joint.

The cut guide 1100 generally includes a body 1105 that defines a first portion 1110 and a second portion 1115 opposite the first portion 1110 along a longitudinal direction L. The first portion 1110 can be said to the spaced from the second portion 1115 in a first direction. Conversely, the second portion 1115 can be said to be spaced from the first portion 1110 in a first direction. The first and second directions can be oriented along the longitudinal direction L. The first and second portions 1110 and 1115 of the body can define respective first and second portions of the cut guide 1100. The cut guide 1100 can further include a paddle 1120 that extends from the body 1105 along a transverse direction T that is substantially perpendicular to the longitudinal direction L. The first portion 1110 can extend from the paddle 1120 in the first direction, and the second portion 1115 can extend from the paddle 1120 in the second direction. The cut guide 1100 may be a single integrally formed component and may comprise a metal, a plastic, or other suitable material.

The paddle 1120 can be sized and shaped to seat within a joint between a first bone and a second bone (e.g., between a metatarsal and a cuneiform or cuboid bone) after removing soft tissue such as the joint capsule around the joint. At least a portion of the paddle 1120 can inwardly taper as it extends to its free end 1121 so as to define a tapered free end 1121. For instance, the paddle 1120 can define opposed first and second longitudinal-facing surfaces 1123*a* and 1123*b*. The first longitudinal facing surface 1123*a* can face the first direction, and the second longitudinal facing surface 1123*a* can face the second direction. In one example, the first longitudinal-facing surface 1123*a* can be substantially planar as it extends from the body 1105 to the free end 1121. At least a portion (such as a distal portion) of the second longitudinal-facing surface 1123*b* can taper toward the first longitudinal-facing surface 1123*a* as it extends to the free end 1121. The tapered free end 1121 may facilitate insertion of the paddle 1120 into the joint. As described above, the paddle 1120 can be monolithic with the body 1105. In other examples, the paddle 1120 can be discrete from the body 1105 and secured to the body 1105.

The body 1105 of the cut guide 1100 defines a bone-facing surface 1105*a* and an outer surface 1105*b* opposite the bone-facing surface 1105*a* along the transverse direction T. can include a cutting slot 1125 that extends through the body 1105 of the cut guide 1100 along the transverse direction T. The cut slot 1125 can be elongate along a lateral direction A that is perpendicular to each of the longitudinal direction L and the transverse direction T. The cutting slot 1125 can pass through the body 1105 from the outer surface 1105*b* to the bone facing surface 1105*a*. The cutting slot 1125 is sized and shaped to serve as a positioning guide that receives a sawblade or other cutting instrument in order to facilitate sequential precise cuts of each of the first and second bones on opposite sides of the joint. For example, the cutting slot 1125 may be positioned at a predetermined spacing distance relative to the paddle 1120 along the longitudinal direction, and in particular in the first direction. Thus, the paddle 1120 can be positioned in the joint in a first orientation such that the cutting slot 1125 is aligned with a base (i.e., joint-facing portion) of the first bone. The cut guide 1100 can therefore receive a cutting instrument that facilitates cutting the base of the first bone when the paddle 1120 is positioned within the joint. In this regard, the first direction can define a distal direction, whereby the first bone is positioned distal of the second bone. Once the first one has been cut, the cutting slot 1125 may be removed from the joint and repositioned in a second orientation whereby the cutting slot 1125 is aligned with the second bone when the paddle 1120 is disposed in the joint. The reversible cut guide can be placed across the dorsal side of the joint in the second orientation. The cut guide 1100 can therefore receive the cutting instrument that facilitates cutting a distal portion (i.e., joint-facing portion) of the second bone when the paddle 1120 is positioned within the joint with the cut guide 1100 in the second orientation. In this regard, the first direction can define a proximal direction opposite the distal direction.

The cutting slot 1125 can have a width that is greater than that of the paddle 1120, The cutting slot can further be parallel to least one of the first and second longitudinal-facing surfaces 1123*a* and 1123*b* of the paddle 1120, or to a direction along which the paddle 1120 extends from the body 1105. In other examples, the cutting slot 1125 can be angled relative at least a portion of each of the first and second longitudinal-facing surfaces 1123*a* and 1123*b* of the paddle 1120. In some embodiments, the cutting slot 1125 can define enlarged terminal sections 1127 its opposed lateral ends that can be configured to receive stop members such as guide wires (e.g., Kirschner wires or K-wires) as the first and/or second bones are cut in order to prevent the cutting blade from making an excessively wide cut in the cutting slot 1125. In particular, the stop members abut the cutting instrument so as to limit the travel of the cutting instrument in the cutting slot 1125 to that region not occluded by the stop members.

The cut guide 1100 can define a first primary temporary bone fixation hole 1112 that extends through the body 1105 from the outer surface 1105*b* to the bone-facing surface 1105*a*. In particular, the first primary temporary bone fixation hole 1112 can extend through the first portion 1110 of the body 1105 along the transverse direction T. The first primary temporary bone fixation hole 1112 can have a substantially circular cross-sectional profile sized to receive a temporary bone fixation element such as a K-wire or pin that temporarily secures the cut guide 1100 to a respective underlying bone as discussed further below. The first primary temporary bone fixation hole 1112 serves as a guide for the temporary bone fixation element that can be inserted through the hole 1112 and into the underlying bone at a predetermined spacing relative to the paddle 1120 and/or relative to the plane along which the underlying bone is cut by a cutting instrument through the cutting slot 1125. Depending on the orientation of the cut guide, the underlying bone can be defined by the first bone or the second bone. Although the example cut guide 1100 of FIGS. 49A-50B includes a single first primary temporary bone fixation hole 1112, in some embodiments the cut guide 1100 may include a plurality of first primary temporary bone fixation holes 1112 to provide additional stability. For example, the cut guide 1100 may include two or more first primary temporary bone fixation holes 1112 aligned along a centerline of the cut guide 1100 perpendicular to the cutting slot 1125. The at least one first primary temporary bone fixation hole 1112 can be aligned along a longitudinal centerline of the guide 1100 (e.g., transverse to the plane of the cut cutting slot 1125).

The first portion 1110 can further include one or more first auxiliary temporary bone fixation holes 1111 that extend through the body 1105 from the outer surface 1105*b* to the bone-facing surface 1105*a*. In particular, the first auxiliary temporary bone fixation holes 1111 can extend through the first portion 1110 of the body 1105 along the transverse direction T. The first auxiliary temporary bone fixation holes 1111 can have a substantially circular cross-sectional profile sized to receive a temporary bone fixation element such as a K-wire or pin that temporarily secures the cut guide 1100 to the underlying bone, as discussed further below. The first auxiliary temporary bone fixation holes 1111 can be offset a predetermined distance from the first primary temporary bone fixation hole 1112 in the first direction in some examples. The first auxiliary temporary bone fixation holes 1111 can further be disposed outboard with respect to the first primary temporary bone fixation hole 1112 along the lateral direction L.

The temporary bone fixation holes 1111 and 1112 may extend parallel to each other or may be angularly offset with respect to each other, thereby defining non-parallel trajectories as they extend through the body 1105. For instance, the first auxiliary temporary bone fixation holes 1111 can be angularly offset with respect to each other. In one example, they can converge toward each other as they extend through the bone plate body 1105 in a direction from the outer surface 1105*b* toward the bone-facing surface 1105*a*. In particular, the first auxiliary temporary bone fixation holes 1111 can be spaced further from each other at the outer surface 1105*b* than they are at the bone-facing surface 1105*a*. The temporary fixation members that extend through the convergent holes 1111 and into the respective underlying bone can provide additional stability as desired.

The cut guide 1100 can define a second temporary bone fixation hole 1117 that extends through the body 1105 from the outer surface 1105*b* to the bone-facing surface 1105*a*. In particular, the second temporary bone fixation hole 1117 can extend through the second portion 1110 of the body 1105 along the transverse direction T. The second temporary bone fixation hole 1117 can have a substantially circular cross-sectional profile sized to receive a temporary bone fixation element such as a K-wire or pin or other structure that temporarily secures the cut guide 1100 to a respective underlying bone as discussed further below. The second temporary bone fixation hole 1117 may have the same diameter as the first temporary bone fixation holes 1111 and 1112.

The second temporary bone fixation hole 1117 serves as a guide for a temporary bone fixation element that can be inserted through the hole 1117 and into the underlying bone at a predetermined spacing relative to the paddle 1120 and/or relative to the plane along which the underlying bone is cut by a cutting instrument through the cutting slot 1125. Depending on the orientation of the cut guide, the underlying bone can be defined by the first bone or the second bone. It should be appreciated that the respective underlying bone of the first temporary bone fixation holes 1111 and 1112 can be defined by one of the first and second bones, and the respective underlying bone of the second temporary bone fixation hole 1117 can be defined by the other of the first and second bones. The second temporary bone fixation hole 1117 can be aligned along a centerline of the cut guide 1100.

The second hole 1117 can extend parallel to one or more up to all of the first holes 1111 and 1112. Thus, the central axes of the first primary temporary bone fixation hole 1112 and the second temporary bone fixation hole 1117 can lie on a common plane. The common plane can be defined by the longitudinal direction L and the transverse direction T in one example. Although the example cut guide 1100 of FIGS. 49A-50B includes a single second temporary bone fixation hole 1117, in some embodiments the cut guide 1100 may include a plurality of second temporary bone fixation holes 1117 to provide additional stability as desired. For example, the cut guide 1100 may include two or more second temporary bone fixation holes aligned along the longitudinal centerline of the cut guide 1100 that is oriented perpendicular to the cutting slot 1125.

The bone-facing surface 1105*a* of the body 1105 can be planar across the second portion 1115 and/or the first portion 1110. Alternatively, the bone-facing surface 1105*a* of the second portion 1115 and/or the first portion 1110 may not be coplanar with the other of the first portion 1110 and the second portion 1115, which in some instances can allow the cut guide 1100 to be placed closer to the first or second bones while allowing space for the osseous anatomy of the first bone and the second bone. Further details are provided in U.S. Pat. No. 10,292,713, which is incorporated herein by reference.

The cut guide 1110 can further include one or more apertures 1109 that extend through the body 1105 from the outer surface 1105*b* to the bone-facing surface 1105*a*. The apertures 1109 can be elongate along the longitudinal direction A or any suitable alternative direction as desired. Thus, the apertures 1109 can define elongate openings at either or both of the bone-facing surface 1105*a* and the outer surface 1105*b*. The apertures 1109 can define regions devoid of cut guide material 1110 to facilitate x-ray visualization and/or any other suitable surgical imaging procedure to confirm and/or monitor the orientation and alignment of the cut guide 1110 during a surgical procedure. The apertures 1109 can intersect the cutting slot 1125 in some examples, and can further intersect the paddle 1120 as desired.

Referring now to FIGS. 50A-50D, the bone fixation kit can include an alternative cut guide 1200 can be configured as a cutting guide and a temporary fixation guide for a joint fusion procedure and particularly for fusion of the TMT joint (for example, fusion of the second or third TMT joint). The cut guide 1200 can be constructed generally as described above with respect to the cut guide 1100 of FIGS. 49A-49D, and reference numerals of the cut guide 1200 corresponding to like elements of the cut guide 1100 have been incremented by 100 for the purposes of clarity and convenience. Accordingly, the description above of the cut guide 1100 applies with equal force and effect to the cut guide 1200 unless otherwise indicated.

Thus, the cut guide 1200 includes a body 1205, that defines a first end 1210 and a second end 1215 opposite the first end along the longitudinal direction. The cut guide 1200 further includes a paddle 1220 that extends from the body 1205 along the transverse direction T, and is sized and shaped to seat within a joint between a first bone and a second bone (e.g., between a metatarsal and a cuneiform or cuboid bone) after removing soft tissue such as the joint capsule around the joint. At least a portion of the paddle 1220 can be tapered at its free end 1221 to facilitate insertion into the joint. The paddle 1220 can be integrally formed with the body 1205 or discrete from and attached to the body 1205. The body 1205 can define a bone-facing surface 1205*a* and an outer surface 1205*b* opposite the bone-facing surface 1205*a* along the transverse direction T.

The cut guide 1200 includes a slot 1225 that extends through the body 1205 from the outer surface 1205*b* to the bone-facing surface 1205*a*. The slot 1225 can be elongate along the lateral direction A. The slot 1225 can receive a cutting instrument in order to facilitate precise cuts of the first and second bones on opposite sides of the joint as described above. The cutting slot 1225 can have enlarged terminal sections 1227 at opposed lateral ends of the cutting slot 1225 may be provided for the placement of additional temporary fixation members during cutting to prevent a cutting instrument from making an excessively wide cut in the cutting slot 1225.

The cut guide 1200 can further include stop holes 1229 that extend through the body 1205 along the longitudinal direction L or along a direction angularly offset with respect to the longitudinal direction L. The stop holes 1229 can intersect the slot 1225. The stop holes 1229 can be spaced from each other along the lateral direction A. The stop holes 1229 can be configured to receive respective stop members, such as temporary fixation members or other structure that limits the range of motion of the cutting instrument in the slot 1225. In particular, the stop members disposed in the stop holes 1229 can abut the cutting instrument in the slot 1225 so as to limit the travel of the cutting instrument in the cutting slot 1225 to that region of the cutting slot 1225 that is not occluded by stop members. The stop holes 1229 can be disposed inward with respect to the enlarged terminal sections 1227 with respect to the lateral direction A, such that stop members disposed in the stop holes 1229 further limit the useful width of the cutting slot 1225 along the lateral direction A with respect to stop members that may be received in the enlarged terminal sections 1227. As shown, the cut guide 1200 does not include apertures more apertures 1109 described above with respect to the cut guide 1100 shown in FIGS. 49A-49D, but could include one or more of the apertures 1109 if desired. Further, the cut guide 1100 can include the stop holes 1229 if desired.

The cut guide 1200 includes a first primary temporary bone fixation hole 1212 that extends through the first portion 1210 of the body 1205 from the outer surface 1205*b* to the bone-facing surface 1205*a* as described above with respect to the first primary temporary bone fixation hole 1112 of the cut guide 1100 of FIGS. 49A-49D. The cut guide 1200 can further include one or more first auxiliary temporary bone fixation holes 1211 that extend through the first portion of the body 1205 from the outer surface 1205*b* to the bone-facing surface 1205*a* as described above with respect to the first auxiliary temporary bone fixation holes 1111 of the cut guide 1100 of FIGS. 49A-49D. The cut guide 1200 can include at least one second temporary bone fixation hole 1217 that extends through the second portion 1215 of the body 1205 from the outer surface 1205*b* to the bone-facing surface 1205*a* along the transverse direction T. The second temporary bone fixation hole 1217 can be as described with respect to the second temporary bone fixation hole 1117 of the cut guide 1100 of FIGS. 49A-49D. The stop holes 1229 can be disposed outboard with respect to all of the temporary fixation holes 1217, 1211, 1212, and 1213 along the lateral direction A as desired.

The cut guide 1200 can further include one or more first offset temporary bone fixation holes 1213 that extend through the first portion 1210 of the body 1205 from the outer surface 1205*b* to the bone-facing surface 1205*a*. During operation, one of the first offset temporary bone fixation holes 1213 can be used instead of the first primary temporary bone fixation hole 1212, if desired, to compensate for a tilt and/or angle of a bone such as a metatarsal. For example, in some implementations, the first primary temporary bone fixation hole 1212 can be used to place a wire and/or drill for a staple hole in a cuneiform bone and, after reversing the cut guide 1200, one of the first offset temporary bone fixation holes 1213 can be used to place a wire and/or drill for a staple hole in the corresponding metatarsal. Accordingly, a subsequently inserted staple used for fixing the cuneiform to the metatarsal will be offset as desired. The proximal pin holes 1211, 1212, and offset proximal pin holes 1213 may extend along the transverse direction T parallel to each other or may be skewed having non-parallel trajectories.

Referring now to FIGS. 51A-51E, the bone fixation kit can further include an example compressor block 1400 is configured to be used in the joint fusion procedures described herein. In some embodiments, the compressor block 1400 may be configured for a combination of realignment and compression of the first and second bones (e.g., a RAC block). In particular, the compressor block 1400 can be used to align the first and second bones after they have been cut either free-hand or using the cut guide 1100 or 1200, or any suitable alternative cut guide. The compressor block 1400 can further be used to draw the first and second bones toward each other. Thus, the compression block 1400 is configured to assist in compressing and fixing a resected joint that has been free-hand cut or cut using the cut guide 1100.

The compressor block 1400 includes a block body 1405 having a bone-facing surface 1404 and an outer surface opposite the bone-facing surface 1404 along the transverse direction T. The outer surface 1402 and/or the bone-facing surface 1404 can be planar or alternative shaped as desired. The block body 1405 defines a proximal end 1405*a* and a distal end 1405*b* opposite the proximal end along the longitudinal direction L. Thus, the block body 1405 and the compressor block 1400 defines a distal direction from the proximal end 1405*a* toward the distal end 1405*b*, and a proximal direction from the distal end 1405*b* toward the proximal end 1405*a*. The proximal and distal directions can be oriented along the longitudinal direction L. The block body 1405, and thus the compressor block 1400, can define a proximal portion 1403 and a distal portion 1407 opposite the proximal portion along the longitudinal direction L. Thus, a distal direction can be defined as a direction from the proximal portion 1403 toward the distal portion 1407, and a proximal direction can be defined as a direction from the distal portion 1407 toward the proximal portion 1403. The proximal portion 1403 can define the proximal end 1405*a*, and the distal portion 1407 can define the distal portion 1405*b*. The distal portion 1407 can be wider than the proximal portion 1403 along the lateral direction A.

The compressor block 1400 can include a first or proximal temporary bone fixation hole 1410 that extends through block body 1405 from the outer surface 1402 to the bone-facing surface 1404. In particular, the proximal temporary bone fixation hole 1410 extends through the proximal portion 1403 of the block body 1405. The proximal temporary bone fixation hole 1410 can extends through the body from the outer surface to the bone-facing surface at a first angle of less than 90 degrees relative to the each of the outer surface and the bone-facing surface. The compressor block 1400 can further include a second or distal temporary bone fixation hole 1415 that extends through block body 1405 from the outer surface 1402 to the bone-facing surface 1404. In particular, the distal temporary bone fixation hole 1415 extends through the distal portion 1407 of the block body 1405. The distal temporary bone fixation hole 1415 can extend through the block body 1405 from the outer surface to the bone-facing surface at the first angle relative to the outer surface and the bone-facing surface.

The proximal temporary bone fixation hole 1410 and the distal temporary bone fixation holes 1415 can be spaced from each other along the longitudinal direction L a first distance that is less than a second distance along which the first primary temporary bone fixation hole 1112 and second temporary bone fixation hole 1117 are spaced from each other along the longitudinal direction L. Further, either or both of the proximal temporary bone fixation hole 1410 and the distal temporary bone fixation holes 1415 can be spaced from the longitudinal center of the compressor block 1400 respective distances that are less than the respective distances along which the first primary temporary bone fixation hole 1112 and second temporary bone fixation hole 1117 are spaced from the longitudinal center of the cut guide 1100.

Further, the proximal temporary bone fixation hole 1410 and the distal temporary bone fixation hole 1415 can be non-parallel and/or are disposed at converging angles as they extend in an inward direction from the outer surface 1402 to the bone-facing surface 1404. Thus, respective openings of the proximal temporary bone fixation hole 1410 and the distal temporary bone fixation hole 1415 at the outer surface 1402 can be spaced a first distance from each other, and respective openings of the proximal temporary bone fixation hole 1410 and the distal temporary bone fixation hole 1415 at the bone-facing surface 1404 can be spaced a second distance from each other that is less than the first distance. Accordingly, as will be described in more detail below, temporary fixation members inserted through the proximal and distal apertures 1410 and 1415 are urged closer together by the compressor block 1400 as the compressor block 1400 slides downward over the temporary fixation members that are received in respective ones of the proximal and distal apertures 1410 and 1415, as is described in more detail below with respect to FIGS. 58-59. The temporary fixation members can be parallel to each other prior to sliding the compressor block 1400 over the temporary fixation members.

The compressor block 1400 can further include a handle attachment aperture 1425 that extends through the block body 1405. The handle attachment aperture 1425 is configured is provided to attach a handle which may assist the user in sliding the compressor block 1400 downward over the temporary fixation members that pass through respective ones of the apertures 1410, 1415 of the compressor block 1400. The handle attachment aperture 1425 can be threaded so as to threadedly mate with the handle. In one example, the handle attachment aperture 1425 extends through the proximal portion 1403 along the lateral direction A, though it should be appreciated that the handle attachment aperture 1425 can extend through any suitable location of the block body 1405 in any suitable direction as desired.

The compressor block 1400 further includes a fixation section 1406 and at least one oblique hole such as a pair of oblique holes 1420 that extend through the fixation section 1406. The fixation section 1406 can be defined by the distal portion 1407 of the block body 1405 in some examples. In one example, the oblique holes 1420 extend from respective first openings at the distal end 1405*b* in an inward direction (defined as a direction from the outer surface 1402 toward the bone-facing surface 1404) as they extend in the proximal direction to second openings at the bone-facing surface 1404. Thus, respective central axes of the oblique holes 1420 can extend along respective linear paths passing diagonally through the joint when the compressor block 1450 is aligned proximate the joint on the first and second temporary fixation members, and the joint can be fixed by inserting an oblique temporary fixation member through the oblique hole and through the joint.

It should be appreciated that the first openings can alternatively be defined by the outer surface 1402 or a lateral side surface as desired. The oblique holes 1420 can be adjacent each other along the lateral direction A. Temporary fixation members can be inserted into the first opening in the oblique holes 1420, respectively, through the respective oblique holes 1420, and out the second ends so as to exit the bone-facing surface 1404 of the compressor block 1400. It should be appreciated that temporary fixation members as described herein can include K-wires, pins, or any suitable alternative structure suitable for temporarily attaching to bone. The oblique holes 1420 can be aligned with each other along the lateral direction A. During operation, the compressor block 1400 causes either or both of the resected first and second bones to travel toward the other of the first and second bones until the first and second bones are placed into contact with each other or into contact with a spacer disposed in the compressed joint. A temporary fixation member inserted through either oblique hole 1420 in the manner described above will extend at an angle through the first and second bones across the compressed joint to temporarily maintain the positions of the first and second bones until the first and second bones can be fixed by a plate or other permanent fixing element.

Referring now to FIGS. 52A-52D, in some embodiments, the fixation section 1406 may include temporary bone fixation slots 1452 rather than oblique holes 1420. In particular, the bone fixation slots 1452 can be defined by a base 1453*a* and internal side surfaces 1453*b* that are spaced from each other and extend from the base 1453*a*. The side surfaces 1453*b* extend from the base 1453*a*. The side surfaces 1453*b* can be spaced from each other along the lateral direction A. The base 1453*a* can taper inwardly as it extends in the proximal direction from the distal surface 1405*b* until the base 1453*a* intersects the bone-facing surface 1404. The base 1453*a* can intersect the bone-facing surface 1404 at a location distal of the opening of the distal temporary bone fixation hole 1415 at the bone-facing surface 1404. The bone fixation slots 1452 can receive a temporary fixation member that extends across the joint between the first and second bones after the bones have been moved toward each other as described above with respect to the oblique holes 1420. However, the temporary bone fixation slots 1452 are configured to receive temporary fixation members that extend through the joint along different trajectories, whereas the oblique holes 1420 receive temporary fixation members that extend through the joint along a fixed trajectory defined by the central axis of the oblique holes 1420. Further, because the temporary fixation slots 1452 are open to the bone-facing surface 1405*b*, the slots 1452 can allow the compression block 1450 to be removed from the underlying bone while the temporary fixation members remain inserted in the bone through one or both of the slots 1452.

Figure 53C:
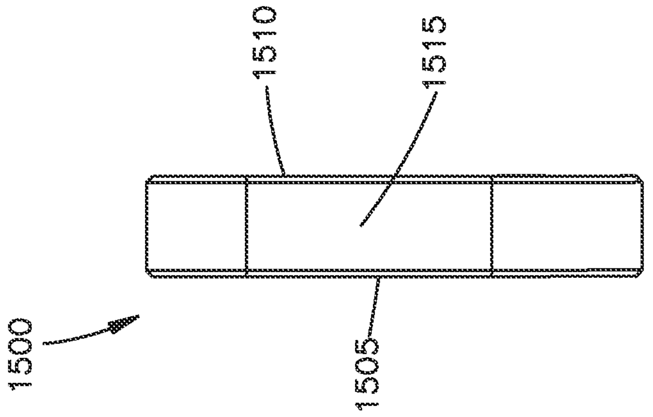
FIG. 53C is a side elevation view of the spacer of FIG. 53A.
Figure 53B:
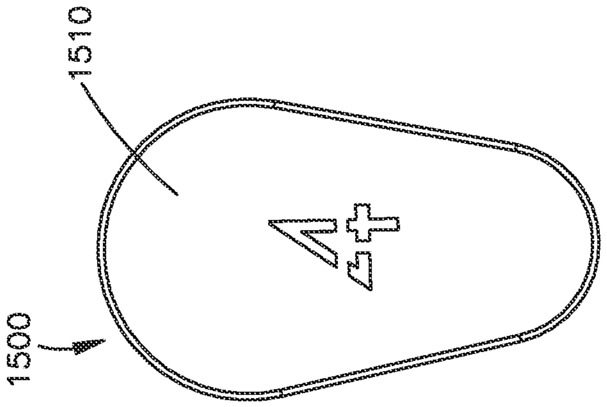
FIG. 53B is a top plan view of the spacer of FIG. 53A.
Figure 53A:
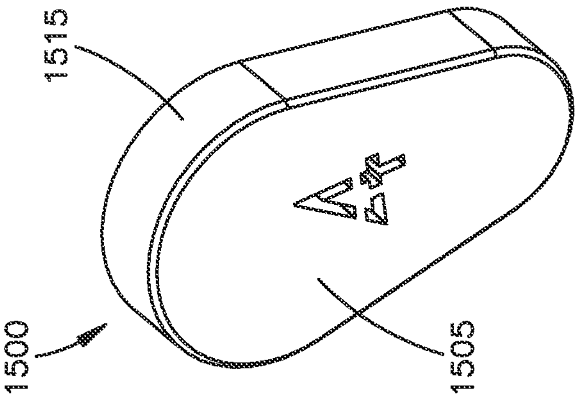
FIG. 53A is a perspective view of a spacer configured to be used between joints in the joint fusion procedures described herein.

With reference to FIGS. 53A-53C, the bone fixation kit can further include a spacer 1500 that is configured to be inserted into a gap between the first and second bones after the first and second bones have been cut. Thus, the spacer 1500 can be placed between respective first and second resected faces of the first bone and the second bone, respectively, in the gap. Thus, the first and second bones can fuse against the spacer 1500. The spacer 1500 can be sized and shaped to position the first and second bone relative to on another in the desired resected position. In some embodiments, the spacer 1500 may have an appropriate thickness to serve as a substitute for removed joint tissue, such as to maintain a preexisting length of the ray of the foot. In some embodiments, the thickness may be selected to correspond to a thickness of tissue removed from the first and second bones by the cutting instrument. The spacer 1500 can include opposed faces 1505 and 1510. One of the faces 1505 and 1510 can define a distal or first bone-facing face, and the other of the faces 1505 and 1510 can define a proximal or second bone-facing face. The opposed faces 1505 and 1510 can be planar in some examples. In various embodiments, the opposed faces 1505 and 1510 may be parallel to each other or may be non-parallel to each other. For example, non-parallel opposed faces 1505 and 1510 may allow the spacer 1500 to serve as a wedge insert for correction conditions such as metatarsus adductus (MTA). The spacer can define an outer periphery 1515 that extends between the opposed faces 1505 and 1510. The outer periphery 1515 can be generally oval or oblong in shape, or can define any suitable alternative shape as desired. The bone fixation kit can include a plurality of spacers 1500 of different sizes, shapes, and/or thicknesses from one of the faces 1505 and 1510 to the other of the faces 1505 and 1510 to fit within different gaps having different sizes and shapes. The spacer 1500 can comprise a generally rigid or elastic material. For instance, the spacer 1500 can comprise a plastic, gel, foam, metal or other suitable material as desired. Further, the faces 1505 and 1510 of the spacer 1500 can include osteoconductive bone growth material and/or bone-growth openings to enhance bone fusion.

Referring now to FIGS. 54-65, a surgical fusion procedure of a joint between a first bone 21 and a second bone 23 will now be described. In one example, the first and second bones 21 and 23 define bones of a human foot 10. For instance, the first bone 21 can define a metatarsal such as the second or third metatarsal, and the second bone 23 can define a cuneiform such as the second or third cuneiform, respectively, such that the joint defines a tarsometatarsal (TMT) joint. It should be appreciated, however, that the first and second bones 21 and 23 can define any anatomical bones as desired. Alternatively, the first and second bones 21 and 23 can instead define bone segments of the same bone.

Figure 54:
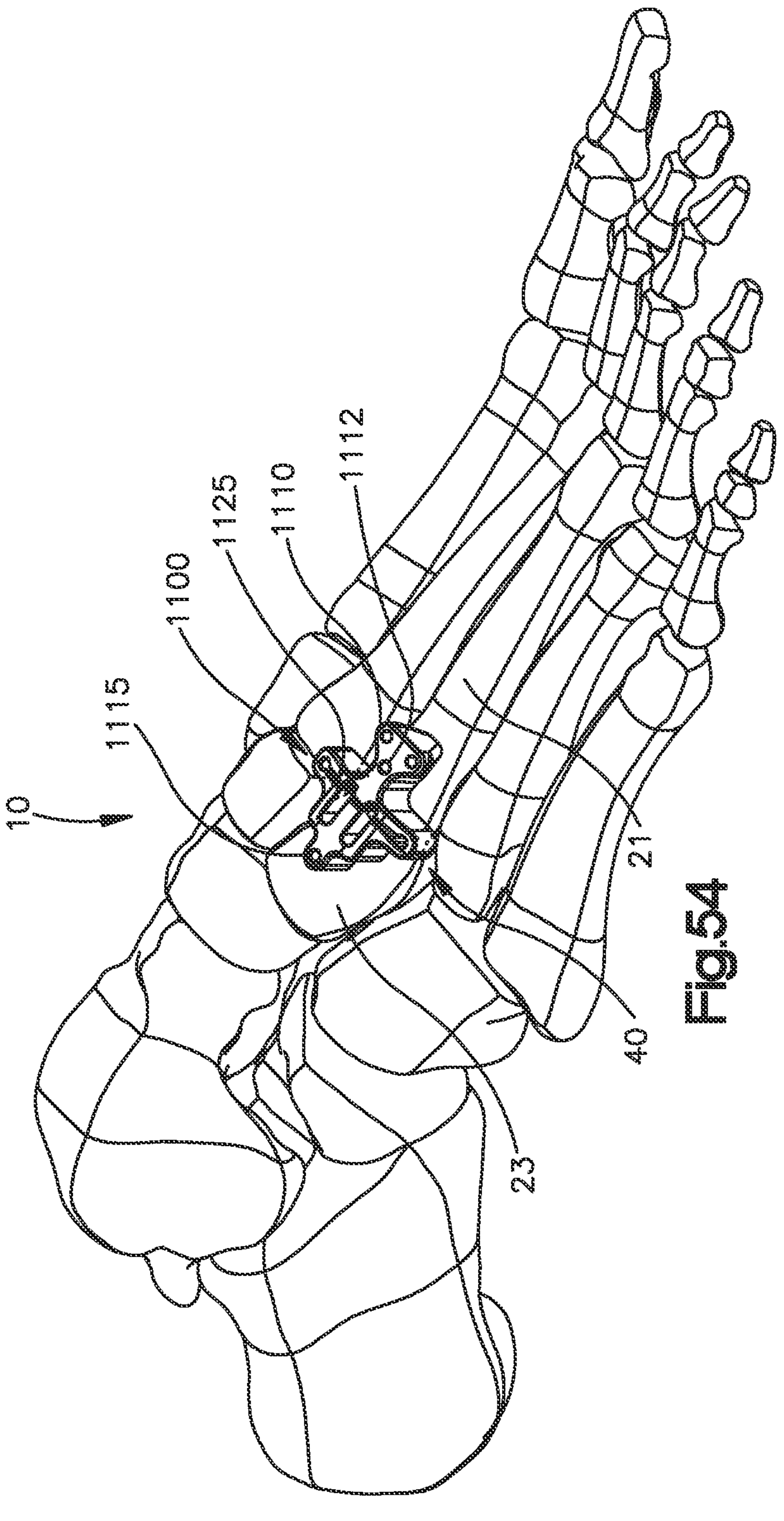
FIG. 54 is a perspective view of the bones of a human foot, showing a step of an example fusion procedure of the tarsometatarsal (TMT) joint performed using the example joint fusion devices disclosed herein, whereby the cut guide of FIG. 49A is placed against first and second bones of the foot that define a joint.
Figure 55:
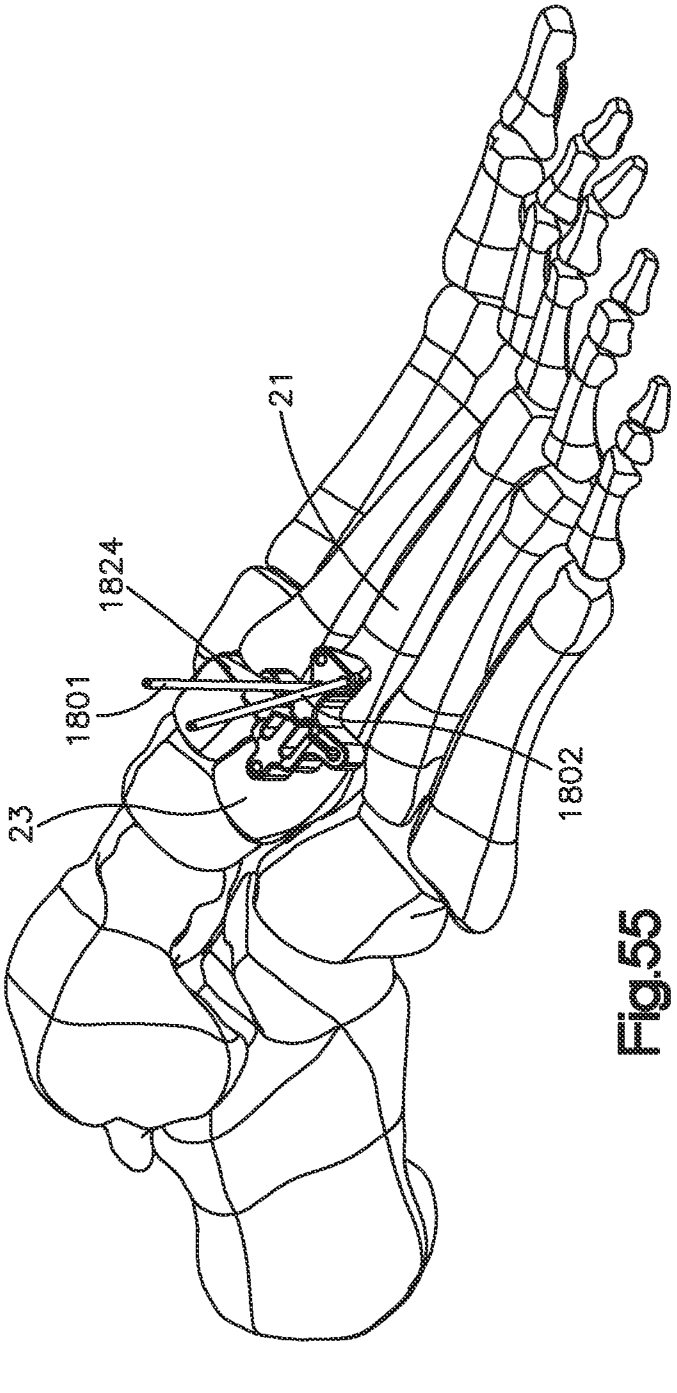
FIG. 55 is a perspective view of the human foot of FIG. 54, showing first and second temporary bone fixation elements inserted into holes of a first portion of the cut guide and into the first bone so as to temporarily secure the cut guide to the foot, and further showing a saw blade positioned in a cutting slot of the cut guide so as to cut a base of the first bone.

As shown in FIG. 54-55, the procedure may begin by placing and temporarily securing the cut guide 1100 to one or both of the first and second bones 21 and 23. Prior to placing the cut guide, the surgeon may prepare the joint by making an incision such as a dorsomedial incisions to expose the joint and excising soft tissue around the joint, such as the joint capsule or other soft tissue, to expose the joint and create a space in which the paddle 1112 of the cut guide 1100 can be seated.

Referring to FIG. 54 in particular, once the joint has been prepared, the cut guide 1100 is placed by seating the paddle 1120 (see FIG. 49A) within the joint between the first and second bones 21 and 23, in a first orientation such that the first portion 1110 is disposed adjacent to or against the first bone 21, and the and the second portion 1115 is disposed adjacent to or against the second bone 23. In particular, the cut guide 1100 can be placed on a dorsal side of the joint in the first orientation. The cutting slot 1125 can be aligned with the base of the first bone 21 when in the first orientation. The paddle 1120 is inserted into the joint such that the longitudinal centerline of the cut guide 1100 is oriented generally along the axis of the first bone 21. The alignment of the cut guide 1100 may be confirmed under fluoroscopy or other suitable imaging technique before proceeding.

Continuing to FIG. 55, when the cut guide 1100 is placed and is suitably aligned in the first orientation whereby the first portion 1110 is aligned with the first bone 21, the second portion 1115 is aligned with the second bone 23, and the cutting slot 1125 is aligned with the base or proximal portion of the first bone 21, the cut guide 1100 can be temporarily secured to the first bone 21. In particular, a first primary temporary bone fixation member 1801 can be inserted through the first primary temporary bone fixation hole 1112 and into or through the first bone 21. The first primary temporary bone fixation member 1801, and all temporary bone fixation members described herein, can be a K-wire or alternative wire, a pin, screw, nail, or any suitable bone fixation member as desired. The bone fixation members can be threaded and configured to threadedly purchase into the underlying bone, or can be smooth and unthreaded as desired. An auxiliary temporary bone fixation member 1802 can be inserted through one of the first auxiliary temporary bone fixation holes 1111 and into or through the first bone 21. It should be appreciated that the temporary bone fixation member 1802 is referred to as auxiliary herein, it can be used to secure the cut guide 1100 to the underlying first bone 21 without the first primary temporary bone fixation member 1801. Optionally, another temporary bone fixation member can be inserted through the second temporary bone fixation hole 1117 and into or through the second bone 23.

It is recognized that when the cut guide 1100 is temporarily secured to either or both of underlying bones 21 and 23 using two temporary bone fixation members, the cut guide 1100 is fixed in place. Thus, while the fixation of the cut guide 1100 is described with respect to insertion of the first and second temporary bone fixation members 1801 and 1802, any two temporary bone fixation members can temporarily secure the cut guide 1100 with respect to the first bone 21 in the first orientation.

With continuing reference to FIG. 55, once the temporary bone fixation members 1801 and 1802 have been inserted into the first and/or second bone 21, the base of the first bone 21 can be cut. In particular, a cutting instrument 1824 can be inserted through the cutting slot 1125 of the cut guide 1100 and into the underlying first bone 21 so as to cut the base of the first bone 21. The cutting instrument can be configured as a saw blade or any suitable instrument as desired.

Figure 56:
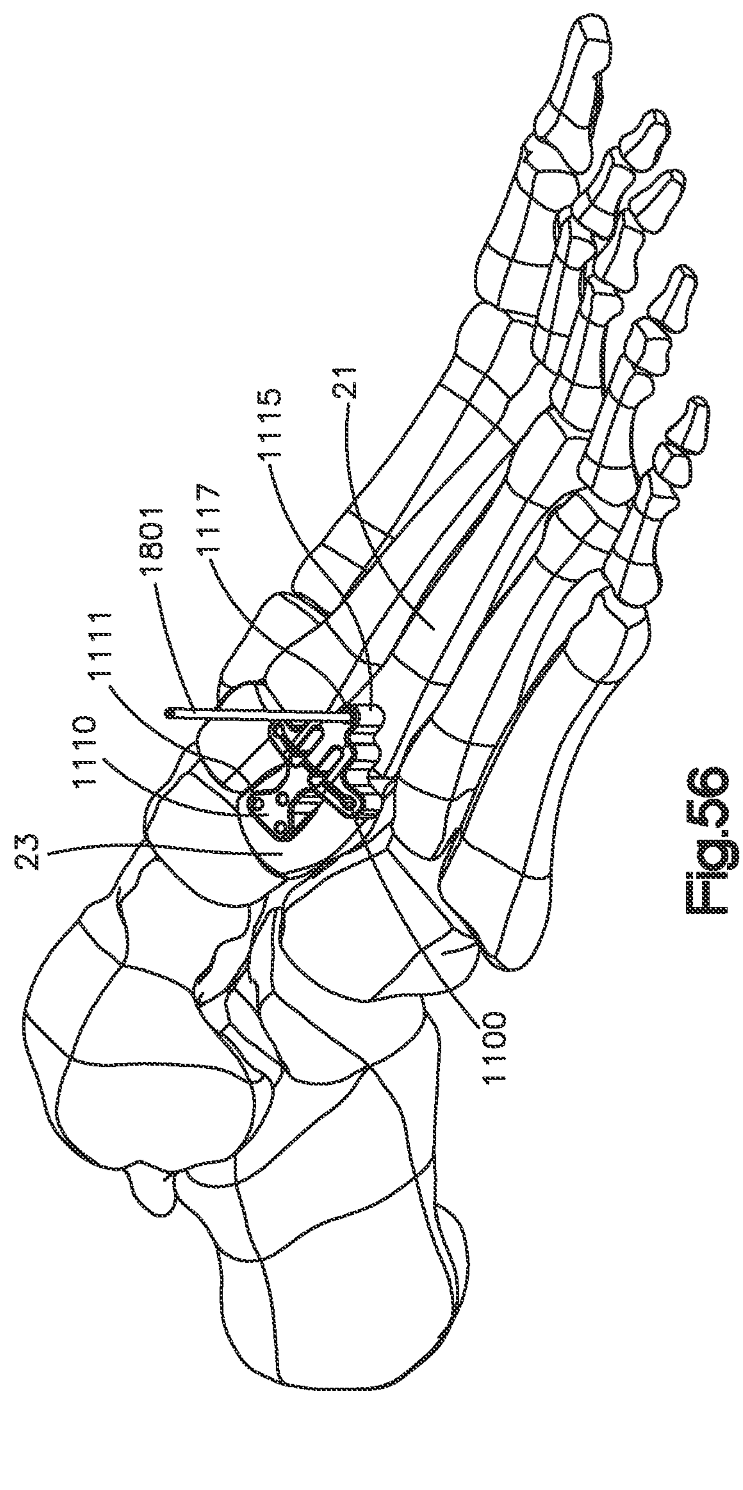
FIG. 56 is a perspective view of the human foot of FIG. 55, showing the cut guide removed and repositioned in a second orientation with the first portion aligned with the second bone and the second portion aligned with the first bone, and further showing a temporary bone fixation element that temporarily secures the second portion to the first bone.
Figure 57:
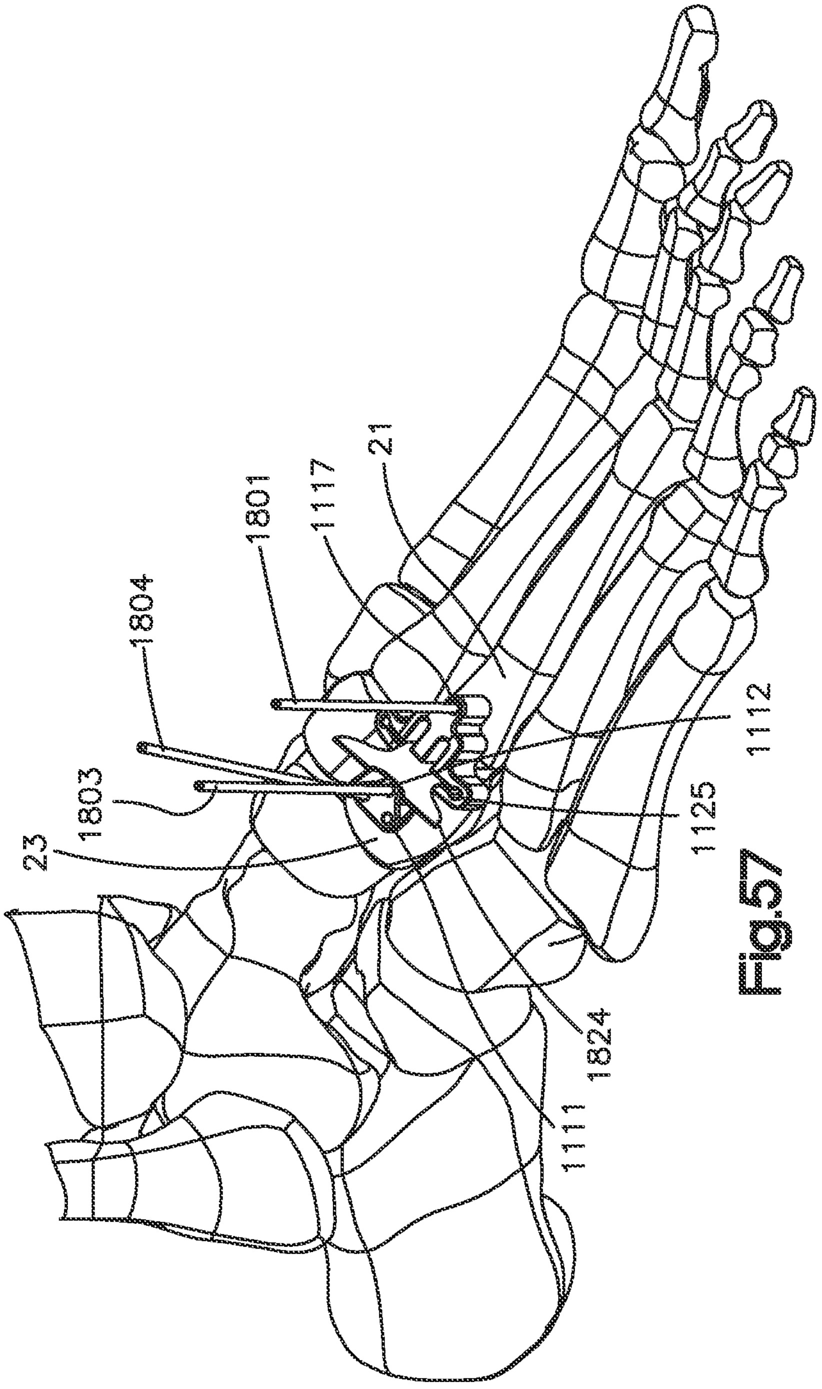
FIG. 57 is a perspective view of the human foot of FIG. 56, showing temporary bone fixation elements that extend through the first portion and into the second bone, and the saw blade in the cutting slot so as to cut a distal portion of the second bone.

Referring now to FIG. 56, the cutting instrument 1824 can then be removed from the cut guide 1100, and the cut guide 1100 can be removed from the temporary fixation members 1801 and 1802. The position of cut guide 1100 can then be reversed into a second orientation opposite the first orientation, whereby the first portion 1110 is aligned with the second bone 23 and the second portion 1115 is aligned with the first bone 21. The cutting slot 1125 can be aligned with the base or distal portion of the second bone 23. Prior to placing cut guide 1100 against the underlying first and second bones 21 and 23 in the second orientation, the bone pin 1802 can be removed from the first bone 21. When the cut guide 1100 is placed adjacent or against the underlying first and second bones 21 and 23, the second temporary bone fixation hole 1117 of the second portion 1115 can receive the first temporary bone fixation member 1801. Otherwise stated, the second portion 1115 can be placed over the first temporary bone fixation member 1801. Another temporary bone fixation member 1803 can be inserted through the first primary temporary bone fixation hole 1112 and into or through the underlying second bone 23. Yet another temporary bone fixation member 1804 can be inserted through a select one of the first auxiliary temporary bone fixation holes 1111 and into or through the second bone 23. The select one of the first auxiliary temporary bone fixation holes 1111 can be selected as that hole 1111 that is best aligned with the underlying second bone 23. The temporary bone fixation member 1804 can extend parallel with the temporary bone fixation member 1803, or can be angularly offset with respect to the temporary bone fixation member 1803.

Once the temporary bone fixation members have been inserted through the cut guide 1100 and into the underlying first and second bones 21 and 23, the base of the second bone 23 can be cut. In particular, the cutting instrument 1824 can be inserted through the cutting slot 1125 of the cut guide 1100 and into the underlying second bone 21 so as to cut the base of the second bone 21. The joint between the first and second bones 21 and 23 can thus be excised by cutting the first and second bones 21 and 23, thereby creating a resected joint 47 (see FIG. 58) between the first and second bones 21 and 23. It should be appreciated that cutting the first and second bones 21 and 23 enlarges the joint therebetween, and presents respective first and second resected faces of the first and second bones 21 and 23.

Figure 58:
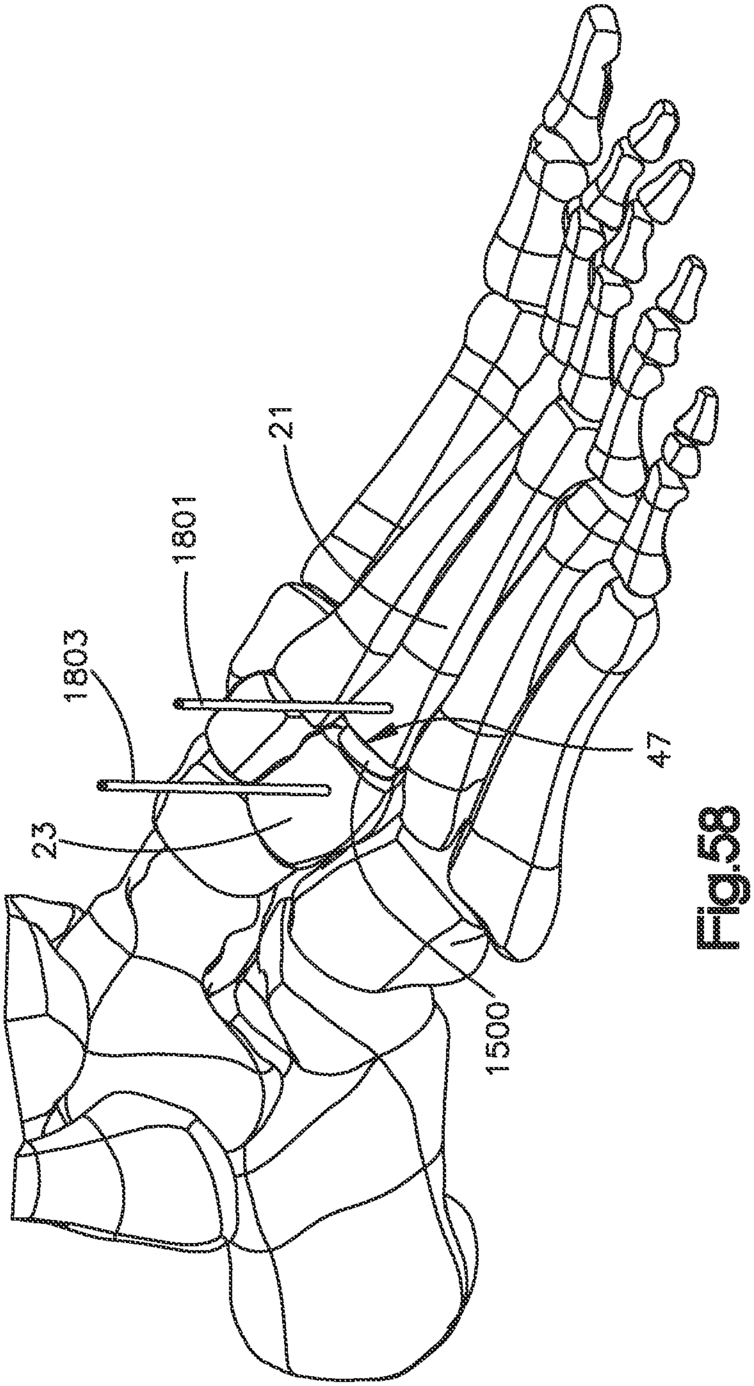
FIG. 58 is a perspective view of the human foot of FIG. 57, showing the saw blade and the cut guide removed, with temporary bone fixation elements remaining inserted into the first and second bones, respectively.

As shown in FIG. 58, the cut guide 1100 can then be removed. The temporary bone fixation member 1804 can be removed from the underlying second bone 23 and the cut guide 1100 prior to removing the cut guide 1100 from the bone, particularly when the temporary bone fixation member 1804 is angularly offset with respect to the temporary bone fixation member 1803. The temporary bone fixation members 1801 and 1803 can be remain fixed to the first and second bones 21 and 23 when the cut guide 1100 is removed. The spacer 1500 can be inserted into the resulting resected joint 47 between the first and second bones 21 and 23, respectively, that has been produced by cutting the first and second bones 21 and 23. The spacer 1500 can fit between the resected first and second faces of the first and second bones 21 and 23, respectively. The spacer 1500 can be sized relatively similar to the resected faces of the first or second bones 21 and 23 as described above. The spacer 1500 can prevent over-compression of the first and second bones 21 and 23 during future compression steps. In particular, the spacer 1500 can serve as a stop member that contacts the first and second resected faces and prevents the first and second bones 21 and 23 from traveling too close together. In some embodiments, the spacer 1500 may be omitted.

Figure 59:
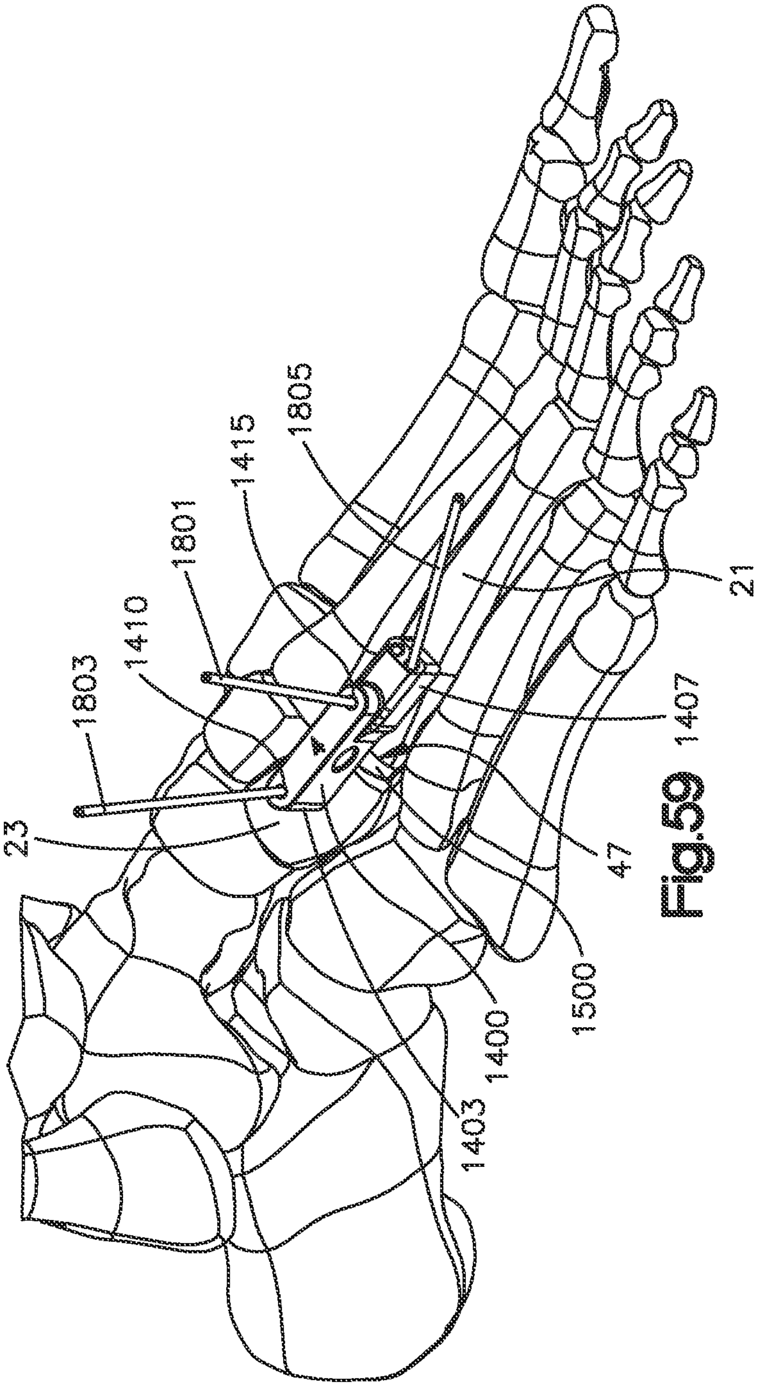
FIG. 59 is a perspective view of the human foot of FIG. 58, showing the compressor block of FIG. 51 applied over the temporary bone fixation elements, and an oblique temporary fixation member inserted through an oblique hole of the compressor block through the compressed joint to temporarily fix the joint in place.

Once the first and second bones 21 and 23 have been cut and the spacer 1500 inserted, if desired, the first and second bones 21 and 23 can be compressed toward each other. In particular, referring now to FIG. 59, the compressor block 1400 can be applied over the temporary bone fixation members 1801 and 1803, which can now be referred to as distal and proximal temporary bone fixation members, respectively. The temporary bone fixation members 1801 and 1803 can extend parallel to each other prior to application of the compressor block 1400. As the compressor block 1400 is applied, the distal temporary bone fixation hole 1415 can receive the temporary bone fixation member 1801 that is inserted into or through (referred to as at least into) the first bone 21, and the proximal temporary bone fixation hole 1410 can receive the temporary bone fixation member 1803 that is inserted into or through (referred to as at least into) the second bone 23. The temporary bone fixation member 1801 can be shorter or longer than the temporary bone fixation member 1803 (e.g., by approximately the height of the compressor block 1400 or more, as shown in FIG. 59). The height of the compressor block can be measured from the bone-facing surface to the opposed outer surface along the transverse direction (see FIG. 51A). In the example of FIG. 59, the compressor block 1400 can be applied to the temporary bone fixation members 1801 and 1803 by first threading the proximal temporary bone fixation holes 1410 onto the temporary bone fixation member 1803 and by inserting the temporary bone fixation member 1801 into the distal temporary bone fixation hole 1415.

As discussed above, unlike the pin holes of the cut guide 1100, the proximal and distal temporary bone fixation holes 1410 and 1415 taper inwardly toward each other along the longitudinal direction as they extend from the outer surface to the bone-facing surface of the cut guide. In particular, the temporary bone fixation members 1803 and 1801 can be inserted into the respective proximal and distal temporary bone fixation holes, respectively, at the bone-facing surface prior to sliding the compressor block 1400 along the temporary bone fixation members 1801 and 1803 toward the resected joint 47. Due to the convergent angle defined by the proximal and distal temporary bone fixation holes 1410 and 1415 (referred to as convergent temporary bone fixation holes), sliding the compressor block 1400 toward the underlying first and second bones 21 and 23 over the temporary bone fixation members 1801 and 1803 draws the temporary bone fixation member 1801 proximally toward to the temporary bone fixation member 1803.

Because the temporary bone fixation member 1801 is secured to the first bone 21, application of the compressor block 1400 causes the first bone 21 to move proximally toward the second bone 23, which thereby reduces the size of the resected joint 47. When the spacer 1500 is disposed in the resected joint 47, the resected faces of the first and second bones 21 and 23 are brought into contact with the respective faces of the spacer 1500 (or into contact with each other if no spacer is used) to an approximated position. Further, convergent temporary fixation holes 1410 and 1415 cause the temporary fixation members 1801 and 1803 to rotate and translate in the sagittal plane so that the plantar side of the resected joint 47 is compressed. This may be desirable, as compression on only the dorsal aspect of the bones 21 and 23 may in some cases cause a plantar gapping of the resected joint 47, which is undesirable for fusion.

Once the bones 21 and 23 have been approximated, an oblique temporary fixation member 1805 is then inserted through one of the oblique holes 1420 such that the oblique temporary fixation member 1805 travels inwardly as it travels proximally through the first bone 21, across the resected joint 47, and into the second bone 23. Thus, the oblique temporary fixation member 1805 temporarily fixes the first and second bones 21 and 23 in place in their approximated position. The temporary bone fixation member 1801 and the temporary bone fixation member 1803 bone pin 1803 can then be removed from the underlying bones 21 and 23 and removed from the compressor block 1400. The compressor block 1400 may then be removed by sliding the compressor block outward along the oblique temporary fixation member 1805, which remains in place to temporarily fix the joint. Alternatively, if the compressor block 1400 includes temporary bone fixation slots 1452 of FIGS. 52A-52D, the compressor block 1400 can be removed from the first and second bones 21 and 23 by moving the compressor block 1400 away from the bones so that the oblique temporary fixation member 1805 exists the slot 1452 out the opening at the bone-facing surface of the compressor block 1400. Any number of oblique hole trajectories could be applied to the compression block 1400 for placement of the oblique temporary bone fixation member.

While the oblique temporary bone fixation holes 1420 (see FIG. 51D) is shown as being disposed at the distal portion 1470 of the compression block 1400 in one example, the oblique temporary bone fixation holes 1420 can alternatively be disposed at the proximal portion 1403 and can thus extend inward as it extends distally. Thus, the oblique temporary fixation member 1805 can be driven inserted through the oblique temporary bone fixation holes 1420 and driven inwardly as it extends distally through the second bone 23, the resected joint 47, and into the first bone 21 to fix the first and second bones 21 and 23 in their approximated position.

Figure 60:
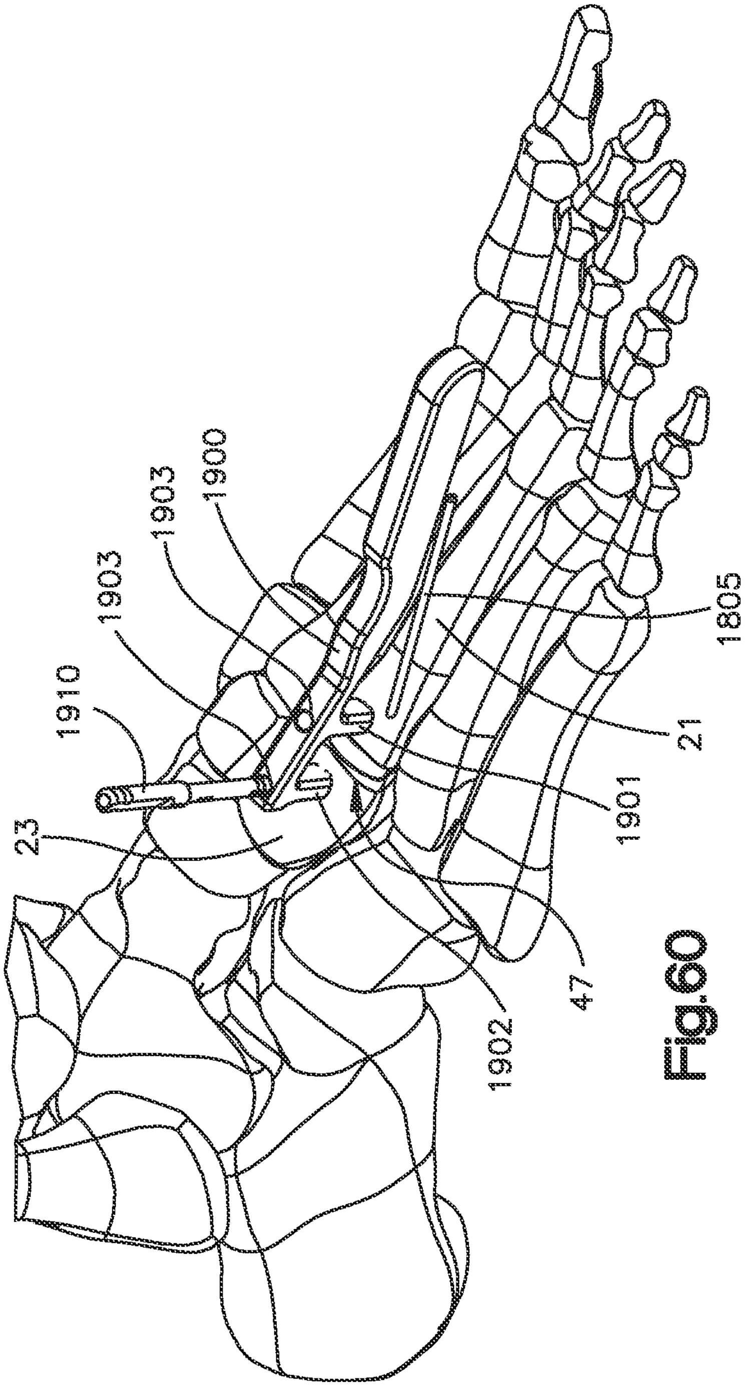
FIG. 60 is a perspective view of the human foot of FIG. 59, showing the compressor block removed, and a drill guide placed across the resected joint.
Figure 61:
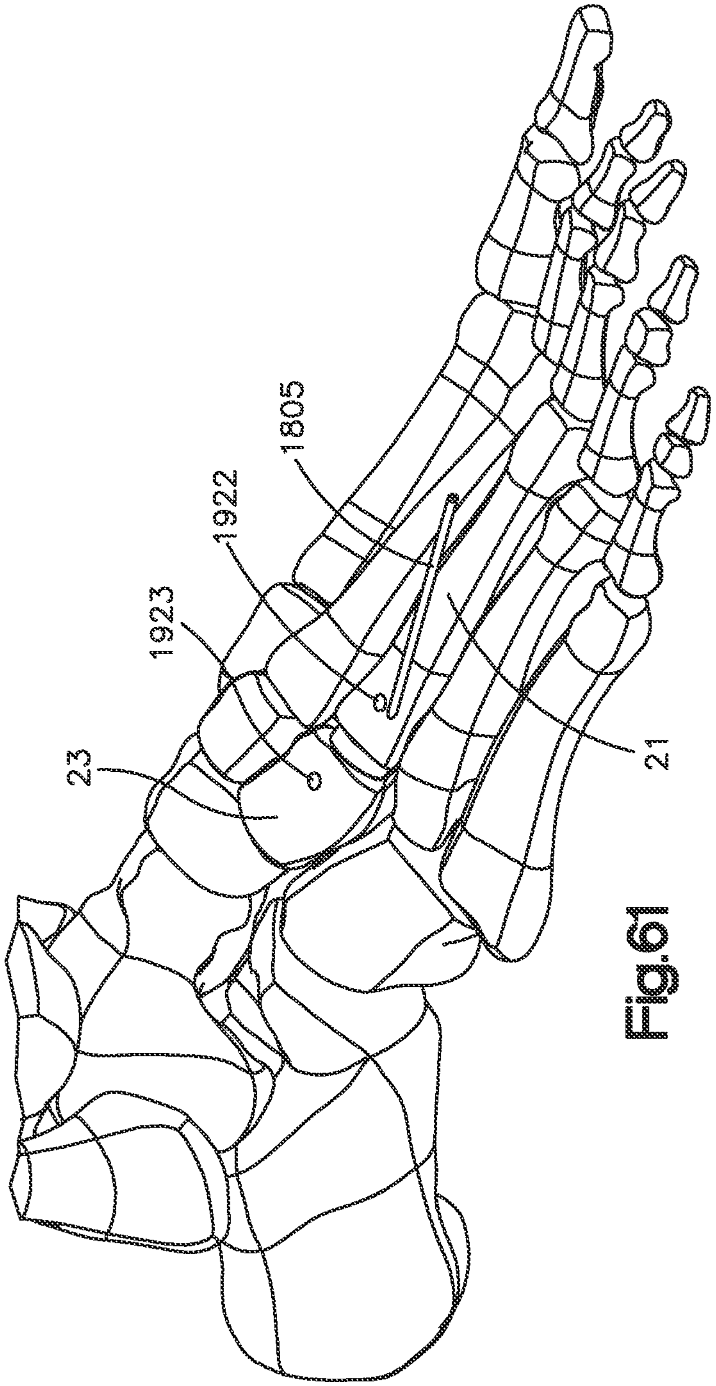
FIG. 61 is a perspective view of the human foot of FIG. 60, showing the pilot holes that have been drilled through the drill guide, and showing the drill guide and temporary bone fixation elements removed.

Referring now to FIGS. 60-61, while the resected joint 47 is fixed in place by the oblique temporary fixation member 1805, a drill guide 1900 can be placed across the resected joint 47. The drill guide 1900 can have first and second legs 1901 and 1902 that can be placed adjacent or against the first bone 21 and the second bone 23, respectively. The drill guide 1900 can define through-holes 1903 that extend through the legs 1901 and 1902. First and second pilot holes 1922 and 1923 are drilled into the first and second bones 21 and 23, respectively, through the through-holes 1903. In particular, a drill 1910 is driven through the through-holes 1903 of the first and second legs 1901 and 1902 to create the pilot holes 1922 and 1923. In some examples, the pilot holes may align with apertures created by insertion of the temporary bone fixation members 1801 and 1803. The drill guide 1900 is further described in U.S. Pat. App. No. 2018/0353172, the entirety of which is hereby incorporated by reference.

Figure 62:
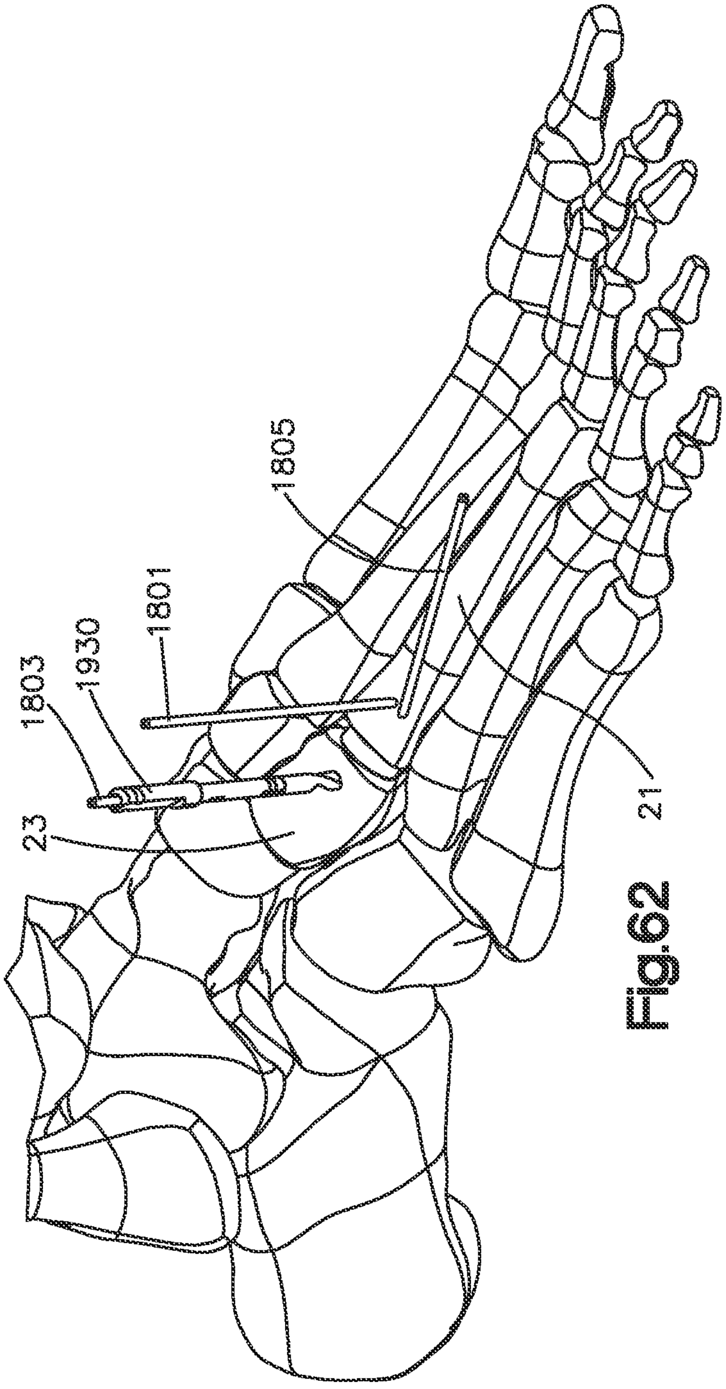
FIG. 62 is a perspective view of the human foot of FIG. 59, showing the compressor block removed and a reamer over one of the temporary bone fixation elements to create a pilot hole in accordance with an alternative embodiment.
Figure 63:
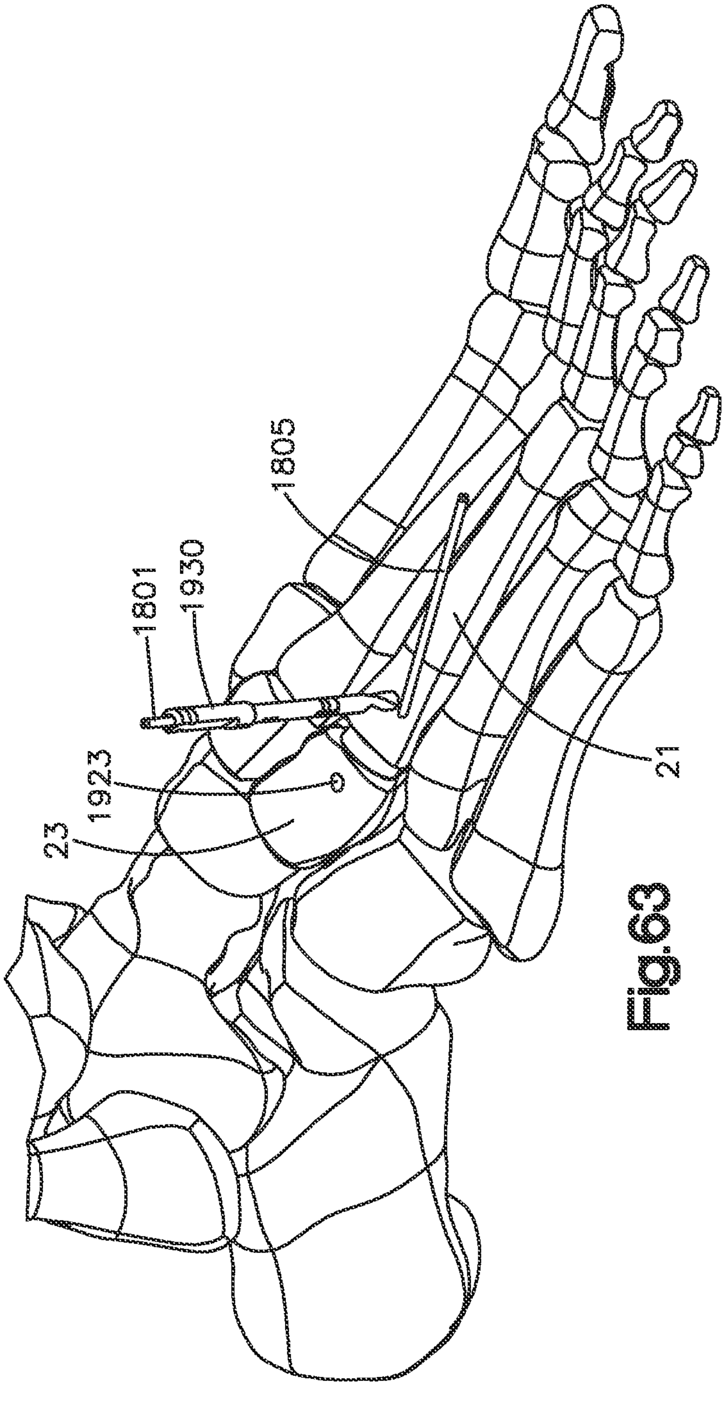

Alternatively, as illustrated in FIGS. 62-63, the first and second pilot holes 1922 and 1923 can be prepared by driving a cannulated reamer 1930 over the temporary bone fixation members 1801 and 1803 and into the underlying first and second bones 21 and 23. The temporary bone fixation members 1801 and 1803 can then be removed. In this regard, it should be appreciated that the temporary bone fixation members 1801 and 1803 can remain in the first and second bones 21 and 23 during removal of the compressor block 1400 due to the fixation of the resected joint 47 by the oblique temporary bone fixation member 1805 (see FIG. 59). Alternatively, the temporary bone fixation members 1801 and 1803 can be removed from the first and second bones 21 and 23 prior to removing the compressor block 1400, and reinserted into the bones 21 and 23 after the compressor block 1400 has been removed. Once the pilot holes 1922 and 1923 have been created, the temporary bone fixation members 1801 and 1803 can be removed from the first and second bones.

Figure 64:
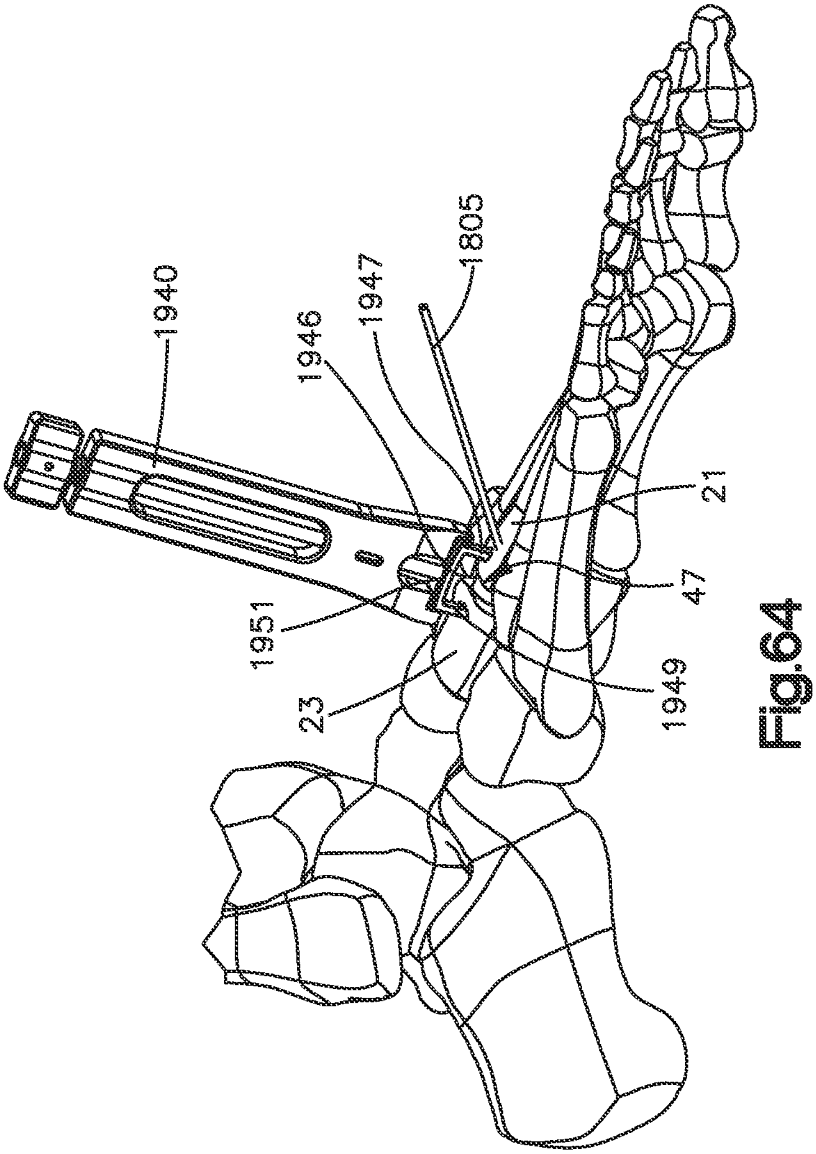
Figure 65:
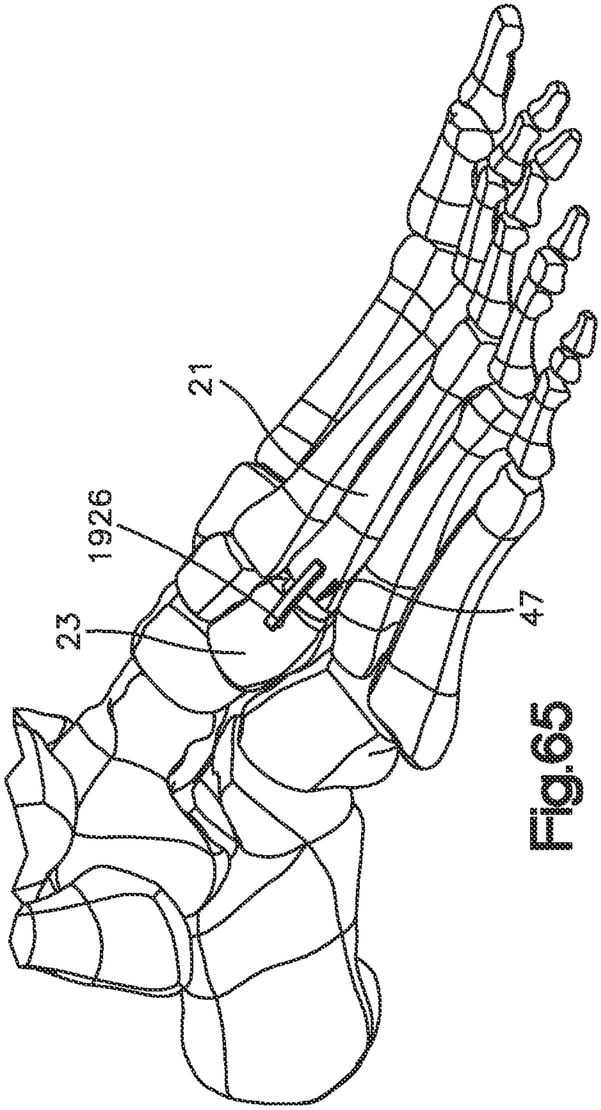

Next, referring to FIGS. 64-65, in order to permanently fix the first bone 21 relative to the second bone 23, a staple 1946 can be inserted across the resected joint. The term "permanently" means that the fixation remains after completion of the surgical procedure. The staple 1946 can be gripped and tensioned using an applicator 1940, as shown and described in U.S. Pat. App. No. 2018/0353172. A first leg 1947 of the staple 1946 can be inserted into the first bone 21 through the first pilot hole 1922. A second leg 1949 of the staple 1946 can be inserted into the second bone 23 through the second pilot hole 1923. A cross-bar 1951 can extend from the first leg 1947 to the second leg 1949 across the resected joint 47. The applicator 1940 can then release the staple 1946. Because the legs 1947 and 1949 of the staple 1946 can be resilient, the legs are drawn together when the applicator 1940 is removed, which allows the staple 1946 to compress the resected joint 47. The staple 1946 is further described in U.S. Publication No. 2018/0317906, which is incorporated herein by reference in its entirety. Alternatively, or in addition, the resected joint 47 may be secured using a bone plate and/or cross screw, or any other desired fixation device suitable for fixing the first bone 21 relative to the second bone 23. A bone plate and staple system may be found in U.S. Pat. No. 10,299,842, which is incorporated herein by reference in its entirety.

FIGS. 66-72 depict a joint 40 between a first bone 20 and a second bone 30. Here, the joint 40 is depicted in the bones of a foot 10. In contrast to the process of FIGS. 54-65, FIGS. 66-72 illustrate an example process of joint fusion that includes a bone plate in combination with a staple. However, it will be understood that the process of FIGS. 66-72 may also be implemented with a bone plate alone, without including a staple as a means of bone fixation.

Figure 66:
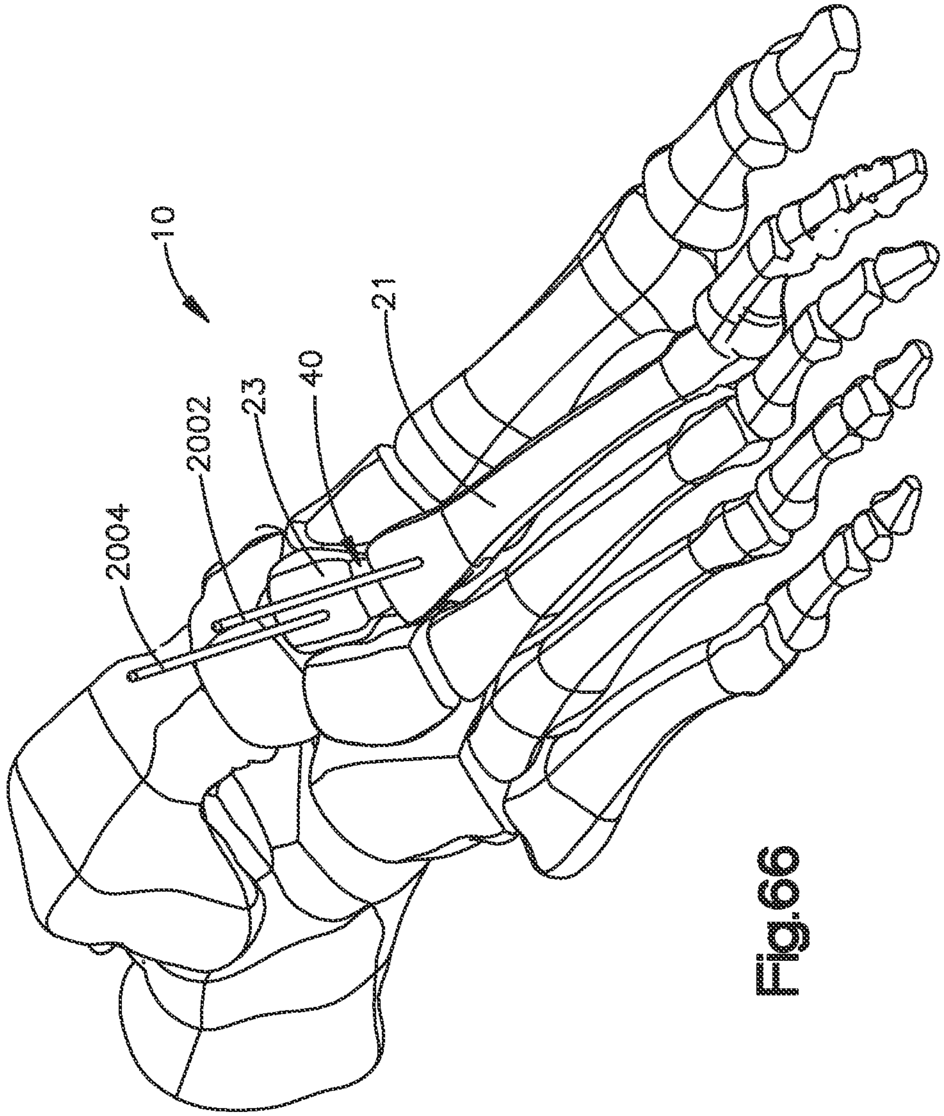

In the initial configuration of FIG. 66, the joint 40 has already been prepared for fixation such as by cutting the facing ends of bones 20 and 30 (e.g., using any of the cut guides disclosed herein). Bone pins 2002, 2004 are positioned partly within bones 20 and 30, respectively. For example, the initial configuration of FIG. 66 may correspond to the configuration shown in FIG. 58. Although not illustrated in FIGS. 66-72, a spacer such as spacer 1500 may be used in conjunction with the process of FIGS. 66-72.

Figure 67:
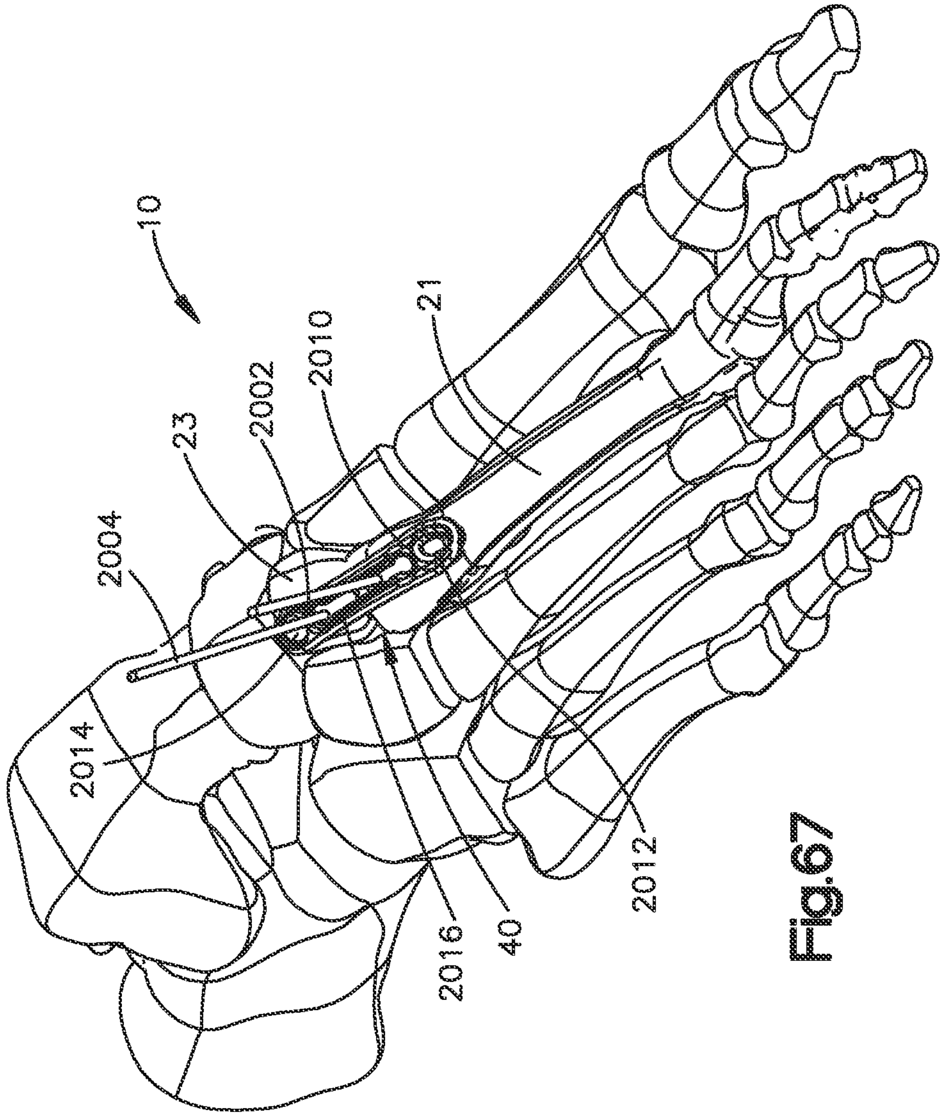

Turning to FIG. 67, a bone plate 2010 can be placed across the joint 40 such that the bone plate 2010 overlays a portion of bones 20 and 30. A distal screw aperture 2012 is positioned over a portion of bone 20 and a proximal screw aperture 2014 is positioned over a portion of bone 30. An intermediate portion of the bone plate 2010 includes a staple aperture 2016 sized and shaped to receive a staple therethrough. In alternative embodiments, the staple aperture 2016 may have other configurations, for example, an elongated open slot suitable for receiving other components such as a non-staple compression plate, or the like.

Figure 68:
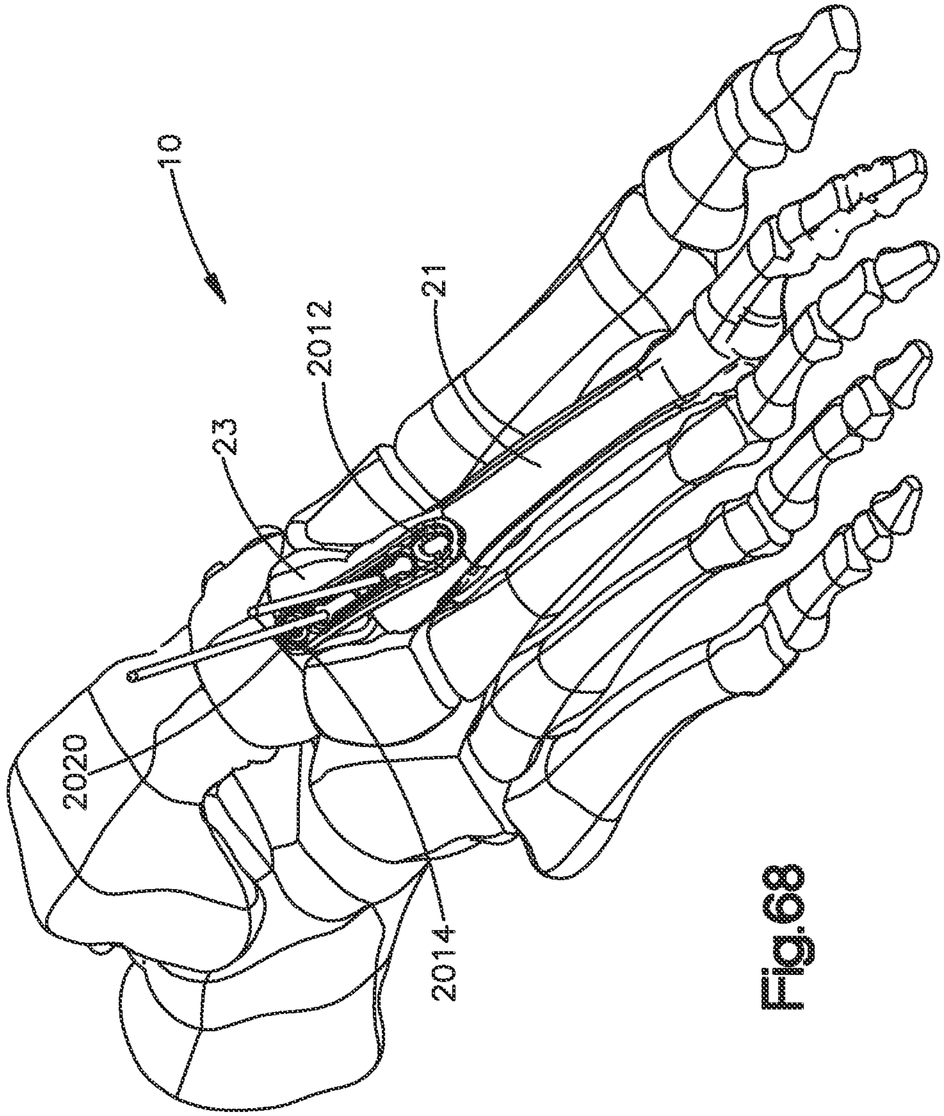
Figure 69:
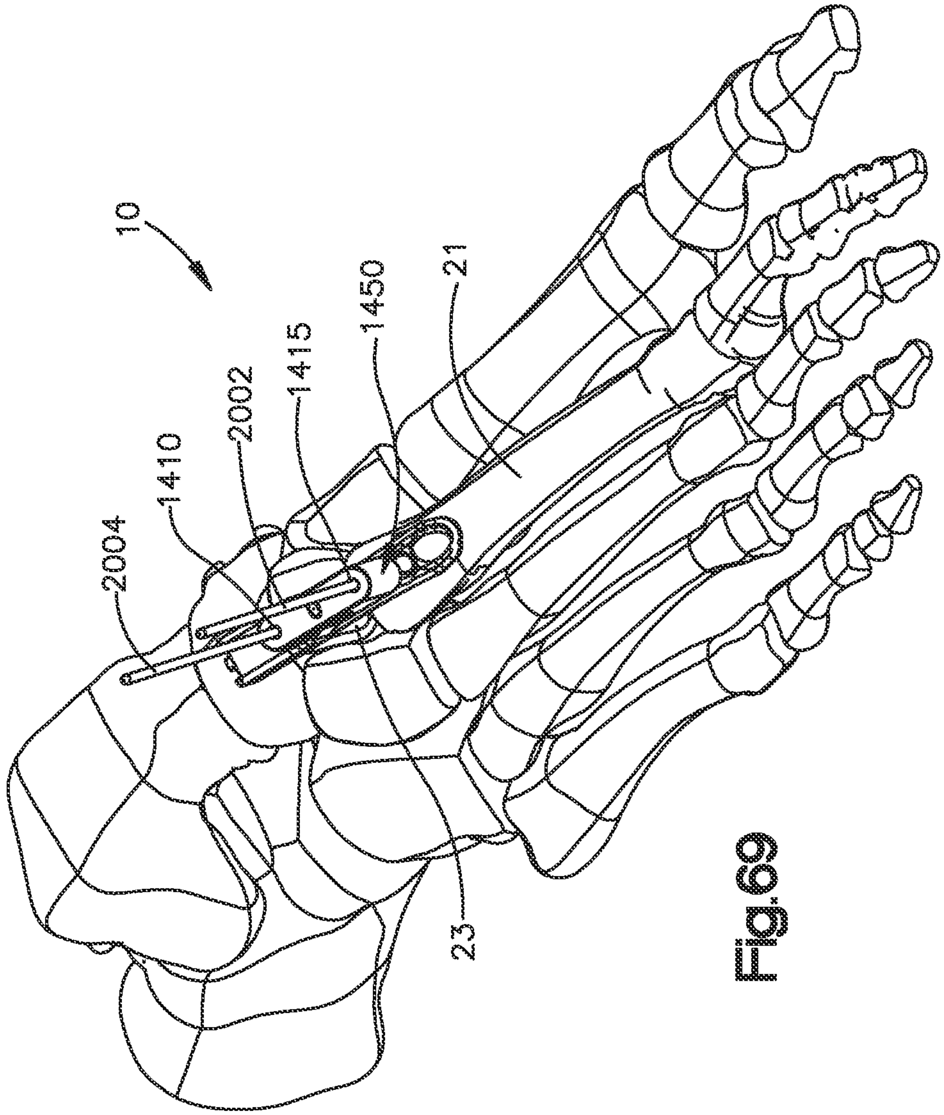

As shown in FIG. 68, a first bone screw 2020 can be driven into bone 30 through the proximal screw aperture 2014 to initially fix the bone plate 2010 to the foot 10. In the configuration shown in FIG. 68, the bone plate 2010 is fixed relative to bone 30 but remains movable relative to bone 20 such that a compression block may be applied prior to fixing the bone plate 2010 to bone 20, as shown in FIG. 69. In alternative embodiments, the first bone screw 2020 can be driven into bone 20 through the distal screw aperture 2012 instead of proximal screw aperture 2014.

FIG. 69 depicts the application of a compression block 1450 over the bone pins 2002, 2004, similar to the application of compressor block 1400 in FIG. 59. Due to the convergent angle of pin holes 1410, 1415 of the compressor block 1450, sliding the compressor block 1450 downward over bone pins 2002, 2004 pulls the bone pins 2002, 2004 closer together, causing bones 20 and 30 to move closer together and into contact either with each other or with a spacer if a spacer is used. In some alternative embodiments, the first bone screw 2020 can be driven into bone 20 or 30 after application of the compression block 1450 over the bone pins 2002, 2004 instead of prior to application of the compression block.

Figure 70:
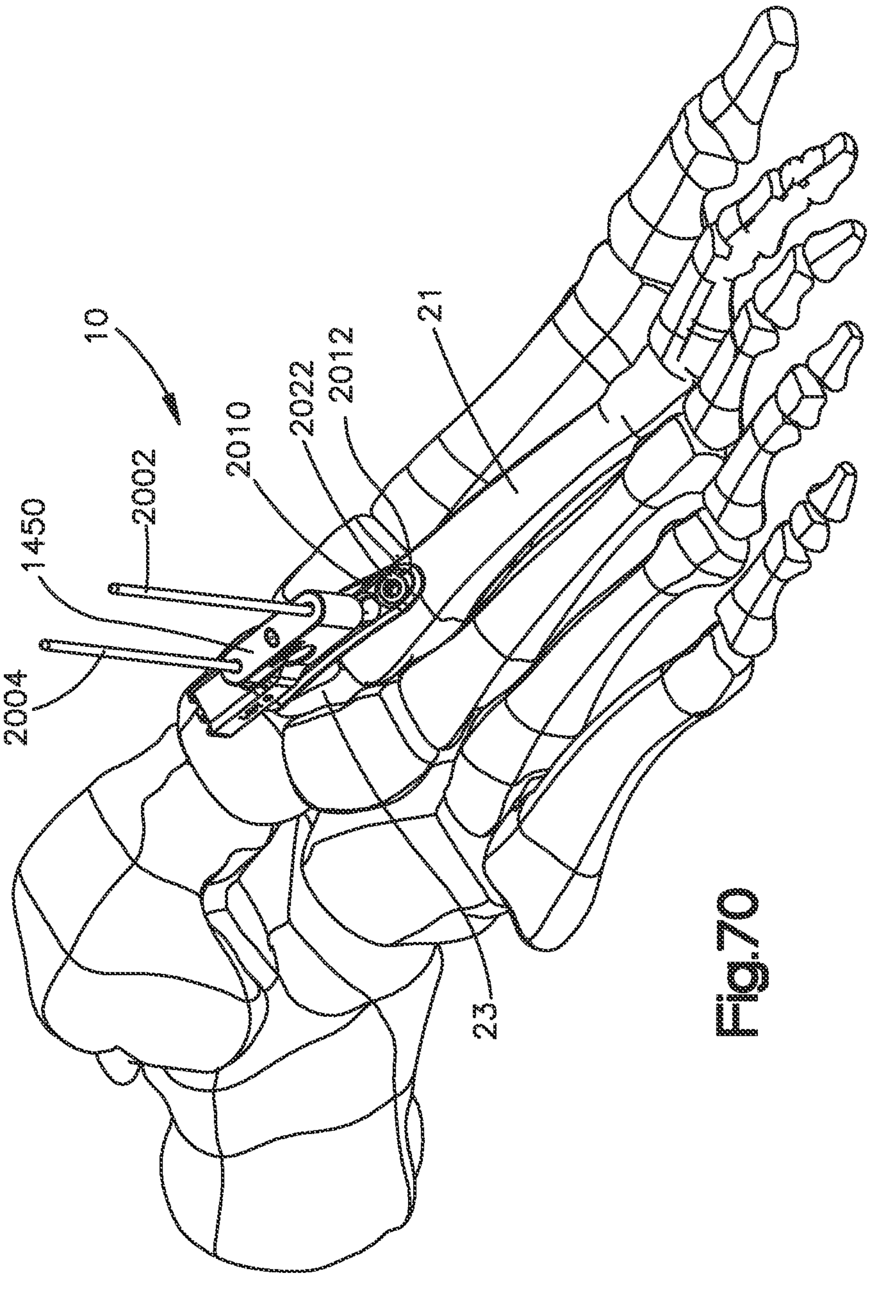
Figure 71:
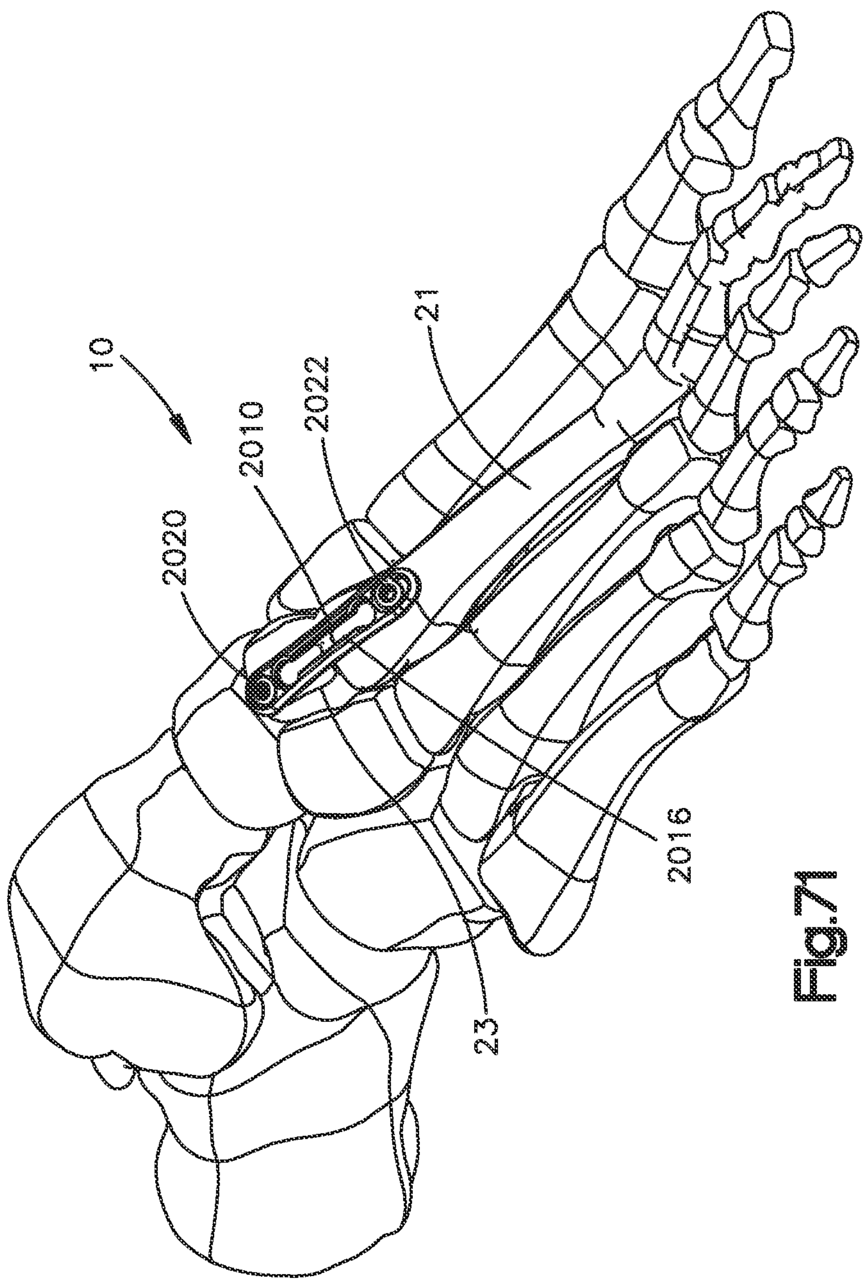
Figure 72:
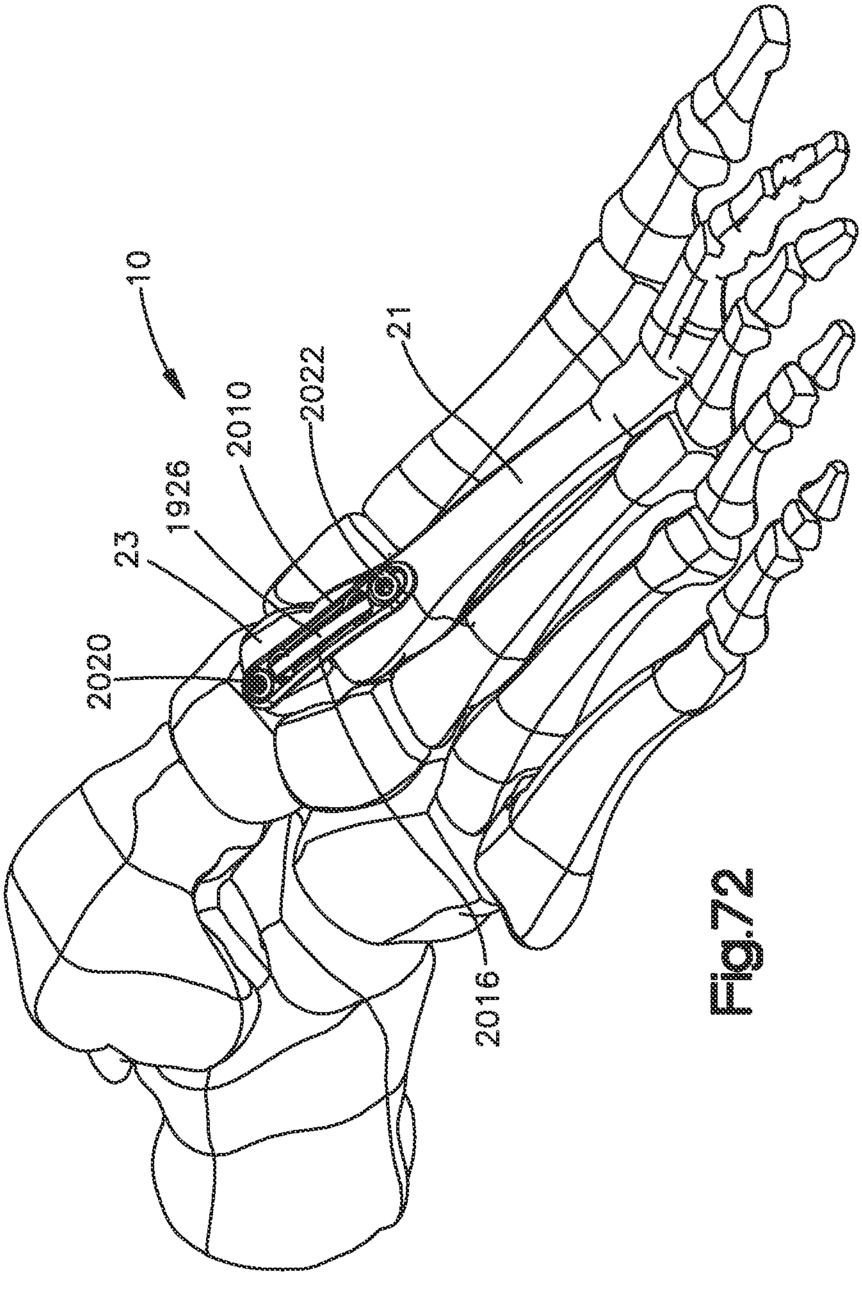

As shown in FIG. 70, a second bone screw 2022 can be driven into bone 20 through the distal screw aperture 2012 while the compression block 1450 retains bone pins 2002 and 2004, maintaining the desired compression of bones 20 and 30. Insertion of the second bone screw 2022 fixes bones 20 and 30 in the desired configuration. The compression block 1450 and bone pins 2002, 2004 can then be removed from the foot 10, as shown in FIG. 71. Continuing with reference to FIG. 72, a staple 1926 can then be inserted through the staple aperture 2016 of the bone plate 2010 (e.g., following preparation and/or drilling for the staple using a process such as that shown in FIGS. 60-63), such that the bones 20 and 30 are fixed relative to one another by the staple 1926, the bone screws 2020 and 2022, and the bone plate 2010.

FIGS. 73A-73E depict an example bone plate 550 configured to be used in the joint fixation procedures described herein. The bone plate 500 can be formed of a variety of metals or alloys. For example, the bone plate may be formed of titanium, a shape-memory alloy such as nitinol, or the like. As will be described in greater detail, the bone plate 550 can be configured to fix two adjacent rays of a foot.

The bone plate 550 is sized and shaped to be applied across Accordingly, the bone plate 550 includes two generally parallel bodies 555 joined by bridges 557. The bodies 555 and bridges 557 may comprise a single integrally formed component. Each body 555 includes a staple aperture 560, a proximal screw aperture 565, and a distal screw aperture 570. Each of the staple apertures 560 includes two holes 562 sized and shaped to accommodate the two legs of a bone staple such that one of the legs is seated within a proximal bone such as a cuneiform bone near the corresponding proximal screw aperture 565 and the other leg is seated within a distal bone such as a corresponding metatarsal near the corresponding distal screw aperture 570.

The staple aperture 560 and each of the screw apertures 565, 570 is shaped to include a countersink to reduce motion of staples and/or screws seated therein. In addition, the countersinks may allow a staple or screw applied therein to not extend significantly above the outer surface of the body 555 of the bone plate 550. A bone-facing surface 551 of the bone plate 550 may be substantially smooth. In addition, the bone plate 550 may be curved, as shown in FIGS. 73A-73E, to match a curvature of the bones of the midfoot. For example, as shown in FIGS. 73D and 73E, the bone plate 550 may have a concave curvature about both the longitudinal and lateral axes.

FIG. 74 is a perspective view of the bones of a foot 10, illustrating an example placement of the bone plate 550. As shown in FIG. 74, the bone plate 550 may be used to fix both the second and third rays of the foot 10. For example, one body 555 of the bone plate 550 fixes the second cuneiform 35 to the second metatarsal 25, and the other body 555 of the bone plate 550 fixes the third cuneiform 37 to the third metatarsal 27, such that the bridges 557 stabilize the second and third rays of the foot relative to each other. In some embodiments, both the second and third TMT joints of the foot 10 may have been excised and prepared using any of the cut guides described herein, or only one of the second and third TMT joints may have been excised. For example, the bone plate 550 may be used to provide additional stability to an excised and fixed joint by securing the joint to another, non-excised joint.

Each of the bodies 555 is secured to its corresponding cuneiform 35 or 37 and its corresponding metatarsal 25 or 27 by a proximal bone screw 2024 through the proximal screw aperture 565, a distal bone screw 2026 through the distal screw aperture 570, and a bone staple 2028 through the staple aperture 560 such that each bone staple 2028 spans a TMT joint.

The embodiments described herein are exemplary. Modifications, rearrangements, substitute processes, etc. may be made to these embodiments and still be encompassed within the teachings set forth herein. Depending on the embodiment, certain acts, events, or functions of any of the methods described herein can be performed in a different sequence, can be added, merged, or left out altogether (e.g., not all described acts or events are necessary for the practice of the method). Moreover, in certain embodiments, acts or events can be performed concurrently rather than sequentially.

The phrases "connected to," "coupled to," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements, and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," "involving," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y and/or Z). Thus, such disjunctive language is not generally intended to, and should not, imply that certain embodiments require at least one of X, at least one of Y or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A in conjunction with a second processor configured to carry out recitations B and C.

While the above detailed description has shown, described, and pointed out novel features as applied to illustrative embodiments, it will be understood that various omissions, substitutions, and changes in the form and details of the devices or algorithms illustrated can be made without departing from the spirit of the disclosure. As will be recognized, certain embodiments described herein can be embodied within a form that does not provide all of the features and benefits set forth herein, as some features can be used or practiced separately from others. All changes which come within the meaning and range of equivalency of the claims are to be embraced within their scope.

What is claimed is:

1. A method of fusing a joint, the method comprising:

inserting a first temporary bone fixation member into a first bone at a first distance from a joint between the first bone and a second bone;

excising the joint to create a resected joint, the excising step comprising:

cutting a base of the first bone adjacent the joint; and cutting a base of a second bone adjacent the joint;

inserting a second temporary bone fixation member into the second bone at a second distance relative to the resected joint;

compressing the joint using a compressor block such that a resected face of the first bone is moved towards a resected face of the second bone;

inserting an oblique temporary fixation member through an oblique hole that extends through the compressor block, and through the joint; and after the step of inserting the oblique temporary fixation member, permanently fixing the first bone to the second bone across the resected joint.

2. The method of claim 1, wherein the first bone is a metatarsal, the second bone is a cuneiform or cuboid bone, and the joint is a tarsometatarsal joint.

3. The method of claim 1, further comprising placing a reversible cut guide across a joint in a first orientation, the reversible cut guide comprising:

a body having a first portion and an opposed second portion;

a primary temporary bone fixation hole that extends through the first portion of the body;

a second temporary bone fixation hole that extends through the second portion of the body parallel to the primary temporary bone fixation hole; and a cutting slot that extends through the body between the primary and second temporary bone fixation holes.

4. The method of claim 3, further comprising inserting an auxiliary bone fixation member into the first bone through an auxiliary bone fixation hole that extends through the first portion of the reversible cut guide.

5. The method of claim 3, wherein in the first orientation the cutting slot is aligned with the base of the first bone, and the excising step further comprises cutting the base of the first bone through the slot.

6. The method of claim 5, wherein the reversible cut guide further includes a paddle that extends from the body between the first and second portions of the cut guide; and the method further comprises inserting the paddle into the joint.

7. The method of claim 6, further comprising removing the reversible cut guide from the first orientation and placing the reversible cut guide across the joint in a second orientation that is opposite the first orientation.

8. The method of claim 7, wherein in the second orientation, the primary temporary bone fixation member extends through the second temporary fixation hole and into first bone, and the second temporary bone fixation member extends through the primary temporary bone fixation hole and into the second bone.

9. The method of claim 8, further comprising inserting another temporary bone fixation member into the second bone through a third temporary bone fixation of the first portion when the cut guide is in the second orientation.

10. The method of claim 7, wherein in the second orientation the cutting slot is aligned with the base of the second bone, and the excising step comprises cutting the base of the second bone through the cutting slot.

11. The method of claim 7, wherein the paddle is inserted in joint, and the primary temporary bone fixation hole defines a second distance relative to the joint when the cut guide is in the second orientation.

12. The method of claim 1, further comprising, prior to compressing the joint, inserting a spacer into the resected joint between the first bone and the second bone.

13. The method of claim 1, wherein the compressor block comprises:

a block body having a bone-facing surface and an opposed outer surface;

a proximal temporary bone fixation hole that extends through the body from the outer surface to the bone-facing surface at a first angle of less than 90 degrees relative to the outer surface and the bone-facing surface; and a distal temporary bone fixation hole extending through the body from the outer surface to the bone-facing surface at the first angle relative to the outer surface and the bone-facing surface, wherein the proximal and distal temporary bone fixation holes converge as they extend from the outer surface to the bone-facing surface.

14. The method of claim 13, wherein compressing the joint comprises:

inserting the first temporary bone fixation member into the distal temporary bone fixation hole at the bone-facing surface;

inserting the second temporary bone fixation member into the proximal temporary bone fixation hole at the bone-facing surface;

sliding the compressor block along the first and second temporary bone fixation members toward the joint.

15. The method of claim 1, wherein the oblique hole defines a linear path passing through the joint when the compressor block is aligned proximate the joint on the temporary bone fixation members.

16. The method of claim 1, further comprising removing the oblique temporary fixation member after permanently fixing the first bone to the second bone.

17. The method of claim 1, wherein the step of permanently fixing the first bone to the second bone comprises placing a staple over the joint such that a first leg of the staple is inserted into the first bone and a second leg of the staple is inserted into the second bone.

18. The method of claim 17, wherein placing the staple includes:

positioning a first guide leg of a drill guide over the first bone;

pre-drilling a first pilot hole in the first bone through the first guide leg;

positioning a second guide leg of the drill guide over the second bone;

pre-drilling a second pilot hole in the second bone through the second guide leg; and inserting the first leg of the staple in the first pilot hole and the second leg of the staple in the second pilot hole.

19. The method of claim 18, wherein placing the staple further includes:

removing the temporary bone fixation members and pre-drilling the pilot holes at the locations of insertion of the temporary bone fixation members.

20. The method of claim 17, wherein placing the staple includes:

pre-drilling a first pilot hole in the first bone using a cannulated reamer over the first temporary bone fixation member;

pre-drilling a second pilot hole in the second bone using the cannulated reamer over the second temporary bone fixation member;

inserting the first leg of the staple in the first pilot hole and the second leg of the staple in the second pilot hole.

21. The method of claim 1, wherein the joint is fixed using a bone plate and a plurality of bone screws, and wherein at least one of the plurality of bone screws is a cross screw extending at an angle of less than 90 degrees relative to the bone plate.

22. The method of claim 1, comprising, prior to compressing the joint:

sliding a bone plate over the first and second temporary bone fixation members; and inserting a first screw through a first aperture in the bone plate into the first or second bone.

23. The method of claim 22, comprising, after compressing the joint, inserting a second screw through a second aperture in the bone plate into the other of the first or second bone.

24. The method of claim 23, comprising inserting a compression staple through the bone plate.

* * * * *